US012807572B2

(12) United States Patent
Chao et al.

(10) Patent No.: US 12,807,572 B2
(45) Date of Patent: Nov. 24, 2026

(54) TROPOLONE DERIVATIVES AND TAUTOMERS THEREOF FOR IRON REGULATION IN ANIMALS

(71) Applicant: Kinesid Therapeutics, Inc., Champaign, IL (US)

(72) Inventors: Jianhua Chao, Palo Alto, CA (US); Stanley J. Hollenbach, Raleigh, NC (US); Michael C. Holmes, Oakland, CA (US); Douglas M. Matje, San Francisco, CA (US); Nicholas M. Snead, San Francisco, CA (US); Gustave Bergnes, Pacifica, CA (US); Kevin T. Mellem, Redwood City, CA (US); David J. Morgans, Jr., Los Altos, CA (US); Walter S. Won, San Mateo, CA (US)

(73) Assignee: Kinesid Therapeutics, Inc., Champaign, IL (US)

( * ) Notice: Subject to any disclaimer, the term of this patent is extended or adjusted under 35 U.S.C. 154(b) by 805 days.

(21) Appl. No.: 17/769,509

(22) PCT Filed: Oct. 16, 2020

(86) PCT No.: PCT/US2020/056056

§ 371 (c)(1),
(2) Date: Apr. 15, 2022

(87) PCT Pub. No.: WO2021/076945

PCT Pub. Date: Apr. 22, 2021

(65) Prior Publication Data

US 2024/0018105 A1 Jan. 18, 2024

Related U.S. Application Data

(60) Provisional application No. 62/916,040, filed on Oct. 16, 2019.

(51) Int. Cl.

| | |
|---|---|
| ***C07D 213/50*** | (2006.01) |
| ***A61P 25/28*** | (2006.01) |
| ***C07C 49/717*** | (2006.01) |
| ***C07C 49/753*** | (2006.01) |
| ***C07C 69/734*** | (2006.01) |
| ***C07D 213/61*** | (2006.01) |
| ***C07D 213/64*** | (2006.01) |
| ***C07D 213/73*** | (2006.01) |
| ***C07D 213/85*** | (2006.01) |
| ***C07D 239/26*** | (2006.01) |
| ***C07D 239/30*** | (2006.01) |
| ***C07D 239/34*** | (2006.01) |
| ***C07D 239/38*** | (2006.01) |

(Continued)

(52) U.S. Cl.

CPC ............ *C07D 213/50* (2013.01); *A61P 25/28* (2018.01); *C07C 49/717* (2013.01); *C07C 49/753* (2013.01); *C07C 69/734* (2013.01); *C07D 213/61* (2013.01); *C07D 213/64* (2013.01); *C07D 213/73* (2013.01); *C07D 213/85* (2013.01); *C07D 239/26* (2013.01); *C07D 239/30* (2013.01); *C07D 239/34* (2013.01); *C07D 239/38* (2013.01); *C07D 239/42* (2013.01); *C07D 263/32* (2013.01); *C07D 277/24* (2013.01); *C07D 409/06* (2013.01); *C07C 2601/18* (2017.05)

(58) Field of Classification Search

CPC .. C07D 213/50; C07D 213/61; C07D 213/64; C07D 213/73; C07D 213/85; C07D 239/26; C07D 239/30; C07D 239/34; C07D 239/38; C07D 239/42; C07D 263/32; C07D 277/24; C07D 409/06; A61P 25/28; C07C 49/717; C07C 49/753; C07C 69/734; C07C 2601/18

USPC ........................................................ 514/274

See application file for complete search history.

(56) References Cited

U.S. PATENT DOCUMENTS

| | | | |
|---|---|---|---|
| 4,110,468 | A | 8/1978 | Bagli et al. |
| 4,152,457 | A | 5/1979 | Bagli et al. |

(Continued)

FOREIGN PATENT DOCUMENTS

| | | | |
|---|---|---|---|
| EP | 1357104 | A1 | 10/2003 |
| JP | H02237964 | A | 9/1990 |

(Continued)

OTHER PUBLICATIONS

Wang et al., Synthesis of 3-(4-aryl-3-cyano-2-methoxypyridin-6-yl)tropolones by the reactions of 3-cinnamoyl-tropolones with malononitrile, 1999, Heterocycles, vol. 51, No. 9, 2093-2102 (Year: 1999).*

(Continued)

*Primary Examiner* — Kristin A Vajda

(74) *Attorney, Agent, or Firm* — Choate, Hall & Stewart LLP; Brian E. Reese; Erica M. D'Amato

(57) ABSTRACT

Disclosed are a series of compounds or their tautomers having a general structure represented by Formula Ia or Ib and pharmaceutically acceptable salts thereof. Also disclosed are pharmaceutical compositions comprising said compounds or tautomers or pharmaceutically acceptable salts thereof. Further disclosure relates to a method of treating a disease or condition associated with iron dysregulation or dysfunctional iron homeostasis, comprising administering to a subject in need thereof a therapeutically effective amount of Formula Ia or Ib compounds or tautomers or pharmaceutically acceptable salts thereof.

19 Claims, No Drawings

(51) Int. Cl.

| | |
|---|---|
| ***C07D 239/42*** | (2006.01) |
| ***C07D 263/32*** | (2006.01) |
| ***C07D 277/24*** | (2006.01) |
| ***C07D 409/06*** | (2006.01) |

(56) References Cited

U.S. PATENT DOCUMENTS

| | | | |
|---|---|---|---|
| 4,183,955 A | 1/1980 | Bagli et al. | |
| 2010/0152301 A1 | 6/2010 | Pommier et al. | |
| 2021/0163393 A1* | 6/2021 | Burke | C07C 49/717 |

FOREIGN PATENT DOCUMENTS

| | | |
|---|---|---|
| JP | 2008158060 A | 7/2008 |
| JP | 2013237618 A | 11/2013 |
| WO | 2013192554 A1 | 12/2013 |
| WO | 2016112381 A1 | 7/2016 |
| WO | 2017156194 A1 | 9/2017 |
| WO | WO-2017/184752 A1 | 10/2017 |
| WO | 2019200314 A2 | 10/2019 |
| WO | WO-2021/076938 A1 | 4/2021 |
| WO | WO-2021/076945 A1 | 4/2021 |

OTHER PUBLICATIONS

Didierjean et al., Inhibition of Human Immunodeficiency Virus Type 1 Reverse Transcriptase, RNase H, and Integrase Activities by Hydroxytropolones, 2005, Antimicrobial Agents and Chemotherapy, vol. 49, No. 12, 4884-4894 (Year: 2005).*

Yoshitaka Shimizu, Effects of Chemicals on the Mitotic Cell in Plant, With Special Reference to Tropoids, 1962, Sci. Rep. Tchoku Univ. Ser. IV (Biol.), 28, 143-180 (Year: 1962).*

Tsunetsugu et al., "On Stevens' Tropolone Synthesis; Hydrolysis of Spirocyclopentadiene- and Sprioindene-Dichloroketen Adducts," J. Chem. Soc., Perkin Translation (1983).

Andrews, "Disorders of Iron Metabolism," New England Journal of Medicine, 1341(26):1986-1995 (1999).

Angawi et al., "Malettinin A: a new antifungal tropolone from an unidentified fungal colonist of Hypoxylon stromata," Tetrahedron Letters, 44(41): 7593-7596 (2003).

Crichton et al., "The Efficacy of Iron Chelators for Removing Iron from Specific Brain Regions and the Pituitary-Ironing out the Brain," Pharmaceuticals, 12(138):1-13 (2019).

Ganz, "Anemia of Inflammation," New England Journal of Medicine, 381(12):1148-1157 (2019).

International Search Report and Written Opinion for International Application No. PCT/US20/56048 mailed Mar. 11, 2021.

International Search Report and Written Opinion for International Application No. PCT/US2020/056056 dated Feb. 22, 2021.

Invitation to Pay Additional Fees for International Application No. PCT/US2020/056056 dated Dec. 18, 2020.

Johnson et al., "Flatiron Mice and Ferroportin Disease," Nutr. Rev., 65(7):341-345 (2007).

Liu et al., "Synthesis of Naturally Occurring Tropones and Tropolones," Tetrahedron, 70(49): 9281-9305 (2014).

Ndayisaba et al., "Iron in Neurodegeneration—Cause or Consequence?" Frontiers in Neuroscience, 13(180):1-15 (2019).

Nemeth et al., "Anemia of Inflammation," Hematol Oncol Clin North Am., 28(4):671-681 (2014).

PubChem CID: 13661167 Create Date: Feb. 8, 2007 (8 pages).

Pubchem., "2-Methyl-7-hydroxy-8H-cyclohepta[b]furan-8-one, CID 102239320." Pubchem Entry(online), National Center for Biotechnology Information, Dec. 25, 2015).

Pubchem., "3-Chloro-2-hydroxycyclohepta-2,4,6-trien-I-one. CID 12324338." Pubchem Entry(online), National Center for Biotechnology Information, Feb. 7, 2007).

Pubchem., "4,6-Dichloro-2-hydroxy-2,4,6-cycloheptatriene-1-one CID 102175376." PubchemEntry (online), National Center for Biotechnology Information, Dec. 24, 2015).

Pubchem., "5-Chloro-2-hydroxy-4,6-dimethylcyclohepta-2,4,6-trien-1-one, CID 13569072." Pubchem Entry (online), National Center for Biotechnology Information, Feb. 8, 2007).

Watanabe et al., "Studies on azulenes. VIII. Troponoids from azulenogens: oxidation of hydroazulenones with selenium dioxide," Pharmaceutical Bulletin, 5(5): 431-434 (1957).

Extended European Search Report for EP Application No. 20876838.2; Oct. 25, 2023, 12 pages.

Grillo Anthony S.; et al: "Restored iron transport by a small molecule promotes absorption and hemoglobinization in animals", Science, vol. 356, No. 6338, May 12, 2017, 20 pages.

Qian Chang-Yi et al: "Hantzsch reaction of 3-(2-bromoacetyl)tropolone. Synthesis of 3-(4-thiazolyl)tropolones", Journal of Heterocyclic Chemistry, vol. 26, No. 3, May 1, 1989, pp. 601-604 (4 pages).

* cited by examiner

TROPOLONE DERIVATIVES AND TAUTOMERS THEREOF FOR IRON REGULATION IN ANIMALS

RELATED APPLICATIONS APPLICATION

This application is a § 371 national stage application based on Patent Cooperation Treaty Application serial number PCT/US20/56056, filed Oct. 16, 2020; which claims the benefit of priority to U.S. Provisional Application 62/916,040, filed Oct. 16, 2019.

FIELD

Provided are compounds, pharmaceutical compositions comprising the compounds, and methods useful for treating a disease or condition associated with iron dysregulation or dysfunctional iron homeostasis.

BACKGROUND

Iron is an essential element in all living systems. Together with oxygen, it forms the basis of life's energy production engine. Iron also needs to be tightly regulated via the endogenous iron homeostasis and metabolism network in order to maintain iron sufficiency; either iron overload or deficiency can cause damages to the cellular systems. Iron overload can lead to many diseases, including primary hemochromatosis (genetically based) and secondary hemochromatosis (resulting from thalassemia, chronic hepatitis C infection or alcoholic liver disease). Iron deficiency, on the other hand, leads to reduced erythropoiesis which subsequently contributes to anemia. One cause of iron deficiency is malabsorption of iron. Another cause is associated with anemia of inflammation, which reduces the systemic functional iron level. Anemia of inflammation has become a key factor of many systemic chronic disease etiologies and contributes to the disease progression in a few classic chronic systemic inflammatory disorders such as chronic kidney disease, inflammatory bowel disease, chronic heart failure, chronic obstructive pulmonary disease, and even cystic fibrosis (Ganz, T. (2019) N. Eng. J. Med. 381(12):1148-57; Andrews, N. C. (1999) N. Eng. J. Med. 341(26):1986-95).

Regulation of systemic iron homeostasis and metabolism is accomplished by a complex network of sensors, transport proteins, storage proteins, carrier protein, and hormones. Two transport proteins that play a critical role in the maintenance and regulation of iron level are divalent metal transport 1 (DMT1) and ferroportin (Fpn1) (Ganz, T (2019) N. Eng. J. Med. 381(12):1148-57; Nemeth, E. et al. (2014) Hematol. Oncol. Clin. North. Am. 28(4):671-81; Johnson, E. E. et al. (2007) Nutr. Rev. 65(7):341-5)

Dietary iron is absorbed into enterocytes via divalent metal transport 1 (DMT1), which transfers iron (Ferrous) across the apical membrane into the cells. DMT1 transport deficiency has been implicated in the malabsorption of iron, resulting in iron deficiency anemia; such a deficiency can also reduce the effectiveness of oral iron treatment for anemia.

At the center of iron homeostasis are the transporter protein ferroportin (FPN1) and the iron regulatory hormone hepcidin. Ferroportin is the only known cellular iron exporter. It facilitates the export of iron (Ferrous) from storage cells and absorptive cells to the blood including hepatocytes, macrophages in the liver and spleen, and enterocytes. Hepcidin is produced in the liver and its main function is to inhibit ferroportin, reducing its iron transport function. Many inflammatory disorders induce an over production of hepcidin, which leads to abnormal suppression of FPN1 function. As a result, high levels of iron are sequestered in the storage cells, lowering functional iron in blood circulation and contributing to anemia.

Iron transport protein DMT1 deficiency contributes to poor absorption of iron and iron deficiency anemia, while iron transport protein FPN1 deficiency leads to the sequestration of iron in storage cells and reduction of functional iron in circulation, compounding anemia of inflammation. Because iron deficiency anemia and anemia of inflammation commonly coexist, and are the most common anemias worldwide, therapeutics targeting to relieve the deficiency in DMT1 and FPN1 function and achieve normalcy in iron homeostasis can be beneficial to people who are living with said anemias.

Deficiency of frataxin in the central nerve system ("CNS") will lead to mitochondrial iron overload and the resulting excess iron creates extra ROS, which causes cellular damage and neurodegeneration. Typical disease associated with deficiency of frataxin in CNS is Friedreich's Ataxia.

Lastly, iron dyshomeostasis is a contributor to iron overload in iron-sensitive brain regions, such as basal ganglia, and induces neuronal damage. High iron levels and iron related pathogenic triggers, though not well understood, have been implicated in neurodegenerative disorders including Parkinson's disease (PD) and Alzheimer's disease (AD). Currently available iron chelators have thus far proven ineffective in removing iron from the brains of neurodegenerative disease (e.g. PD) patients. New small molecule therapies that can relieve the brain iron overload condition and restore iron homeostasis are much needed (Ndaylsaba. A. et al. (2019) Front. Neurosci. 13:180; Crichton. R. R (2019) Pharmaceuticals 12:138)

It is unexpectedly found that the Formula Ia and Ib compounds, tautomers thereof, and pharmaceutically acceptable salts of either (for example tropolone derivatives, their tautomers, and pharmaceutically acceptable salts of either) can effectively regulate Fe(III) efflux across liposomes and increase Fe absorption in DMT1-deficient Caco-2 cells. It was also found that Formula Ia and Ib compounds and tautomers thereof, and pharmaceutically acceptable salts of either, demonstrate desirable ADME and DMPK characteristics.

SUMMARY

Provided are compounds, pharmaceutical compositions comprising the compounds, and methods useful for treating a disease or condition associated with iron dysregulation or dysfunctional iron homeostasis.

In certain embodiments, the present disclosure provides a compound or a tautomer thereof, or a pharmaceutically acceptable salt of either, represented by Formula Ia:

Formula Ia

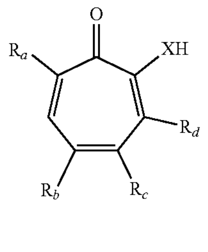

wherein:

X represents sulfur or oxygen;

$R_a$, $R_b$, $R_c$, and $R_d$ independently represent hydrogen, halo, alkyl, substituted alkyl, heteroalkyl, alkoxy, substituted alkoxy, alkoxyalkyl, substituted alkoxyalkyl, aryloxy, substituted aryloxy, heteroaryloxy, substituted heteroaryloxy, cycloalkyl, substituted cycloalkyl, heterocycloalkyl, substituted heterocycloalkyl, alkenyl, substituted alkenyl, heteroalkenyl, cycloalkenyl, substituted cycloalkenyl, heterocycloalkenyl, substituted heterocycloalkenyl, alkynyl, substituted alkynyl, heteroalkynyl, aryl, substituted aryl, heteroaryl, or substituted heteroaryl;

at least one of $R_a$, $R_b$, $R_c$, and $R_d$ is aryloxy, substituted aryloxy, heteroaryloxy, substituted heteroaryloxy, aryl, substituted aryl, heteroaryl, substituted heteroaryl; and provided that $R_a$, $R_b$, $R_c$, and $R_d$ are not all hydrogen.

In certain embodiments, the present disclosure provides a compound or a tautomer thereof, or a pharmaceutically acceptable salt of either, represented by Formula Ib:

Formula Ib

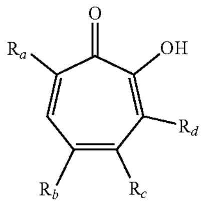

wherein:

$R_a$, $R_b$, $R_c$, and $R_d$ independently represent hydrogen, halo, alkyl, substituted alkyl, heteroalkyl, alkoxy, substituted alkoxy, alkoxyalkyl, substituted alkoxyalkyl, cycloalkyl, substituted cycloalkyl, heterocycloalkyl, substituted heterocycloalkyl, alkenyl, substituted alkenyl, heteroalkenyl, cycloalkenyl, substituted cycloalkenyl, heterocycloalkenyl, substituted heterocycloalkenyl, alkynyl, substituted alkynyl, heteroalkynyl, aryl, substituted aryl, heteroaryl, or substituted heteroaryl;

at least one of $R_b$, $R_c$, and $R_d$ is aryl, substituted aryl, heteroaryl, or substituted heteroaryl; and provided that $R_a$, $R_b$, $R_c$, and $R_d$ are not all hydrogen.

In certain embodiments, in Formula Ia or Ib, each of $R_b$, $R_c$, and $R_d$ that is aryl, substituted aryl, heteroaryl or substituted heteroaryl is represented by Formula II:

Formula II

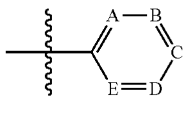

each of A, B, C, D, and E independently represents CH, N, or CR;

for each instance of Formula II the total number of nitrogen atoms among A, B, C, D, and E is 0, 1, or 2; and each instance of R independently represents halo, alkyl, substituted alkyl, heteroalkyl, substituted heteroalkyl, cycloalkyl, substituted cycloalkyl, heterocycloalkyl, substituted heterocycloalkyl, hydroxy, alkoxy, substituted alkoxy, alkoxyalkyl, substituted alkoxyalkyl, cycloalkoxy, substituted cycloalkoxy, cyano, amino, alkenyl, substituted alkenyl, heteroalkenyl, cycloalkenyl, substituted cycloalkenyl, heterocycloalkenyl, substituted heterocycloalkenyl, alkynyl, substituted alkynyl, or heteroalkynyl.

In certain embodiments, in Formula II, each instance of R independently represents chloro, fluoro, bromo, iodo, cyano, trifluoromethyl, amino, hydroxy, (C1-C12)alkyl, (C3-C12)cycloalkyl, (C1-C12)alkoxy, (C3-12)cycloalkoxy, or (C3-C12)heterocycloalkyl; and heterocycloalkyl comprises one or two oxygen atoms, one or two nitrogen atoms, one or two sulfur atoms, or any combination of two atoms selected from the group consisting of oxygen, nitrogen, and sulfur atoms.

In certain embodiments, the present disclosure provides a pharmaceutical composition, comprising a compound described herein or its tautomer in a pharmaceutically acceptable carrier.

In certain embodiments, the present disclosure provides a method of treating a disease or condition associated with iron dysregulation or dysfunctional iron homeostasis, comprising administering to a subject in need thereof a therapeutically effective amount of a compound or tautomer described herein.

DETAILED DESCRIPTION

Aspects of the present disclosure relate to a compound or a tautomer thereof, or a pharmaceutically acceptable salt of either, represented by Formula Ia:

Formula Ia

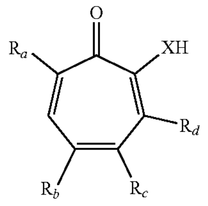

wherein:

X represents sulfur or oxygen;

$R_a$, $R_b$, $R_c$, and $R_d$ independently represent hydrogen, halo, alkyl, substituted alkyl, heteroalkyl, alkoxy, substituted alkoxy, alkoxyalkyl, substituted alkoxyalkyl, aryloxy, substituted aryloxy, heteroaryloxy, substituted heteroaryloxy, cycloalkyl, substituted cycloalkyl, heterocycloalkyl, substituted heterocycloalkyl, alkenyl, substituted alkenyl, heteroalkenyl, cycloalkenyl, substituted cycloalkenyl, heterocycloalkenyl, substituted heterocycloalkenyl, alkynyl, substituted alkynyl, heteroalkynyl, aryl, substituted aryl, heteroaryl, or substituted heteroaryl;

at least one of $R_a$, $R_b$, $R_c$, and $R_d$ is aryloxy, substituted aryloxy, heteroaryloxy, substituted heteroaryloxy, aryl, substituted aryl, heteroaryl, substituted heteroaryl; and provided that $R_a$, $R_b$, $R_c$, and $R_d$ are not all hydrogen.

Aspects of the present disclosure relate to a compound or a tautomer thereof, or a pharmaceutically acceptable salt of either, represented by Formula Ib:

Formula Ib

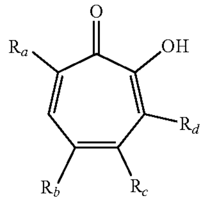

wherein:

$R_a$, $R_b$, $R_c$, and $R_d$ independently represent hydrogen, halo, alkyl, substituted alkyl, heteroalkyl, alkoxy, substituted alkoxy, alkoxyalkyl, substituted alkoxyalkyl, cycloalkyl, substituted cycloalkyl, heterocycloalkyl, substituted heterocycloalkyl, alkenyl, substituted alkenyl, heteroalkenyl, cycloalkenyl, substituted cycloalkenyl, heterocycloalkenyl, substituted heterocycloalkenyl, alkynyl, substituted alkynyl, heteroalkynyl, aryl, substituted aryl, heteroaryl, or substituted heteroaryl;

at least one of $R_b$, $R_c$, and $R_d$ is aryl, substituted aryl, heteroaryl, or substituted heteroaryl; and provided that $R_a$, $R_b$, $R_c$, and $R_d$ are not all hydrogen.

In certain embodiments, in Formula I, each of $R_b$, $R_c$, and $R_d$ that is aryl, substituted aryl, heteroaryl or substituted heteroaryl is represented by Formula II:

Formula II

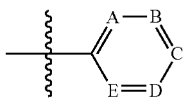

each of A, B, C, D, and E independently represents CH, N, or CR;

for each instance of Formula II the total number of nitrogen atoms among A, B, C, D, and E is 0, 1, or 2; and each instance of R independently represents halo, alkyl, substituted alkyl, heteroalkyl, substituted heteroalkyl, cycloalkyl, substituted cycloalkyl, heterocycloalkyl, substituted heterocycloalkyl, hydroxy, alkoxy, substituted alkoxy, alkoxyalkyl, substituted alkoxyalkyl, cycloalkoxy, substituted cycloalkoxy, cyano, amino, alkenyl, substituted alkenyl, heteroalkenyl, cycloalkenyl, substituted cycloalkenyl, heterocycloalkenyl, substituted heterocycloalkenyl, alkynyl, substituted alkynyl, or heteroalkynyl.

In certain embodiments, in Formula II, each instance of R independently represents chloro, fluoro, bromo, iodo, cyano, trifluoromethyl, amino, hydroxy, (C1-C12)alkyl (C3-C12)cycloalkyl, (C1-C12)alkoxy, (C3-12)cycloalkoxy, or (C3-C12)heterocycloalkyl; and heterocycloalkyl comprises one or two oxygen atoms, one or two nitrogen atoms, one or two sulfur atoms, or any combination of two atoms selected from the group consisting of oxygen, nitrogen, and sulfur atoms.

One aspect of the present disclosure relates to a pharmaceutical composition, comprising a compound described herein or its tautomer in a pharmaceutically acceptable carrier.

One aspect of the present disclosure relates to a method of treating a disease or condition associated with iron dysregulation or dysfunctional iron homeostasis, comprising administering to a subject in need thereof a therapeutically effective amount of a compound or tautomer described herein. In one embodiment, the disease or condition associated with iron dysregulation or dysfunctional iron homeostasis comprises anemia, iron deficiency anemia, anemia of inflammation, anemia of chronic inflammatory disorders, anemia of chronic kidney disease, anemia in inflammatory bowel disease, chemotherapy-induced anemia, cancer associated anemia, primary hemochromatosis, secondary hemochromatosis, liver failure, Parkinson's disease, or Alzheimer's disease. In one embodiment, the disease or condition associated with iron dysregulation or dysfunctional iron homeostasis is liver failure; and the liver failure is chronic or acute. In one embodiment, the disease or condition associated with iron dysregulation or dysfunctional iron homeostasis is selected from the group consisting of anemia of chronic inflammation, inflammatory bowel disease, chronic heart failure, chronic obstructive pulmonary disease, anemia of chronic kidney disease, rheumatoid arthritis, primary hemochromatosis, secondary hemochromatosis, and lupus. In one embodiment, the disease or condition associated with iron dysregulation or dysfunctional iron homeostasis is a CNS disease, such as Friedreich's Ataxia.

In one aspect, one or more compounds of the present disclosure can be used in the treatment of anemia of inflammation, for example the anemia of inflammation in chronic kidney disease (CKD), either as monotherapy or in combination with another therapy, such as e.g., one or more standard of care therapies.

In one aspect, one or more compounds of the present disclosure can be used in the treatment of chemotherapy-induced anemia where a functional iron-deficiency develops in the setting of inflammation that leads to the iron sequestration in macrophages and enterocytes and reduces iron availability for bone marrow in the erythrocyte production.

In one aspect, one or more compounds of the present disclosure can be also applied in the prevention of acute chronic liver failure (ACLF) in patients of cirrhosis where anemia is a contributing factor.

In another aspect, one or more compounds of the present disclosure may also be applied, in combination with other therapies, in the treatment of neurodegenerative diseases such as Parkinson's (PD) and Alzheimer's disease (AD), where iron dysregulation contributes to disease progression.

In another aspect, one or more compounds of the present disclosure can be applied to mobilize extra iron out of the CNS of a subject and, therefore, can be applied to treat conditions that include excess iron in the CNS, such as, but not necessarily limited to, Friedreich's Ataxia.

DEFINITIONS

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., C1-C30 for straight chain, C3-C30 for branched chain), and alternatively, about 20 or fewer. In one embodiment, the term "alkyl" refers to a C1-C10 straight-chain alkyl group. In one embodiment, the term "alkyl" refers to a C1-C6 straight-chain alkyl group. In one embodiment, the term "alkyl" refers to a C3-C12 branched-chain alkyl group. In one embodiment, the term "alkyl" refers to a C3-C8, branched-chain alkyl group. Cycloalkyls have from about 3 to about 10 carbon atoms in their ring structure, and alternatively about 5, 6, or 7 carbons in the ring structure.

The term "alkenyl" or "alkenyl group" means a group formed by removing a hydrogen from a carbon of an alkene, where an alkene is an acyclic or cyclic compound consisting entirely of hydrogen atoms and carbon atoms, and including at least one carbon-carbon double bond. An alkenyl group may include one or more substituent groups.

The term "alkynyl group" means a group formed by removing a hydrogen from a carbon of an alkyne, where an alkyne is an acyclic or cyclic compound consisting entirely of hydrogen atoms and carbon atoms, and including at least one carbon-carbon triple bond. An alkynyl group may include one or more substituent groups.

The term "substituent" or "substituent group" means a group that replaces one or more hydrogen atoms in a molecular entity. Except as may be specified otherwise, substituent groups can include, without limitation, alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, and silyloxy.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "heterocyclyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this disclosure, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The term "alkoxy" or "alkoxy group" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "cycloalkylalkyl" as used herein refers to an alkyl group substituted with one or more cycloalkyl groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as triflurомethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

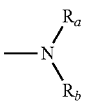 and 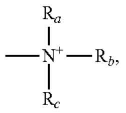

wherein $R_a$, $R_b$, and $R_c$ each independently represent a hydrogen, an alkyl, an alkenyl, $—(CH_2)_x—R_d$, or $R_a$ and $R_b$, taken together with the N atom to which they are attached complete a heterocycle having from 4 to 8 atoms in the ring structure; Rd represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ ach independently represent a hydrogen, an alkyl, an alkenyl, or $—(CH_2)_x—R_d$. In one embodiment, the term "amino" refers to $—NH_2$.

The term "acyl" is a term of an and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of an and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "carbonyl" as used herein refers to —C(O)—.

The term "thiocarbonyl" as used herein refers to —C(S)—.

The term "alkylthio" as used herein refers to alkyl-S—.

The term "aryl" is a term of art and as used herein refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In one embodiment, the term "aryl" refers to a phenyl group.

The term "heteroaryl" is a term of art and as used herein refers to a monocyclic, bicyclic, and polycyclic aromatic group having one or more heteroatoms in the ring structure, for example, pyrrole, furan, thiophene, imidazole, oxazole, thiazole, triazole, pyrazole, pyridine, pyrazine, pyridazine and pyrimidine, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" or "arylalkyl" is a term of art and as used herein refers to an alkyl group substituted with an aryl group.

The term "heteroaralkyl" or "heteroarylalkyl" is a term of art and as used herein refers to an alkyl group substituted with a heteroaryl group.

The term "alkoxy" as used herein means an alkyl group, as defined herein, appended to the parent molecular moiety through an oxygen atom. Representative Examples of alkoxy include, but are not limited to, methoxy, ethoxy, propoxy, 2-propoxy, butoxy, tert-butoxy, pentyloxy, and hexyloxy.

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "fluoroalkyl" as used herein refers to an alkyl group, as defined herein, wherein some or all of the hydrogens are replaced with fluorines.

The term "halo" is a term of art and as used herein refers to —F, —Cl, —Br, or —I.

The term "hydroxy" is a term of art and as used herein refers to —OH.

Certain compounds contained in compositions of the present disclosure may exist in particular geometric or stereoisomeric forms. In addition, compounds of the present disclosure may also be optically active. The present disclosure contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

If, for instance, a particular enantiomer of compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds.

For purposes of this disclosure, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this disclosure pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula Ia or Ib. As another example, the salt may comprise less than one inorganic or organic acid molecule per molecule of base, such as two molecules of compound of Formula Ia or Ib per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in Remington's Pharmaceutical Sciences by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

In some aspects, the present disclosure provides a compound or a tautomer thereof, or a pharmaceutically acceptable salt of either, represented by Formula Ia:

Formula Ia

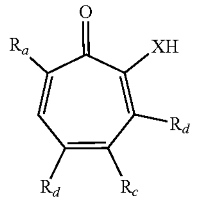

wherein:

X represents sulfur or oxygen;

$R_a$, $R_b$, $R_c$, and $R_d$ independently represent hydrogen, halo, alkyl, substituted alkyl, heteroalkyl, alkoxy, substituted alkoxy, alkoxyalkyl, substituted alkoxyalkyl, aryloxy, substituted aryloxy, heteroaryloxy, substituted heteroaryloxy, cycloalkyl, substituted cycloalkyl, heterocycloalkyl, substituted heterocycloalkyl, alkenyl, substituted alkenyl, heteroalkenyl, cycloalkenyl, substituted cycloalkenyl, heterocycloalkenyl, substituted heterocycloalkenyl, alkynyl, substituted alkynyl, heteroalkynyl, aryl, substituted aryl, heteroaryl, or substituted heteroaryl;

at least one of $R_a$, $R_b$, $R_c$, and $R_d$ is aryloxy, substituted aryloxy, heteroaryloxy, substituted heteroaryloxy, aryl, substituted aryl, heteroaryl, substituted heteroaryl; and provided that $R_a$, $R_b$, $R_c$, and $R_d$ are not all hydrogen.

In certain embodiments, in Formula Ia, at least one of $R_a$, $R_b$, $R_c$, and $R_d$ is aryl, substituted aryl, heteroaryl, substituted heteroaryl.

In certain embodiments, in Formula Ia, at least one of $R_b$, $R_c$, and $R_d$ is aryl, substituted aryl, heteroaryl, substituted heteroaryl.

In some aspects, the present disclosure provides a compound or a tautomer thereof, or a pharmaceutically acceptable salt of either, represented by Formula Ib:

Formula Ib

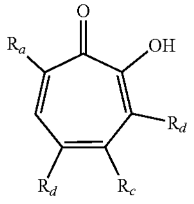

wherein:

$R_a$, $R_b$, $R_c$, and $R_d$ independently represent hydrogen, halo, alkyl, substituted alkyl, heteroalkyl, alkoxy, substituted alkoxy, alkoxyalkyl, substituted alkoxyalkyl, cycloalkyl, substituted cycloalkyl, heterocycloalkyl, substituted heterocycloalkyl, alkenyl, substituted alkenyl, heteroalkenyl, cycloalkenyl, substituted cycloalkenyl, heterocycloalkenyl, substituted heterocycloalkenyl, alkynyl, substituted alkynyl, heteroalkynyl, aryl, substituted aryl, heteroaryl, or substituted heteroaryl;

at least one of $R_b$, $R_c$, and $R_d$ is aryl, substituted aryl, heteroaryl, or substituted heteroaryl; and provided that $R_a$, $R_b$, $R_c$, and $R_d$ are not all hydrogen.

In certain embodiments, in Formula Ia or Ib, each of $R_b$, $R_c$, and $R_d$ that is aryl, substituted aryl, heteroaryl or substituted heteroaryl is represented by Formula II:

Formula II

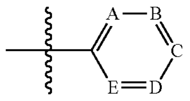

each of A, B, C, D, and E independently represents CH, N, or CR;

for each instance of Formula II the total number of nitrogen atoms among A, B, C, D, and E is 0, 1, or 2; and each instance of R independently represents halo, alkyl, substituted alkyl, heteroalkyl, substituted heteroalkyl, cycloalkyl, substituted cycloalkyl, heterocycloalkyl, substituted heterocycloalkyl, hydroxy, alkoxy, substituted alkoxy, alkoxyalkyl, substituted alkoxyalkyl, cycloalkoxy, substituted cycloalkoxy, cyano, amino, alkenyl, substituted alkenyl, heteroalkenyl, cycloalkenyl, substituted cycloalkenyl, heterocycloalkenyl, substituted heterocycloalkenyl, alkynyl, substituted alkynyl, or heteroalkynyl.

In certain embodiments, in Formula II, each instance of R independently represents chloro, fluoro, bromo, iodo, cyano, trifluoromethyl, amino, hydroxy, (C1-C12)alkyl, (C3-C12)cycloalkyl, (C1-C12)alkoxy, (C3-12)cycloalkoxy, or (C3-C12)heterocycloalkyl; and heterocycloalkyl comprises one or two oxygen atoms, one or two nitrogen atoms, one or two sulfur atoms, or any combination of two atoms selected from the group consisting of oxygen, nitrogen, and sulfur atoms.

In certain embodiments, in Formula Ia or Ib, $R_a$, $R_b$, and $R_d$ represent hydrogen; and $R_c$ represents an aryl, substituted aryl, heteroaryl, or substituted heteroaryl according to Formula II.

In certain embodiments, wherein the compound of Formula Ia or Ib is selected from the group consisting of:

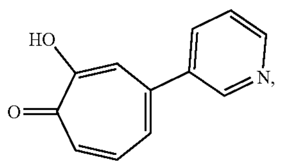

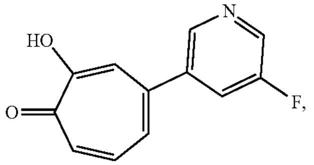

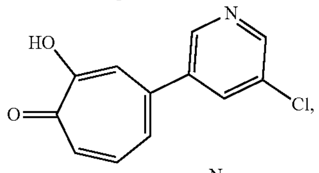

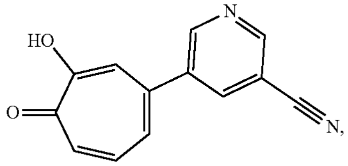

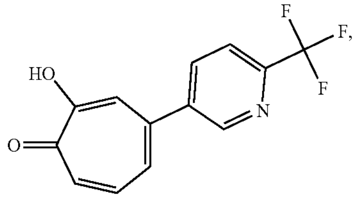

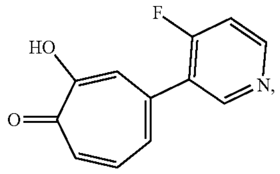

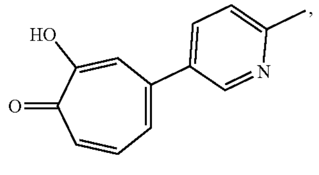

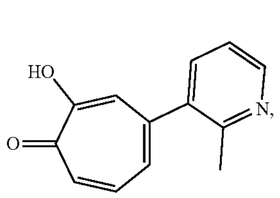

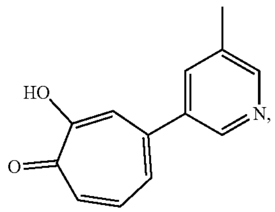

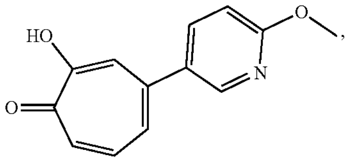

-continued
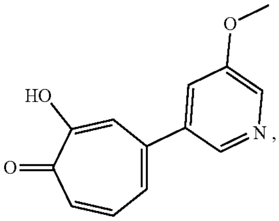
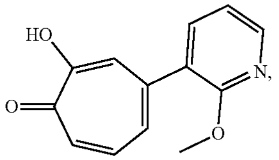
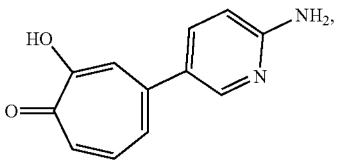
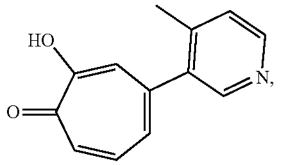
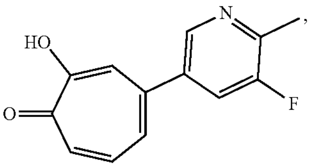
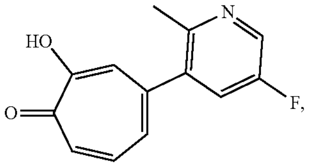
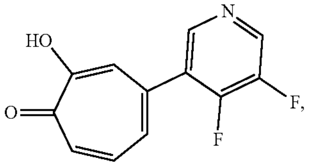
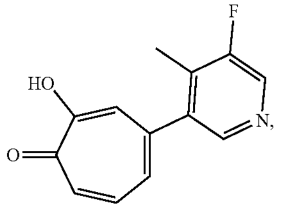
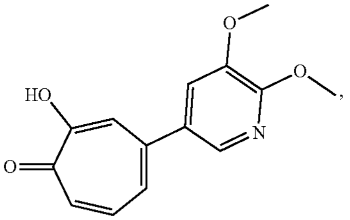
-continued
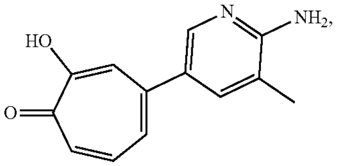
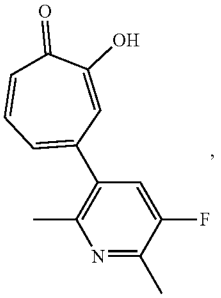
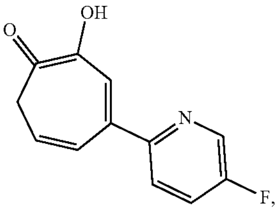
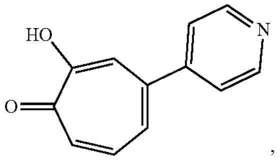
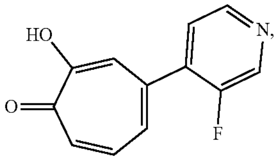
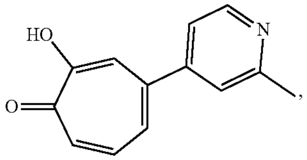
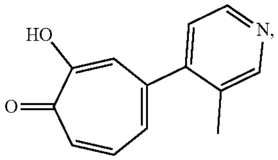
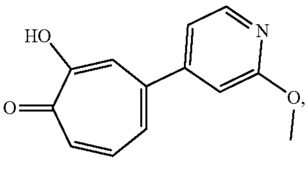
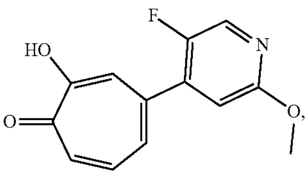
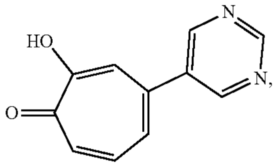
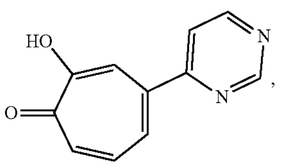
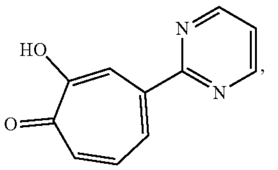

-continued
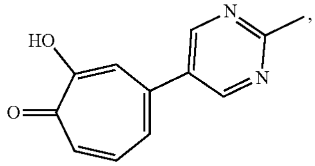,
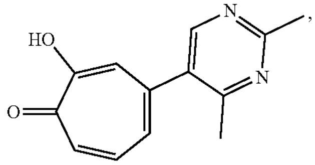,
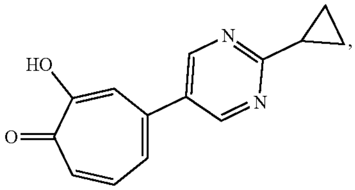,
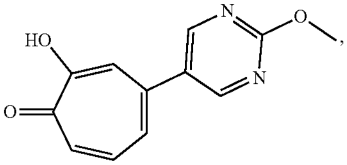,
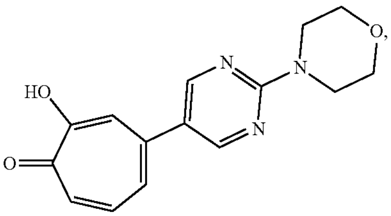,
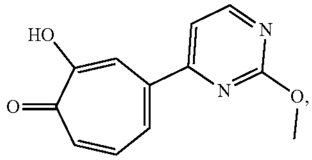, and
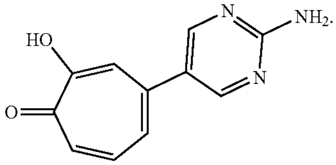.
In certain embodiments, in Formula Ia or Ib,
$R_a$, $R_c$, and $R_d$ represent hydrogen; and
$R_b$ represents an aryl, substituted aryl, heteroaryl, or substituted heteroaryl according to Formula II.
In certain embodiments, wherein the compound of Formula Ia or Ib is selected from the group consisting of:
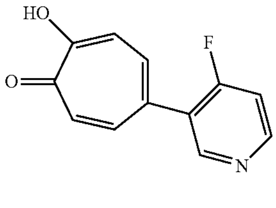,
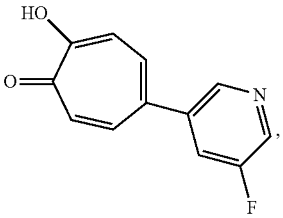,
-continued
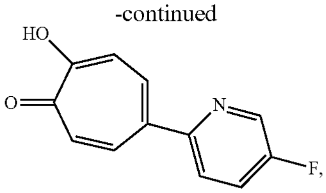,
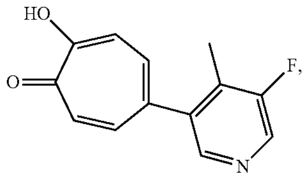,
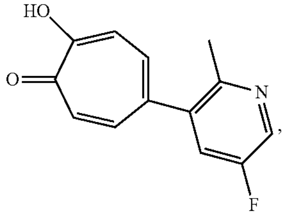,
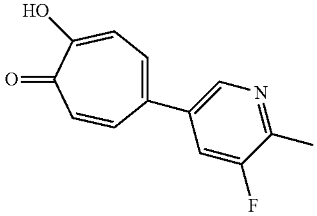,
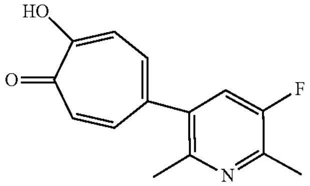,
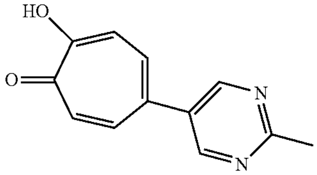,
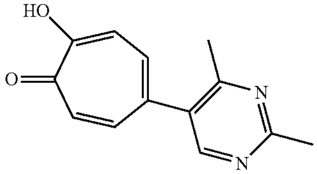,
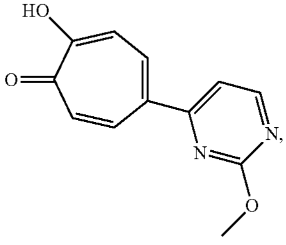,
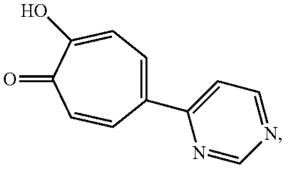, and -continued

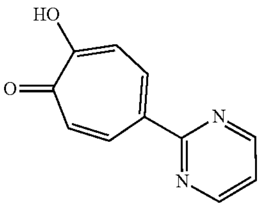

In certain embodiments, in Formula Ia or Ib, $R_a$, $R_b$, and $R_c$ represent hydrogen; and $R_d$ represents an aryl, substituted aryl, heteroaryl, or substituted heteroaryl according to Formula II.

In certain embodiments, wherein the compound of Formula Ia or Ib is selected from the group consisting of:

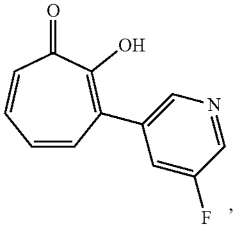
,
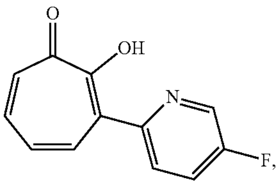

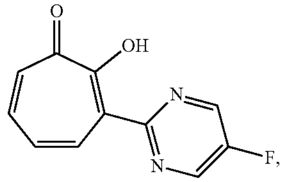

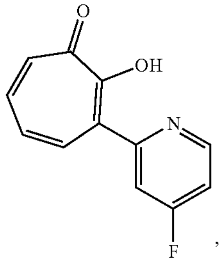
,
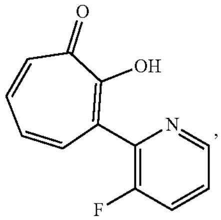
,
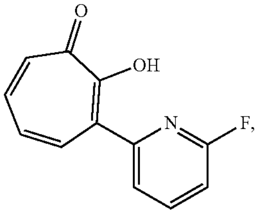

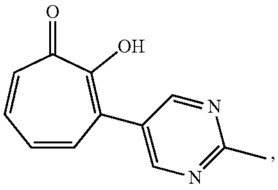
, and

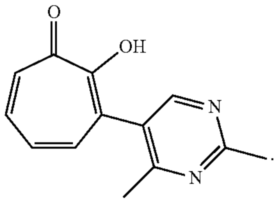

In certain embodiments, wherein the compound of Formula Ia or Ib is selected from the group consisting of:

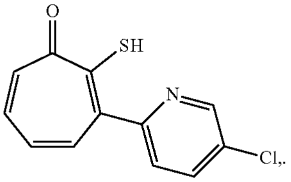

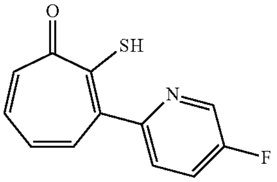

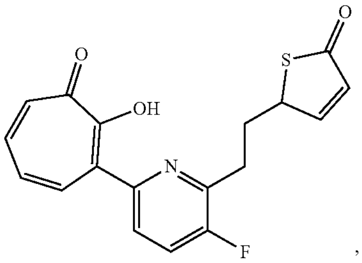
, and

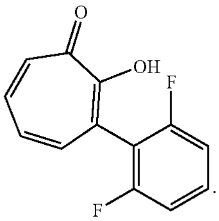

In certain embodiments, in Formula Ia or Ib, $R_a$ represents alkyl;

one and only one of $R_b$, $R_c$, and $R_d$ represents aryl, substituted aryl, heteroaryl, or substituted heteroaryl according to Formula II; and two of $R_b$, $R_c$, and $R_d$ represent hydrogen.

In certain embodiments, wherein the compound of Formula Ia or Ib is selected from the group consisting of:

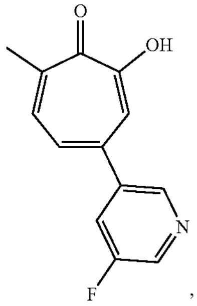
,
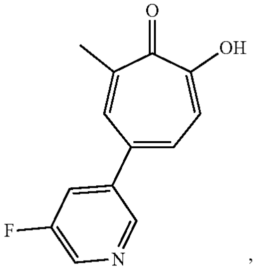
,

-continued

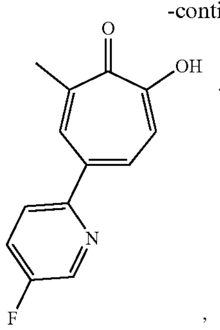

,

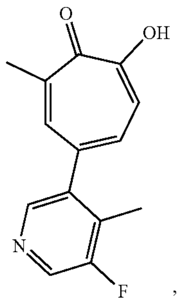

, and

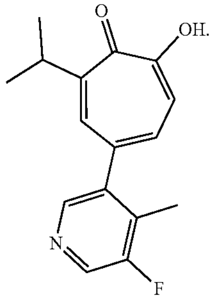

In certain embodiments, in Formula Ia or Ib, $R_a$ represents an aryl, substituted aryl, heteroaryl, or substituted heteroaryl according to Formula II;

one and only one of $R_b$, $R_c$, and $R_d$ represents alkyl; and two of $R_b$, $R_c$, and $R_d$ represent hydrogen.

In certain embodiments, wherein the compound of Formula Ia or Ib is selected from the group consisting of:

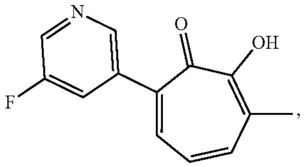

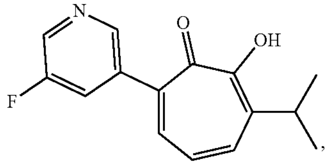

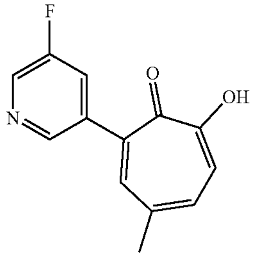

and

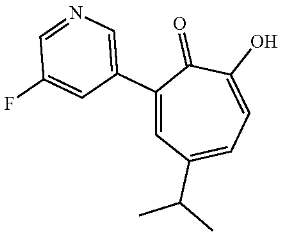

In certain embodiments, in Formula Ia or Ib, $R_a$ represents an aryl, substituted aryl, heteroaryl, or substituted heteroaryl according to Formula II; and each of $R_b$, $R_c$, and $R_d$ represent hydrogen.

In certain embodiments, in Formula Ia or Ib, the compound or tautomer is selected from the group consisting of:

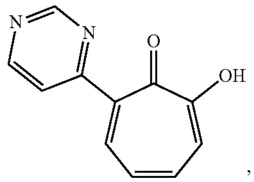

,

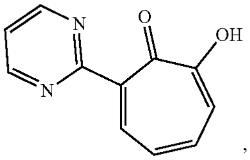

, and

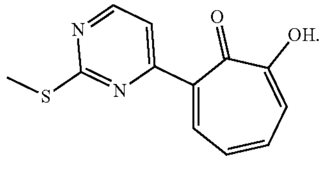

In certain embodiments, in Formula Ia or Ib, at least one of $R_a$, $R_b$, $R_c$, and $R_d$ is aryloxy, substituted aryloxy, heteroaryloxy, or substituted heteroaryloxy.

In certain embodiments, in Formula Ia or Ib, at least one of $R_b$, $R_c$, and $R_d$ is aryloxy, substituted aryloxy, heteroaryloxy, or substituted heteroaryloxy.

In certain embodiments, in Formula Ia or Ib, each of $R_b$, $R_c$, and $R_d$ that is aryloxy, substituted aryloxy, heteroaryloxy, or substituted heteroaryloxy is represented by Formula IIa Formula IIa

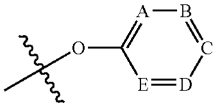

each of A, B, C, D, and E independently represents CH, N, or CR;

for each instance of Formula II the total number of nitrogen atoms among A, B, C, D, and E is 0, 1, or 2; and each instance of R independently represents halo, alkyl, substituted alkyl, heteroalkyl, substituted heteroalkyl, cycloalkyl, substituted cycloalkyl, heterocycloalkyl, substituted heterocycloalkyl, hydroxy, alkoxy, substituted alkoxy, alkoxyalkyl, substituted alkoxyalkyl, cycloalkoxy, substituted cycloalkoxy, cyano, amino, alkenyl, substituted alkenyl, heteroalkenyl, cycloalkenyl, substituted cycloalkenyl, heterocycloalkenyl, substituted heterocycloalkenyl, alkynyl, substituted alkynyl, or heteroalkynyl.

In certain embodiments, in Formula Ia or Ib, each instance of R independently represents chloro, fluoro, bromo, iodo, cyano, trifluoromethyl, amino, hydroxy, (C1-C12)alkyl, (C3-C12)cycloalkyl, (C1-C12)alkoxy, (C3-12)cycloalkoxy, or (C3-C12)heterocycloalkyl; and heterocycloalkyl comprises one or two oxygen atoms, one or two nitrogen atoms, one or two sulfur atoms, or any combination of two atoms selected from the group consisting of oxygen, nitrogen, and sulfur atoms.

In certain embodiments, in Formula Ia or Ib, $R_a$, $R_b$, and $R_d$ represent hydrogen; and $R_c$ represents an aryloxy, substituted aryloxy, heteroaryloxy, or substituted heteroaryloxy according to Formula IIa.

In certain embodiments, in Formula Ia or Ib, $R_a$, $R_c$, and $R_d$ represent hydrogen; and $R_b$ represents an aryloxy, substituted aryloxy, heteroaryloxy, or substituted heteroaryloxy according to Formula IIa.

In certain embodiments, in Formula Ia or Ib, $R_a$, $R_b$, and $R_c$ represent hydrogen; and $R_d$ represents an aryloxy, substituted aryloxy, heteroaryloxy, or substituted heteroaryloxy according to Formula IIa.

In certain embodiments, in Formula Ia or Ib, $R_a$ represents alkyl;

one and only one of $R_b$, $R_c$, and $R_d$ represents an aryloxy, substituted aryloxy, heteroaryloxy, or substituted heteroaryloxy according to Formula IIa; and two of $R_b$, $R_c$, and $R_d$ represent hydrogen.

In certain embodiments, in Formula Ia or Ib, $R_a$ represents an aryl, substituted aryl, heteroaryl, or substituted heteroaryl according to Formula IIa;

one and only one of $R_b$, $R_c$, and $R_d$ represents alkyl; and two of $R_b$, $R_c$, and $R_d$ represent hydrogen.

In certain embodiments, in Formula Ia or Ib, $R_a$ represents an aryl, substituted aryl, heteroaryl, or substituted heteroaryl according to Formula IIa; and each of $R_b$, $R_c$, and $R_d$ represent hydrogen.

In certain embodiments, in Formula Ia or Ib, the compound or tautomer is selected from the group consisting of:

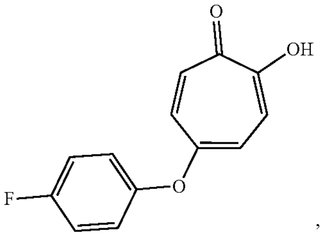

,

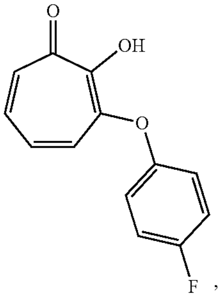

,

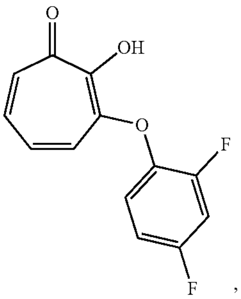

,

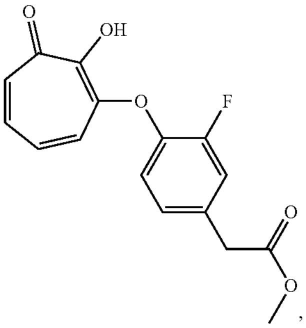

,

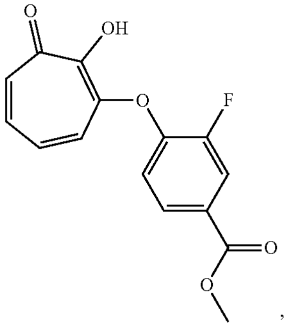

,

-continued

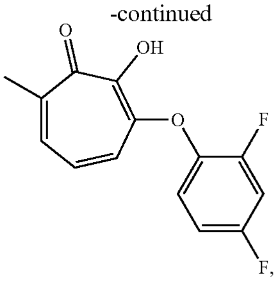

, and

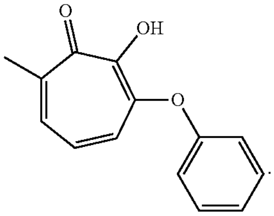

.

In certain embodiments, in Formula Ia or Ib, each of $R_b$, $R_c$, and $R_d$ that is heteroaryl or substituted heteroaryl is represented by Formula IIb:

Fromula IIb

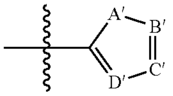

A' represents O or S;

each of B', C', and D' independently represents CH, N, or CR; and each instance of R independently represents halo, alkyl, substituted alkyl, heteroalkyl, substituted heteroalkyl, cycloalkyl, substituted cycloalkyl, heterocycloalkyl, substituted heterocycloalkyl, hydroxy, alkoxy, substituted alkoxy, alkoxyalkyl, substituted alkoxyalkyl, cycloalkoxy, substituted cycloalkoxy, cyano, amino, alkenyl, substituted alkenyl, heteroalkenyl, cycloalkenyl, substituted cycloalkenyl, heterocycloalkenyl, substituted heterocycloalkenyl, alkynyl, substituted alkynyl, or heteroalkynyl.

In certain embodiments, in Formula Ia or Ib, each of $R_b$, $R_c$, and $R_d$ that is heteroaryl or substituted heteroaryl is represented by Formula IIc:

Fromula IIc

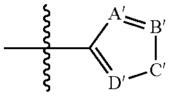

C' represents O or S;

each of A', B', and D' independently represents CH, N, or CR; and each instance of R independently represents halo, alkyl, substituted alkyl, heteroalkyl, substituted heteroalkyl, cycloalkyl, substituted cycloalkyl, heterocycloalkyl, substituted heterocycloalkyl, hydroxy, alkoxy, substituted alkoxy, alkoxyalkyl, substituted alkoxyalkyl, cycloalkoxy, substituted cycloalkoxy, cyano, amino, alkenyl, substituted alkenyl, heteroalkenyl, cycloalkenyl, substituted cycloalkenyl, heterocycloalkenyl, substituted heterocycloalkenyl, alkynyl, substituted alkynyl, or heteroalkynyl.

In certain embodiments, in Formula Ia or Ib, each of $R_b$, $R_c$, and $R_d$ that is heteroaryl or substituted heteroaryl is represented by Formula IId:

Fromula IId

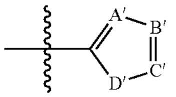

D' represents O or S;

each of A', B', and C' independently represents CH, N, or CR; and each instance of R independently represents halo, alkyl, substituted alkyl, heteroalkyl, substituted heteroalkyl, cycloalkyl, substituted cycloalkyl, heterocycloalkyl, substituted heterocycloalkyl, hydroxy, alkoxy, substituted alkoxy, alkoxyalkyl, substituted alkoxyalkyl, cycloalkoxy, substituted cycloalkoxy, cyano, amino, alkenyl, substituted alkenyl, heteroalkenyl, cycloalkenyl, substituted cycloalkenyl, heterocycloalkenyl, substituted heterocycloalkenyl, alkynyl, substituted alkynyl, or heteroalkynyl.

In certain embodiments, in Formula Ia or Ib, each of $R_b$, $R_c$, and $R_d$ that is heteroaryl or substituted heteroaryl is represented by Formula IIe:

Formula IIe

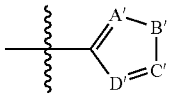

B' represents O or S;

each of A', C', and D' independently represents CH, N, or CR; and each instance of R independently represents halo, alkyl, substituted alkyl, heteroalkyl, substituted heteroalkyl, cycloalkyl, substituted cycloalkyl, heterocycloalkyl, substituted heterocycloalkyl, hydroxy, alkoxy, substituted alkoxy, alkoxyalkyl, substituted alkoxyalkyl, cycloalkoxy, substituted cycloalkoxy, cyano, amino, alkenyl, substituted alkenyl, heteroalkenyl, cycloalkenyl, substituted cycloalkenyl, heterocycloalkenyl, substituted heterocycloalkenyl, alkynyl, substituted alkynyl, or heteroalkynyl.

In certain embodiments, in Formula Ia or Ib, each instance of R independently represents chloro, fluoro, bromo, iodo, cyano, trifluoromethyl, amino, hydroxy, (C1-C12)alkyl, (C3-C12)cycloalkyl, (C1-C12)alkoxy, (C3-12)cycloalkoxy, or (C3-C12)heterocycloalkyl; and heterocycloalkyl comprises one or two oxygen atoms, one or two nitrogen atoms, one or two sulfur atoms, or any combination of two atoms selected from the group consisting of oxygen, nitrogen, and sulfur atoms.

In certain embodiments, in Formula Ia or Ib, $R_a$, $R_b$, and $R_d$ represent hydrogen; and $R_c$ represents a heteroaryl or substituted heteroaryl according to any one of Formulas IIb-IIe.

In certain embodiments, in Formula Ia or Ib, $R_a$, $R_c$, and $R_d$ represent hydrogen; and $R_b$ represents a heteroaryl or substituted heteroaryl according to any one of Formulas IIb-IIe.

In certain embodiments, in Formula Ia or Ib, $R_a$, $R_b$, and $R_c$ represent hydrogen; and $R_d$ represents a heteroaryl or substituted heteroaryl according to any one of Formulas IIb-IIe.

In certain embodiments, in Formula Ia or Ib, $R_a$ and $R_c$ represent hydrogen;

$R_b$ represents halo, alkyl or substituted alkyl.

$R_d$ represents a heteroaryl or substituted heteroaryl according to any one of Formulas IIb-IIe.

In certain embodiments, in Formula Ia or Ib, $R_a$ represents halo or alkyl;

one and only one of $R_b$, $R_c$, and $R_d$ represents a heteroaryl or substituted heteroaryl according to any one of Formulas IIb-IIe; and two of $R_b$, $R_c$, and $R_d$ represent hydrogen.

In certain embodiments, in Formula Ia or Ib, $R_a$ represents a heteroaryl or substituted heteroaryl according to any one of Formulas IIb-IIe;

one and only one of $R_b$, $R_c$, and $R_d$ represents alkyl; and two of $R_b$, $R_c$, and $R_d$ represent hydrogen.

In certain embodiments, in Formula Ia or Ib, $R_a$ represents a heteroaryl or substituted heteroaryl according to any one of Formulas IIb-IIe; and each of $R_b$, $R_c$, and $R_d$ represent hydrogen.

In certain embodiments, in Formula Ia or Ib, the compound or tautomer is selected from the group consisting of:

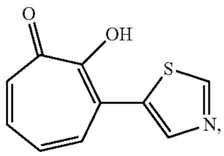,
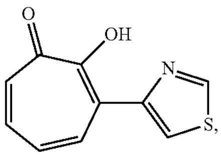,
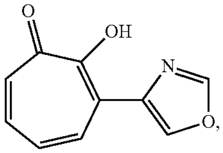,
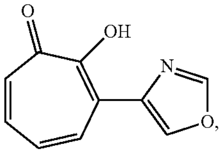,
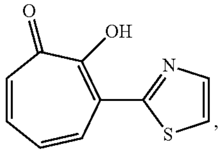,
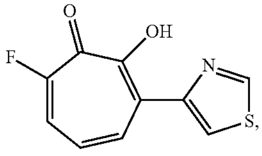,
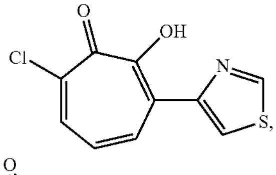,
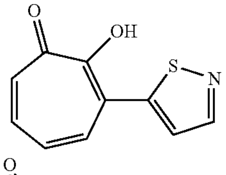,
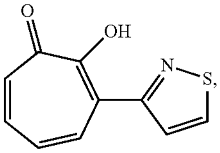,
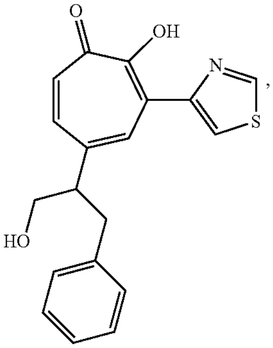, and -continued

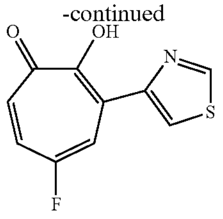

Representative compounds of Formula Ia and Formula Ib are tropolone derivatives, their tautomers, and pharmaceutically acceptable salts of either.

In certain embodiments, compounds of the present disclosure and tautomers thereof, and pharmaceutically acceptable salts of either, demonstrate desirable Absorption, Distribution, Metabolism, Excretion (ADME) and/or Drug Metabolism and Pharmacokinetics (DMPK) characteristics, demonstrating certain advantages desireable for further drug development. ADME and DMPK characteristics of a compound may be assessed by a variety of different assays that are known to the relevant ordinarily skilled artisan.

Useful such assays include, but are not limited to e.g., those measurements made in PK studies, such as rodent and non-human primate PK studies, including e.g., mouse (such as mouse 6-hour PK studies), rat PK studies, cynomolgus or rhesus PK studies, or the like. Useful measurements obtained in such PK studies include but are not limited to e.g., maximum concentration ($C_{max}$) reflecting the "peak" of a drug observed after its administration that can reflect not only the rate but also the extent of absorption, area under the curve (AUC) representing the area under the plot of tissue (e.g., plasma) concentration against time after drug administration which is of particular use in estimating bioavailability of drugs and drug total clearance, half-life ($t_{1/2}$) or the period of time required for the concentration or amount of drug to be reduced to exactly one-half of a given concentration or amount that indicates the persistence of the drug in its volume of distribution, and the like. Compounds of the present disclosure displayed improved PK characteristics, e.g., as measured by PK assays, including but not limited to e.g., where such compounds have improved PK characteristics as compared to a reference compound, such as hinokitiol.

Further examples of useful assays include metabolic stability assays, such as but not limited to e.g., liver microsomal clearance assays which provide measurement such as, but not limited to e.g., liver microsomal clearance half-life ($t_{1/2}$), liver microsomal intrinsic clearance ($CL_{int}$), and the like. Such measurements are useful in assessing various characteristics of a subject compound, such as e.g., the availability of an intact compound to provide a pharmacological effect. A compound having a longer microsomal clearance half-life ($t_{1/2}$), e.g., than a reference compound, will provide better exposure of the intact compound and greater availability to produce the relevant pharmacological effect. A compound having a less microsomal clearance, e.g., as measured by liver microsomal intrinsic clearance ($CL_{int}$), will similarly result in greater exposure of the intact compound available for an increase in the relevant pharmacological effect, e.g., as compared to that of a reference compound with a higher liver microsomal intrinsic clearance ($CL_{int}$). Other useful assays include in vitro hepatocyte metabolic stability assays. Compounds of the present disclosure displayed desireable characteristics in in vitro hepatocyte metabolic stability assays, including e.g., decreased metabolic clearance and increased systemic exposure. Compounds of the present disclosure displayed improved clearance characteristics, e.g., as measured by metabolic stability assays, including but not limited to e.g., where such compounds have improved clearance characteristics as compared to a reference compound, such as hinokitiol.

In certain embodiments, the compound of Formula Ia or Formula Ib has a human liver microsomal clearance half-life ($t_{1/2}$) of greater than 9 minutes. In certain embodiments, the compound of Formula Ia or Formula Ib has a human liver microsomal clearance half-life ($t_{1/2}$) of greater than 12 minutes. In certain embodiments, the compound of Formula Ia and Formula Ib has a human liver microsomal clearance half-life ($t_{1/2}$) of greater than 25 minutes. In certain embodiments, the compound of Formula Ia or Formula Ib has a human liver microsomal clearance half-life ($t_{1/2}$) of greater than 50 minutes. In certain embodiments, the compound of Formula Ia or Formula Ib has a human liver microsomal clearance half-life ($t_{1/2}$) of greater than 100 minutes. In certain embodiments, the compound of Formula Ia or Formula Ib has a human liver microsomal clearance half-life ($t_{1/2}$) of greater than 120 minutes. In certain embodiments, the compound of Formula Ia or Formula Ib a human liver microsomal clearance half-life ($t_{1/2}$) of greater than 150 minutes. In some instances, a compound of Formula Ia or Formula Ib of the present disclosure may have a human liver microsomal clearance half-life ($t_{1/2}$) of greater than 9 minutes, including but not limited to e.g., 10 min. or more, such as e.g., greater than 11 min., greater than 12 min., greater than 13 min., greater than 14 min., greater than 15 min., greater than 20 min., greater than 25 min., greater than 30 min., greater than 35 min., greater than 40 min., greater than 45 min., greater than 50 min., greater than 55 min., greater than 60 min., greater than 65 min., greater than 70 min., greater than 75 min., greater than 80 min., greater than 85 min., greater than 90 min., greater than 95 min., greater than 100 min., greater than 105 min., greater than 110 min., greater than 115 min., greater than 120 min., greater than 125 min., greater than 130 min., greater than 135 min., greater than 140 min., greater than 145 min., or greater than 150 min. or more. In some instances, a compound of Formula Ia or Formula Ib of the present disclosure may have a human liver microsomal clearance half-life ($t_{1/2}$) that is greater than a reference compound, such as but not limited to e.g., one or more of the reference compounds described herein, such as but not limited to e.g., hinokitiol.

In certain embodiments, the compound of Formula Ia or Formula Ib has a human liver microsomal intrinsic clearance ($CL_{int}$) of less than 120 μL/min/mg protein. In certain embodiments, the compound of Formula Ia or Formula Ib has a human liver microsomal intrinsic clearance ($CL_{int}$) of less than 50 μL/min/mg protein. In certain embodiments, the compound of Formula Ia or Formula Ib has a human liver microsomal intrinsic clearance ($CL_{int}$) of less than 46 μL/min/mg protein. In certain embodiments, the compound of Formula Ia or Formula Ib has a human liver microsomal intrinsic clearance ($CL_{int}$) of less than 43 μL/min/mg protein. In certain embodiments, the compound of Formula Ia or Formula Ib has a human liver microsomal intrinsic clearance ($CL_{int}$) of less than 25 μL/min/mg protein. In certain embodiments, the compound of Formula Ia or Formula Ib has a human liver microsomal intrinsic clearance ($CL_{int}$) of less than 12 μL/min/mg protein. In some instances, a compound of Formula Ia or Formula Ib of the present disclosure may have a human liver microsomal intrinsic clearance ($CL_{int}$) of less than 120 μL/min/mg protein, including but not limited to e.g., 119 μL/min/mg protein or less, such as e.g., less than 118 μL/min/mg protein, less than 117 μL/min/mg protein, less than 116 μL/min/mg protein, less than 115 μL/min/mg protein, less than 110 μL/min/mg protein, less than 105 μL/min/mg protein, less than 100 μL/min/mg protein, less than 95 μL/min/mg protein, less than 90 μL/min/mg protein, less than 85 μL/min/mg protein, less than 80 μL/min/mg protein, less than 75 μL/min/mg protein, less than 70 μL/min/mg protein, less than 65 μL/min/mg protein, less than 60 μL/min/mg protein, less than 55 μL/min/mg protein, less than 50 μL/min/mg protein, less than 45 μL/min/mg protein, less than 40 μL/min/mg protein, less than 35 μL/min/mg protein, less than 30 μL/min/mg protein, less than 25 μL/min/mg protein, less than 20 μL/min/mg protein, less than 15 μL/min/mg protein, or less than 10 μL/min/mg protein or less. In some instances, a compound of Formula Ia or Formula Ib of the present disclosure may have a human liver microsomal intrinsic clearance ($CL_{int}$) that is less than a reference compound, such as but not limited to e.g., one or more of the reference compounds described herein, such as but not limited to e.g., hinokitiol.

In certain embodiments, the compound of Formula Ia or Formula Ib has a 6-hour PK Cmax greater than 1000 ng/mL. In certain embodiments, the compound of Formula Ia or Formula Ib has a 6-hour PK Cmax greater than 1500 ng/mL. In certain embodiments, the compound of Formula Ia or Formula Ib has a 6-hour PK Cmax greater than 2000 ng/mL. In certain embodiments, the compound of Formula Ia or Formula Ib has a 6-hour PK Cmax greater than 2500 ng/mL. In certain embodiments, the compound of Formula Ia or Formula Ib has a 6-hour PK Cmax greater than 3000 ng/mL. In certain embodiments, the compound of Formula Ia or Formula Ib has a 6-hour PK Cmax greater than 3500 ng/mL. In certain embodiments, the compound of Formula Ia or Formula Ib has a 6-hour PK Cmax greater than 4000 ng/mL. In certain embodiments, the compound of Formula Ia or Formula Ib has a 6-hour PK Cmax greater than 5000 ng/mL. In certain embodiments, the compound of Formula Ia or Formula Ib has a 6-hour PK Cmax greater than 7500 ng/mL. In certain embodiments, the compound of Formula Ia or Formula Ib has a 6-hour PK Cmax greater than 10,000 ng/mL. In certain embodiments, the compound of Formula Ia or Formula Ib has a 6-hour PK Cmax greater than 15,000 ng/mL. In some instances, a compound of Formula Ia or Formula Ib of the present disclosure may have a 6-hour PK Cmax of greater than 1000 ng/mL, including but not limited to e.g., 1100 ng/mL or more, such as e.g., greater than 1200 ng/mL, greater than 1300 ng/mL, greater than 1400 ng/mL, greater than 1500 ng/mL, greater than 1600 ng/mL, greater than 1700 ng/mL, greater than 1800 ng/mL, greater than 1900 ng/mL, greater than 2000 ng/mL, greater than 2200 ng/mL, greater than 2400 ng/mL, greater than 2600 ng/mL, greater than 2800 ng/mL, greater than 3000 ng/mL, greater than 3200 ng/mL, greater than 3400 ng/mL, greater than 3600 ng/mL, greater than 3800 ng/mL, greater than 4000 ng/mL, greater than 4500 ng/mL, greater than 5000 ng/mL, greater than 5500 ng/mL, greater than 6000 ng/mL, greater than 6500 ng/mL, greater than 7000 ng/mL, greater than 7500 ng/mL, greater than 8000 ng/mL, greater than 8500 ng/mL, greater than 9000 ng/mL, greater than 9500 ng/mL, greater than 10000 ng/mL, greater than 10500 ng/mL, greater than 11000 ng/mL, greater than 11500 ng/mL, greater than 12000 ng/mL, greater than 12500 ng/mL, greater than 13000 ng/mL, greater than 13500 ng/mL, greater than 14000 ng/mL, greater than 14500 ng/mL, or greater than 15000 ng/mL or more. In some instances, a compound of Formula Ia or Formula Ib of the present disclosure may have a 6-hour PK Cmax that is greater than a reference compound, such as but not limited to e.g., one or more of the reference compounds described herein, such as but not limited to e.g., hinokitiol.

In certain embodiments, the compound of Formula Ia or Formula Ib has a 6-hour PK $AUC_{last}$ 0-6 hr greater than 590 hr*ng/mL. In certain embodiments, the compound of Formula Ia or Formula Ib has a 6-hour PK $AUC_{last}$ 0-6 hr greater than 700 hr*ng/mL. In certain embodiments, the compound of Formula Ia or Formula Ib has a 6-hour PK $AUC_{last}$ 0-6 hr greater than 1000 hr*ng/mL. In certain embodiments, the compound of Formula Ia or Formula Ib has a 6-hour PK $AUC_{last}$ 0-6 hr greater than 1500 hr*ng/mL. In certain embodiments, the compound of Formula Ia or Formula Ib has a 6-hour PK $AUC_{last}$ 0-6 hr greater than 5000 hr*ng/mL. In certain embodiments, the compound of Formula Ia or Formula Ib has a 6-hour PK $AUC_{last}$ 0-6 hr greater than 10,000 hr*ng/mL. In certain embodiments, the compound of Formula Ia or Formula Ib has a 6-hour PK $AUC_{last}$ 0-6 hr greater than 20,000 hr*ng/mL. In certain embodiments, the compound of Formula Ia or Formula Ib has a 6-hour PK $AUC_{last}$ 0-6 hr greater than 45,000 hr*ng/mL. In some instances, a compound of Formula Ia or Formula Ib of the present disclosure may have a 6-hour PK $AUC_{last}$ 0-6 hr of greater than 590 hr*ng/mL, including but not limited to e.g., 600 hr*ng/mL or more, such as e.g., greater than 700 ng/mL, greater than 800 ng/mL, greater than 900 ng/mL, greater than 1000 ng/mL, greater than 1500 ng/mL, greater than 2000 ng/mL, greater than 2500 ng/mL, greater than 3000 ng/mL, greater than 3500 ng/mL, greater than 4000 ng/mL, greater than 4500 ng/mL, greater than 5000 ng/mL, greater than 5500 ng/mL, greater than 6000 ng/mL, greater than 6500 ng/mL, greater than 7000 ng/mL, greater than 7500 ng/mL, greater than 8000 ng/mL, greater than 8500 ng/mL, greater than 9000 ng/mL, greater than 9500 ng/mL, greater than 10000 ng/mL, greater than 12000 ng/mL, greater than 14000 ng/mL, greater than 16000 ng/mL, greater than 18000 ng/mL, greater than 20000 ng/mL, greater than 22000 ng/mL, greater than 24000 ng/mL, greater than 26000 ng/mL, greater than 28000 ng/mL, greater than 30000 ng/mL, greater than 32000 ng/mL, greater than 34000 ng/mL, greater than 36000 ng/mL, greater than 38000 ng/mL, or greater than 40000 ng/mL or more. In some instances, a compound of Formula Ia or Formula Ib of the present disclosure may have a 6-hour PK $AUC_{last}$ 0-6 hr that is greater than a reference compound, such as but not limited to e.g., one or more of the reference compounds described herein, such as but not limited to e.g., hinokitiol.

In certain embodiments, the compound of Formula Ia or Formula Ib has a 6-hour PK $t_{1/2}$ greater than 1 hr. In certain embodiments, the compound of Formula Ia or Formula Ib has a 6-hour PK $t_{1/2}$ greater than 1.3 hr. In certain embodiments, the compound of Formula Ia or Formula Ib has a 6-hour PK $t_{1/2}$ greater than 1.5 hr. In certain embodiments, the compound of Formula Ia or Formula Ib has a 6-hour PK $t_{1/2}$ greater than 2 hr. In certain embodiments, the compound of Formula Ia or Formula Ib has a 6-hour PK $t_{1/2}$ greater than 2.5 hr. In certain embodiments, the compound of Formula Ia or Formula Ib has a 6-hour PK $t_{1/2}$ greater than 3 hr. In some instances, a compound of Formula Ia or Formula Ib of the present disclosure may have a 6-hour PK $t_{1/2}$ of greater than 1 hr, including but not limited to e.g., 1.1 hr or more, such as e.g., greater than 1.2 hr, greater than 1.3 hr, greater than 1.4 hr, greater than 1.5 hr, greater than 1.6 hr, greater than 1.7 hr, greater than 1.8 hr, greater than 1.9 hr, greater than 2 hr, greater than 2.1 hr, greater than 2.2 hr, greater than 2.3 hr, greater than 2.4 hr, greater than 2.5 hr, greater than 2.6 hr, greater than 2.7 hr, greater than 2.8 hr, greater than 2.9 hr, greater than 3 hr, greater than 3.1 hr, greater than 3.2 hr, greater than 3.3 hr, greater than 3.4 hr, greater than 3.5 hr, greater than 3.6 hr, greater than 3.7 hr, greater than 3.8 hr, greater than 3.9 hr, greater than 4 hr, greater than 4.1 hr, greater than 4.2 hr, greater than 4.3 hr, greater than 4.4 hr, greater than 4.5 hr, greater than 4.6 hr, greater than 4.7 hr, greater than 4.8 hr, greater than 4.9 hr, or greater than 5 hr or more. In some instances, a compound of Formula Ia or Formula Ib of the present disclosure may have a 6-hour PK $t_{1/2}$ that is greater than a reference compound, such as but not limited to e.g., one or more of the reference compounds described herein, such as but not limited to e.g., hinokitiol.

In certain embodiments, a compound of Formula Ia or Formula Ib of the present disclosure may have a combination of two or more, including three or more, four or more, etc., of the herein described, including aforementioned, characteristics. For example, a compound of the present disclosure may, in some instances, have two or more, three or more, or four or more, of human liver microsomal clearance half-life ($t_{1/2}$), human liver microsomal intrinsic clearance ($CL_{int}$), 6 hour PK Cmax, 6 hour PK $AUC_{last}$ 0-6 hr, and 6-hour PK $t_{1/2}$ greater or less than, as relevant, a threshold value disclosed herein, including above.

EXEMPLIFICATION

The present disclosure now being generally described, it will be more readily understood by reference to the following, which is included merely for purposes of illustration of certain aspects and embodiments of the present disclosure, and is not intended to limit the present disclosure.

A. Synthesis of Tropolone Intermediates

Preparation of Building Block BB1: 2-(benzyloxy)-5-bromocyclohepta-2,4,6-trien-1-one

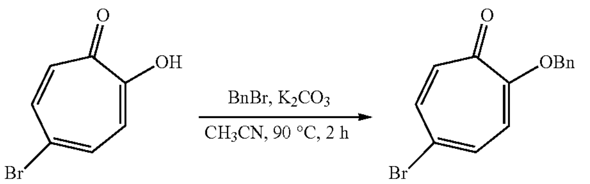

BB1a BB1

To a mixture of BB1a (commercially available) (10.9 g, 54.2 mmol, 1 eq) and $K_2CO_3$ (22.5 g, 163 mmol, 3 eq) in MeCN (200 mL) was added benzyl bromide (13.9 g, 81.3 mmol, 1.5 eq) in one portion at 25 °C under $N_2$. The mixture was stirred at 90 °C for 2 hours. TLC (petroleum ether: EtOAc=3:1) indicated the staring material was consumed completely and one new spot was formed. After cooling, the reaction mixture was filtered, and the filtrate was concentrated under reduced pressure to dryness. The residue was purified by silica gel column chromatography eluting with Petroleum ether/Ethyl acetate (20/1 to 3/1) to give BB1 (8 g, 50.7%) as a yellow solid $^1$H NMR (400 MHz, DMSO-d6) δ ppm 7.54-7.44 (m, 2H), 7.43-7.33 (m, 5H), 6.94-6.88 (m, 2H), 5.18 (s, 2H).

Preparation of Building Block BB2: 4-bromo-2-hydroxycyclohepta-2,4,6-trien-1-one

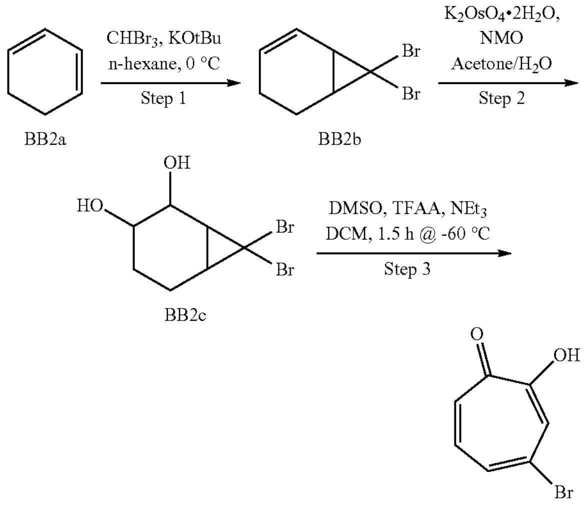

BB2a BB2b BB2c BB2

Step 1:

To a solution of 1,3-cyclohexadiene BB2a (76 g, 949.6 mmol, 1.2 eq) and KOtBu (151 g, 1.35 mol, 1.7 eq) in n-hexane (500 mL) was added bromoform (200 g, 791.4 mmol, 1 eq) dropwise at 0 °C. The mixture was stirred at 0 °C for 1 h, and then continued at 25 °C. 2 hours. TLC (100% petroleum ether) showed BB2a (Rf=0.9) was consumed completely, and a new spot was observed (Rf=0.8). The mixture was poured into water (500 mL), and the aqueous mixture was extracted with petroleum ether (300 mL×3). The combined organic phases were washed with brine (200 mL×2), dried over $Na_2SO_4$ and concentrated under reduced pressure to dryness. The residue was purified by silica gel column chromatography eluting with Petroleum ether/Ethyl acetate (100:0 to 100:1) to give BB2b (180 g, 90%) as a colorless oil.

Step 2:

To a stirred solution of NMO (58.6 g, 500 mmol, 1.4 eq) in acetone (500 mL) and water (100 mL) was added BB2b (90 g, 357 mmol, 1 eq). A solution of $K_2OsO_4 \cdot 2H_2O$ (500 mg, 1.36 mmol, 0.004 eq) in water (30 mL) was added under $N_2$. The resulting mixture was stirred at 15 °C for 16 hr under a $N_2$ balloon. TLC (petroleum ether:EtOAc=1:1) indicated BB2b (Rf=0.9) was consumed completely and a new product spot was observed (Rf=0.3). $Na_2SO_3$ (15 g) was added to quench the reaction at 0 °C. The mixture was concentrated to remove acetone. Brine (500 mL) was added to the residue, then the aqueous mixture was extracted with EtOAc (200 mL×3). The combined organic layers were washed with brine (200 mL), dried over $Na_2SO_4$, and concentrated under reduced pressure to dryness. The residue was purified by silica gel column chromatography eluting with Petroleum ether/Ethyl acetate (10:1 to 1:1) to provide BB2c (70 g, 68.5%) as a white solid.

Step 3:

To a solution of DMSO (26.2 g, 335 mmol, 8 eq) in DCM (300 mL) was added TFAA (70.5 g, 335 mmol, 8 eq) dropwise at −60 °C under $N_2$, the resulting colorless mixture was stirred at −60 °C for 15 min. A solution of 7,7-dibromonorcarane-2,3-diol BB2c (12 g, 41.9 mmol, 1 eq) in DMSO (10 mL) was added to the above mixture dropwise at a temperature below −60 °C. The mixture was stirred at −60 °C for another 1.5 hours. $Et_3N$ (59.5 g, 588 mmol, 14 eq) was added dropwise, the resulting yellow solution was stirred at −60 °C for another 2 hours, then warmed to 25 °C. Reaction was continued at room temperature for 16 hours. TLC (EtOAc) indicated BB2c (Rf=0.6) was consumed completely, and a new spot was detected (Rf=0.2). Water (500 mL) was added to the mixture and the aqueous layer was extracted with DCM (200 mL×2). The combined organic phases were washed with brine (200 mL×2), dried over $Na_2SO_4$, and evaporated under vacuo to dryness. The residue was purified by silica gel column chromatography eluting with Petroleum ether/Ethyl acetate (50:1 to 20:1) to afford BB2 (5 g, 59.2%) as a yellow solid; $^1H$ NMR: 400 MHz $CDCl_3$, δ 7.70-7.75 (m, 1H), 7.31-7.38 (m, 1H), 7.21-7.25 (m, 1H), 7.08-7.15 (m, 1H).

Preparation of Building Block BB5: 4-bromo-7-oxocyclohepta-1,3,5-trien-1-yl tert-butyl carbonate

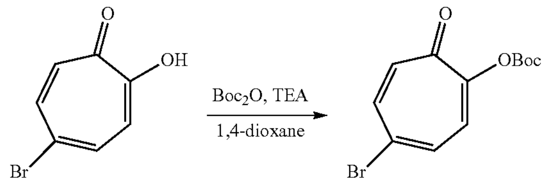

BB1a BB5

To a stirred solution of BB1a (5 g, 24.9 mmol, 1 eq) in dioxane (10 mL) was added TEA (10.1 g, 99.5 mmol, 4 eq) and $Boc_2O$ (16.3 g, 74.6 mmol, 3 eq) in one portion at 25 °C under $N_2$. The mixture was heated to 118 °C and stirred for 1 hour. TLC (petroleum ether:EtOAc=5:1) indicated the starting material was consumed completely and one major new spot with lower polarity detected. After cooling, the mixture was concentrated under reduced pressure to dryness. The residue was purified by silica gel column chromatography (petroleum ether:EtOAc=20:1 to 8:1) to give building block BB5 (5 g, 33.4%) as a yellow solid; $^1H$ NMR (400 MHz, DMSO-d6) δ ppm 7.75-7.55 (m, 2H), 7.35-7.2 (m, 2H), 7.1-6.9 (m, 2H), 1.45 (s, 9H).

Preparation of Building Block BB6: 3-bromo-7-oxocyclohepta-1,3,5-trien-1-yl tert-butyl carbonate

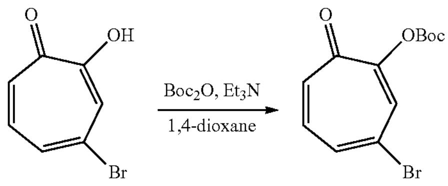

BB2 BB6 or

-continued

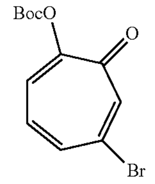

BB6x

To a solution of BB2 (19 g, 94.5 mmol, 1 eq) in 1,4-dioxane (100 mL) was added $Boc_2O$ (51.6 g, 236 mmol, 2.5 eq) and $Et_3N$ (38.2 g, 378 mmol, 4 eq). The mixture was heated to 100 °C and stirred for 2 hours. TLC (petroleum ether:EtOAc=3:1) indicated BB2 (Rf=0.1) was consumed completely and a new spot (Rf=0.8) was observed. After cooling to room temperature, the mixture was concentrated under reduced pressure to dryness. The residue was purified by silica gel column chromatography (Petroleum ether/Ethyl acetate=20:1 to 3:1) twice to afford building block BB6 (12 g, 40.6%) as a brown oil; $^1H$ NMR 400 MHz, CD3OD, δ ppm 7.709-7.705 (m, 1H), 7.508-7.365 (m, 1H), 7.316-7.262 (m, 1H), 7.02-6.98 (m, 1H), 1.51 (s, 9H).

Preparation of Building Block BB7

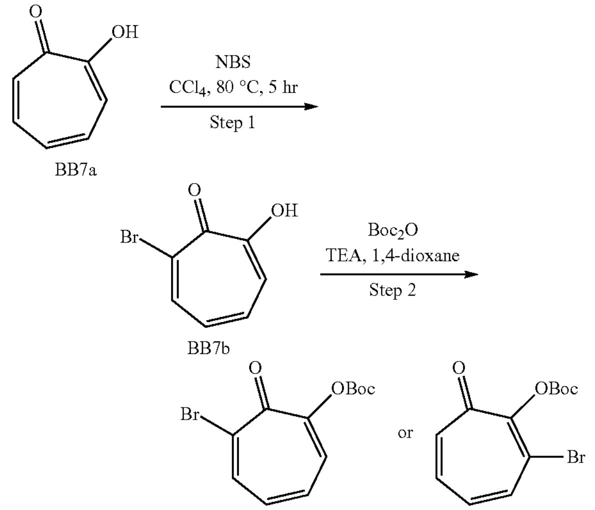

BB7a BB7b BB7

Step 1:

To a solution of BB7a (20 g, 164 mmol, 1 eq) in $CCl_4$ (400 mL) was added NBS (26.1 g, 147 mmol, 0.9 eq) in portions at 25 °C under $N_2$. The mixture was heated and stirred at 80 °C for 5 hrs. LCMS showed the starting material was almost consumed. After cooling, a saturated aq. sodium thiosulfate solution (300 mL) was added drop-wise and the mixture was stirred for another 10 min. The aqueous mixture was extracted with dichloromethane (200 mL×3). The combined organic phases were washed with water (100 mL×2), brine (100 mL), dried over anhydrous $Na_2SO_4$, filtered and concentrated under reduced pressure to dryness to afford crude BB7b (20 g, crude) as an off-white solid.

Step 2:

To a solution of crude BB7b (20 g, 100 mmol, 1 eq) in dioxane (200 mL) was added $Boc_2O$ (43.6 g, 200 mmol, 2 eq) and TEA (20.2 g, 200 mmol, 2 eq) at 25 °C under $N_2$.

The mixture was heated and stirred at 100 °C for 2 hr. LCMS showed the starting material was almost consumed and desired product mass was observed. After cooling, water (100 mL) was added and stirred for 10 min. The aqueous mixture was extracted with ethyl acetate (300 mL×3). The combined organic phases were washed with water (200 mL×2), brine (300 mL), dried over anhydrous $Na_2SO_4$, filtered and concentrated under reduced pressure to dryness. The residue was purified by silica gel column chromatography (Petroleum ether:Ethyl acetate=20:1 to 5:1) twice to afford building block BB7 (10 g, 33.3% yield, 90% purity) as a yellow oil; $^1$H NMR (400 MHz, DMSO-d6) δ ppm 8.50-8.48 (m, 1H), 7.64-7.61 (m, 1H), 7.36-7.31 (m, 1H), 7.16-7.11 (m, 1H), 1.47 (s, 9H).

Preparation of Building Block BB8: tert-butyl (4-iodo-7-oxocyclohepta-1,3,5-trien-1-yl) carbonate

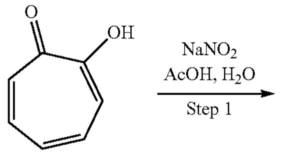

BB7a

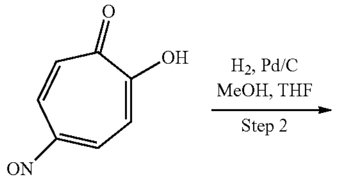

BB8a

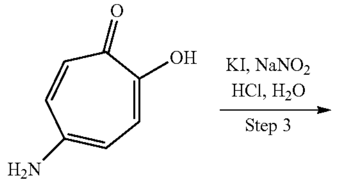

BB8b

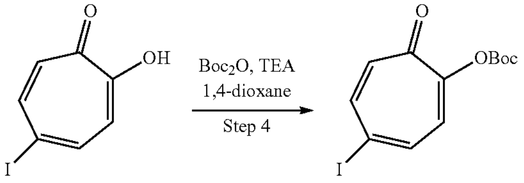

BB8c BB8

Step 1:

To a mixture of Tropolone BB7a (100 g, 819 mmol, 1 eq) in AcOH (600 mL) and $H_2O$ (200 mL) was added a solution of $NaNO_2$ (84.7 g, 1.23 mol, 1.5 eq) in $H_2O$ (400 mL) dropwise at 0 °C. The mixture was stirred at 0 °C for 1 hr. LCMS showed the starting material was consumed. A yellow precipitate was collected by filtration and rinsed with $H_2O$ (200 mL) to give the intermediate BB8a (106 g, 85.7%) as a yellow solid which was used in the next step without further purification Step 2:

To a solution of BB8a (10 g, 66.2 mmol, 1 eq) in MeOH (300 mL) and THE (600 mL) was added 10% Pd/C (3.52 g, 0.05 eq) under $N_2$. The system was degassed and purged with $H_2$ three times. The mixture was stirred under a hydrogen balloon (15 psi) at 15 °C for 4 hrs. TLC (DCM: MeOH=10:1) showed the starting material was consumed completely. The reaction mixture was filtered through a pad of Celite and the filter cake was washed with MeOH (100 mL×2). The combined filtrates were concentrated under reduced pressure to give BB8b (9 g, crude) as a yellow solid, which was used in the next step directly.

Step 3:

To a solution of BB8b (30 g, 218 mmol, 1 eq) in $H_2O$ (600 mL) and HCl (600 mL) was added $NaNO_2$ (30.2 g, 437 mmol, 2 eq) in $H_2O$ (300 mL) drop-wise at 0 °C. The mixture was stirred at 0 °C for 15 min. After that, a solution of KI (109 g, 656 mmol, 3 eq) in $H_2O$ (300 mL) was added to drop-wise at 0 °C. The reaction mixture was stirred at 15 °C for 16 hours. TLC (Ethyl acetate:MeOH=1:1) showed a new product spot was formed. The mixture was filtered, and the filter cake was washed with EtOAc (500 mL). The mixture was separated, the aqueous phase was extracted with EtOAc (1 L×3). The combined organic phase and organic extracts were washed with Sat. $NaHSO_3$ (1 L×3), water (1 L×3) and brine (1 L×2), dried over $Na_2SO_4$ and concentrated under reduced pressure to give intermediate BB8c (29 g, crude). The crude material was purified by silica gel column chromatography eluting with petroleum ether: EtOAc (10:1 to 0:1) to give intermediate BB8c (15 g, 27.6%) as a yellow solid.

Step 4:

To a mixture of BB8c (30 g, 121 mmol, 1 eq) and $Et_3N$ (61.1 g, 605 mmol, 5 eq) in 1,4-dioxane (500 mL) was added $Boc_2O$ (79.1 g, 363 mmol, 3 eq) drop-wise at 20 °C. The mixture was stirred at 110 °C for 2 hrs. TLC (MeOH/Ethyl acetate=1:1) showed the starting material was consumed completely and TLC (Petroleum ether/Ethyl acetate=5:1) showed a new product spot was observed (Rf=0.5). After cooling, the mixture was concentrated under reduced pressure to dryness. The residue was purified by silica gel column chromatography eluting with petroleum ether:EtOAc (50:1 to 10:1) to afford the building block BB8 (23 g, 54%) as a yellow solid; $^1$H NMR (400 MHz, DMSO-d6) δ ppm 7.84-7.81 (m, 2H), 7.054 (brs, 1H), 6.81 (brs, 1H), 1.45 (s, 9H).

Preparation of Building Block BB10: tert-butyl (7-oxo-3-(4,4,5,5-tetramethyl-1,3,2-dioxaborolan-2-yl)cyclohepta-1,3,5-trien-1-yl) carbonate

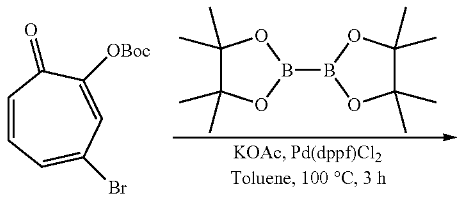

BB6

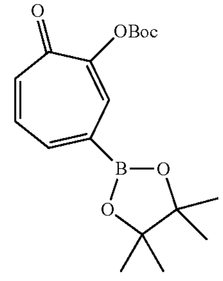
BB10

To a solution of building block BB6 (4 g, 13.3 mmol, 1 eq) in toluene (50 mL) was added bis(pinacolato)diboron (Pin2B2, 3.54 g, 13.9 mmol, 1.05 eq), KOAc (1.96 g, 19.9 mmol, 1.5 eq) and Pd(dppf)$Cl_2$ (972 mg, 1.33 mmol, 0.1 eq) under $N_2$. The system was degassed and recharged with nitrogen for three times. The mixture was heated and stirred at 100 °C for 3 hours under nitrogen. TLC (Petroleum ether:Ethyl acetate=5:1 and 1:1) indicated starting material was consumed completely and one major new spot with larger polarity was detected. After cooling, the reaction solution was filtered through a pad of Celite and the filter cake was washed with $CH_2Cl_2$ (50 mL×2). The combined filtrates were washed with brine (20 mL), dried over $Na_2SO_4$, filtered and concentrated under reduced pressure to give the crude product. The crude product was purified by silica gel column chromatography eluting with Petroleum ether:Ethyl acetate (20:1 to 2:1) to give building block BB10 (2.7 g, 7.75 mmol, 58.4%) as a yellow gum.

Preparation of Building Block 12

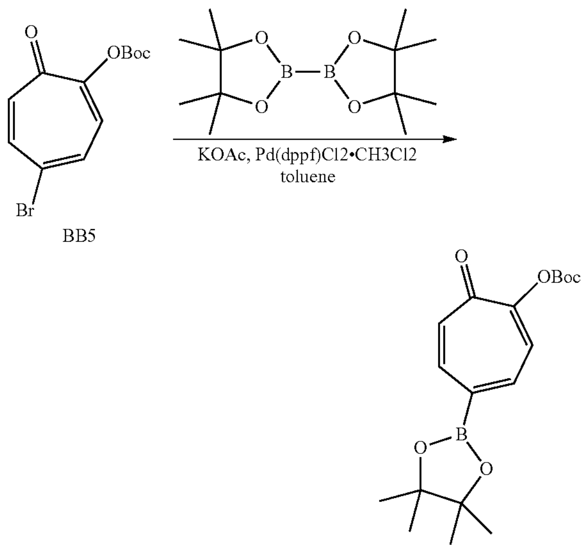

BB5

BB12

A mixture of building block BB5 (1.00 g, 3.32 mmol, 1.00 eq), 4,4,4',4',5,5,5',5'-octamethyl-2,2'-bi(1,3,2-dioxaborolane) (927 mg, 3.65 mmol, 1.10 eq) and KOAc (651 mg, 6.64 mmol, 2.00 eq) in toluene (20.0 mL) was degassed and purged with $N_2$. To the mixture was added Pd(dppf) $Cl_2 \cdot CH_2Cl_2$ complex (542 mg, 664 umol, 0.20 eq), and the mixture was stirred at 120 °C for 1 hour under $N_2$ atmosphere. Reaction progress was monitored by TLC (petroleum ether:EtOAc (3:1, product Rf=0.1). The reaction mixture was filtered and concentrated to dryness under vacuum. The residue was purified by silica gel column chromatography eluting with petroleum ether:EtOAc (100:1 to 9:1) to afford BB12 (1.40 g, crude) as a white solid.

B. Synthesis of Tropolone Derivatives

In certain embodiments, tropolone intermediates obtained in section A (immediately above). were further reacted with various reagents to produce tropolone derivatives. The synthesis, purification, and characterization of each representative tropolone derivative are described in detail in the following examples.

Example 1: Preparation of 4-(5-fluoropyridin-3-yl)-2-hydroxycyclohepta-2,4,6-trien-1-one (Ex.1)

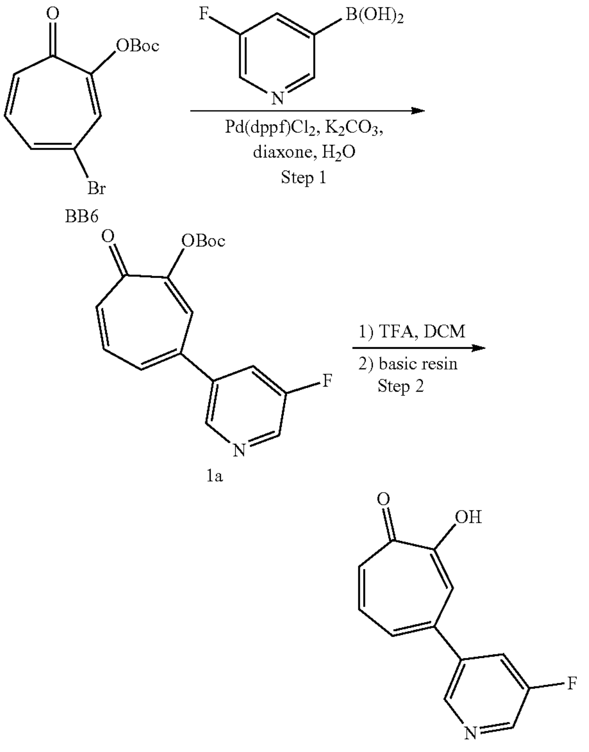

BB6

1a

Ex. 1

Step 1:

To a solution of building block BB6 (0.6 g, 1.99 mmol, 1 eq) and (5-fluoro-3-pyridyl) boronic acid (421 mg, 2.99 mmol, 1.5 eq) in dioxane (10 mL) and $H_2O$ (2 mL) was added Pd(dppf)$Cl_2$ (145 mg, 199 umol, 0.1 eq) and $K_2CO_3$ (688 mg, 4.98 mmol, 2.5 eq) at 20 °C under $N_2$ atmosphere. The system was degassed and charged with nitrogen three times. The reaction was monitored by LCMS. After cooling to room temperature, water (15 mL) was added and the mixture extracted with EtOAc (10 mL×3). The combined organic phases were washed with brine (100 mL) and dried over anhydrous $Na_2SO_4$. After filtering, the filtrate was concentrated under reduced pressure to dryness. The residue was purified by silica gel column chromatography, eluting with petroleum ether:EtOAc (10:1 to 7:3) to afford 1a (0.3 g, 45.1% yield, 95% purity) as a yellow solid.

Step 2:

To a solution of 1a (0.3 g, 945 umol, 1 eq) in DCM (5 mL) was added TFA (3 mL) at 25 °C. The mixture was stirred at 25 °C for 0.5 hour. The reaction was monitored by TLC (petroleum ether:EtOAc=1:1, product Rf=0.5). The reaction mixture was concentrated under vacuum, and the crude product was dissolved in DCM (5 mL) and treated with Amberlyst A21 ion-exchange resin (0.2 g) and stirred at 25 °C for 0.5 hour. After filtering, the filtrate was concentrated under reduced pressure to dryness. The residue was dissolved in a mixture of $CH_3CN$ (1 mL) and pure water (2 mL) to provide Ex.1 (103 mg, 49.7% yield, 99% purity) as a yellow solid after lyophilization overnight; $^1H$ NMR: 400 MHz $CD_3OD$, δ 8.67 (s, 1H), 8.57 (d, J=2.8 Hz, 1H), 7.95

(td, J=1.6, 9.6 Hz, 1H), 7.61 (dd, J=10.4 Hz, 1H), 7.55 (d, J=1.6 Hz, 1H), 7.41-7.28 (m, 2H); LCMS: m/z $[M+1]^+$=218.0.

Example 2: Preparation of 4-(4,5-difluoropyridin-3-yl)-2-hydroxycyclohepta-2,4,6-trien-1-one (Ex.2)

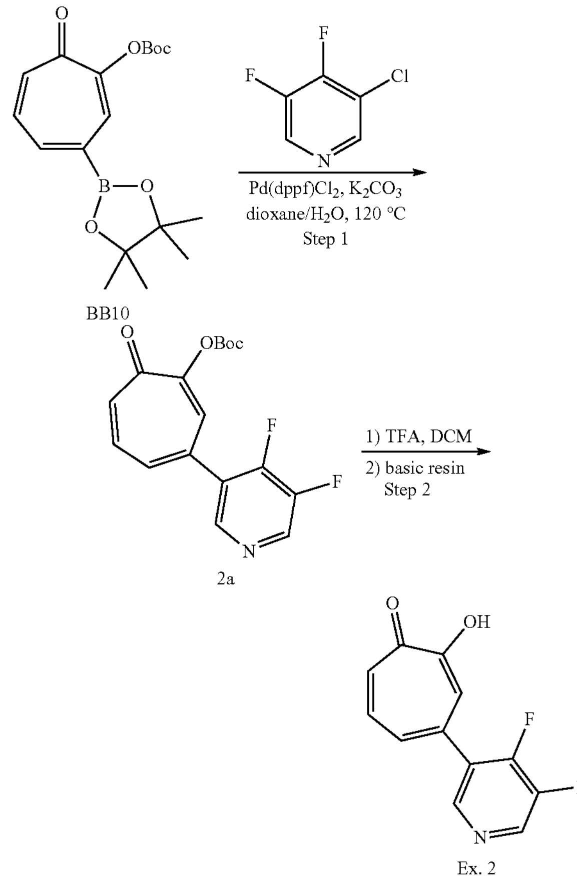

Step 1:

To a mixture of building block BB10 (300 mg, 861 umol, 1.00 eq) and 3-chloro-4,5-difluoro-pyridine (154 mg, 1.03 mmol, 1.2 eq) in a mixture of dioxane and $H_2O$ (17:1, 3 mL) was added $Cs_2CO_3$ (562 mg, 1.72 mmol, 2 eq) and Pd(dppf) $Cl_2 \cdot CH_2Cl_2$ (141 mg, 172 umol, 0.20 eq) in one portion at 25 °C under $N_2$ atmosphere. The system was degassed and charged with nitrogen three times. The mixture was heated to and stirred at 120 °C for 0.5 hour under $N_2$ atmosphere. The reaction was monitored by LCMS. After cooling to room temperature, water (10 mL) was added and the mixture extracted with EtOAc (50 mL×3). The combined organic phases were washed with water (10 mL), brine (10 mL), and dried over anhydrous $Na_2SO_4$. After filtering, the filtrate was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to afford 2a (20 mg, 6.92% yield) as a yellow solid.

Step 2:

To a solution of 2a (20 mg, 60 umol, 1 eq) in $CH_2Cl_2$ (1 mL) was added TFA (0.5 mL) in one portion at 0 °C, and the mixture was warmed to and stirred at 25 °C for 1 hour. The reaction was monitored by TLC (petroleum ether:EtOAc=1:1). The reaction mixture was diluted with $CH_2Cl_2$ (10 mL) and concentrated under reduced pressure to dryness below 10 °C. The residue was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2), and the filtrate was concentrated under reduced pressure to provide Ex.2 (10 mg, 71.4% yield) as a yellow solid; $^1H$ NMR: 400 MHz $CD_3OD$, δ 7.17-7.28 (m, 1H) 7.34-7.47 (m, 2H) 7.53-7.65 (m, 1H) 8.48-8.58 (m, 1H) 8.69 (br d, J=8.4 Hz, 1H); LCMS: m/z $[M+1]^+$=236.0.

Example 3: Preparation of 4-(5-fluoropyridin-2-yl)-2-hydroxycyclohepta-2,4,6-trien-1-one (Ex.3)

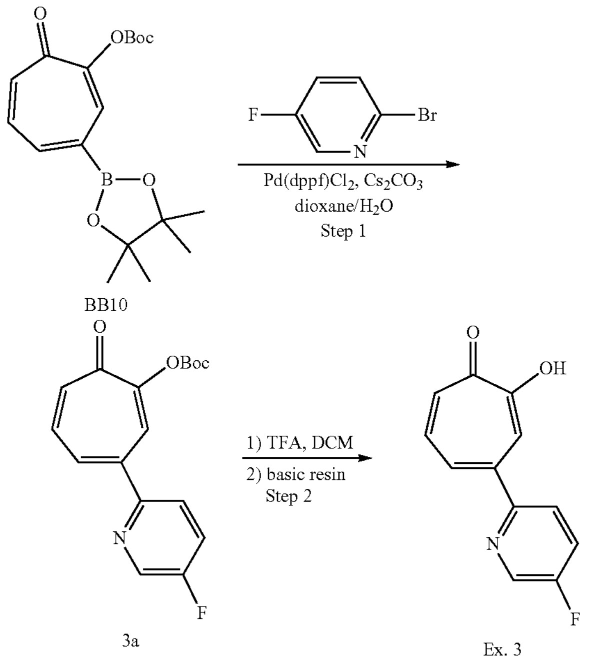

Step 1:

To a mixture of building block BB10 (0.30 g, 861 umol, 1.00 eq), 2-bromo-5-fluoro-pyridine (182 mg, 1.03 mmol, 1.20 eq) in a mixture of dioxane and $H_2O$ (17:1, 3 mL) were added $Cs_2CO_3$ (562 mg, 1.72 mmol, 2.00 eq) and Pd(dppf) $Cl_2 \cdot CH_2Cl_2$ (35.0 mg, 43.0 umol, 0.05 eq) under $N_2$. The system was degassed and charged with nitrogen three times. The mixture was heated to and stirred at 110 °C for 5 hours under $N_2$ atmosphere. The reaction was monitored by LCMS. After cooling to room temperature, water (10 mL) was added and the mixture extracted with EtOAc (50 mL×3). The combined organic phases were washed with water (10 mL) and brine (10 mL), and dried over anhydrous $Na_2SO_4$. After filtering, the filtrate was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to afford 3a (50 mg, 18.2% yield) as a brown solid.

Step 2:

To a solution of 3a (50 mg, 157 umol, 1.00 eq) in $CH_2Cl_2$ (1 mL) were added TFA (0.5 mL) and $Et_3SiH$ (55.0 mg, 472 umol, 3.00 eq). The mixture was stirred at 25 °C for 1 hour.

The reaction was monitored by TLC (EtOAc). The mixture was diluted with $CH_2Cl_2$ (10 mL) and concentrated under reduced pressure to dryness. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2) and the filtrate was concentrated under reduced pressure to provide Ex.3 (25 mg, 73.1%) as a brown solid; $^1$H NMR: 400 MHz DMSO-$d_6$, δ 7.25 (d, J=11.2 Hz, 1H) 7.51-7.59 (m, 1H) 7.62-7.70 (m, 1H) 7.84-7.93 (m, 2H) 8.10 (m, 1H) 8.67-8.75 (m, 1H); LCMS: m/z $[M+1]^+$=218.0.

Example 4: Preparation of 5-(6-hydroxy-5-oxocyclohepta-1,3,6-trien-1-yl)nicotinonitrile (Ex.4)

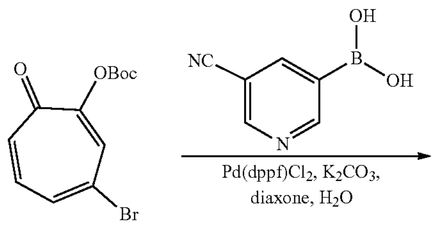

BB6

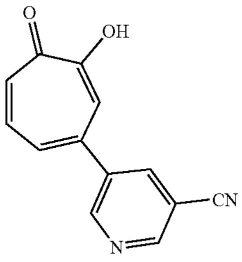

Ex. 4

To a mixture of building block BB6 (200 mg, 664 umol, 1.00 eq), (5-cyano-3-pyridyl)boronic acid (118 mg, 796 umol, 1.20 eq) in a mixture of dioxane and $H_2O$ (17:1, 3 mL) were added $Cs_2CO_3$ (433 mg, 1.33 mmol, 2.00 eq) and Pd(dppf)$Cl_2$·$CH_2Cl_2$ (27.0 mg, 33.2 umol, 0.05 eq) under $N_2$. The system was degassed and charged with nitrogen three times. The mixture was heated to and stirred at 110 °C for 5 hours under $N_2$ atmosphere. The reaction was monitored by TLC (EtOAc). After cooling to room temperature, water (10 mL) was added and the mixture extracted with EtOAc (50 mL×3). The combined organic phases were washed with water (10 mL) and brine (10 mL), and dried over anhydrous $Na_2SO_4$. After filtering, the filtrate was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to afford Ex.4 (11 mg, 46.2 umol, 6.96% yield) as a yellow solid; $^1$H NMR: 400 MHz $CD_3OD$, δ 6.71-6.75 (m, 1H) 6.96-7.02 (m, 1H) 7.06-7.11 (m, 1H) 7.23-7.31 (m, 1H) 8.37-8.40 (m, 1H) 8.89-8.91 (m, 1H) 8.98 (d, J=2.0 Hz, 1H); LCMS: m/z $[M+1]^+$=225.0.

Example 5: Preparation of 2-hydroxy-4-(2-methylpyridin-4-yl)cyclohepta-2,4,6-trien-1-one

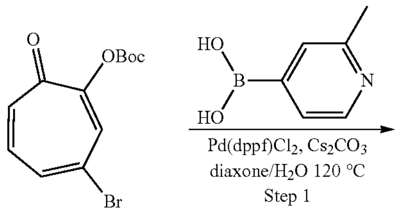

BB6

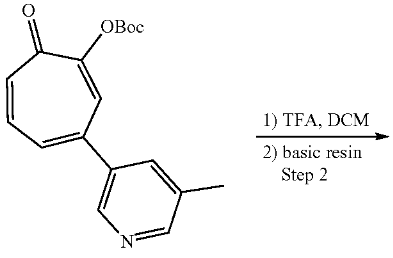

5a

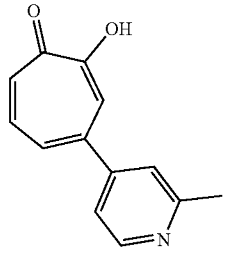

Ex. 5

Step 1:

To a mixture of building block BB6 (150 mg, 498 umol, 1.00 eq), (2-methyl-4-pyridyl)boronic acid (82.0 mg, 597 umol, 1.20 eq) in a mixture of dioxane and $H_2O$ (17:1, 2 mL) were added $Cs_2CO_3$ (325 mg, 996 umol, 2.00 eq) and Pd(dppf)$Cl_2$·$CH_2Cl_2$ (81.0 mg, 99.6 umol, 0.20 eq) under $N_2$. The system was degassed and charged with nitrogen three times. The mixture was stirred at 120 °C for 1.5 hours under $N_2$ atmosphere. The reaction was monitored by LCMS. After cooling to room temperature, water (10 mL) was added and the mixture extracted with EtOAc (50 mL×3). The combined organic phases were washed with water (10 mL) and brine (10 mL), and dried over anhydrous $Na_2SO_4$. After filtering, the filtrate was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to afford 5a (40 mg, 25.6% yield) as a yellow solid.

Step 2:

To a solution of 5a (40 mg, 127 umol, 1.00 eq) in $CH_2Cl_2$ (1 mL) was added TFA (0.5 mL) and $Et_3SiH$ (45.0 mg, 382 umol, 3 eq) in one portion at 0 °C. The mixture was warmed to room temperature and stirred at 25 °C for 1 hour. The reaction was monitored by TLC (EtOAc). The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2), and the filtrate was concentrated under reduced pressure to provide Ex.5 (11.5 mg, 42.2% yield) as a yellow solid; $^1H$ NMR: 400 MHz DMSO-$d_6$, δ 2.55 (s, 3H) 7.22-7.31 (m, 2H) 7.40 (d, J=1.6 Hz, 1H) 7.43-7.47 (m, 1H) 7.51 (s, 1H) 7.53-7.57 (m, 1H) 8.55 (d, J=5.6 Hz, 1H); LCMS: m/z $[M+1]^+$=214.1.

Example 6: Preparation of 4-(5-fluoro-2-methoxy-pyridin-4-yl)-2-hydroxycyclohepta-2,4,6-trien-1-one (Ex.6)

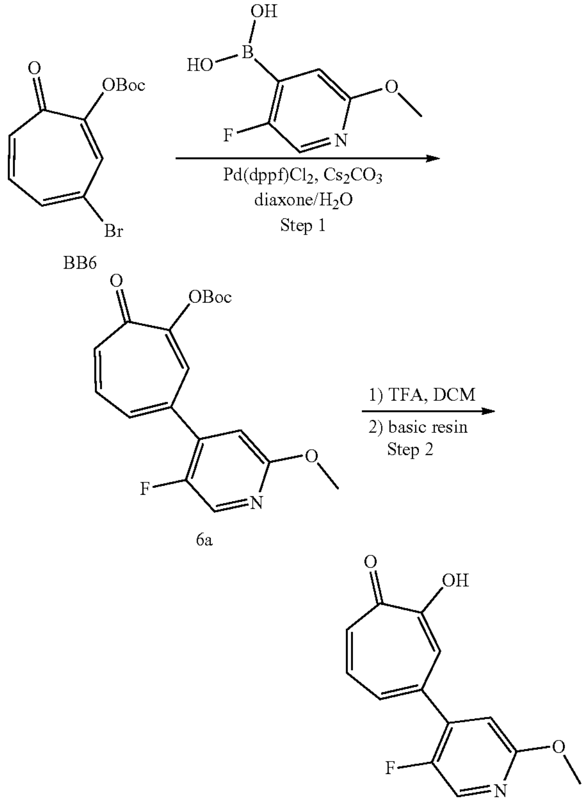

BB6

6a

Ex. 6

Step 1:

To a mixture of building block BB6 (200 mg, 664 umol, 1.00 eq), (5-fluoro-2-methoxy-4-pyridyl) boronic acid (136 mg, 796 umol, 1.20 eq), $Cs_2CO_3$ (433 mg, 1.33 mmol, 2 eq) in a mixture of dioxane and $H_2O$ (17:1, 4 mL) was added $Pd(dppf)Cl_2 \cdot CH_2Cl_2$ (27.0 mg, 33.2 umol, 0.05 eq) under $N_2$. The system was degassed and charged with nitrogen three times, and the mixture was heated to and stirred at 120 °C for 4 hours under $N_2$ atmosphere. The reaction was monitored by LCMS. After cooling to room temperature, the mixture was filtered through a pad of Celite and the filter cake washed with $CH_2Cl_2$ (20 mL×2). The mixture was concentrated under reduced pressure to dryness. The residue was purified by prep-TLC (EtOAc) to give 6a (100 mg, 43.3% yield) as a yellow oil.

Step 2:

To a solution of 6a (100 mg, 287 umol, 1.00 eq) in $CH_2Cl_2$ (1 mL) was added TFA (0.5 mL) and $Et_3SiH$ (100 mg, 863 umol, 3.00 eq) in one portion at 0 °C. The mixture was warmed to room temperature and stirred at 25 °C for 3 hours. The reaction was monitored by TLC (EtOAc). The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) 25 °C for another 0.5 hour. After filtering, the cake was washed with $CH_2Cl_2$ (5 mL×2), and the filtrate was concentrated under reduced pressure to provide Ex.6 (42.5 mg, 59.7% yield) as a yellow solid; $^1H$ NMR: 400 MHz DMSO-$d_6$, δ 3.87 (s, 3H) 6.98-7.05 (m, 1H) 7.09-7.17 (m, 1H) 7.24-7.31 (m, 2H) 7.46-7.55 (m, 1H) 8.24 (s, 1H); LCMS: m/z $[M+1]^+$=248.0.

Example 7: Preparation of 2-hydroxy-4-(pyridin-4-yl)cyclohepta-2,4,6-trien-1-one (Ex.7)

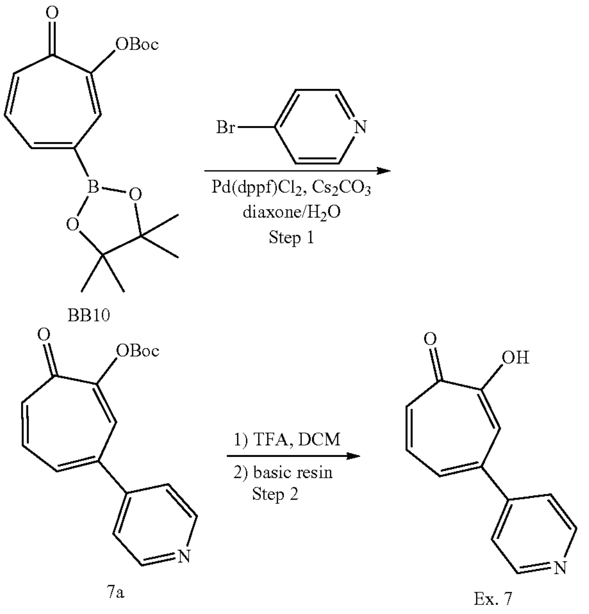

BB10

7a

Ex. 7

Step 1:

To a mixture of building block BB10 (250 mg, 717 umol, 1.00 eq), 4-bromopyridine (136 mg, 861 umol, 1.20 eq) in a mixture of dioxane and $H_2O$ (17:1, 4 mL), were added $Cs_2CO_3$ (468 mg, 1.44 mmol, 2.00 eq) and Pd(dppf) $Cl_2 \cdot CH_2Cl_2$ (117 mg, 143 umol, 0.20 eq) under $N_2$. The system was degassed and charged with nitrogen three times, and the mixture was heated to and stirred at 120 °C for 0.5 hour under $N_2$ atmosphere. The reaction was monitored by LCMS showed. After cooling to room temperature, the mixture was filtered through a pad of Celite, and the filter cake was washed with $CH_2Cl_2$ (20 mL×2). The washes were then concentrated under reduced pressure to dryness and the resulting residue purified by prep-TLC (EtOAc:MeOH=10:1) to give 7a (60 mg, 27.9% yield) was as a brown oil.

Step 2:

To a solution of 7a (50 mg, 167 umol, 1 eq) in $CH_2Cl_2$ (1 mL) was added TFA (0.5 mL) in one portion at 0 °C. The mixture was warmed to room temperature and stirred at 25 °C for 1 hour. The reaction was monitored by TLC (EtOAc). The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2) and the filtrate was concentrated under reduced pressure to provide Ex.7 (19 mg, 57.1% yield) as a brown solid; $^1H$ NMR: 400 MHz DMSO-$d_6$, δ 7.28 (t, J=10.8 Hz, 2H) 7.41 (d, J=1.2 Hz, 1H) 7.49-7.59 (m, 1H) 7.62-7.70 (m, 2H) 8.65-8.74 (m, 2H); LCMS: m/z $[M+1]^+$=200.0.

Example 8: Preparation of 2-hydroxy-4-(2-methoxypyridin-4-yl)cyclohepta-2,4,6-trien-1-one (Ex.8)

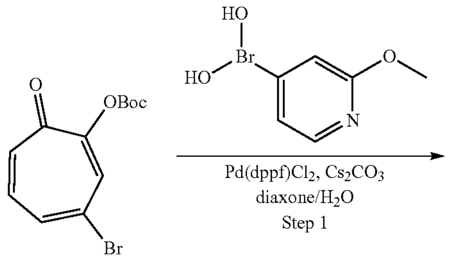

BB6

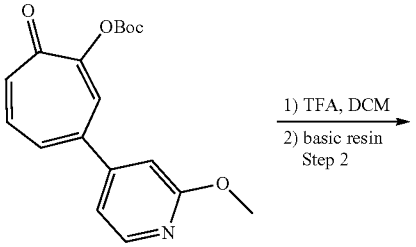

8a

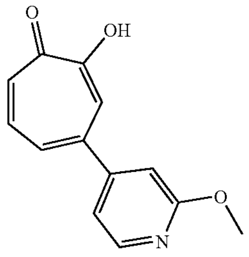

Ex. 8

Step 1:

To a mixture of building block BB6 (150 mg, 498 umol, 1.00 eq) and (2-methoxy-4-pyridyl)boronic acid (76.0 mg, 498 umol, 1.00 eq) in 1,4-dioxane (2 mL) and $H_2O$ (0.3 mL) were added $Cs_2CO_3$ (324 mg, 996 umol, 2.00 eq) and Pd(dppf)$Cl_2$·$CH_2Cl_2$ (40.0 mg, 49.8 umol, 0.10 eq) under $N_2$. The system was degassed and charged with nitrogen three times. The mixture was heated to and stirred at 120 °C for 0.5 hour under $N_2$ atmosphere. The reaction was monitored by TLC (petroleum ether:EtOAc=3:1, product Rf=0.4). After cooling to room temperature, the mixture was filtered through a pad of Celite, and the filter cake was washed with $CH_2Cl_2$ (20 mL×2). The mixture was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to give compound 8a (57 mg, 34.8% yield) as a yellow solid.

Step 2:

To a solution of 8a (57 mg, 173 umol, 1 eq) in $CH_2Cl_2$ (1 mL) was added $Et_3SiH$ (60.0 mg, 519 umol, 3.00 eq) and TFA (3 mL) in one portion at 20 °C. The mixture was stirred at 20 °C for 3 hours. The reaction was monitored by TLC (EtOAc, product Rf=0.1). The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2) and the filtrate was concentrated under reduced pressure to provide compound Ex.8 (28.5 mg, 71.8% yield) as a brown solid; $^1H$ NMR: 400 MHz $CD_3OD$, δ 8.24 (d, J=5.6 Hz, 1H), 7.64-7.56 (m, 1H), 7.52 (d, J=1.2 Hz, 1H), 7.40-7.30 (m, 2H), 7.18 (m, 1H), 7.02 (s, 1H), 3.98 (s, 3H), 4.00-3.96 (m, 1H); LCMS: m/z $[M+1]^+$=230.1.

Example 9: Preparation of 2-hydroxy-4-(3-methylpyridin-4-yl)cyclohepta-2,4,6-trien-1-one (Ex.9)

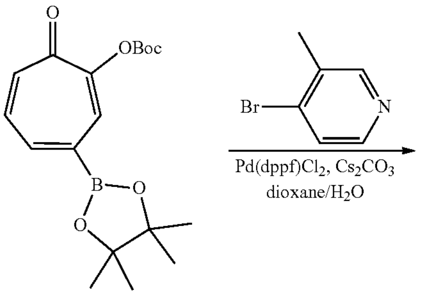

BB10

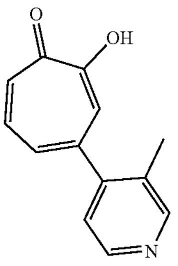

Ex. 9

Step 1:

To a mixture of building block BB10 (250 mg, 717 umol, 1.00 eq), 4-bromo-3-methyl-pyridine (224 mg, 1.08 mmol, 1.50 eq, HCl salt) and $Cs_2CO_3$ (1.17 g, 3.59 mmol, 5 eq) in 1,4-dioxane (2 mL) and $H_2O$ (1 mL) was added Pd(dppf)$Cl_2$·$CH_2Cl_2$ (117 mg, 143 umol, 0.20 eq) in one portion at 25 °C under $N_2$ atmosphere. The system was degassed and charged with nitrogen three times. The mixture was heated to and stirred at 120 °C for 0.5 hour under $N_2$ atmosphere. The reaction was monitored by LCMS. After cooling to room temperature, the mixture was filtered through a pad of Celite and the filter cake washed with $CH_2Cl_2$ (30 mL×3). The filtrate was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to give compound Ex.9 (10 mg, 6.53% yield) directly as a brown solid; $^1H$ NMR: 400 MHz $CD_3OD$, δ 8.48 (s, 1H), 8.46-8.42 (m, 1H), 7.48-7.42 (m, 1H), 7.32-7.28 (m, 1H), 7.28-7.22 (m, 1H), 7.10-7.08 (m, 1H), 6.86-6.80 (m, 1H), 2.28 (s, 3H); LCMS: m/z $[M+1]^+$=214.0.

Example 10: Preparation of 2-hydroxy-4-(5-methoxypyridin-3-yl)cyclohepta-2,4,6-trien-1-one (Ex.10)

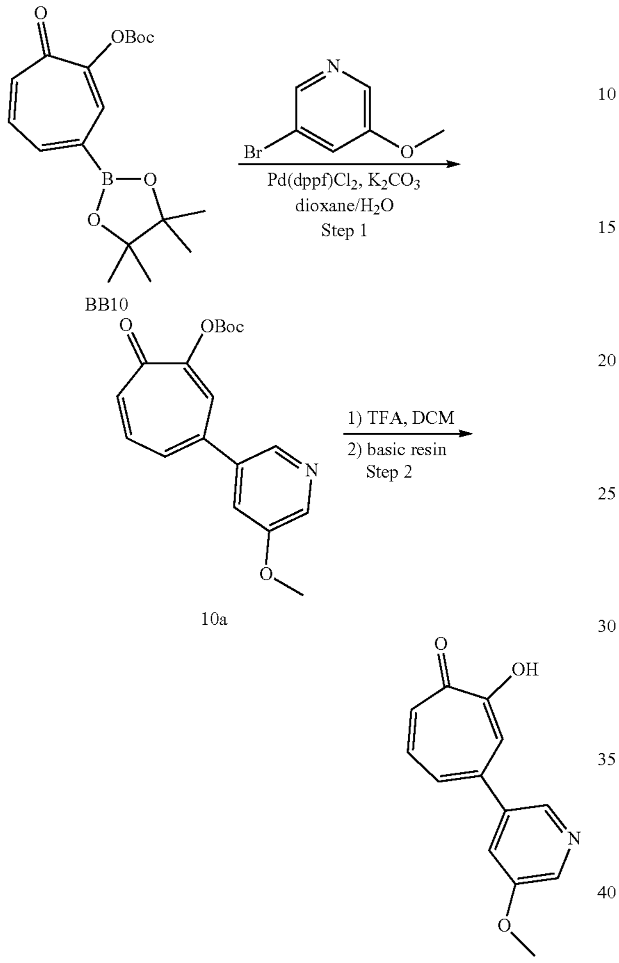

BB10

10a

Ex. 10

Step 1:

To a mixture of building block BB10 (0.3 g, 862 umol, 1 eq) and 3-bromo-5-methoxy-pyridine (242 mg, 1.29 mmol, 1.5 eq) in dioxane (5 mL) and $H_2O$ (1 mL) were added $K_2CO_3$ (357 mg, 2.58 mmol, 3 eq) and Pd(dppf)$Cl_2$ (63 mg, 86.2 umol, 0.1 eq) in one portion at 25 °C under $N_2$ atmosphere. The system was degassed and charged with nitrogen three times. The mixture was heated to and stirred at 110 °C for 0.5 hour under $N_2$ atmosphere. The reaction was monitored by LCMS. After cooling to room temperature, water (15 mL) was added and the mixture extracted with EtOAc (10 mL×3). The combined organic phases were washed with brine (30 mL) and dried over anhydrous $Na_2SO_4$. After filtering, the filtrate was concentrated under reduced pressure to dryness. The residue was purified by silica gel column chromatography (petroleum ether: EtOAc=30:70) to give 10a (30 mg, 10.6% yield) as a yellow oil.

Step 2:

To a solution of 10a (30 mg) in DCM (5 mL) was added TFA (2 mL) in one portion at 0 °C. The mixture was warmed to room temperature and stirred at 25 °C for 0.5 hour. The reaction was monitored by TLC (petroleum ether:EtOAc=1:1). The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 at 25 °C for another 0.5 hour. After filtering, the cake was washed with $CH_2Cl_2$ (5 mL×2), and the filtrate was concentrated under reduced pressure to provide Ex.10 (13 mg, 61.4% yield) as yellow a solid; $^1H$ NMR: 400 MHz $CDCl_3$, δ 8.41 (dd, J=2.4, 8.0 Hz, 2H), 7.55 (d, J=1.6 Hz, 1H), 7.53-7.45 (m, 1H), 7.39-7.32 (m, 2H), 7.21 (d, J=10.0 Hz, 1H), 3.95 (s, 3H); LCMS: m/z $[M+1]^+$ =230.1.

Example 11: Preparation of 2-hydroxy-4-(pyridin-3-yl)cyclohepta-2,4,6-trien-1-one (Ex.11)

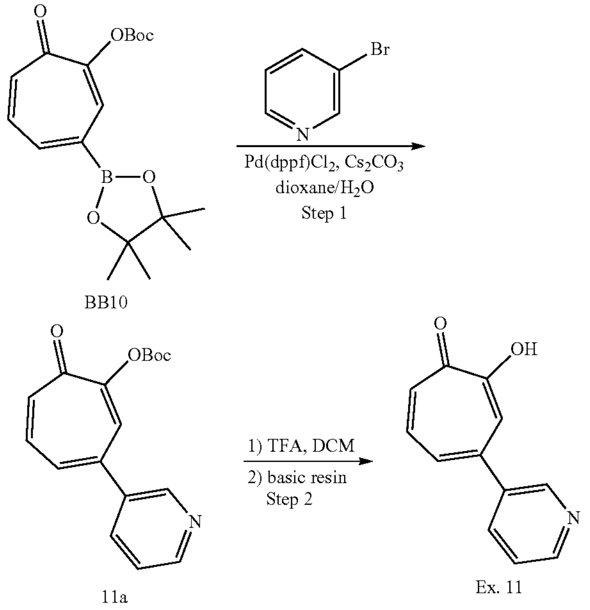

BB10

11a

Ex. 11

Step 1:

To a solution of building block BB10 (200 mg, 574 umol, 1.00 eq), 3-bromopyridine (109 mg, 689 umol, 66.4 uL, 1.20 eq) in a mixture of dioxane and $H_2O$ (17:1, 4 mL) were added $Cs_2CO_3$ (374 mg, 1.15 mmol, 2.00 eq) and Pd(dppf) $Cl_2 \cdot CH_2Cl_2$ (93.8 mg, 114 umol, 0.20 eq) under $N_2$. The system was degassed and charged with nitrogen three times, and the mixture was heated to and stirred at 120 °C for 0.5 hour under $N_2$ atmosphere. The reaction was monitored by LCMS. After cooling to room temperature, the mixture was filtered through a pad of Celite, and the filter cake was washed with $CH_2Cl_2$ (20 mL×2). The mixture was concentrated under reduced pressure to dryness. The residue was purified by prep-TLC (MeOH:EtOAc=10:1) to give 11a (80 mg, 46.5% yield) as a yellow oil.

Step 2:

To a solution of 11a (80 mg) in $CH_2Cl_2$ (2 mL) was added TFA (1 mL) in one portion, and the resulting mixture was stirred at 25 °C for 1 hour. The reaction was monitored by TLC (MeOH:EtOAc=10:1). The mixture was concentrated under reduced pressure to dryness, and then re-dissolved in $CH_2Cl_2$ (10 mL). Amberlyst A21 (20 mg) was added to above solution and the mixture stirred for another 20 min. After filtering, the cake was washed with $CH_2Cl_2$ (10 mL×2), and the filtrate was concentrated under reduced pressure to give Ex.11 (38.5 mg, 72.4% yield) as a yellow solid; $^1$H NMR: 400 MHz DMSO-$d_6$, δ 7.20-7.31 (m, 2H) 7.39-7.44 (m, 1H) 7.47-7.58 (m, 2H) 8.08 (br d, J=8.0 Hz, 1H) 8.66 (d, J=4.8 Hz, 1H) 8.85 (d, J=2.4 Hz, 1H); LCMS: m/z $[M+1]^+$=200.1.

Example 12: Preparation of 4-(5,6-dimethoxypyridin-3-yl)-2-hydroxycyclohepta-2,4,6-trien-1-one

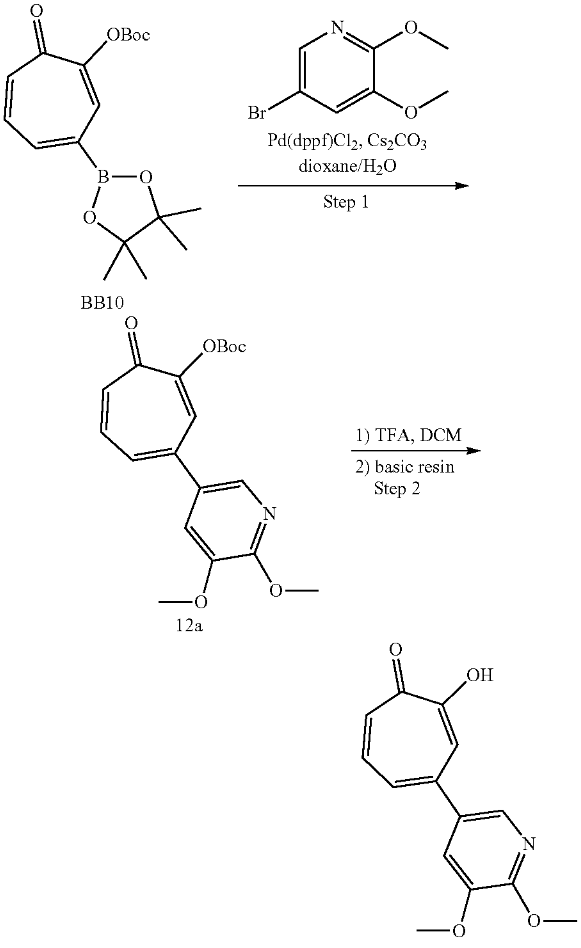

BB10
12a
Ex. 12

Step 1:

To a mixture of building block BB10 (150 mg, 430 umol, 1.00 eq) and 5-bromo-2,3-dimethoxy-pyridine (113 mg, 516 umol, 1.20 eq) in a mixture of dioxane and $H_2O$ (17:1, 3 mL) were added $Cs_2CO_3$ (281 mg, 861 umol, 2.00 eq) and Pd(dppf)$Cl_2$·$CH_2Cl_2$ (70 mg, 86.1 umol, 0.20 eq) under $N_2$. The system was degassed and charged with nitrogen three times, and the mixture was heated to and stirred at 120 °C for 0.5 hour under $N_2$ atmosphere. The reaction was monitored by LCMS. After cooling to room temperature, the mixture was filtered through a pad of Celite and the filter cake washed with $CH_2Cl_2$ (20 mL×2). The mixture was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to give 12a (30 mg, 19.3% yield) as a yellow solid.

Step 2:

To a solution of 12a (30 mg) in $CH_2Cl_2$ (1 mL) was added TFA (0.5 mL) in one portion, and the mixture was stirred at 25 °C for 1 hour. The reaction was monitored by TLC (EtOAc). The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2) and the filtrate concentrated under reduced pressure to provide Ex.12 (12 mg, 55.6% yield) as a yellow solid; $^1$H NMR: 400 MHz DMSO-$d_6$, δ 3.88 (s, 3H) 3.92 (s, 3H) 7.13-7.22 (m, 1H) 7.26-7.34 (m, 1H) 7.42-7.58 (m, 3H) 7.95 (s, 1H); LCMS: m/z $[M+1]^+$=260.0.

Example 13: Preparation of 4-(6-aminopyridin-3-yl)-2-hydroxycyclohepta-2,4,6-trien-1-one (Ex.13)

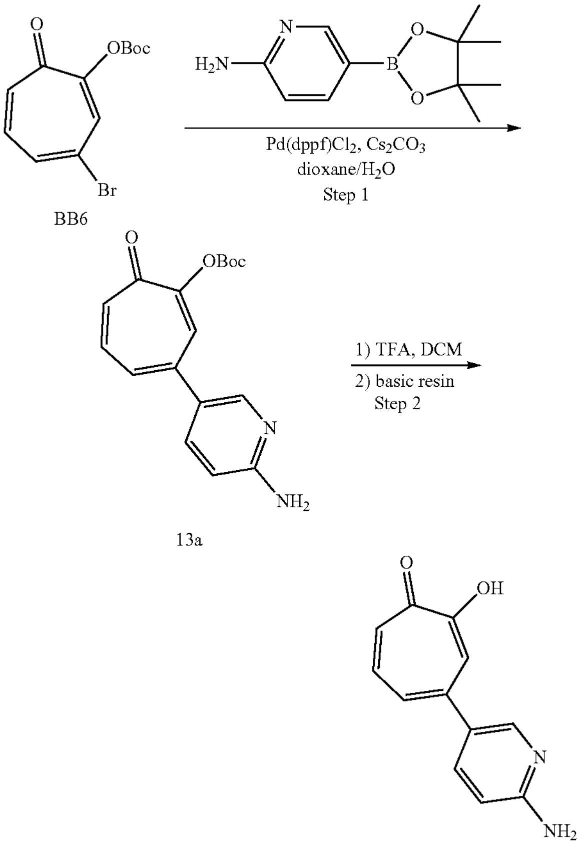

BB6
13a
Ex. 13

Step 1:

To a mixture of building block BB6 (300 mg, 996 umol, 1.00 eq), 5-(4,4,5,5-tetramethyl-1,3,2-dioxaborolan-2-yl)pyridin-2-amine (263 mg, 1.20 mmol, 1.20 eq) and $Cs_2CO_3$ (649 mg, 1.99 mmol, 2.00 eq) in 1,4-dioxane (2.5 mL) and $H_2O$ (0.5 mL) was added Pd(dppf)$Cl_2$·$CH_2Cl_2$ (163 mg, 199 umol, 0.20 eq) in one portion at 25 °C under $N_2$ atmosphere. The system was degassed and charged with nitrogen three times. The mixture was heated to and stirred at 120 °C for 0.5 hour. The reaction was monitored by LCMS. After cooling to room temperature, the mixture was filtered through a pad of Celite and the filter cake washed with $CH_2Cl_2$ (30 mL×3). The filtrate was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to provide compound 13a (117 mg, 37.36% yield) as a yellow solid.

Step 2:

To a solution of 13a (30 mg) in $CH_2Cl_2$ (0.5 mL) was added TFA (0.25 mL) in one portion at 20 °C under $N_2$. The mixture was stirred at 20 °C for 1 hour. The reaction was monitored by LCMS. The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2) and the filtrate was concentrated under reduced pressure to provide compound Ex.13 (14 mg, 68.5% yield) as a yellow solid; $^1H$ NMR: 400 MHz $CD_3OD$, δ 8.20 (d, J=2.0 Hz, 1H), 7.80-7.74 (m, 1H), 7.53 (s, 2H), 7.27 (s, 2H), 6.68 (d, J=8.8 Hz, 1H); LCMS: m/z $[M+1]^+$=215.1.

Example 14: Preparation of 2-hydroxy-4-(4-methylpyridin-3-yl)cyclohepta-2,4,6-trien-1-one (Ex.14)

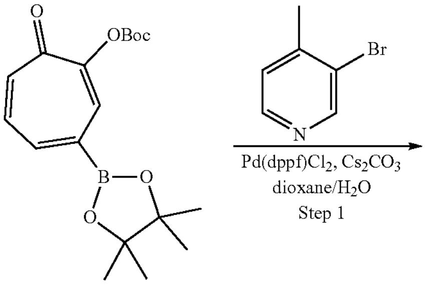

BB10

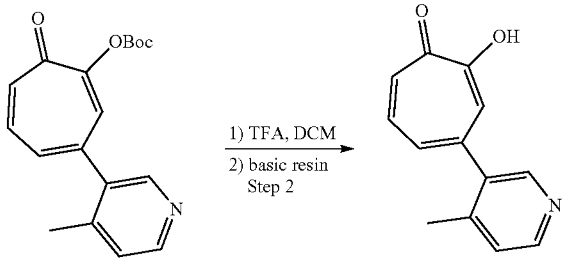

14a

Ex. 14

Step 1:

To a mixture of building block BB10 (200 mg, 574 umol, 1.00 eq), 3-bromo-4-methylpyridine (118 mg, 689 umol, 1.20 eq) and $Cs_2CO_3$ (374 mg, 1.15 mmol, 2.00 eq) in a mixture of dioxane and $H_2O$ (17:1, 2 mL) was added $Pd(dppf)Cl_2$ (84.0 mg, 114 umol, 0.20 eq) at 20 °C under $N_2$ atmosphere. The system was degassed and charged with nitrogen three times. The mixture was heated to and stirred at 120 °C for 20 min. The reaction was monitored by TLC (petroleum ether:EtOAc=10:1, product Rf=0.50). After cooling to room temperature, the mixture was filtered through a pad of Celite and the filter cake washed with $CH_2Cl_2$ (30 mL×3). The filtrate was concentrated under reduced pressure to dryness. The residue was purified by prep-TLC (EtOAc:MeOH=10:1) to give 14a (74 mg, 39.8% yield, 97.0% purity) as a yellow oil.

Step 2:

To a solution of 14a (74 mg) in dichloromethane (1 mL) was added TFA (0.2 mL) in one portion at 20 °C. The mixture was stirred at 20 °C for 1 hour. The reaction was monitored by LCMS. The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2) and the filtrate concentrated under reduced pressure to provide Ex.14 (20.5 mg, 40.7% yield) as yellow a solid; $^1H$ NMR: 400 MHz DMSO-$d_6$, δ 8.47 (d, J=4.8 Hz, 1H), 8.41 (s, 1H), 7.46 (t, J=10.4 Hz, 1H), 7.35 (d, J=5.2 Hz, 1H), 7.27 (d, J=11.2 Hz, 1H), 7.12 (s, 1H), 6.97 (d, J=9.6 Hz, 1H), 2.25 (s, 3H); LCMS: m/z $[M+1]^+$=214.0.

Example 15: Preparation of 5-(5-fluoropyridin-3-yl)-2-hydroxycyclohepta-2,4,6-trien-1-one (Ex.14)

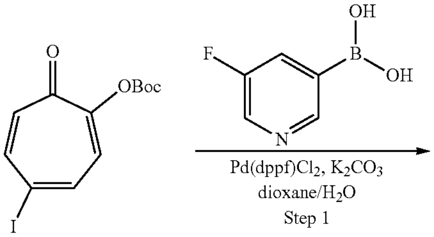

BB8

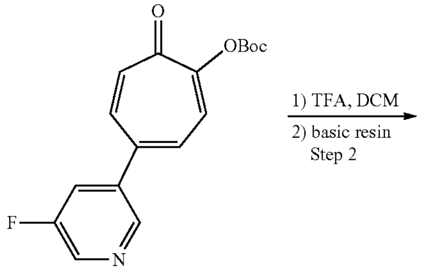

15a

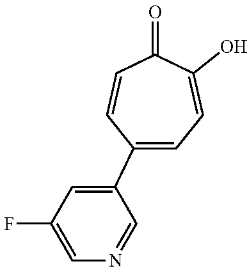

Ex. 15

Step 1:

To a mixture of building block BB8 (150 mg, 431 umol, 1 eq) and (5-fluoropyridin-3-yl)boronic acid (91 mg, 646 umol, 1.5 eq) in dioxane (5 mL) and $H_2O$ (1 mL) were added $K_2CO_3$ (119 mg, 862 umol, 2 eq) and $Pd(dppf)Cl_2{\cdot}CH_2Cl_2$ (35 mg, 43 umol, 0.1 eq) in one portion at 25 °C under $N_2$ atmosphere. The system was degassed and charged with nitrogen three times. The mixture was heated to and stirred at 110 °C for 0.5 hours. The reaction was monitored by TLC (petroleum ether:EtOAc=5:1). After cooling to room temperature, the reaction mixture was quenched by addition water (20 mL) and extracted with EtOAc (20 mL×3). The combined organic layers were washed with brine (20 mL×2), dried over $Na_2SO_4$, filtered and concentrated under reduced pressure. The resulting residue was purified by silica gel column chromatography eluting with petroleum ether:EtOAc (20:1 to 5:1) to give 15a (80 mg, 252 umol, 29.3% yield) as yellow a solid.

Step 2:

To a solution of 15a (80 mg) in $CH_2Cl_2$ (2 mL) was added TFA (0.4 mL) in one portion at 0 °C under $N_2$. The mixture was warmed to room temperature and stirred at 25 °C for 1 hour. The reaction was monitored by TLC (petroleum ether: EtOAc=5:1). The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2), and the filtrate was concentrated under reduced pressure to provide Ex.15 (23 mg, 42.0% yield) as yellow a solid; $^1H$ NMR: 400 MHz $CD_3OD$, δ 7.44 (d, J=11.6 Hz, 2H) 7.77 (d, J=12.0 Hz, 2H) 7.91 (m, 1H) 8.51 (d, J=2.8 Hz, 1H) 8.64 (s, 1H); LCMS: m/z $[M+1]^+$=218.0.

Example 16: Preparation of 4-(5-fluoropyridin-3-yl)-2-hydroxy-7-methylcyclohepta-2,4,6-trien-1-one (Ex.16)

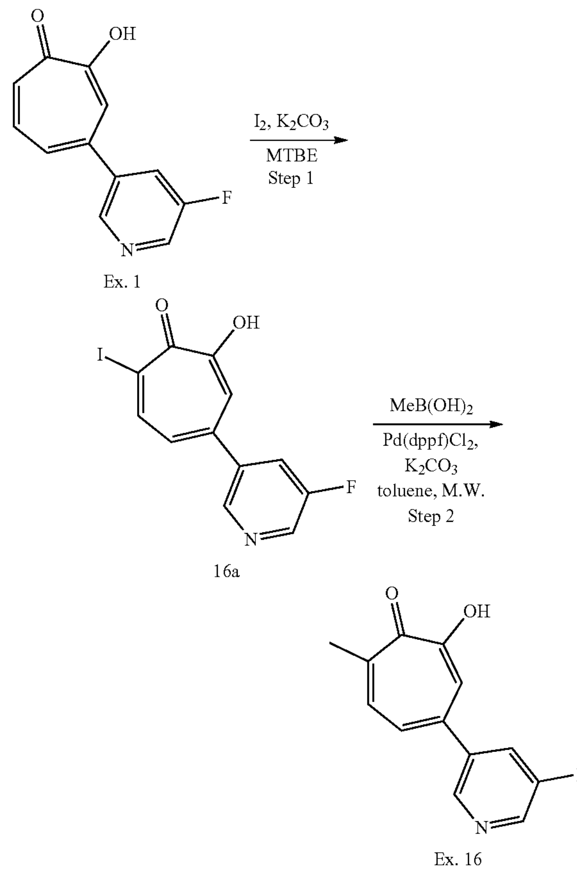

Step 1:

To a mixture of Ex.1 (0.33 g, 1.52 mmol, 1 eq) in methyl tert-butyl ether (MTBE, 5 mL) was added $K_2CO_3$ (419 mg, 3.04 mmol, 2 eq) and 12 (347 mg, 1.37 mmol, 0.9 eq) in one portion at 25 °C. The mixture was stirred at 25 °C for 20 hours. The reaction was monitored by LCMS. The mixture was filtered through a pad of Celite and the filter cake washed with MTBE (10 mL×3). The filtrate was concentrated under reduced pressure to dryness to give crude 16a (0.5 g, 80% purity) as a black solid.

Step 2:

A mixture of 16a (0.5 g, 1.17 mmol, 1 eq), methylboronic acid (348 mg, 5.83 mmol, 5 eq), Pd(dppf)$Cl_2$ (85 mg, 116.59 umol, 0.1 eq) and $K_2CO_3$ (402 mg, 2.91 mmol, 2.5 eq) were taken up into a microwave tube in toluene (10 mL) at 20 °C under $N_2$ atmosphere. The sealed tube was heated to and stirred at 110 °C for 2 hours under microwave conditions. The reaction was monitored by LCMS. The reaction mixture was filtered through a pad of Celite, and the filter cake was washed with $CH_2Cl_2$ (10 mL×2). The filtrate was concentrated under reduced pressure to dryness. The residue was purified by prep-HPLC {column: Nano-micro Kromasil C18 (100*30 mm, 5 um); mobile phase: [water (0.10% TFA)-ACN]; B %: 30%-60%, 10 min} to provide Ex.16 (13 mg, 4.77% yield) as yellow a solid; $^1H$ NMR: 400 MHz $CD_3OD$, δ 8.68 (s, 1H), 8.56 (d, J=2.4 Hz, 1H), 7.96 (br d, J=9.2 Hz, 1H), 7.78 (br d, J=10.0 Hz, 1H), 7.58 (s, 1H), 7.28 (br d, J=9.6 Hz, 1H), 2.47 (s, 3H); LCMS: m/z $[M+1]^+$=231.9.

Example 17: Preparation of 4-(5-chloropyridin-3-yl)-2-hydroxycyclohepta-2,4,6-trien-1-one (Ex.17)

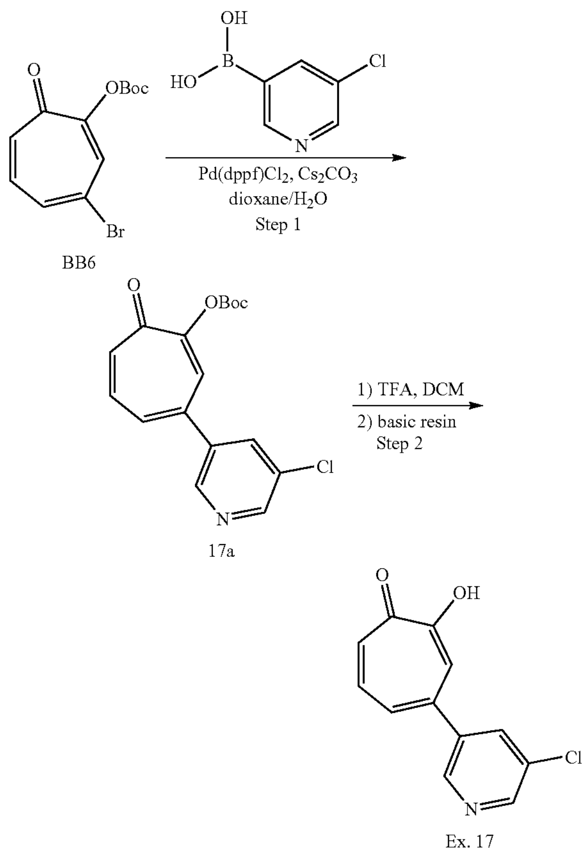

Step 1:

To a mixture of building block BB6 (200 mg, 664 umol, 1 eq), (5-chloro-3-pyridyl)boronic acid (125 mg, 796 umol, 1.2 eq) and $Cs_2CO_3$ (432 mg, 1.33 mmol, 2 eq) in dioxane (4 mL) and $H_2O$ (1 mL) was added $Pd(dppf)Cl_2 \cdot CH_2Cl_2$ (27 mg, 33.2 umol, 0.05 eq) under $N_2$ atmosphere. The system was degassed and charged with nitrogen three times. The mixture was heated to and stirred at 120 °C for 20 min under $N_2$. After cooling to room temperature, the mixture was filtered through a pad of Celite, and the filter cake was washed with $CH_2Cl_2$ (10 mL×3). The filtrate was concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to give 17a (40 mg, 18.0% yield) and Ex.17 (24 mg, 15.5% yield) as a white solid.

Step 2:

To a solution of 17a (40.0 mg) in dichloromethane (2 mL) were added TFA (0.1 mL) and $Et_3SiH$ (42 mg, 3 eq) in one portion at 25 °C. The mixture was stirred at 25 °C for 2 hours. The reaction was monitored by LCMS. The reaction mixture was diluted with $CH_2Cl_2$ (10 mL) and concentrated under reduced pressure to dryness below 10 °C. The crude product was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2), and the filtrate was concentrated under reduced pressure to provide Ex.17 (12.0 mg, 42.8% yield) as a yellow solid; $^1H$ NMR: 400 MHz $CD_3OD$, δ 8.69 (d, J=10.4 Hz, 1H), 8.64 (d, J=10.4 Hz, 1H), 8.08 (t, J=2.0 Hz, 1H), 7.30-7.36 (m, 1H), 7.18 (br s, 1H), 7.06 (br d, J=11.2 Hz, 1H), 6.84 (br d, J=9.6 Hz, 1H); LCMS: m/z $[M+1]^+$=234.0.

Example 18: Preparation of 2-hydroxy-4-(6-methylpyridin-3-yl)cyclohepta-2,4,6-trien-1-one (Ex.18)

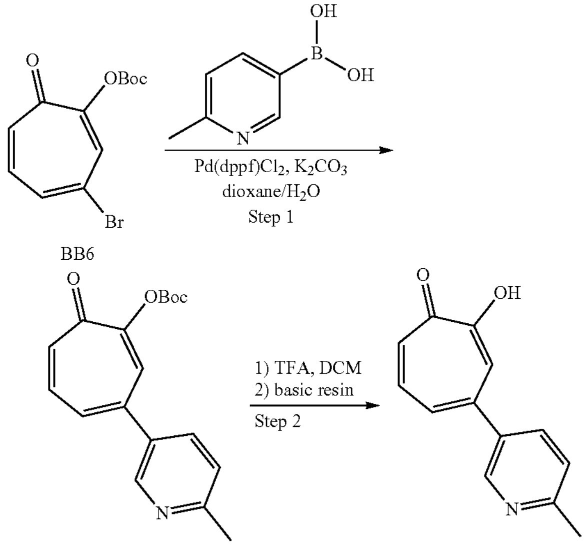

BB6

18a

Ex. 18

Step 1:

To a mixture of building block BB6 (50 mg, 166.04 umol, 1 eq), (6-methyl-3-pyridyl)boronic acid (28 mg, 199.25 umol, 1.2 eq) and $Cs_2CO_3$ (108 mg, 332 umol, 2 eq) in dioxane (1 mL) and water (0.1) was added Pd(dppf) $Cl_2 \cdot CH_2Cl_2$ (7 mg, 8.4 umol, 0.05 eq) in one portion at 25 °C under $N_2$ atmosphere. The system was degassed and charged with nitrogen three times. The mixture was heated to and stirred at 110 °C for 1 hour. The reaction was monitored by TLC (petroleum ether:EtOAc=3:1). After cooling to room temperature, the mixture was filtered through a pad of Celite, and the filter cake was washed with $CH_2Cl_2$ (5 mL×2). The filtrate was concentrated under reduced pressure to dryness. The residue was purified by prep-TLC (petroleum ether:EtOAc=1:2) to give 18a (25 mg, 48.1% yield) as a yellow solid.

Step 2:

To a solution of 18a (80 mg) in DCM (2 mL) was added TFA (0.2 mLq) in one portion at 25 °C. The mixture was stirred at 25 °C for 2 hours. The reaction was monitored by TLC (petroleum ether:EtOAc=3:1). The reaction mixture was diluted with $CH_2Cl_2$ (10 mL) and concentrated under reduced pressure to dryness below 10 °C. The mixture was re-dissolved in $CH_2Cl_2$ (10 mL) and stirred with Amberlyst A21 (0.2 g) for another 0.5 hour. After filtering, the cake was washed with $CH_2Cl_2$ (5 mL×2) and the filtrate was concentrated under reduced pressure to provide desired product Ex.18 (47 mg, 86.33% yield) as a yellow solid; $^1H$ NMR: 400 MHz $CD_3OD$, δ 8.65 (d, J=2.0 Hz, 1H), 7.99 (dd, J=8.0, 2.4 Hz, 1H), 7.59 (dd, J=11.2, 10.0 Hz, 1H), 7.53-7.55 (m, 1H), 7.43 (d, J=8.0 Hz, 1H), 7.28-7.36 (m, 2H), 2.60 (s, 3H); LCMS: m/z $[M+1]^+$=214.1.

Example 19: Preparation of 2-hydroxy-4-(6-methoxypyridin-3-yl)cyclohepta-2,4,6-trien-1-one (Ex.19)

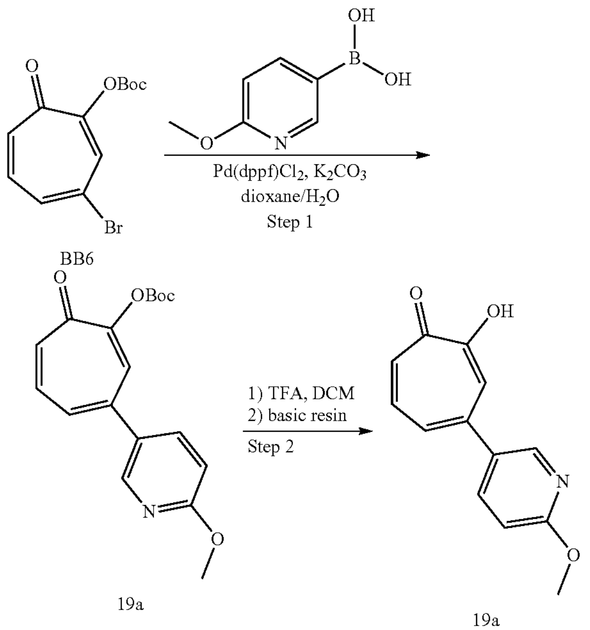

BB6

19a

19a

Step 1:

To a mixture of building block BB6 (150 mg, 0.5 mmol, 1 eq) and (6-methoxy-3-pyridyl)boronic acid (92 mg, 0.6 mmol, 1.2 eq) in dioxane (2.0 mL) and water (0.2 mL) were added $K_2CO_3$ (140 mg, 0.1 mmol, 2 eq) and $Pd(dppf)Cl_2$ (21 mg, 25 umol, 0.05 eq) in one portion at 25 °C under $N_2$ atmosphere. The system was degassed and charged with nitrogen three times. The mixture was heated to and stirred at 120 °C for 3 hours. The reaction was monitored by TLC (petroleum ether:EtOAc=3:1). After cooling to room temperature, the mixture was filtered through a pad of Celite, and the filter cake was washed with $CH_2Cl_2$ (30 mL×3). The filtrate was concentrated under reduced pressure to dryness. The residue was purified by prep-TLC (petroleum ether: EtOAc=1:2) to give 19a (105 mg, 64% yield) as an off-white solid.

Step 2:

To a solution of 19a (100 mg) in $CH_2Cl_2$ (2 mL) was added TFA (0.2 mL) in one portion at 0 °C. The mixture was warmed to room temperature and stirred at 25 °C for 1 hour. The reaction was monitored by TLC (petroleum ether: EtOAc=3:1). The reaction mixture was diluted with $CH_2Cl_2$ (10 mL) and concentrated under reduced pressure to dryness below 10 °C. The mixture was re-dissolved in $CH_2Cl_2$ (10 mL) and stirred with Amberlyst A21 (0.1 g) for another 0.5 hour. After filtering, the cake was washed with $CH_2Cl_2$ (5 mL×2) and the filtrate was concentrated under reduced pressure to provide desired product Ex.19 (65 mg, 93.4% yield) as a yellow solid; $^1$H NMR: 400 MHz $CD_3OD$, δ 8.40 (d, J=2.4 Hz, 1H), 7.96 (dd, J=8.8, 2.8 Hz, 1H), 7.54-7.60 (m, 1H), 7.54 (d, J=1.2 Hz, 1H), 7.53-7.54 (m, 1H), 7.32 (s, 1H), 7.29 (s, 1H), 6.93 (d, J=8.8 Hz, 1H), 3.98 (s, 3H); LCMS: m/z $[M+1]^+$=230.0.

Example 20: Preparation of 4-(5-fluoro-2,6-dimethylpyridin-3-yl)-2-hydroxycyclohepta-2,4,6-trien-1-one (Ex.20)

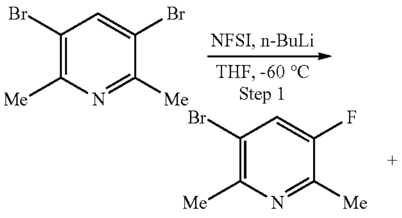

20a

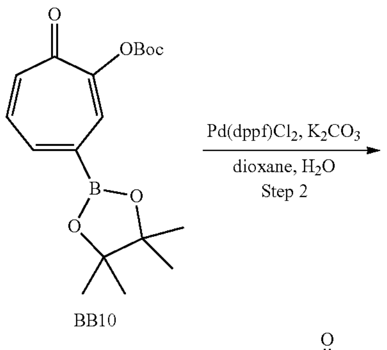

BB10

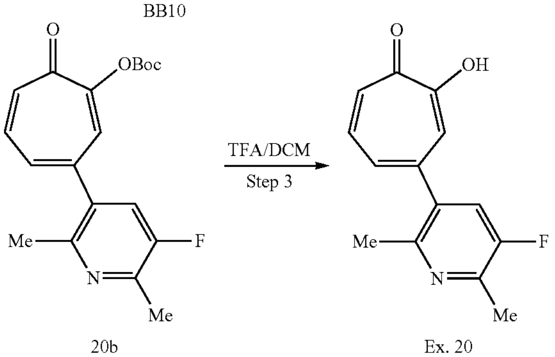

20b

Ex. 20

Step 1:

To a solution of 3,5-dibromo-2,6-dimethylpyridine (650 mg, 2.45 mmol, 1.00 eq) in THF (10 mL) was added n-BuLi (2.5 M, 1.08 mL, 1.10 eq) drop-wise at −60 °C under $N_2$ atmosphere. The mixture was stirred at −60 °C for 10 min after which NFSI (928 mg, 2.94 mmol, 1.20 eq) was added at −60 °C. The resulting yellow solution was stirred at −60 °C for 15 min. The reaction was monitored by TLC (petroleum ether:EtOAc=10:1, product Rf=0.55). The mixture was quenched with sat.$NH_4Cl$ (10 mL) at −60 °C and then extracted with EtOAc (10 mL×2). The combined organic phases were washed with brine (10 mL), dried over $Na_2SO_4$, filtered and concentrated under reduced pressure to dryness. The residue was purified by prep-TLC (petroleum ether: EtOAc=10:1) to give 20a (200 mg, 980 umol, 39.9% yield) as colorless gum.

Step 2:

To a mixture of building block BB10 (200 mg, 574 umol, 1.00 eq) and 20a (100 mg, 490 umol, 0.85 eq) in dioxane (3 mL) and water (0.05 mL) were added $K_2CO_3$ (199 mg, 1.45 mmol, 2.52 eq) and Pd(dppf)$Cl_2$·$CH_2Cl_2$ (46.9 mg, 57.4 umol, 0.10 eq) in one portion at 25 °C under $N_2$ atmosphere. The system was degassed and charged with nitrogen three times. The mixture was heated to and stirred at 120 °C for 1 hour under $N_2$. The reaction was monitored by TLC (petroleum ether:EtOAc=2:1, product Rf=0.4). After cooling to room temperature, water (10 mL) was added and the mixture extracted with EtOAc (15 mL×2). The combined organic phases were washed with brine (10 mL), dried over $Na_2SO_4$ and concentrated under reduced pressure to dryness. The residue was purified by prep-TLC (petroleum ether: EtOAc=2:1) to give 20b (100 mg, crude) as light yellow gum.

Step 3:

A mixture of 20b (100 mg) and TFA (0.2 mL) in DCM (2 mL) was stirred at 20 °C for 1 hour. The reaction was monitored by TLC (petroleum ether:EtOAc=2:1, product Rf=0.4). The reaction mixture was diluted with $CH_2Cl_2$ (10 mL) and concentrated under reduced pressure to dryness below 10 °C. The yellow residue gum was purified by prep-HPLC {column: Nano-micro Kromasil C18 (100*30 mm, Sum); mobile phase: [water (0.1% TFA)-ACN]; B %: 5%-15%, 10 min} to give Ex.20 (15.0 mg, 21.1% yield) as a yellow gum after lyophilization; $^1$H NMR: 400 MHz $CDCl_3$, δ 7.52-7.37 (m, 3H), 7.25 (d, J=1.2 Hz, 1H), 6.93 (d, J=9.6 Hz, 1H), 6.52 (br s, 2H), 2.66 (d, J=2.8 Hz, 3H), 2.54 (s, 3H); LCMS: m/z $[M+1]^+$=246.1.

Example 21: Preparation of 5-(5-fluoro-2,6-dimethylpyridin-3-yl)-2-hydroxycyclohepta-2,4,6-trien-1-one (Ex.21)

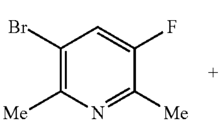

20a

-continued

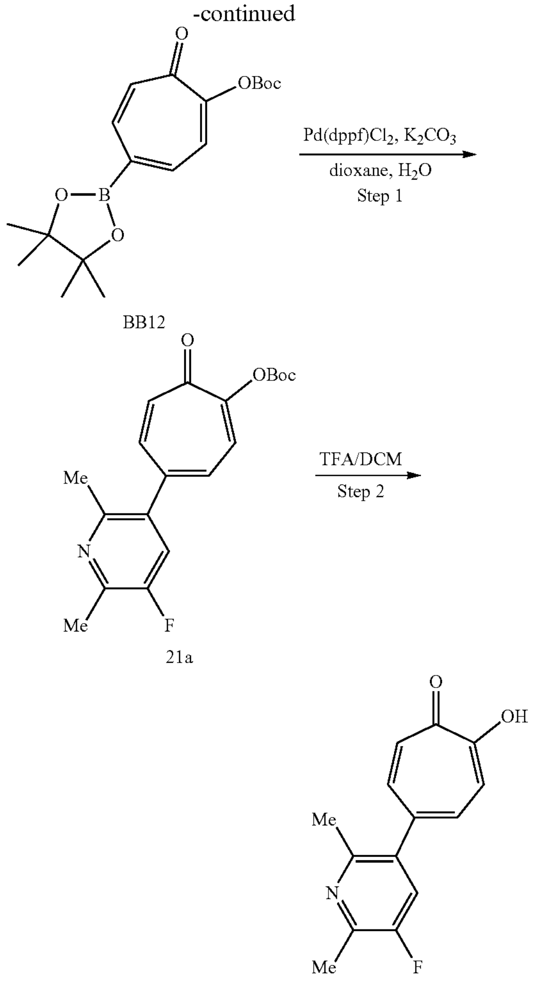

BB12

21a

Ex. 21

Step 1:

To a mixture of building block BB12 (200 mg, 574 umol, 1.00 eq) and 20a (0.10 g, 489 umol, 0.85 eq) in dioxane (3 mL) and water (0.05 mL) were added $K_2CO_3$ (199 mg, 1.45 mmol, 2.52 eq) and Pd(dppf)$Cl_2 \cdot CH_2Cl_2$ (47 mg, 57.4 umol, 0.10 eq) in one portion at 25 °C under $N_2$ atmosphere. The system was degassed and charged with nitrogen three times. The mixture was heated to 120 °C under $N_2$ for 1 hour. The reaction was monitored by TLC (petroleum ether:EtOAc=2:1, product Rf=0.4). After cooling to room temperature, water (10 mL) was added and the mixture extracted with EtOAc (15 mL×2). The combined solution was washed with brine (10 mL), dried over $Na_2SO_4$ and concentrated under reduced pressure to dryness. The residue was purified by prep-HPLC {column: Nano-micro Kromasil C18 (100*30 mm, Sum); mobile phase: [water (0.1% TFA)-ACN]; B %: 15%-40%, 10 min} to give 21a (30.0 mg, 15.1% yield) as light yellow gum.

Step 2:

A mixture of 21a (30 mg) and TFA (99.0 mg, 868 umol, 10.0 eq) in DCM (3 mL) was stirred at 20 °C for 1 hour. The reaction was monitored by TLC (petroleum ether:EtOAc=2:1, product Rf=0.4). The reaction mixture was diluted with $CH_2Cl_2$ (10 mL) and concentrated under reduced pressure to dryness below 10 °C. The mixture was re-dissolved in MeCN (2 mL) and distilled $H_2O$ (2 mL) and then lyophilized to give Ex.21 (20.0 mg, 93.8% yield, TFA salt) as yellow gum; $^1H$ NMR: 400 MHz $CDCl_3$, δ 9.63 (br s, 1H), 9.76-9.49 (m, 1H), 7.75 (d, J=8.2 Hz, 1H), 7.48-7.40 (m, 2H), 7.31 (d, J=11.6 Hz, 2H), 2.78 (d, J=2.4 Hz, 3H), 2.65 (s, 3H); LCMS: m/z $[M+1]^+$=246.1.

Example 22: Preparation of 5-(5-fluoropyridin-2-yl)-2-hydroxycyclohepta-2,4,6-trien-1-one (Ex.22)

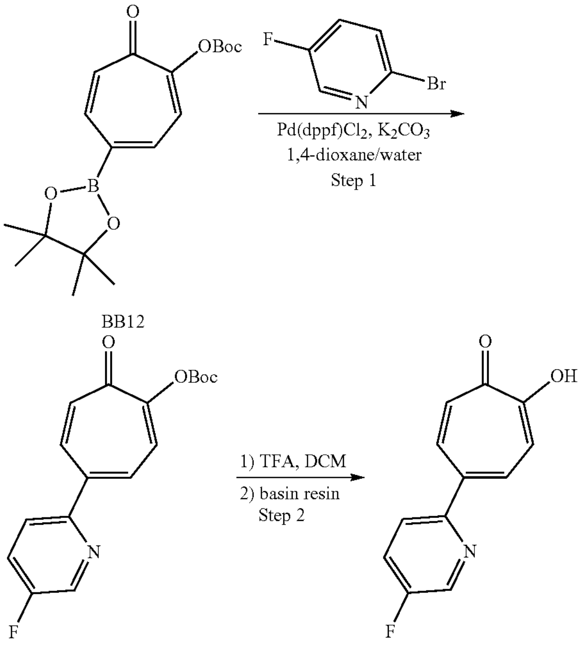

BB12

22a

Ex. 22

Step 1:

To a mixture of building block BB12 (250 mg, 718 umol, 1 eq) and 2-bromo-5-fluoro-pyridine (190 mg, 1.08 mmol, 1.5 eq) in 1,4-dioxane (5 mL) and water (1 mL) were added $K_2CO_3$ (248 mg, 1.79 mmol, 2.5 eq) and Pd(dppf)$Cl_2 \cdot CH_2Cl_2$ (60 mg, 71.8 umol, 0.1 eq) in one portion at 25 °C under $N_2$ atmosphere. The system was degassed and charged with nitrogen three times. The mixture was heated to and stirred at 110 °C for 0.5 hour under $N_2$ atmosphere. The reaction was monitored by TLC (petroleum ether:EtOAc=3:1). After cooling to room temperature, water (10 mL) was added and the mixture extracted with EtOAc (20 mL×3). The combined organic phases were dried over anhydrous $Na_2SO_4$ and filtered. The filtrate was concentrated under reduced pressure to give a residue. The residue was purified by silica gel column chromatography (Petroleum ether:EtOAc=20:1 to 3:1) to afford 22a (175 mg, 76.8% yield) as a yellow oil.

Step 2:

To a solution of 22a (35 mg, 110 umol, 1 eq) in DCM (2 mL) was added TFA (1 mL) in one portion at 20 °C under $N_2$. The mixture was stirred at 20 °C for 0.5 hour. The reaction was monitored by TLC (Petroleum ether:EtOAc=3:1). The reaction mixture was diluted with $CH_2Cl_2$ (10 mL) and concentrated under reduced pressure to dryness below 10 °C. The mixture was re-dissolved in $CH_2Cl_2$ (5 mL) and stirred with Amberlyst A21 (0.1 g) at 25 °C for another 0.5 hour. After filtering, the cake was washed with $CH_2Cl_2$ (5 mL×2) and the filtrate was concentrated under reduced pressure to provide Ex.22 (12 mg, 55 umol, 49.6% yield) as a white solid; $^1H$ NMR: 400 MHz $CDCl_3$, δ 7.45-7.46 (m, 1H) 7.47-7.49 (m, 1H) 7.49-7.55 (m, 1H) 7.69 (dd, J=8.8, 4.0 Hz, 1H) 8.04-8.09 (m, 2H) 8.56 (d, J=2.8 Hz, 1H); LCMS: m/z $[M+1]^+$=218.1.

Example 23: Preparation of sodium 4-(5-fluoro-4-methylpyridin-3-yl)-7-oxocyclohepta-1,3,5-trien-1-olate (Ex.23)

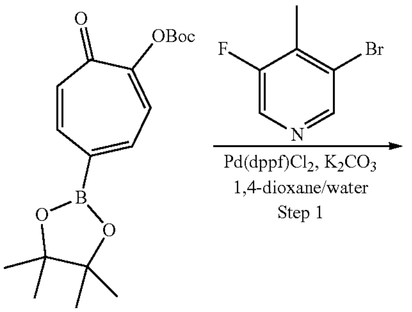

BB12

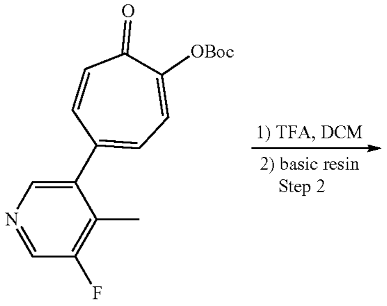

23a

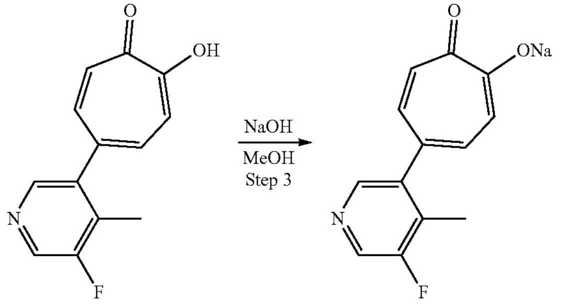

23b

Ex. 23

Step 1:

To a mixture of building block BB12 (600 mg, 1.72 mmol, 1.00 eq), 3-bromo-5-fluoro-4-methyl-pyridine (360 mg, 1.90 mmol, 1.10 eq) and $K_2CO_3$ (595 mg, 4.31 mmol, 2.50 eq) in 1,4-dioxane (5 mL) and $H_2O$ (1 mL) was added Pd(dppf)$Cl_2$·$CH_2Cl_2$ (141 mg, 172 umol, 0.10 eq) in one portion at 25 °C under $N_2$ atmosphere. The system was degassed and charged with nitrogen three times. The mixture was heated to and stirred at 120 °C for 0.5 hour. The reaction was monitored by TLC (petroleum ether:EtOAc=3:1, product Rf=0.4). After cooling to room temperature, the reaction mixture was filtered and the filtrate concentrated under vacuum to give a residue. The residue was purified by silica gel column chromatography (petroleum ether:EtOAc=20:1 to 3:1) to obtain 23a (300 mg, 52.6% yield) as a yellow solid.

Step 2:

To a solution of 23a (400 mg) in $CH_2Cl_2$ (2 mL) was added TFA (1 mL) in one portion at 0 °C. The mixture was warmed to room temperature and stirred at 20 °C for 0.5 hour. The reaction was monitored by TLC (petroleum ether: EtOAc=1:1, product Rf=0.1). The reaction mixture was diluted with $CH_2Cl_2$ (10 mL) and concentrated under reduced pressure to dryness below 10 °C. The residue was re-dissolved in $CH_2Cl_2$ (10 mL) and stirred with Amberlyst A21 (1 g) for another 0.5 hour. After filtering, the cake was washed with $CH_2Cl_2$ (5 mL×2) and the filtrate was concentrated under reduced pressure to provide crude product 23b (230 mg, 82.4% yield) as a yellow solid.

Step 3:

To a solution of 23b (230 mg, 1 mmol, 1 eq) in MeOH (3 mL) was added NaOH (5 M, 200 uL, 1 eq). The mixture was stirred at 40 °C for 0.5 hour. The reaction mixture was concentrated under reduced pressure to remove MeOH. The crude product was slurried with acetone (10 mL) at 25 °C and stirred for another 30 min. After filtering, the solid was washed with acetone (10 mL×2), collected and dried under vacuum to provide Ex.23 (205 mg, 81.0% yield) as a yellow solid; $^1H$ NMR: 400 MHz $D_2O$, δ 8.26 (s, 1H), 8.15 (s, 1H), 7.24 (d, J=12.0 Hz, 2H), 7.08 (d, J=12.0 Hz, 2H), 2.19 (d, J=2.0 Hz, 3H); LCMS: m/z $[M+1]^+$=232.1.

Example 24: Preparation of 2-(5-fluoropyridin-3-yl)-7-hydroxycyclohepta-2,4,6-trien-1-one (Ex.24)

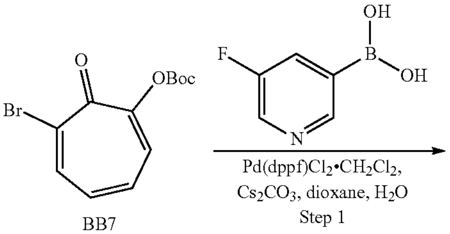

BB7

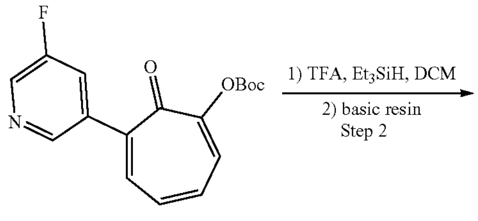

24a

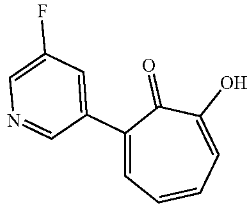

Ex. 24

Step 1:

To a mixture of building block BB7 (250 mg, 0.84 mmol, 1 eq) and (5-fluoro-3-pyridyl)boronic acid (128 mg, 910 umol, 1.1 eq) in dioxane (2.5 mL) and $H_2O$ (0.2 mL) were added $Cs_2CO_3$ (540 mg, 1.66 mmol, 2 eq) and Pd(dppf) $Cl_2$·$CH_2Cl_2$ (130 mg, 166. umol, 0.2 eq) in one portion at 25 °C under $N_2$ atmosphere. The system was degassed and charged with nitrogen three times. The mixture was heated to and stirred at 80 °C for 3 hours under $N_2$ atmosphere. The reaction was monitored by TLC (petroleum ether:EtOAc=3:1). After cooling to room temperature, the mixture was filtered through a pad of Celite, and the filter cake was washed with $CH_2Cl_2$ (30 mL×3). The filtrate was concentrated under reduced pressure to dryness. The residue was purified by silica gel column chromatography (petroleum ether:EtOAc=20:1 to 4:1) to afford 24a (60 mg, 21.9% yield) as a yellow solid.

Step 2:

To a solution of 24a (30 mg, 94.54 umol, 1 eq) in DCM (1 mL) were added TFA (0.5 mL) and $Et_3SiH$ (220 mg, 1.88 mmol, 0.3 mL, 20 eq). The mixture was stirred at 25 °C for 1 hour. The reaction was monitored by TLC (petroleum ether:EtOAc=3:1). The reaction mixture was concentrated under reduced pressure. The mixture was re-dissolved in $CH_2Cl_2$ (10 mL) and stirred with Amberlyst A21 (0.1 g) for another 0.5 hour. After filtering, the cake was washed with $CH_2Cl_2$ (5 mL×2), and the filtrate was concentrated under reduced pressure to dryness. The mixture was re-dissolved in MeCN (2 mL) and distilled $H_2O$ (2 mL) and then lyophilized to give compound Ex.24 (14 mg, 33.2% yield) as a yellow solid; $^1H$ NMR: 400 MHz $CDCl_3$, δ=8.55-8.50 (m, 2H), 7.73-7.68 (m, 1H), 7.61 (d, J=10.0 Hz, 1H), 7.47-7.43 (m, 2H), 7.18-7.11 (m, 1H); LCMS m/z $[M+1]^+$=218.1.

Example 25: Preparation of 4-(5-fluoropyridin-2-yl)-7-hydroxy-2-methylcyclohepta-2,4,6-trien-1-one (Ex.25)

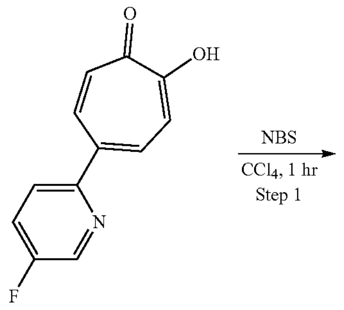

Ex. 22

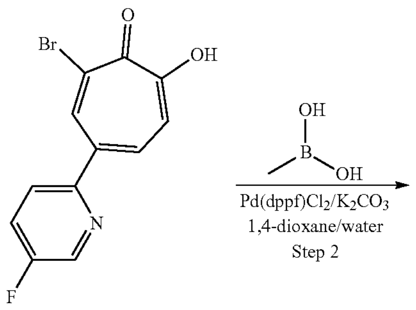

25a

-continued

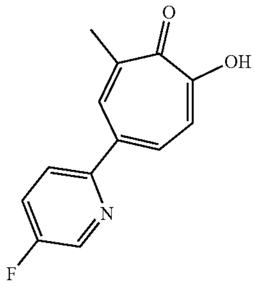

Ex. 25

Step 1:

To a solution of Ex.22 (400 mg, 1.84 mmol, 1 eq) in $CCl_4$ (5 mL) was added NBS (164 mg, 921 umol, 0.5 eq) in one portion at 25 °C. The system was degassed and charged with nitrogen three times. The mixture was heated to and stirred at 80 °C for 1 hour. The reaction was monitored by TLC (petroleum ether:EtOAc=3:1) until the majority of the starting material was consumed. After cooling to room temperature, the reaction mixture was diluted with dichloromethane (10 mL) and water (0.1 mL), and then directly concentrated under reduced pressure to give 25a (500 mg, crude) as a yellow solid.

Step 2:

To a mixture of 25a (160 mg, 404 umol, 1 eq) and methylboronic acid (242 mg, 4.04 mmol, 10 eq) in dioxane (5 mL) and $H_2O$ (1 mL) were added $K_2CO_3$ (112 mg, 808 umol, 2 eq) and Pd(dppf)$Cl_2$·$CH_2Cl_2$ (33 mg, 40.3 umol, 0.1 eq) in one portion at 25 °C under $N_2$ atmosphere. The system was degassed and charged with nitrogen three times. The mixture was heated to and stirred at 118 °C for 0.5 hour under $N_2$ atmosphere. After cooling to room temperature, water (30 mL) was added and the mixture extracted with EtOAc (20 mL×3). The combined organic phases were dried over anhydrous $Na_2SO_4$ and filtered. The filtrate was concentrated under reduced pressure to dryness. The residue was purified by prep-HPLC {column: Nano-micro Kromasil C18 (100*30 mm, Sum); mobile phase: [water (0.1% TFA)-ACN]; B %: 35%-65%, 10 min} to give Ex.25 (11 mg, 11.7% yield, TFA salt) as a yellow solid; $^1H$ NMR: 400 MHz $CD_3OD$, δ 2.53 (s, 3H) 7.45 (d, J=11.2 Hz, 1H) 7.70 (td, J=8.8, 2.8 Hz, 1H) 7.91 (dd, J=8.8, 4.8 Hz, 1H) 7.97-8.02 (m, 1H) 8.32-8.34 (m, 1H) 8.55 (d, J=2.8 Hz, 1H); LCMS: m/z $[M+1]^+$=232.1.

Example 26: Preparation of 3-(5-fluoropyridin-2-yl)-2-hydroxycyclohepta-2,4,6-trien-1-one (Ex.26)

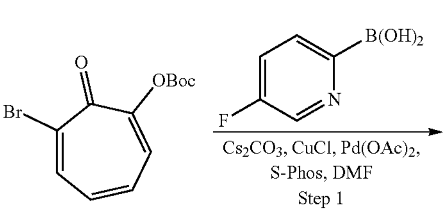

BB7

-continued

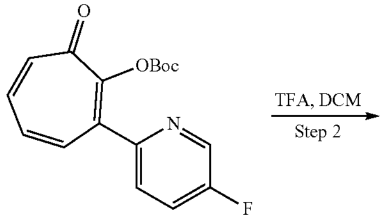

26a

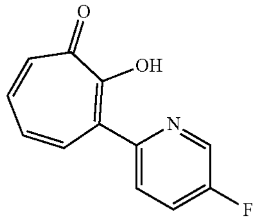

Ex. 26

Step 1:

To a solution of building block BB7 (300 mg, 996 umol, 1 eq) in DMF (5 mL) were added (5-fluoro-2-pyridyl)-boronic acid (280 mg, 1.99 mmol, 2 eq), CuCl (98 mg, 996 umol, 1 eq), $Cs_2CO_3$ (1.30 g, 3.98 mmol, 4 eq), 2-dicyclo-hexylphosphino-2',6'-dimethoxybiphenyl (S-Phos, 163 mg, 398 umol, 0.4 eq), and $Pd(OAc)_2$ (22 mg, 99 umol, 0.1 eq) in one portion at 25 °C under $N_2$ atmosphere. The system was degassed and charged with nitrogen three times. The mixture was heated to and stirred at 100 °C for 2 hours under $N_2$ atmosphere. The reaction was monitored by LCMS. After cooling to room temperature, water (10 mL) was added and the mixture extracted with EtOAc (20 mL×3). The combined organic phases were washed with water (20 mL), brine (20 mL), dried over anhydrous $Na_2SO_4$. After filtering, the filtrate was concentrated under reduced pressure to give a residue. The residue was purified by silica gel column chromatography (petroleum ether:EtOAc=20:1 to 3:1) to afford 26a (100 mg, 31.6% yield) as a yellow oil.

Step 2:

To a solution of 26a (50 mg, 157 umol, 1 eq) in dichloromethane (2 mL) was added TFA (2 mL). The mixture was stirred at 25 °C for 0.5 hour. The reaction was monitored by TLC (EtOAc:petroleum ether=1:1). The reaction mixture was diluted with $CH_2Cl_2$ (10 mL) and concentrated under reduced pressure to dryness below 10 °C. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to obtain Ex.26 (25 mg, 72.9% yield) as a brown solid; $^1H$ NMR: 400 MHz $CDCl_3$, 8.63 (s, 1H) 8.11-8.20 (m, 2H) 7.58-7.70 (m, 1H) 7.42-7.54 (m, 2H) 7.19-7.26 (m, 1H); LCMS: m/z $[M+1]^+$=218.1.

Example 27: Preparation of 7-(5-fluoropyridin-3-yl)-2-hydroxy-3-methylcyclohepta-2,4,6-trien-1-one

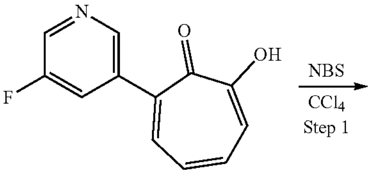

24b

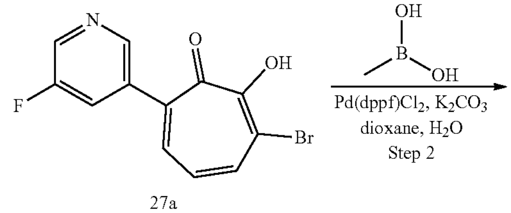

27a

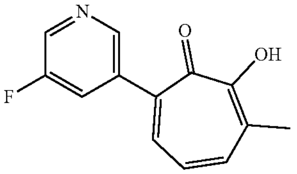

Ex. 27

Step 1:

To a solution of 24b (100 mg, 460 umol, 1 eq) in $CCl_4$ (5 mL) was added NBS (41 mg, 230 umol, 0.5 eq) in one portion at 25 °C under $N_2$ atmosphere. The system was degassed and charged with nitrogen three times. The mixture was heated to and stirred at 80 °C for 0.5 hour. The reaction was monitored by LCMS. After cooling to room temperature, water (10 mL) was added and the mixture extracted with EtOAc (10 mL×3). The combined organic layers were washed with brine (10 mL), dried over anhydrous $Na_2SO_4$, filtered and concentrated under reduced pressure to give 27a (0.4 g, crude) as a yellow solid.

Step 2:

To a mixture of 27a (200 mg, 675 umol, 1 eq) and methylboronic acid (404 mg, 6.75 mmol, 10 eq) in dioxane (5 mL) and $H_2O$ (1 mL) was added $K_2CO_3$ (187 mg, 1.35 mmol, 2 eq) and $Pd(dppf)Cl_2 \cdot CH_2Cl_2$ (55 mg, 68 umol, 0.1 eq) in one portion at 25 °C under $N_2$ atmosphere. The system was degassed and charged with nitrogen three times. The mixture was heated to and stirred at 118 °C for 0.5 hour. After cooling to room temperature, water (10 mL) was added and the mixture extracted with EtOAc (10 mL×3). The combined organic layers were dried over anhydrous $Na_2SO_4$, filtered and concentrated under reduced pressure to give a residue. The residue was purified by prep-HPLC {column: Welch Xtimate C18 (100*25 mm, 3 um); mobile phase: [water (0.1% TFA)-ACN]; B %: 20%-50%, 10.5 min} to give Ex.27 (17 mg, 10.6% yield, TFA salt) as a yellow solid; $^1H$ NMR: 400 MHz $CD_3OD$, δ 2.50 (s, 3H) 7.08-7.17 (m, 1H) 7.56-7.67 (m, 2H) 7.89-7.95 (m, 1H) 8.50-8.59 (m, 2H); LCMS: m/z $[M+1]^+$=232.1.

Example 28: Preparation of 2-(5-fluoropyridin-3-yl)-7-hydroxy-4-methylcyclohepta-2,4,6-trien-1-one (Ex.28)

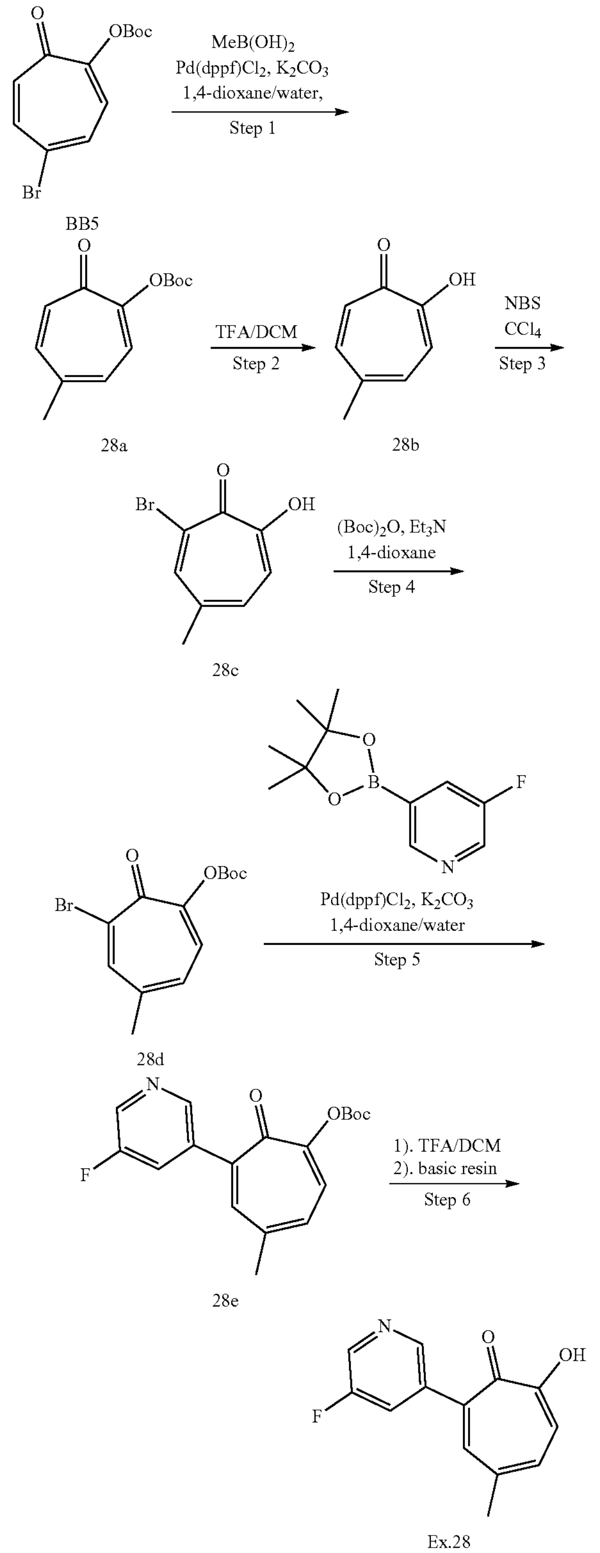

Step 1:

To a mixture of building block BB5 (500 mg, 1.66 mmol, 1 eq), methyl boronic acid (994 mg, 16.6 mmol, 10 eq) and $K_2CO_3$ (459 mg, 3.32 mmol, 2 eq) in dioxane (20 mL) and $H_2O$ (4 mL) was added Pd(dppf)$Cl_2$·$CH_2Cl_2$ (136 mg, 166 umol, 0.1 eq) in one portion at 25 °C under $N_2$. The system was degassed and recharged with nitrogen, repeated the process three times. The resulting mixture was heated and stirred at 118 °C for 30 min. TLC (Petroleum ether:Ethyl acetate=3:1) showed the starting material was consumed completely and a new spot was observed. The reaction mixture was poured into $H_2O$ (100 mL) and extracted with ethyl acetate (50 mLx3). The combined organic phases were washed with brine (50 mL), dried over anhydrous $Na_2SO_4$, filtered and concentrated under reduced pressure to a residue. The residue was purified by silica gel column chromatography eluting with Petroleum ether/Ethyl acetate (20/1 to 4/1) to give 28a (320 mg, 81.5%) as a white solid. Two parallel reactions were carried out, and a total of 800 mg of 28a was obtained.

Step 2:

To a solution of 28a (800 mg, 3.39 mmol, 1 eq) in DCM (8 mL) was added TFA (4.11 g, 36 mmol, 10.6 eq) in one portion at 0 °C. The mixture was warmed and stirred at 25 °C for 0.5 h. TLC (Petroleum ether:Ethyl acetate=3:1) indicated the starting material was consumed completely and a new spot was observed. The reaction mixture was concentrated under reduced pressure to give 28b (422 mg, 91.5%) as a yellow solid, which was used directly in the next step without further purification.

Step 3:

To a solution of 28b (422 mg, 3.10 mmol, 1 eq) in $CCl_4$ (8 mL) was added NBS (386 mg, 2.17 mmol, 0.7 eq) in one portion at 20 °C under $N_2$. The mixture was heated and stirred at 80 °C for 0.5 h. LCMS showed the desired product mass was detected but some starting material remained. After cooling, the mixture was filtered through a pad of Celite and the filter cake was washed with $CH_2Cl_2$ (20 mLx3). The filtrate was concentrated under reduced pressure to dryness. The residue was re-dissolve in $CH_2Cl_2$ (50 mL) and washed with water (10 mL), brine (10 mL), dried over anhydrous $Na_2SO_4$, filtered and concentrated under reduced pressure to give 28c (350 mg, crude) as a yellow solid, which was used directly in the next step.

Step 4:

To a mixture of crude 28c (150 mg, 697 umol, 1 eq) in dioxane (8 mL) was added TEA (282 mg, 2.79 mmol, 4 eq) and $(Boc)_2O$ (457 mg, 2.09 mmol, 480 uL, 3 eq) in one portion at 25 °C under $N_2$. The mixture was heated and stirred at 118 °C for 30 min. TLC (Petroleum ether:Ethyl acetate=3:1) showed the starting material was consumed completely and two major new spots with lower polarity was detected. The mixture was concentrated to a residue. The residue was purified by silica gel column chromatography (Petroleum ether/Ethyl acetate=20/1 to 4/1) to give 28d (95 mg, 43.2%) as a yellow oil. A total of 200 mg of 28d was obtained from 2 batches of synthesis.

Step 5:

To a mixture of 28d (200 mg, 634 umol, 1 eq), 3-fluoro-5-(4,4,5,5-tetramethyl-1,3,2-dioxaborolan-2-yl)pyridine (212 mg, 952 umol, 1.5 eq) and $K_2CO_3$ (175 mg, 1.27 mmol, 2 eq) in dioxane (10 mL) and $H_2O$ (2 mL) was added Pd(dppf)$Cl_2$·$CH_2Cl_2$ (52 mg, 63 umol, 0.1 eq) in one portion under $N_2$. The system was degassed and recharged with nitrogen, repeated the process three times. The mixture was heated and stirred at 118 °C for 30 min. LCMS showed desired product mass was observed and the starting material was consumed. The reaction mixture was poured into $H_2O$ (20 mL) and extracted with ethyl acetate (10 mL×3). The combined organic phases were washed with brine (15 mL), dried over anhydrous $Na_2SO_2$, filtered and concentrated under reduced pressure to give a residue. The residue was purified by silica gel column chromatography eluting with Petroleum ether/Ethyl acetate (20/1 to 3/1) to provide 28d (95 mg, 45.2%) as a white solid.

Step 6:

To a solution of 28d (95 mg) in DCM (5 mL) was added TFA (1 mL) in one portion at 0 °C under $N_2$. The mixture was warmed and stirred at 25 °C for 30 min. TLC (Petroleum ether:Ethyl acetate=3:1) showed the starting material was consumed completely and a new spot with larger polar was observed. The reaction mixture was diluted with $CH_2Cl_2$ (10 mL) and concentrated under reduced pressure to dryness at a temperature below 10 °C. The mixture was redissolved in MeCN (2 mL) and distilled $H_2O$ (2 mL) and then lyophilized to afford the titled product Ex.28 (62 mg, 93.5%, a TFA salt) as a yellow solid; $^1H$ NMR: 400 MHz DMSO-$d_6$, δ 8.52-8.62 (m, 2H), 7.87-7.95 (m, 1H), 7.60 (d, J=1.2 Hz, 1H), 7.30-7.39 (m, 1H), 7.21-7.29 (m, 1H), 2.41 (s, 3H); LC-MS: m/z $[M+H]^+$=232.1.

Example 29: Preparation of 2-hydroxy-4-(pyrimidin-5-yl)cyclohepta-2,4,6-trien-1-one (Ex.29)

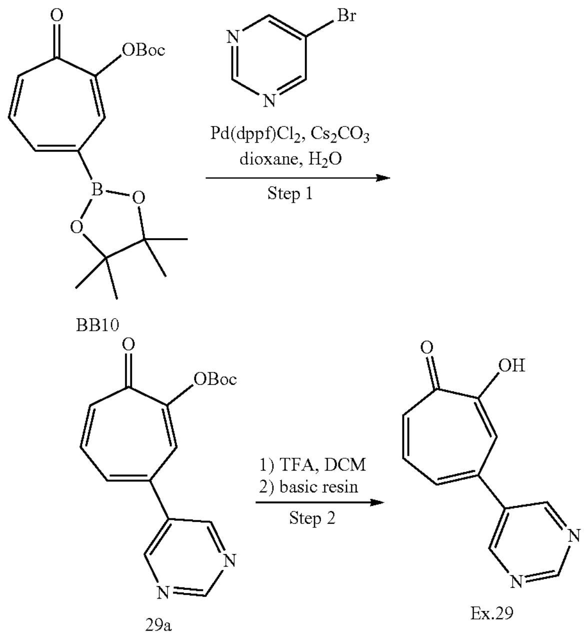

BB10 29a Ex.29

Step 1:

To a stirred mixture of building block BB10 (200 mg, 575 umol, 1.00 eq), 5-bromopyrimidine (109 mg, 689 umol, 1.20 eq) and $Cs_2CO_3$ (374 mg, 1.15 mmol, 2.00 eq) in dioxane (2 mL) and $H_2O$ (0.5 mL) was added Pd(dppf)$Cl_2$·$CH_2Cl_2$ complex (93.8 mg, 114 umol, 0.20 eq) under $N_2$ atmosphere. The system was degassed and recharged with nitrogen, repeated the process three times. The resulting mixture was then heated and stirred at 120 °C for 20 min. TLC {petroleum ether:EtOAc=10:1, Rf (product)=0.50)} indicated starting material BB10 was consumed completely and a new product spot was observed. After cooling, the mixture was filtered through a pad of Celite and the filtration cake was washed with $CH_2Cl_2$ (30 mL×3). The combined filtrates were concentrated under reduced pressure to dryness. The residue was purified by prep-TLC (EtOAc/MeOH=10/1) to afford 29a (70 mg, 38.1%) as a yellow oil.

Step 2:

To a solution of 29a (70 mg) in DCM (1 mL) was added TFA (0.2 mL) in one portion at 20 °C. The mixture was stirred at 20 °C for 1 h. LCMS indicated 29a was consumed completely. The reaction mixture was diluted with $CH_2Cl_2$ (10 mL) and concentrated under reduced pressure to dryness at a temperature below 10 °C. The residue was re-dissolved in $CH_2Cl_2$ (5 mL), treated with Amberlyst A21 (0.1 g), and stirred at 25 °C for another 0.5 hr. After filtering, the solid cake was washed with $CH_2Cl_2$ (5 mL×2) and the combined filtrate and washings were concentrated under reduced pressure to provide the titled product Ex.29 (16 mg, 34.3%) as a yellow solid; $^1H$ NMR: 400 MHz DMSO-d6, δ 9.26 (s, 1H), 9.10 (s, 2H), 7.56-7.47 (m, 2H), 7.32-7.24 (m, 2H); LC-MS: m/z $[M+H]^+$=201.0.

Example 30: Preparation of 2-hydroxy-4-(2-methoxypyrimidin-5-yl)cyclohepta-2,4,6-trien-1-one (Ex.30)

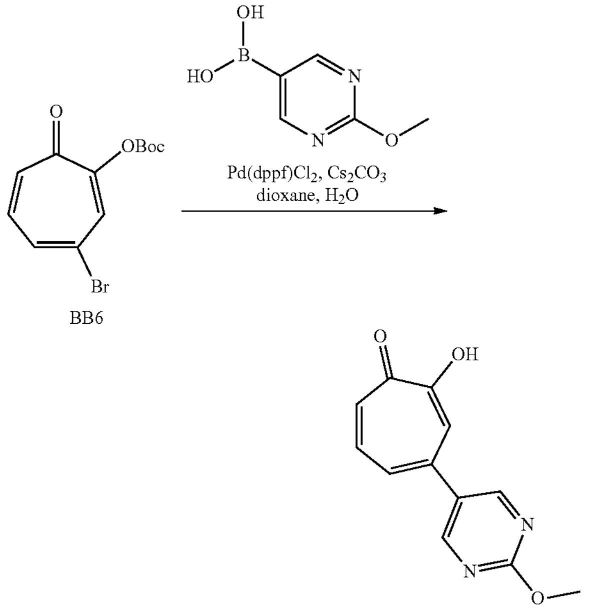

BB6 Ex.30

To a stirred mixture of building block BB6 (300 mg, 996 umol, 1.00 eq), (2-methoxypyrimidin-5-yl)boronic acid (230 mg, 1.49 mmol, 1.50 eq) and $Cs_2CO_3$ (649 mg, 1.99 mmol, 2.00 eq) in 1,4-dioxane (2.5 mL) and $H_2O$ (0.5 mL) was added Pd(dppf)$Cl_2$·$CH_2Cl_2$ complex (163 mg, 199 umol, 0.20 eq) in one portion at 25 °C under $N_2$ atmosphere. The system was degassed and recharged with nitrogen, the process was repeated three times. The resulting mixture was heated and stirred at 120 °C for 0.5 hr. LC-MS showed BB6 was consumed completely and a desired product mass was detected. The Boc protecting group was cleaved during the Suzuki coupling reaction under the current condition. After cooling, the mixture was filtered through a pad of Celite and the filter cake was washed with $CH_2Cl_2$ (30 mL×3). The combined filtrate and washings were concentrated under reduced pressure to dryness. The residue was purified by prep-HPLC (neutral condition) to afford the titled product Ex.30 (20 mg, 8.71%) as a yellow solid; $^1$H NMR: 400 MHz $CD_3OD$, δ 8.85 (s, 2H), 7.64-7.52 (m, 2H), 7.38-7.26 (m, 2H), 4.08 (s, 3H); LC-MS: m/z $[M+H]^+$=231.0.

Example 31: Preparation of 2-hydroxy-4-(2-methylpyrimidin-5-yl)cyclohepta-2,4,6-trien-1-one (Ex.31)

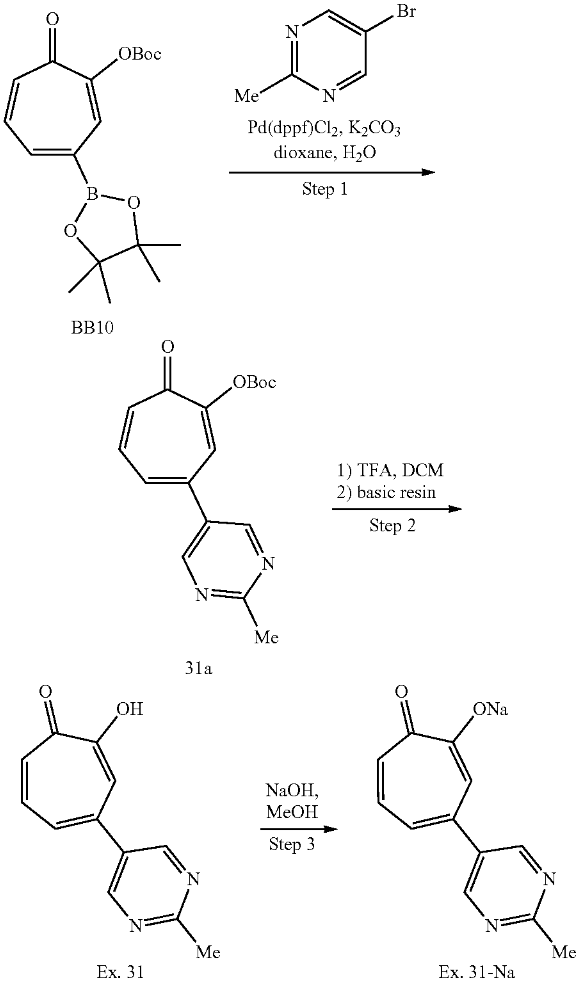

BB10

31a

Ex. 31

Ex. 31-Na

Step 1:

To a stirred mixture of building block BB10 (0.50 g, 1.44 mmol, 1.00 eq), 5-bromo-2-methyl-pyrimidine (273 mg, 1.58 mmol, 1.10 eq) and $K_2CO_3$ (496 mg, 3.59 mmol, 2.50 eq) in 1,4-dioxane (5 mL) and $H_2O$ (1 mL) was added Pd(dppf)$Cl_2$·$CH_2Cl_2$ (117 mg, 143 umol, 0.10 eq) under $N_2$ atmosphere. The system was degassed and then recharged with nitrogen, repeated the process three times. The resulting mixture was heated and stirred at 120 °C for 0.5 hour under $N_2$ atmosphere. Reaction progress was monitored by TLC which showed BB10 was consumed completely and one new spot was formed. After cooling, the mixture was filtered through a pad of Celite and the filter cake was washed with $CH_2Cl_2$ (10 mL×3). The filtrate was concentrated under a reduced pressure to dryness. The residue was purified by silica gel column chromatography eluting with Petroleum ether/Ethyl acetate (from 100/1 to 0/1) to provide 31a (300 mg, 66.4%) as a yellow solid.

Step 2:

To a solution of 31a (350 mg) in dichloromethane (2 mL) was added TFA (1 mL). The mixture was stirred at 20 °C for 0.5 hr. TLC analysis of the reaction mixture indicated 31a was consumed completely and one new spot was formed. The reaction mixture was diluted with $CH_2Cl_2$ (10 mL) and concentrated under reduced pressure to dryness at a temperature below 10 °C. The residue was re-dissolved in $CH_2Cl_2$ (10 mL), treated with Amberlyst A21 (0.1 g), and stirred for another 0.5 hr. After filtering, the solid cake was washed with $CH_2Cl_2$ (5 mL×2), and the filtrate was concentrated under reduced pressure to provide the titled product Ex.31 (220 mg, 92.2%) as a yellow solid.

Step 3:

To a solution of Ex.31 (220 mg, 1.03 mmol, 1.00 eq) in MeOH (2 mL) was added 5 M NaOH (206 uL, 1.00 eq) at 25 °C. The mixture was warmed and stirred at 40 °C for 0.5 hr. The reaction mixture was concentrated under reduced pressure to remove MeOH. The crude product was triturated with acetone at 25 °C and stirred for another 30 min. After filtering, the solid cake was washed with acetone (5 mL×2), the solids were collected and dried in vacuum to provide the sodium salt of the titled product Ex.31-Na (230 mg, 95%) as a yellow solid; $^1$H NMR: 400 MHz $D_2O$, δ 8.85 (s, 2H), 7.42-7.34 (m, 1H), 7.16 (s, 1H), 7.07 (d, J=11.2 Hz, 1H), 6.89 (br d, J=10.0 Hz, 1H), 2.70 (s, 3H); LC-MS: m/z $[M+H]^+$=215.

Example 32: Preparation of 4-(2,4-dimethylpyrimidin-5-yl)-2-hydroxycyclohepta-2,4,6-trien-1-one (Ex.32)

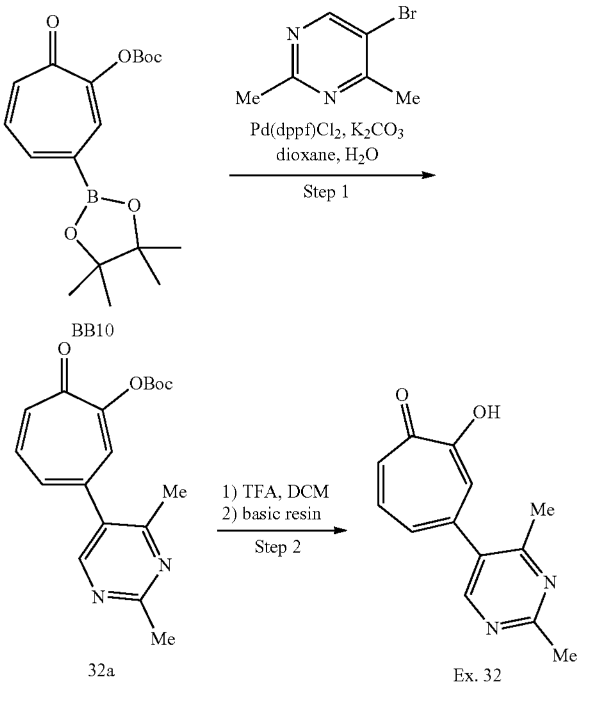

BB10

32a

Ex. 32

Step 1:

To a stirred mixture of building block BB10 (0.20 g, 574 umol, 1.00 eq), 5-bromo-2,4-dimethyl-pyrimidine (107 mg, 574 umol, 1.00 eq), $K_2CO_3$ (158 mg, 1.15 mmol, 2.00 eq) in dioxane (4 mL) and water (1 mL) was added Pd(dppf)$Cl_2$ (10 mg, 14.1 umol, 0.2 eq) under $N_2$ atmosphere. The system was degassed and recharged with nitrogen, the process was repeated three times. The resulting mixture was heated and stirred at 100 °C for 5 hrs. Reaction progress was monitored by LCMS, a major peak with desired mass was observed. After cooling, water (10 mL) was added and the aqueous mixture was extracted with EtOAc (20 mL×2). The combined organic extracts were washed with brine (10 mL), dried over $Na_2SO_4$, filtered and concentrated under reduced pressure to dryness to give a yellow gum. This crude product was purified by silica gel column chromatography eluting with Petroleum ether:Ethyl acetate (1:1) to provide 32a (60 mg, 31.8%) as a yellow gum.

Step 2:

To a solution of 32a (60 mg, 182 umol, 1.00 eq) in DCM (4 mL) was added TFA (1 mL) in one portion at 0 °C. The mixture was warmed and stirred at 25 °C for 1 hr. TLC (petroleum ether:EtOAc=3:1) showed 32a was consumed completely. The reaction mixture was diluted with $CH_2Cl_2$ (10 mL) and concentrated under reduced pressure at a temperature below 10 °C to dryness. The residue was re-dissolved in $CH_2Cl_2$ (10 mL), and treated with Amberlyst A21 (0.1 g), and stirred for another 0.5 hr. After filtering, the solid cake was washed with $CH_2Cl_2$ (5 mL×2), and the combined filtrate and washings were concentrated under reduced pressure to afford the titled product Ex.32 (35 mg, 83.9%) as a yellow solid; $^1$H NMR: 400 MHz $CD_3OD$, δ 8.25-7.92 (m, 1H), 7.81-7.55 (m, 2H), 7.50 (br s, 1H), 7.30 (br d, J=9.2 Hz, 1H), 1.60-1.48 (m, 9H); LC-MS: m/z $[M+H]^+$=229.1.

Example 33: Preparation of 2-hydroxy-5-(2-methylpyrimidin-5-yl)cyclohepta-2,4,6-trien-1-one (Ex.33)

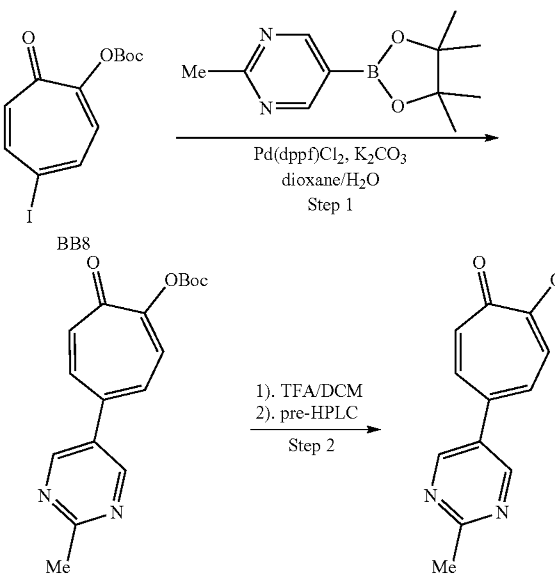

BB8 33a Ex. 33

Step 1:

To a mixture of building block BB8 (300 mg, 862 umol, 1.00 eq), 2-methyl-5-(4,4,5,5-tetramethyl-1,3,2-dioxaborolan-2-yl)pyrimidine (284 mg, 1.29 mmol, 1.50 eq) and $K_2CO_3$ (238 mg, 1.72 mmol, 2.00 eq) in dioxane (10 mL) and $H_2O$ (2 mL) was added Pd(dppf)$Cl_2$·$CH_2Cl_2$ (70.0 mg, 86.1 umol, 0.1 eq) under $N_2$ atmosphere. The system was degassed and then recharged with nitrogen, repeated three times. The resulting mixture was heated and stirred at 118 °C for 30 min. LC-MS showed the starting material BB8 was consumed completely. After cooling, the reaction mixture was poured into $H_2O$ (50 mL), and the aqueous mixture was extracted with ethyl acetate (15 mL×3). The combined organic extracts were dried over anhydrous $Na_2SO_4$, filtered and concentrated under reduced pressure to dryness. The residue was purified by silica gel column chromatography eluting with Petroleum ether/Ethyl acetate (100/1 to 3/1) to give intermediate 33a (140 mg, crude) as a yellow solid.

Step 2:

To a solution of crude 33a (100 mg) in DCM (4 mL) was added TFA (1 mL) in one portion at 25 °C. The mixture was stirred at 25 °C for 30 min. TLC {Petroleum ether/Ethyl acetate=1/1, Rf (33a)=0.4, Rf (product)=0} showed the starting material was consumed completely. The reaction mixture was diluted with $CH_2Cl_2$ (5 mL) and concentrated under reduced pressure to dryness at a temperature below 10 °C. The residue was purified by prep-HPLC (column: Nano-micro Kromasil C18 100*30 mm 5 um; mobile phase: [water (0.1% TFA)-ACN]; B %: 50%-65%, 10 min) to give the titled product Ex.33 (13.0 mg, 19.1%) as a yellow solid; $^1$H NMR: 400 MHz $CD_3OD$, δ 8.92 (s, 2H), 7.75 (d, J=12.0 Hz, 2H), 7.43 (d, J=12.0 Hz, 2H), 2.74 (s, 3H); LC-MS: m/z $[M+H]^+$=215.1.

Example 34: Preparation of 2-hydroxy-3-(2-methylpyrimidin-5-yl)cyclohepta-2,4,6-trien-1-one (Ex.34)

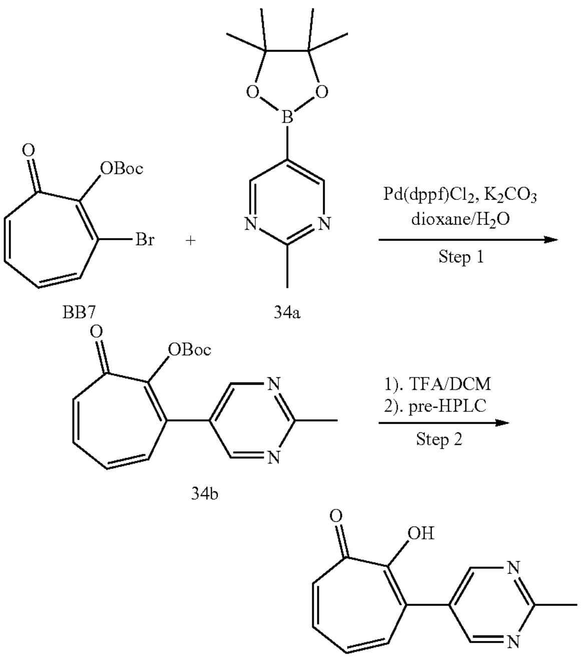

BB7 34a 34b Ex. 34

Step 1:

To a mixture of building block BB7 (250 mg, 664 umol, 1 eq), boronic pinacol ester 34a (219 mg, 996 umol, 1.5 eq) and $K_2CO_3$ (229 mg, 1.66 mmol, 2.5 eq) in dioxane (5 mL)

and $H_2O$ (1 mL) was added Pd(dppf)$Cl_2$ (49 mg, 66 umol, 0.1 eq) in one portion at 20 °C under a $N_2$ atmosphere. The system was degassed and recharged with nitrogen, repeated two more times. The resulting mixture was heated and stirred at 110 °C for 30 min. LCMS showed the starting material was consumed and the desired product mass was detected. After cooling, water (10 mL) was added and the aqueous mixture was extracted with EtOAc (10 mL×3). The combined organic extracts were washed with brine (10 mL), dried over $Na_2SO_4$, filtered and concentrated under reduced pressure to dryness. The residue was purified by prep-TLC ($SiO_2$, Ethyl acetate, Rf=0.5) to give 34b (80 mg, 38.3% yield) as a yellow oil.

Step 2:

To a solution of 34b (80 mg, 254 umol, 1 eq) in $CH_2Cl_2$ (5 mL) was added TFA (3.08 g, 27.01 mmol, 2 mL, 106 eq). The mixture was stirred at 20 °C for 0.5 hr. LCMS showed the starting material was consumed completely and the desired product mass was detected. The reaction mixture was diluted with $CH_2Cl_2$ (10 mL) and concentrated under reduced pressure to dryness at a temperature below 10 °C. The residue was re-dissolved in $CH_2Cl_2$ (5 mL), treated with Amberlyst A21 (0.1 g), and then stirred at 25 °C for another 0.5 hr. After filtering, the solid cake was washed with $CH_2Cl_2$ (5 mL×2) and the combined filtrates were concentrated under reduced pressure to afford the titled product Ex.34 (22 mg, 40.4%) as a yellow solid; $^1H$ NMR: 400 MHz $CD_3OD$, δ 8.86 (s, 2H), 7.78-7.72 (m, 1H), 7.55-7.47 (m, 1H), 7.45-7.39 (m, 1H), 7.24-7.17 (m, 1H), 2.76-2.74 (m, 3H); LC-MS: m/z $[M+H]^+$=215.0.

Example 35: Preparation of 5-(2,4-dimethylpyrimidin-5-yl)-2-hydroxycyclohepta-2,4,6-trien-1-one (Ex.35)

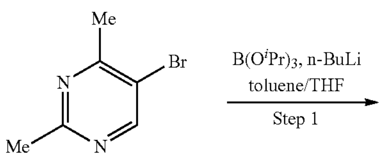

35a

35b

+

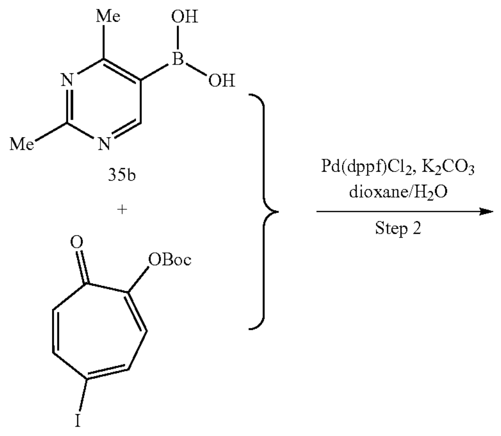

BB8

-continued

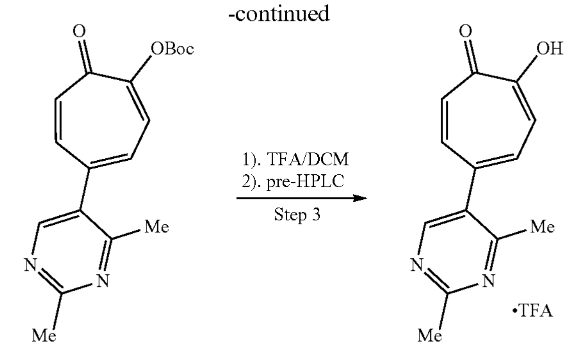

35c

Ex. 35

Step 1:

To a mixture of 35a (100 mg, 535 umol, 1.00 eq) and tri-isopropyl borate (131 mg, 695 umol, 1.30 eq) in toluene (4 mL) and THE (1 mL) was added n-BuLi (2.5 M, 278 uL, 1.3 eq) dropwise at −78 °C under a $N_2$ atmosphere. The mixture was stirred at −78 °C for 30 min and then warmed to −20 °C and stirred for another 0.5 hour. TLC (Petroleum ether/Ethyl acetate=3/1) indicated the 35a was consumed completely and a new product spot was formed. The reaction mixture was quenched with 1 N HCl aqueous solution (1 mL) carefully at −20 °C and then warmed to 0 °C. The mixture was basified to pH 7 using solid $NaHCO_3$ at 0 °C and the resulting mixture was concentrated under reduced pressure to dryness. The residue was re-dissolved in dichloromethane/MeOH (10:1, 10 mL) and stirred for 10 min. After filtering, the filtrate was concentrated under reduced pressure to give the boronic acid 35b (180 mg, crude) as a white solid.

Step 2:

To a mixture of BB8 (150 mg, 431 umol, 1.00 eq) and boronic acid 35b (98 mg, 646 umol, 1.5 eq) in dioxane (5 mL) and $H_2O$ (1 mL) was added $K_2CO_3$ (119 mg, 862 umol, 2.00 eq) and Pd(dppf)$Cl_2$·$CH_2Cl_2$ (35.0 mg, 43 umol, 0.10 eq) in one portion at 20 °C under a $N_2$ atmosphere. The system was degassed and then recharged with nitrogen, repeated three times. The resulting mixture was heated and stirred at 120 °C for 0.5 hours. TLC (EtOAc) indicated the starting material BB8 was consumed completely and one major new spot with larger polarity was formed. After cooling, the reaction mixture was quenched by water (10 mL) and then extracted with EtOAc (20 mL×3). The combined organic extracts were washed with brine (10 mL×3), dried over $Na_2SO_4$, filtered and concentrated under reduced pressure to dryness. The residue was purified by prep-TLC (EtOAc, Rf=0.4) to provide 35c (45 mg, 31.8%) as a yellow solid.

Step 3:

To a mixture of 35c (45 mg) in $CH_2Cl_2$ (4 mL) was added TFA (0.25 mL) in one portion at 0 °C. The mixture was warmed and stirred at 25 °C for 0.5 hour. TLC (EtOAc) indicated the starting material was consumed completely. The reaction mixture was diluted with $CH_2Cl_2$ (10 mL) and concentrated under reduced pressure to dryness at a temperature below 10 °C. Then the mixture was re-dissolved in MeCN (2 mL) and distilled $H_2O$ (2 mL), and lyophilized to afford the titled compound Ex.35 (43.0 mg, 91.6%, TFA salt) as a yellow solid; $^1H$ NMR: 400 MHz $CD_3OD$, δ 8.61 (s, 1H), 7.49 (d, J=11.6 Hz, 2H), 7.39 (d, J=12.0 Hz, 2H), 2.75 (s, 3H), 2.52 (s, 3H); LC-MS: m/z $[M+H]^+$=229.0.

Example 36: Preparation of 3-(2,4-dimethylpyrimidin-5-yl)-2-hydroxycyclohepta-2,4,6-trien-1-one (Ex.36)

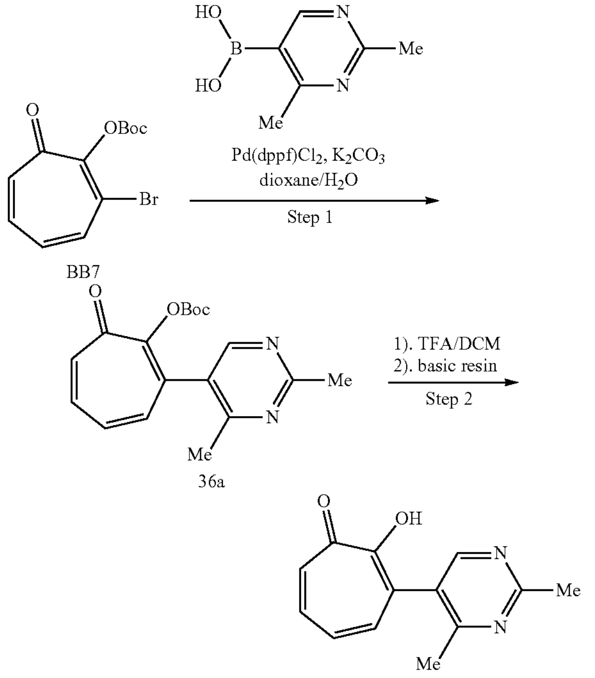

BB7 36a Ex. 36

Step 1:

To a mixture of building block BB7 (150 mg, 498 umol, 1.00 eq) and (2,4-dimethylpyrimidin-5-yl)boronic acid (133 mg, 747 umol, 1.50 eq) in dioxane (5 mL) and $H_2O$ (1 mL) was added $K_2CO_3$ (206 mg, 1.49 mmol, 3.00 eq) and $Pd(dppf)Cl_2$ (36.0 mg, 49.8 umol, 0.10 eq) at 25 °C under a $N_2$ atmosphere. The system was degassed and recharged with nitrogen, repeated the process three times. The resulting mixture was heated and stirred at 110 °C for 0.5 hr. Reaction progress was monitored by LCMS which showed the starting material BB7 was nearly consumed completely and a major peak with desired mass was observed. After cooling, water (10 mL) was added and the aqueous mixture was extracted with ethyl acetate (10 mL×3). The combined organic extracts were washed with brine (30 mL), dried over anhydrous $Na_2SO_4$. After filtering, the filtrate was concentrated under reduced pressure to dryness. The residue was purified by prep-TLC to afford 36a (80.0 mg, 46.9%) as yellow solid.

Step 2:

To a solution of 36a (80.0 mg) in dichloromethane (3 mL) was added TFA (3 mL) 25 °C. The mixture was stirred at 25 °C for 0.5 hr. LCMS showed the starting material was consumed almost completely and a major peak with desired mass was observed. The reaction mixture was diluted with $CH_2Cl_2$ (2 mL) and concentrated under reduced pressure to dryness at a temperature below 10 °C. The residue was re-dissolved in $CH_2Cl_2$ (5 mL), treated with Amberlyst A21 (1 g), and stirred for another 0.5 hr. After filtering, the solid cake was washed with $CH_2Cl_2$ (10 mL×2) and the combined filtrates were concentrated under reduced pressure to dryness. The residue was triturated with n-hexane (5 mL×2) to give the titled product Ex.36 (11.0 mg, 19.5%, 99.8% purity) as a yellow solid; $^1H$ NMR: 400 MHz DMSO-$d_6$, δ 8.42 (s, 1H), 7.50-7.57 (m, 2H), 7.36 (d, J=10.4 Hz, 1H), 7.13 (t, J=9.6 Hz, 1H), 2.62 (s, 3H), 2.21 (s, 3H); LC-MS: m/z $[M+H]^+$=229.1.

Example 37: Preparation of 2-cyclopropyl-5-(4,4,5,5-tetramethyl-1,3,2-dioxaborolan-2-yl)pyrimidine (Ex.37)

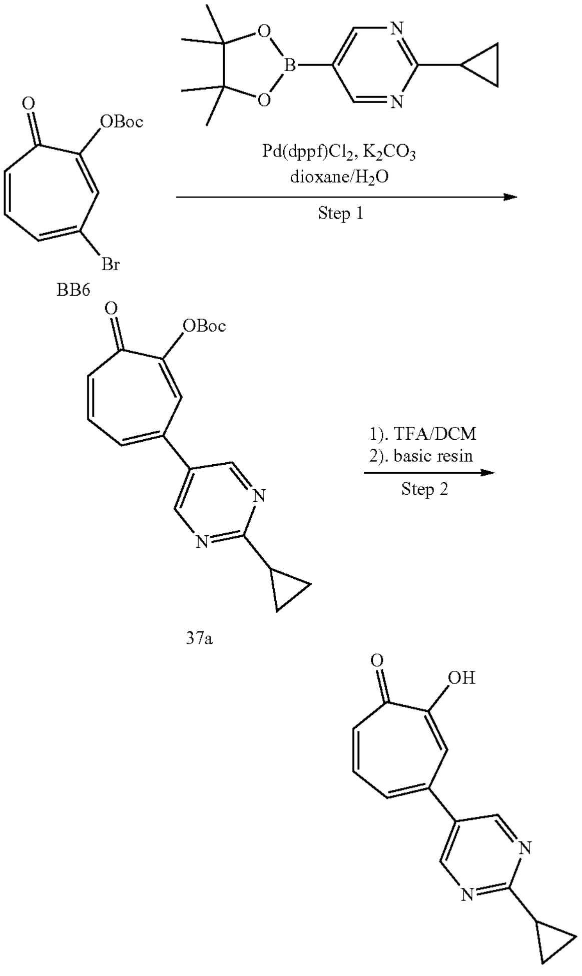

BB6 37a Ex. 37

Step 1:

To a mixture of build block BB6 (300 mg, 996 umol, 1.00 eq) and 2-cyclopropyl-5-(4,4,5,5-tetramethyl-1,3,2-dioxaborolan-2-yl)pyrimidine (367 mg, 1.49 mmol, 1.50 eq) in dioxane (10 mL) and $H_2O$ (2 mL) was added $K_2CO_3$ (413 mg, 2.99 mmol, 3.00 eq) and $Pd(dppf)Cl_2$ (72.0 mg, 99.6 umol, 0.10 eq) in one portion at 25 °C under a $N_2$ atmosphere. The system was degassed and recharged with nitrogen, repeated three times. The resulting mixture was heated and stirred at 100 °C for 0.5 hr under a $N_2$ atmosphere. LCMS showed the starting material was consumed completely and the desired product mass was observed. After cooling, water (10 mL) was added and the aqueous mixture was extracted with ethyl acetate (10 mL×3). The combined organic phases were washed with brine (30 mL), dried over anhydrous $Na_2SO_4$. After filtering, the filtrate was concentrated under reduced pressure to dryness. The residue was purified by prep-TLC (Petroleum ether/Ethyl acetate=4/1) to give 37a (40 mg, 11.8%) as a yellow solid.

Step 2:

To a solution of 37a (40 mg) in DCM (5 mL) was added TFA (1 mL) in one portion at 25 °C. The mixture was stirred at 25 °C for 30 min. LCMS showed the starting material was consumed completely. The reaction mixture was diluted with $CH_2Cl_2$ (10 mL) and concentrated under reduced pressure to dryness at a temperature below 10 °C. The residue was re-dissolved in $CH_2Cl_2$ (10 mL), treated with Amberlyst A21 (0.1 g), and stirred for another 0.5 hr. After filtering, the solids were washed with $CH_2Cl_2$ (5 mL×2) and the filtrate was concentrated under reduced pressure to afford the titled product Ex.37 (12.0 mg, 42.6%) as a yellow solid; $^1$H NMR: 400 MHz $CD_3OD$, δ 8.86 (s, 2H), 7.67-7.56 (m, 1H), 7.54 (d, J=1.6 Hz, 1H), 7.40-7.22 (m, 2H), 2.39-2.23 (m, 1H), 1.24-1.10 (m, 4H); LC-MS: m/z $[M+H]^+$=241.1.

Example 38: Preparation of 2-hydroxy-5-(2-methoxypyrimidin-4-yl)cyclohepta-2,4,6-trien-1-one (Ex.38)

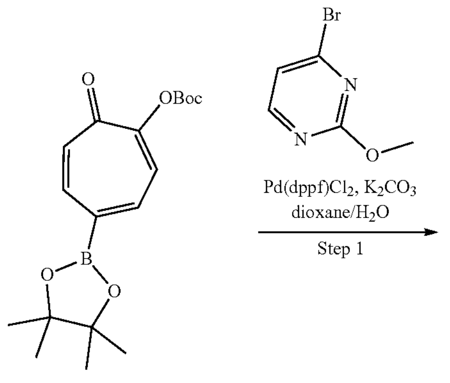

BB12

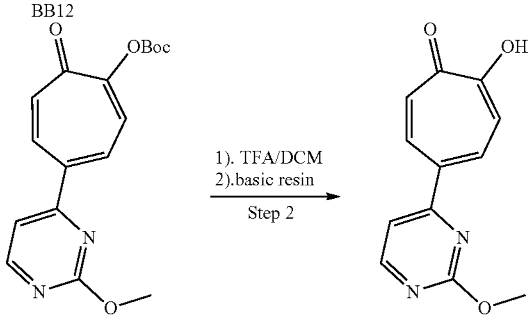

38a

Ex. 38

Step 1:

To a mixture of building block BB12 (100 mg, 287 umol, 1.00 eq) and 4-bromo-2-methoxypyrimidine (54.0 mg, 287 umol, 1.00 eq) in dioxane (5 mL) and $H_2O$ (1 mL) was added $K_2CO_3$ (79.0 mg, 575 umol, 2.00 eq) and Pd(dppf) $Cl_2{\cdot}CH_2Cl_2$ (23.0 mg, 29.0 umol, 0.10 eq) in one portion at 20 °C under a $N_2$ atmosphere. The system was degassed and recharged with nitrogen, repeated the process three times. The resulting mixture was heated and stirred at 120 °C for 0.5 hours. TLC (Petroleum ether/Ethyl acetate=1/1) showed the starting material was consumed completely and one major new spot with larger polarity was detected. After cooling, the reaction mixture was quenched by addition of water (50 mL) at 20 °C. The aqueous mixture was extracted with EtOAc (20 mL×3). The combined organic extracts were washed with brine (10 mL×2), dried over $Na_2SO_4$, filtered and concentrated under reduced pressure to dryness. The residue was purified by silica gel column chromatography eluting with Petroleum ether/Ethyl acetate (20/1 to 3/1) to give 38a (50.0 mg, 52.7%) as a yellow solid.

Step 2:

To a solution of 38a (50.0 mg, 151 umol, 1.00 eq) in $CH_2Cl_2$ (3 mL) was added TFA (0.5 mL) in one portion at 0 °C under $N_2$. The mixture was warmed and stirred at 25 °C for 1 h. TLC ($CH_2Cl_2$/MeOH=10/1) indicated the starting material was consumed completely and one major new spot with larger polarity was formed. The reaction mixture was diluted with $CH_2Cl_2$ (10 mL) and concentrated under reduced pressure to dryness at a temperature below 10 °C. The residue was re-dissolved in MeCN (2 mL) and distilled $H_2O$ (2 mL) and then lyophilized to afford the titled product Ex.38 (38.0 mg, 72.9%, a TFA salt) as a yellow solid; $^1$H NMR: 400 MHz $CD_3OD$, δ 8.62 (d, J=5.2 Hz, 1H), 8.35 (d, J=12.4 Hz, 2H), 7.61 (d, J=5.2 Hz, 1H), 7.45 (d, J=12.0 Hz, 2H), 4.11 (s, 3H); LC-MS: m/z $[M+H]^+$=231.1.

Example 39: Preparation of 2-hydroxy-4-(2-methoxypyrimidin-4-yl)cyclohepta-2,4,6-trien-1-one (Ex.39)

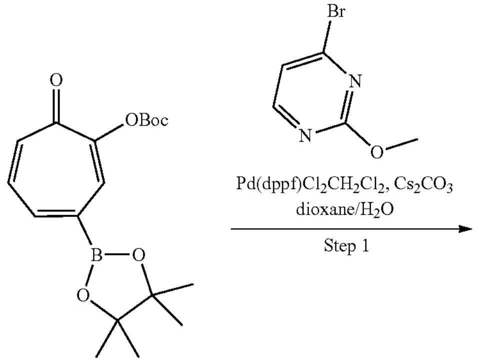

BB10

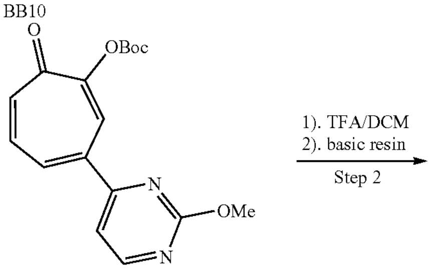

39a

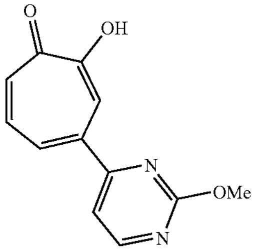

Ex. 39

Step 1:

To a mixture of building block BB10 (200 mg, 574 umol, 1.00 eq) and 4-bromo-2-methoxypyrimidine (130 mg, 689 umol, 1.20 eq) in dioxane/$H_2O$=(17/1, 2 mL) was added $Cs_2CO_3$ (374 mg, 1.15 mmol, 2.00 eq) and Pd(dppf)$Cl_2 \cdot CH_2Cl_2$ (94 mg, 114 umol, 0.20 eq) in one portion at 25 °C under a $N_2$ atmosphere. The system was degassed and refilled with $N_2$ for 3 times. The resulting mixture was stirred at 120 °C for 20 min under $N_2$ atmosphere. TLC {EtOAc, Rf (product)=0.5} indicated starting material BB10 was consumed completely. After cooling, the mixture was filtered through a pad of Celite and the filter cake was washed with $CH_2Cl_2$ (10 mL×3). The combined filtrate and washings were concentrated under reduced pressure to dryness. The crude product was purified by prep-TLC{EtOAc, Rf (product)=0.45} to provide 39a (70.0 mg, 36.1%) as a yellow oil.

Step 2:

To a solution of 39a (54.0 mg) in dichloromethane (2 mL) was added TFA (1 mL) at 20 °C. The mixture was stirred at 20 °C for 1 h. TLC (EtOAc) indicated the starting material was consumed completely and one major new spot with larger polarity was detected. The reaction mixture was diluted with $CH_2Cl_2$ (10 mL) and concentrated under reduced pressure to dryness at a temperature below 10 °C. The residue was re-dissolved in MeCN (2 mL) and distilled $H_2O$ (2 mL) and then lyophilized to afford the titled product Ex.39 (38.0 mg, a TFA salt) as a yellow solid; $^1$H NMR: 400 MHz DMSO-$d_6$, δ 8.65 (d, J=4.8 Hz, 1H), 8.04 (s, 1H), 7.77 (m, 1H), 7.67-7.59 (m, 2H), 7.37 (d, J=11.2 Hz, 1H), 4.08 (s, 3H); LC-MS: m/z $[M+H]^+$=231.1.

Example 40: Preparation of 2-hydroxy-7-(2-(methylthio)pyrimidin-4-yl)cyclohepta-2,4,6-trien-1-one (Ex.40)

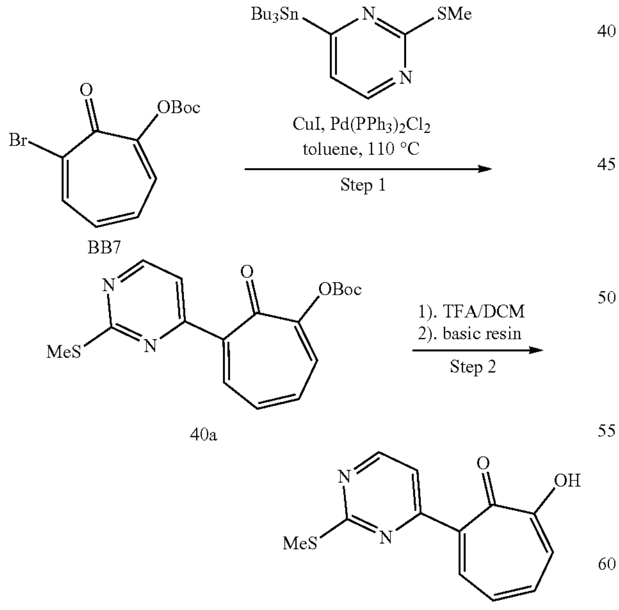

BB7

40a

Ex. 40

Step 1:

To a mixture of building block BB7 (100 mg, 332 umol, 1.00 eq) and 2-(methylthio)-4-(tributylstannyl)pyrimidine (138 mg, 332 umol, 1.00 eq) in toluene (12 mL) was added CuI (25.0 mg, 133 umol, 0.40 eq) and $Pd(PPh_3)_2Cl_2$ (47.0 mg, 66.0 umol, 0.20 eq) in one portion at 25 °C under nitrogen. The system was degassed and recharged with nitrogen, repeated the process three times. The resulting mixture was heated and stirred at 110 °C for 2.5 hrs under $N_2$ atmosphere. After cooling, the mixture was filtered through a pad of Celite and the filter cake was washed with $CH_2Cl_2$ (30 mL×3). The combined filtrate and washings were concentrated under reduced pressure to dryness. The residue was purified by prep-HPLC (neutral condition, column: Waters Xbridge BEH C18 100*25 mm*5 um; mobile phase: [water (10 mM $NH_4HCO_3$)-ACN]; B %: 45%-65%, 20 min) to give 40a (55.0 mg, 159 umol, 47.8%) as a yellow solid.

Step 2:

To a solution of 40a (25.0 mg, 72.1 umol, 1.00 eq) in dichloromethane (1 mL) was added TFA (462 mg, 4.05 mmol, 56.1 eq) at 20 °C under $N_2$ atmosphere. The mixture was stirred at 20 °C for 1 hr. The reaction mixture was diluted with $CH_2Cl_2$ (5 mL) and concentrated under reduced pressure to dryness at a temperature below 10 °C. The residue was re-dissolved in acetonitrile (1 mL) and $H_2O$ (2 mL) and then lyophilized to afford the titled product Ex.40 (15.0 mg, 82.0%) as a yellow solid; $^1$H NMR: 400 MHz DMSO-$d_6$, δ 8.67-8.72 (m, 1H), 7.99-8.08 (m, 1H), 7.64-7.69 (m, 1H), 7.50-7.57 (m, 1H), 7.31 (s, 1H), 7.17 (s, 1H), 2.54-2.59 (m, 3H); LC-MS: m/z $[M+H]^+$=247.1.

Example 41: Preparation of 4-(2-aminopyrimidin-5-yl)-2-hydroxycyclohepta-2,4,6-trien-1-one (Ex.41)

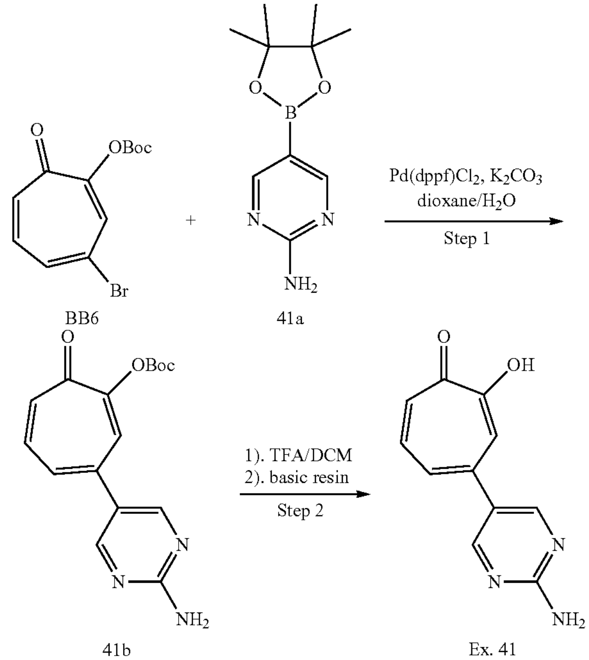

BB6

41a

41b

Ex. 41

Step 1:

To a mixture of building block BB6 (300 mg, 996 umol, 1 eq), 41a (330 mg, 1.49 mmol, 1.5 eq) and $K_2CO_3$ (344 mg, 2.49 mmol, 2.5 eq) in dioxane (5 mL) and $H_2O$ (1 mL) was added Pd(dppf)$Cl_2$ (73 mg, 100 umol, 0.1 eq) in one portion at 20 °C under $N_2$ atmosphere. The system was degassed and recharged with nitrogen, repeated the process three times. The resulting mixture was heated and stirred at 110 °C for 30 min under $N_2$ atmosphere. LCMS showed the starting material was consumed completely and the desired product mass was detected. The reaction mixture was quenched by addition water (10 mL) and extracted with EtOAc (10 mL×3). The combined organic extracts were washed with brine (10 mL), dried over $Na_2SO_4$, concentrated under reduced pressure to dryness. The residue was purified by silica gel column chromatography eluting with Petroleum ether/Ethyl acetate (10:1 to 0:1) to provide 41b (100 mg, 31.8% yield) as a yellow solid.

Step 2:

To a solution of 41b (100 mg) in dichloromethane (5 mL) was added TFA (2 mL) at 20 °C. The mixture was stirred at 20 °C for 0.5 hr. LCMS showed the starting material was consumed completely and the desired product mass was detected. The reaction mixture was concentrated under reduced pressure to dryness. The residue was purified by prep-HPLC (TFA condition; column: Luna C8 100*30 5 u; mobile phase: [water (0.1% TFA)-ACN]; B %: 1%-20%, 10 min) to afford the titled product Ex.41 (11 mg, 16.1%, TFA salt) as a white solid; $^1$H NMR: 400 MHz DMSO-$d_6$, δ 8.7 (s, 2H), 7.4-7.5 (m, 2H), 7.25-7.3 (d, 1H), 7.10-7.2 (d, 1H); LC-MS: m/z $[M+H]^+$=216.0.

Example 42: Preparation of 2-hydroxy-4-(2-morpholinopyrimidin-5-yl)cyclohepta-2,4,6-trien-1-one (Ex.42)

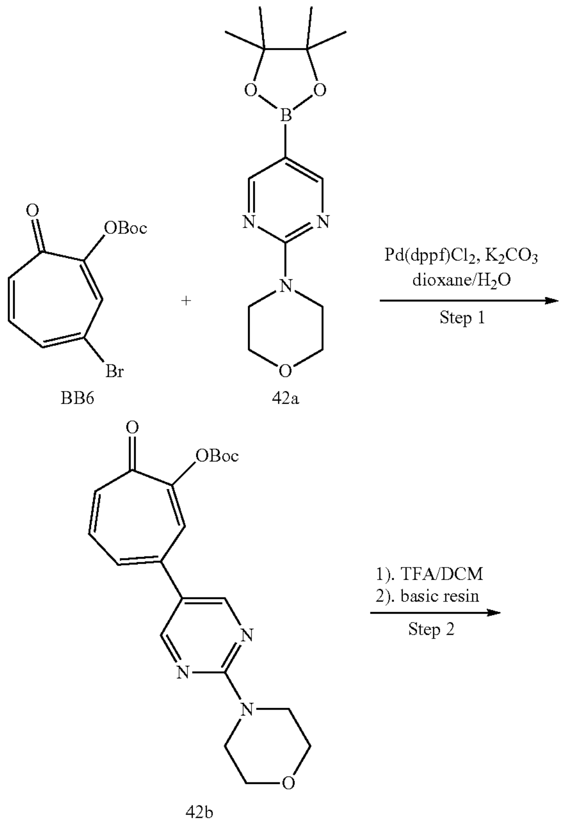

BB6

42a

42b

-continued

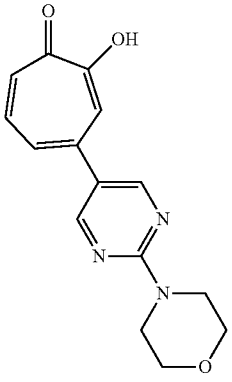

Ex. 42

Step 1:

To a mixture of building block BB6 (0.3 g, 996 umol, 1 eq) and 42a (435 mg, 1.49 mmol, 1.5 eq) in dioxane (10 mL) and $H_2O$ (2 mL) was added $K_2CO_3$ (413 mg, 2.99 mmol, 3 eq) and Pd(dppf)$Cl_2$ (72 mg, 99.62 umol, 0.1 eq) at 25 °C under $N_2$ atmosphere. The system was degassed and recharged with nitrogen, repeated the process three times. The resulting mixture was heated and stirred at 100 °C for 0.5 hr under a $N_2$ atmosphere. LCMS showed the starting material was consumed completely and the desired product mass was observed. After cooling, water (15 mL) was added and the aqueous mixture was extracted with ethyl acetate (10 mL×3). The combined organic extracts were washed with brine (30 mL), dried over anhydrous $Na_2SO_4$, filtered and concentrated under reduced pressure to dryness. The residue was purified by silica gel column chromatography eluting with Petroleum ether/Ethyl acetate (90/10 to 70/30) to give 42b (0.10 g, 24.4%) as a yellow oil.

Step 2:

To a solution of 42b (100 mg) in DCM (5 mL) was added TFA (1 mL) at 25 °C. The mixture was stirred at 25 °C for 30 min. LCMS showed the starting material was consumed completely and the desired product mass was observed. The reaction mixture was diluted with $CH_2Cl_2$ (10 mL) and concentrated under reduced pressure to dryness at a temperature below 10 °C. The residue was re-dissolved in $CH_2Cl_2$ (5 mL), treated with Amberlyst A21 (0.2 g) and stirred at 25 °C for another 0.5 hr. After filtering, the solid cake was washed with $CH_2Cl_2$ (5 mL×2) and the combined filtrates were concentrated under reduced pressure to afforded the titled product Ex.42 (24 mg, 32.7%) as a yellow solid; $^1$H NMR: 400 MHz $CD_3OD$, δ 8.66 (s, 2H), 7.61-7.50 (m, 2H), 7.37-7.23 (m, 2H), 3.92-3.85 (m, 4H), 3.81 (br d, J=5.2 Hz, 1H), 3.79-3.73 (m, 4H); LC-MS: m/z $[M+H]^+$=286.1.

Example 43: Preparation of 2-hydroxy-4-(pyrimidin-2-yl)cyclohepta-2,4,6-trien-1-one (Ex.43)

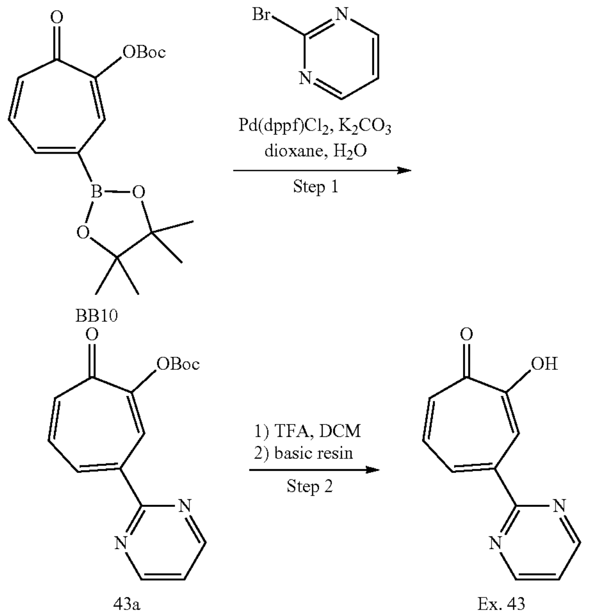

Step 1:

To a mixture of building block BB10 (150 mg, 430 umol, 1 eq) and 2-bromopyrimidine (102 mg, 646 umol, 1.5 eq) in dioxane (5 mL) and $H_2O$ (1 mL) was added $K_2CO_3$ (178 mg, 1.29 mmol, 3 eq) and Pd(dppf)$Cl_2$ (31 mg, 43.1 umol, 0.1 eq) at 20 °C under a $N_2$ atmosphere. The system was degassed and recharged with nitrogen, repeated the process three times. The resulting mixture was heated and stirred at 120 °C for 0.5 h under $N_2$. LCMS showed the starting material was almost consumed completely and a major peak with desired mass was observed. After cooling, water (20 mL) was added and the aqueous mixture was extracted with ethyl acetate (20 mL×3). The combined organic phases were washed with brine (70 mL), dried over anhydrous $Na_2SO_4$. After filtering, the filtrate was concentrated under reduced pressure to give a residue. The residue was purified by prep-TLC (Petroleum ether/Ethyl acetate=1/2, Rf=0.3) to give 43a (70 mg, 54.1%) as a yellow oil.

Step 2:

To a solution of 43a (70 mg, 233 umol, 1 eq) in DCM (2 mL) was added TFA (1 mL) at 20 °C. The mixture was stirred at 20 °C for 30 min. TLC showed the starting material was consumed completely and a new spot was observed. The reaction mixture was diluted with $CH_2Cl_2$ (10 mL) and concentrated under reduced pressure to dryness at a temperature below 10 °C. The residue was re-dissolved in $CH_2Cl_2$ (10 mL), treated with Amberlyst A21 (0.2 g) and stirred for another 0.5 hr. After filtering, the solid cake was washed with $CH_2Cl_2$ (5 mL×2) and the filtrates were concentrated under reduced pressure to afford the titled product Ex.43 (34 mg, 72.9%) as a yellow solid; $^1H$ NMR: 400 MHz DMSO-$d_6$, δ 9.00 (d, J=4.8 Hz, 2H), 8.40 (d, J=1.6 Hz, 1H), 8.34-8.24 (m, 1H), 7.65 (dd, J=10.0, 11.2 Hz, 1H), 7.59 (t, J=4.8 Hz, 1H), 7.32 (d, J=11.2 Hz, 1H); LC-MS: m/z $[M+H]^+$=201.1.

Example 44: Preparation of 2-hydroxy-5-(pyrimidin-2-yl)cyclohepta-2,4,6-trien-1-one (Ex.44)

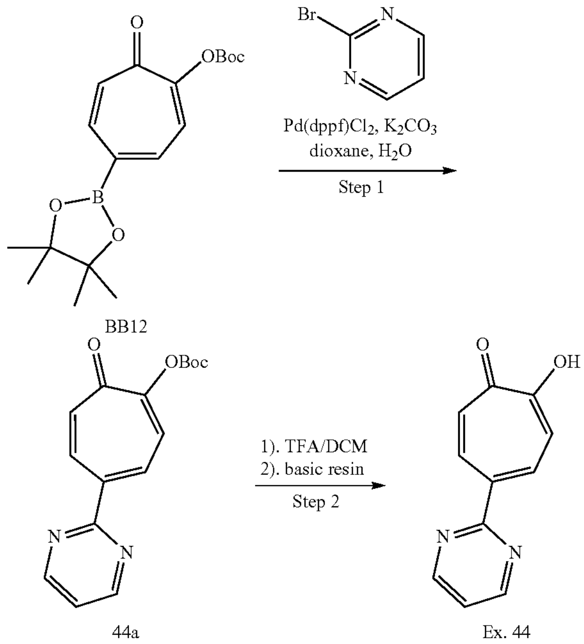

Step 1:

To a mixture of building block BB12 (200 mg, 574 umol, 1.00 eq), 2-bromopyrimidine (109 mg, 689 umol, 1.20 eq) and $K_2CO_3$ (198 mg, 1.44 mmol, 2.50 eq) in dioxane: $H_2O$=17:1 (4 mL) was added Pd(dppf)$Cl_2$·$CH_2Cl_2$ (46.9 mg, 57.4 umol, 0.10 eq) under $N_2$. The system was degassed and recharged with nitrogen, repeated three times, and then the resulting mixture was heated and stirred at 120 °C for 0.5 hr under $N_2$. LCMS showed the starting material was consumed completely and the desired product mass was observed. After cooling, the mixture was filtered through a pad of Celite and the filter cake was washed with $CH_2Cl_2$ (20 mL×2). The combined filtrates were concentrated under reduced pressure to a residue, which was purified by prep-TLC ($SiO_2$, petroleum ether:EtOAc=1:2) to give 44a (90 mg, 299 umol, 52.1%) as a yellow solid.

Step 2:

To a solution of 44a2 (90 mg, 299 umol, 1.00 eq) in $CH_2Cl_2$ (1 mL) was added TFA (0.5 mL). The mixture was stirred at 25 °C for 1 h. TLC (petroleum ether:EtOAc=1:2) indicated the staring material was consumed completely and one new spot was formed. The reaction mixture was diluted with $CH_2Cl_2$ (10 mL) and concentrated under reduced pressure to dryness at a temperature below 10 °C. The residue was re-dissolved in $CH_2Cl_2$ (10 mL) and treated with Amberlyst A21 (0.1 g). After stirring for 0.5 hr, the suspension was filtered, the solid cake was washed with $CH_2Cl_2$ (5 mL×2). The combined filtrates were concentrated under reduced pressure to afford the tilted product Ex.44 (52 mg, 86.7%) as a yellow solid; $^1H$ NMR: 400 MHz DMSO-$d_6$, δ 7.36-7.40 (m, 2H) 7.48 (t, J=4.8 Hz, 1H) 8.65-8.70 (m, 2H) 8.92 (d, J=4.8 Hz, 2H); LC-MS: m/z $[M+H]^+$=201.1.

Example 45: Preparation of 2-hydroxy-4-(pyrimidin-2-yl)cyclohepta-2,4,6-trien-1-one (Ex.45)

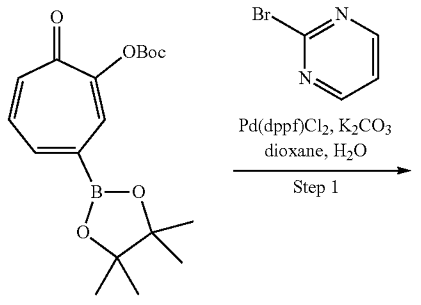

BB10

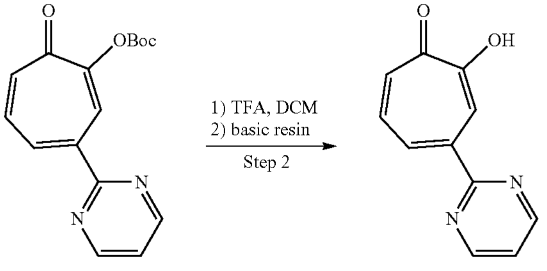

45a

Ex. 45

Step 1:

To a mixture of building block BB10 (150 mg, 430 umol, 1 eq) and 2-bromopyrimidine (102 mg, 646 umol, 1.5 eq) in dioxane (5 mL) and $H_2O$ (1 mL) was added $K_2CO_3$ (178 mg, 1.29 mmol, 3 eq) and Pd(dppf)$Cl_2$ (31 mg, 43.1 umol, 0.1 eq) at 20 °C under a $N_2$ atmosphere. The system was degassed and recharged with nitrogen, repeated three times. The mixture was heated and stirred at 120 °C for 0.5 h under $N_2$. LCMS showed the starting material was almost consumed completely and a major peak with the desired product mass was observed. After cooling, water (20 mL) was added and then extracted with ethyl acetate (20 mL×3). The combined organic extracts were washed with brine (70 mL), dried over anhydrous $Na_2SO_4$. After filtering, the filtrate was concentrated under reduced pressure to give a residue. The residue was purified by prep-TLC (Petroleum ether/Ethyl acetate=1/2, Rf=0.3) to give 45a (70 mg, 54.1%) as a yellow oil.

Step 2:

To a solution of 45a (70 mg, 233 umol, 1 eq) in DCM (2 mL) was added TFA (1 mL) at 20 °C. The mixture was stirred at 20 °C for 30 min. TLC showed the starting material was consumed completely and a new spot was observed. The reaction mixture was diluted with $CH_2Cl_2$ (10 mL) and concentrated under reduced pressure to dryness at a temperature below 10 °C. The residue was re-dissolved in $CH_2Cl_2$ (10 mL), added Amberlyst A21 (0.2 g) and stirred for another 0.5 hr. After filtering, the cake was washed with $CH_2Cl_2$ (5 mL×2) and the filtrate was concentrated under reduced pressure to afford the titled product Ex.45 (34 mg, 72.9%) as a yellow solid; $^1$H NMR: 400 MHz DMSO-$d_6$, δ 9.00 (d, J=4.8 Hz, 2H), 8.40 (d, J=1.6 Hz, 1H), 8.34-8.24 (m, 1H), 7.65 (dd, J=10.0, 11.2 Hz, 1H), 7.59 (t, J=4.8 Hz, 1H), 7.32 (d, J=11.2 Hz, 1H); LC-MS: m/z $[M+H]^+$=201.1.

Example 46: Preparation of 4-(5-fluoro-4-methylpyridin-3-yl)-2-hydroxycyclohepta-2,4,6-trien-1-one (Ex.46)

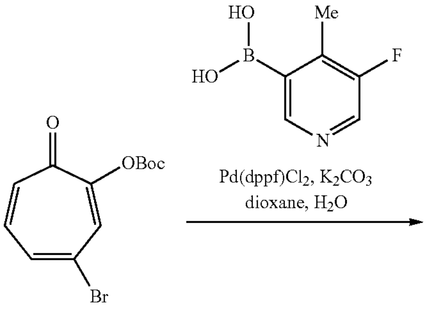

BB6

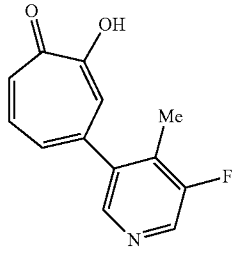

Ex. 46

To a stirred mixture of building block BB6 (50 mg, 1.66 mmol, 1.00 eq), (5-fluoro-4-methylpyridin-3-yl)boronic acid (38.59 mg, 2.49 mmol, 1.50 eq) and $K_2CO_3$ (68.84 mg, 4.98 mmol, 3.00 eq) in 1,4-dioxane (1.5 mL) and $H_2O$ (0.3 mL) was added Pd(dppf)$Cl_2$·$CH_2Cl_2$ complex (27.12 mg, 0.33 mmol, 0.20 eq) in one portion at 25 °C under $N_2$ atmosphere. The system was degassed and recharged with nitrogen, the process was repeated three times. The resulting mixture was heated and stirred under microwave conditions at 120 °C for 1 hr. LC-MS showed BB6 was consumed completely and a desired product mass was detected. The Boc protecting group was cleaved during the Suzuki coupling reaction under the current condition. After cooling, the mixture was filtered through a pad of Celite and the filter cake was washed with $CH_2Cl_2$ (10 mL×3). The combined filtrate and washings were concentrated under reduced pressure to dryness. The residue was purified by prep-HPLC (neutral condition) to afford the titled product Ex.46 (33.21 mg, 8.71%) as a yellow solid; $^1$H NMR: 500 MHz DMSO, δ 8.55 (d, 1H), 8.33 (s, 1H), 7.46 (dd, 1H), 7.25 (d, 1H), 7.13 (d, 1H), 6.98 (d, 1H), 2.18 (d, 3H); LC-MS: m/z $[M+H]^+$=232.0.

Example 47: Preparation of 2-hydroxy-7-(pyrimidin-4-yl)cyclohepta-2,4,6-trien-1-one (Ex.47)

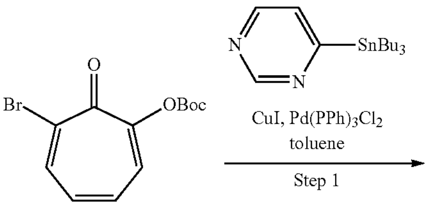

BB7

-continued

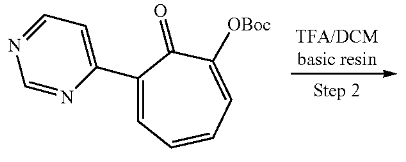

47a

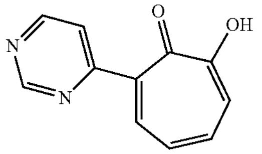

Ex. 47

Step 1:

To a mixture of building block BB7 (200 mg, 664 umol, 1 eq) and tributyl(pyrimidin-4-yl)stannane (270 mg, 730 umol, 1.1 eq) in dry toluene (3 mL) was added CuI (51 mg, 265 umol, 0.4 eq) and $Pd(PPh_3)_2Cl_2$ (93 mg, 132 umol, 0.2 eq) at 25 °C under $N_2$. The mixture was degassed and recharged with nitrogen, repeated three times. The resulting mixture was heated and stirred at 120 °C for 2 hours. TLC (Petroleum ether:Ethyl acetate=1:1) showed the starting material was consumed completely and one major new spot was detected. After cooling, the mixture was filtered through a pad of Celite and the filter cake was washed with EtOAc (30 mL×3). The filtrates were concentrated under reduced pressure to dryness. The residue was purified by prep-HPLC (column: Waters Xbridge 150×25 5 u; mobile phase: [water (0.1% TFA)-ACN]; B %: 25%-55%, 20 min) to provide 47a (40 mg, 20.1%) as a yellow solid.

Step 2:

To a mixture of 47a (40 mg) in DCM (1 mL) was added TFA (152 mg, 1.33 mmol, 10 eq) at 25 °C. The mixture was stirred at 25 °C for 1 h. TLC (Petroleum ether:Ethyl acetate=1:1) showed the starting material was consumed completely and one major new spot was detected. The reaction mixture was diluted with $CH_2Cl_2$ (10 mL) and concentrated under reduced pressure to dryness at a temperature below 10 °C. The residue was re-dissolved in $CH_2Cl_2$ (5 mL), treated with Amberlyst A21 (0.1 g), and stirred at 25 °C for another 0.5 hr. After filtering, the solid cake was washed with $CH_2Cl_2$ (5 mL×2) and the filtrates were concentrated under reduced pressure to provide the titled product Ex.47 (16 mg, 60.0%) as a yellow solid; $^1H$ NMR: 400 MHz $CD_3OD$, δ 9.26 (s, 1H), 8.82 (d, J=5.2 Hz, 1H), 8.19-8.06 (m, 2H), 7.63-7.53 (m, 1H), 7.42 (d, J=10.4 Hz, 1H), 7.25 (t, J=10.0 Hz, 1H); LC-MS: m/z $[M+H]^+$=201.0.

Example 48: Preparation of 2-hydroxy-4-(pyrimidin-4-yl)cyclohepta-2,4,6-trien-1-one (Ex.48)

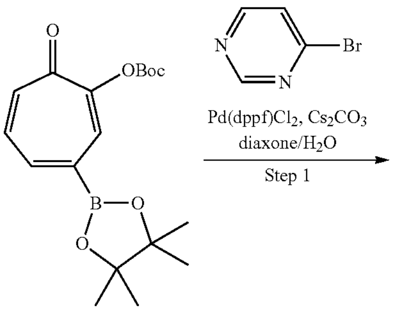

BB10

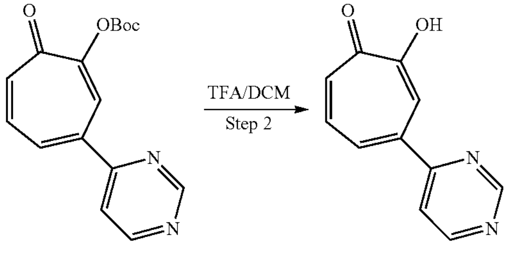

48a

Ex. 48

Step 1:

To a mixture of building block BB10 (300 mg, 861 umol, 1 eq) and 4-bromopyrimidine (164 mg, 1.03 mmol, 1.2 eq) in dioxane (0.7 mL) and $H_2O$ (0.1 mL) was added $Cs_2CO_3$ (561 mg, 1.72 mmol, 2 eq) and $Pd(dppf)Cl_2{\cdot}CH_2Cl_2$ (141 mg, 172 umol, 0.2 eq) at 25 °C under $N_2$. The system was degassed and recharged with nitrogen, repeated the process three times. The resulting mixture was heated and stirred at 120 °C for 30 min. TLC (Petroleum ether:Ethyl acetate=3:1) showed the starting material was consumed completely and a new spot was observed. After cooling, the mixture was filtered through a pad of Celite and the filter cake was washed with ethyl acetate (20 mL×3). The filtrate was concentrated under reduced pressure to dryness. The residue was purified by prep-HPLC (column: Waters Xbridge 150*25 5 u; mobile phase: [water (10 mM $NH_4HCO_3$)-ACN]; B %: 40%-60%, 10.5 min) to afford 48a (30 mg, 11.6%) as a yellow solid.

Step 2:

To a mixture of 48a (30 mg, 99.9 umol, 1 eq) in DCM (3 mL) was added TFA (114 mg, 999 umol, 10 eq) at 25 °C. The mixture was stirred at 25 °C for 1 h. TLC (Petroleum ether:Ethyl acetate=5:1) showed the starting material was consumed completely and one major new spot was detected. The reaction mixture was diluted with $CH_2Cl_2$ (10 mL) and concentrated under reduced pressure to dryness at a temperature below 10 °C. The residue was redissolved in MeCN (2 mL) and distilled $H_2O$ (2 mL) and then lyophilized to afford the titled product Ex.48 (28.5 mg, 91%, a TFA salt) as a yellow solid; $^1H$ NMR: 400 MHz $CD_3OD$, δ 9.29 (s, 1H), 8.90 (d, J=5.6 Hz, 1H), 8.12-8.00 (m, 2H), 7.82 (d, J=10.4 Hz, 1H), 7.73-7.62 (m, 1H), 7.42 (d, J=11.2 Hz, 1H); LC-MS: m/z $[M+H]^+$=201.0.

Example 49: Preparation of 2-hydroxy-5-(pyrimidin-4-yl)cyclohepta-2,4,6-trien-1-one (Ex.49)

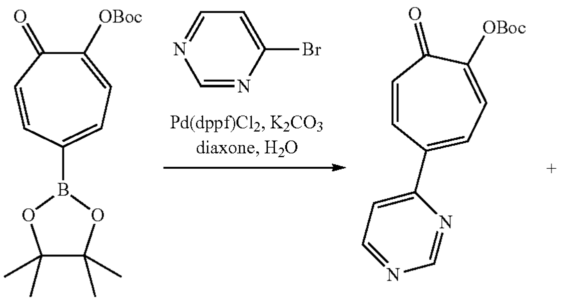

BB12

49a

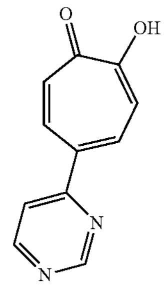

Ex. 49

To a mixture of building block BB12 (165 mg, 0.47 mmol, 1 eq), 4-bromopyrimidine (100 mg, 0.65 mmol 1.3 eq) and $K_2CO_3$ (140 mg, 1 mmol, 2 eq) in dioxane (2 mL) and $H_2O$ (0.17 mL) was added Pd(dppf)$Cl_2$·$CH_2Cl_2$ (140.72 mg, 172.32 umol, 0.2 eq)) at 25 °C under a $N_2$ atmosphere. The system was degassed and recharged with nitrogen, repeated the process three times. The reaction mixture was heated and stirred at 120 °C for 3 hours. TLC (Petroleum ether:Ethyl acetate=3:1) showed the starting material was consumed completely and a new spot was observed. After cooling, the mixture was filtered through a pad of Celite and the filter cake was washed with $CH_2Cl_2$ (30 mL×3). The filtrates were concentrated under reduced pressure to dryness. The residue was purified by prep-HPLC (column: Waters Xbridge 150×25 5 u; mobile phase: [water (10 mM $NH_4HCO_3$)-ACN]; B %: 20%-40%, 20 min) to give the titled product Ex.49 (13.5 mg, 5.7%) as a yellow solid; $^1$H NMR: 400 MHz DMSO-$d_6$, δ 9.25 (s, 1H), 8.88 (d, J=4.8 Hz, 1H), 8.27 (br d, J=11.2 Hz, 2H), 8.06 (br d, J=5.2 Hz, 1H), 7.34 (br d, J=11.2 Hz, 2H); LC-MS: m/z $[M+H]^+$=201.0.

Example 50: Preparation of 4-(3-fluoropyridin-4-yl)-2-hydroxycyclohepta-2,4,6-trien-1-one (Ex.50)

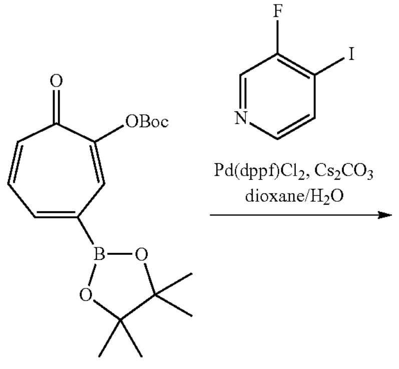

BB10

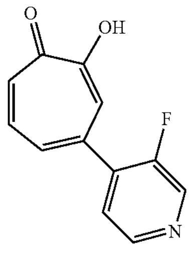

Ex. 50

To a mixture of building block BB10 (200 mg, 574 umol, 1 eq), 3-fluoro-4-iodo-pyridine (150 mg, 690 umol, 1.2 eq) in 1,4-dioxane (4 mL) and $H_2O$ (0.5 mL) was added $Cs_2CO_3$ (380 mg, 1.15 mmol, 2 eq) and Pd(dppf)$Cl_2$ (24 mg, 28.7 umol, 0.05 eq) in one portion at 25 °C under a $N_2$ atmosphere. The system was degassed and recharged with nitrogen, repeated the process three times. The resulting mixture was heated and stirred at 120 °C for 25 min. LCMS showed desired product mass and all starting material was consumed. After cooling to 25 °C, water (20 mL) was added and the aqueous mixture was extracted with $CH_2Cl_2$ (15 mL×3). The combined organic extracts were washed with water (10 mL), brine (10 mL), dried over anhydrous $Na_2SO_4$, filtered and concentrated under reduced pressure to dryness. The residue was purified by prep-HPLC (neutral condition, column: Welch Xtimate C18 100*25 mm*3 um; liquid phases: [A—10 mM $NH_4HCO_3$ in $H_2O$; B—CAN; B %: 40%-70%, 12 min]) to afford the titled product Ex.50 (25.6 mg, 20.5%) as a yellow solid (note: the Boc group was cleaved during the reaction); $^1$H NMR: 400 MHz $CDCl_3$, δ 8.62 (d, J=2.0 Hz, 1H), 8.52-8.57 (m, 1H), 7.47-7.54 (m, 1H), 7.39-7.47 (m, 2H), 7.36 (dd, J=6.4, 5.2 Hz, 1H), 7.15 (dd, J=9.6, 0.88 Hz, 1H); LC-MS: m/z $[M+H]^+$=218.0.

Example 51: Preparation of 5-(4-fluoropyridin-3-yl)-2-hydroxycyclohepta-2,4,6-trien-1-one (Ex.51)

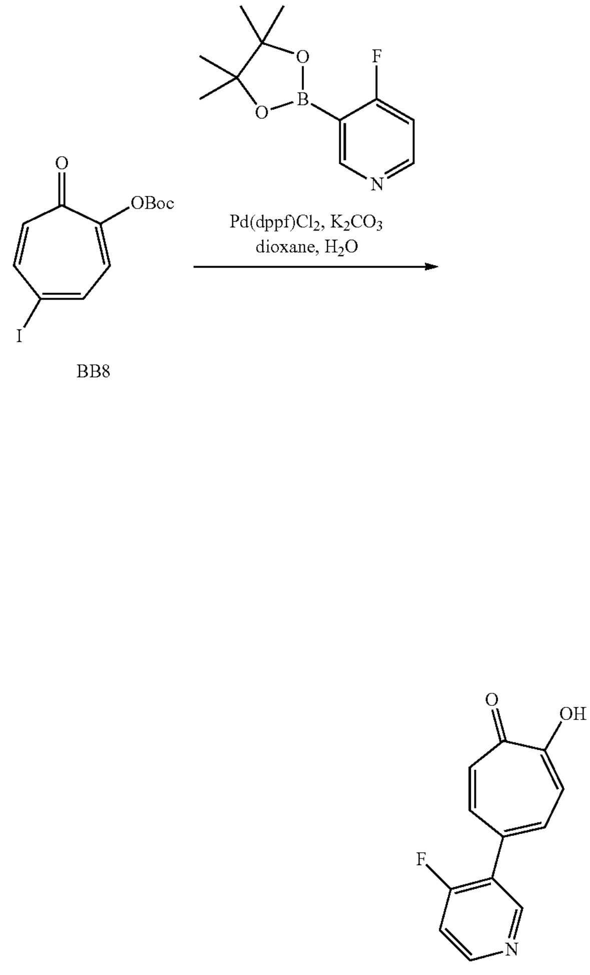

BB8

Ex. 51

To a stirred mixture of building block BB8 (50 mg, 1.44 mmol, 1.00 eq), 4-fluoro-3-(4,4,5,5-tetramethyl-1,3,2-dioxaborolan-2-yl)pyridine (48.05 mg, 2.15 mmol, 1.50 eq) and $K_2CO_3$ (59.55 mg, 4.31 mmol, 3.00 eq) in 1,4-dioxane (1.5 mL) and $H_2O$ (0.3 mL) was added Pd(dppf)$Cl_2$·$CH_2Cl_2$ complex (23 mg, 0.29 mmol, 0.20 eq) in one portion at 25 °C under $N_2$ atmosphere. The system was degassed and recharged with nitrogen, the process was repeated three times. The resulting mixture was heated and stirred under microwave conditions at 120 °C for 1 hr. LC-MS showed BB8 was consumed completely and a desired product mass was detected. The Boc protecting group was cleaved during the Suzuki coupling reaction under the current condition. After cooling, the mixture was filtered through a pad of Celite and the filter cake was washed with $CH_2Cl_2$ (10 mL×3). The combined filtrate and washings were concentrated under reduced pressure to dryness. The residue was purified by prep-HPLC (neutral condition) to afford the titled product Ex.51 (33.21 mg, 8.71%) as a yellow solid; $^1H$ NMR: 500 MHz DMSO, δ 8.70 (d, 1H), 8.63 (dd, 1H), 7.55 (m, 2H), 7.47 (dd, 1H), 7.26 (d, 2H); LC-MS: m/z $[M+H]^+$=217.9.

Example 52: Preparation of 4-(4-fluoropyridin-3-yl)-2-hydroxycyclohepta-2,4,6-trien-1-one (Ex.52)

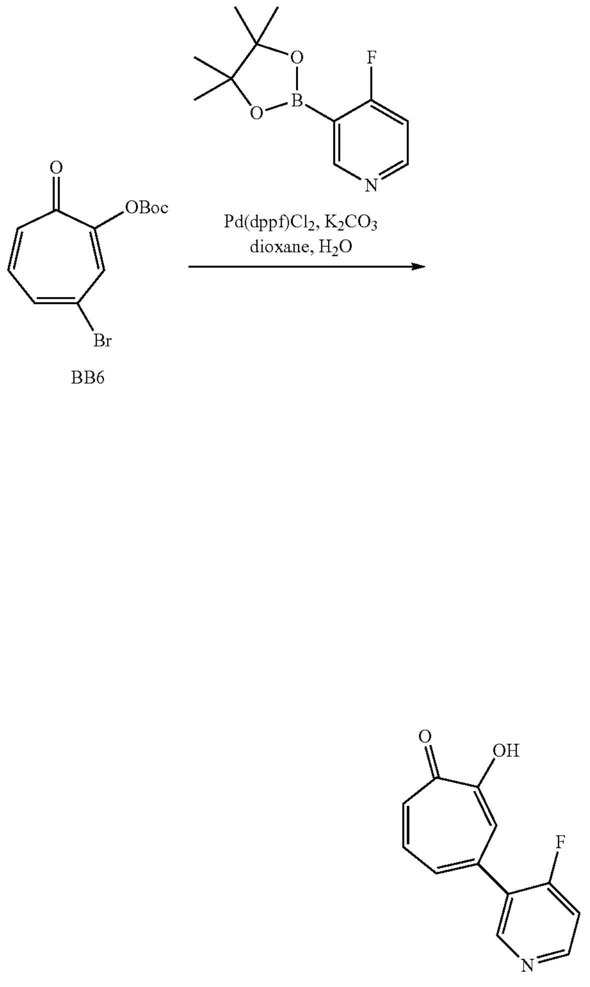

BB6

Ex. 52

To a stirred mixture of building block BB6 (50 mg, 1.66 mmol, 1.00 eq), 4-fluoro-3-(4,4,5,5-tetramethyl-1,3,2-dioxaborolan-2-yl)pyridine (55.55 mg, 2.49 mmol, 1.50 eq) and $K_2CO_3$ (68.84 mg, 4.98 mmol, 3.00 eq) in 1,4-dioxane (1.5 mL) and $H_2O$ (0.3 mL) was added Pd(dppf)$Cl_2$·$CH_2Cl_2$ complex (27.12 mg, 0.33 mmol, 0.20 eq) in one portion at 25 °C under $N_2$ atmosphere. The system was degassed and recharged with nitrogen, the process was repeated three times. The resulting mixture was heated and stirred under microwave conditions at 120 °C for 1 hr. LC-MS showed BB6 was consumed completely and a desired product mass was detected. The Boc protecting group was cleaved during the Suzuki coupling reaction under the current condition. After cooling, the mixture was filtered through a pad of Celite and the filter cake was washed with $CH_2Cl_2$ (10 mL×3). The combined filtrate and washings were concentrated under reduced pressure to dryness. The residue was purified by prep-HPLC (neutral condition) to afford the titled product Ex.52 (33.21 mg, 8.71%) as a yellow solid; 500 MHz DMSO, δ 8.73 (d, 1H), 8.68 (dd, 1H), 7.50 (ddd, 2H), 7.27 (m, 1H), 7.14 (dd, 1H); LC-MS: m/z $[M+H]^+$=217.9.

Example 53: Preparation of 2-hydroxy-4-(2-methylpyridin-3-yl)cyclohepta-2,4,6-trien-1-one (Ex.53)

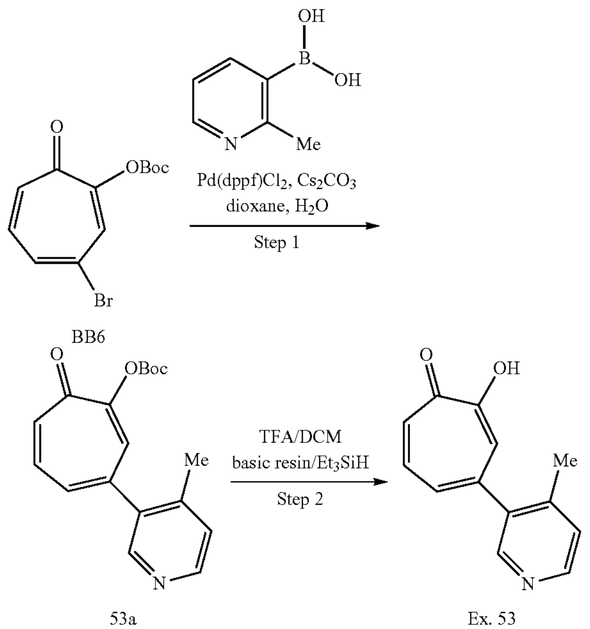

BB6

53a

Ex. 53

Step 1:

To a mixture of building block BB6 (150 mg, 498 umol, 1 eq) and (2-methyl-3-pyridyl)boronic acid (81 mg, 597 umol, 1.2 eq) in dioxane (2.1 mL) and $H_2O$ (0.1 mL) was added Pd(dppf)$Cl_2$·$CH_2Cl_2$ (81 mg, 99.6 umol, 0.2 eq) and $Cs_2CO_3$ (324 mg, 996 umol, 2 eq) at 25 °C under $N_2$. The mixture was degassed and recharged with nitrogen, repeated three times. The resulting mixture was heated and stirred at 120 °C for 30 minutes. TLC (Petroleum ether:Ethyl acetate=1:1) showed the starting material was consumed completely and one major new spot was detected. The mixture was filtered, and the filter cake was washed with ethyl acetate (10 mL×2). The combined filtrates were washed with brine (10 mL), dried over $Na_2SO_4$, filtered and concentrated under reduced pressure to dryness. The residue was purified by prep-TLC ($SiO_2$, Ethyl acetate, Rf=0.4) to give 53a (99 mg, 63.4%) as a yellow oil.

Step 2:

To a solution of 53a in DCM (5 mL) was added TFA (360 mg, 3.16 mmol, 10 eq) and $Et_3SiH$ (110 mg, 947 umol, 3 eq) at 25 °C. The mixture was stirred at 25 °C for 1 h. TLC (Petroleum ether:Ethyl acetate=1:1) showed the starting material was consumed completely and one major new spot was detected. The reaction mixture was diluted with $CH_2Cl_2$ (10 mL) and concentrated under reduced pressure to dryness below 10 °C. The residue was redissolved in $CH_2Cl_2$ (10 mL), treated with Amberlyst A21 (0.1 g) and stirred for another 0.5 hr. After filtering, the solid cake was washed with $CH_2Cl_2$ (5 mL×2) and the filtrates were concentrated under reduced pressure to dryness. The residue was re-dissolved in MeCN (2 mL) and distilled $H_2O$ (2 mL) and then lyophilized to afford the titled product Ex.53 (40.6 mg, 60.2%) as a light yellow solid; $^1H$ NMR: 400 MHz $CD_3OD$, δ 8.56 (dd, J=1.6, 5.2 Hz, 1H), 7.92 (dd, J=1.6, 7.6 Hz, 1H), 7.61-7.50 (m, 2H), 7.38 (d, J=11.2 Hz, 1H), 7.28 (d, J=1.2 Hz, 1H), 7.07 (dd, J=0.8, 10.0 Hz, 1H), 2.53 (s, 3H); LC-MS: m/z $[M+H]^+$=214.1.

Example 54: Preparation of 2-hydroxy-4-(2-methoxypyridin-3-yl)cyclohepta-2,4,6-trien-1-one (Ex.54)

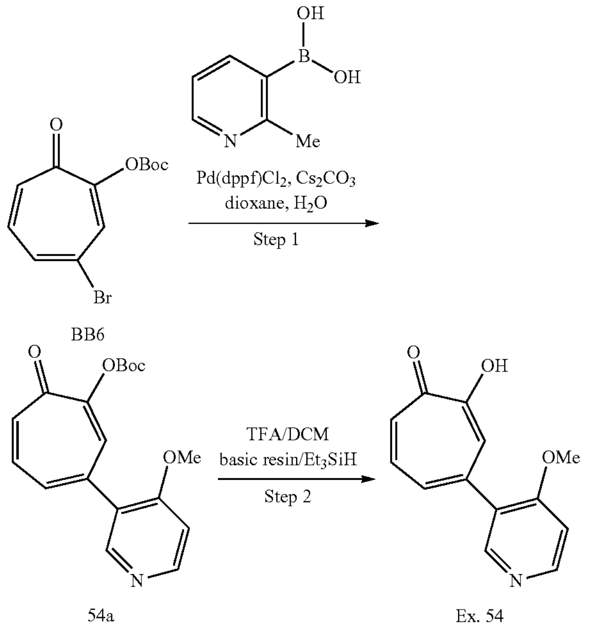

BB6

54a

Ex. 54

Step 1:

To a mixture of building block BB6 (200 mg, 664 umol, 1 eq) and (2-methoxy-3-pyridyl)boronic acid (121 mg, 796 umol, 1.2 eq) in dioxane (2.8 mL) and $H_2O$ (0.2 mL) was added $Cs_2CO_2$ (432 mg, 1.33 mmol, 2 eq) and Pd(dppf)$Cl_2$·$CH_2Cl_2$ (108 mg, 132 umol, 0.2 eq) at 25 °C under $N_2$. The mixture was degassed and recharged with nitrogen, repeated three times. The resulting mixture was heated and stirred at 120 °C for 25 minutes. TLC (Petroleum ether:Ethyl acetate=1:1) showed the starting material was consumed completely and one major new spot was detected. After cooling, the mixture was filtered, and the filter cake was washed with ethyl acetate (10 mL×2). The combined filtrates were washed with brine (10 mL), dried over $Na_2SO_4$, filtered and concentrated under reduced pressure to dryness. The residue was purified by prep-TLC ($SiO_2$, Petroleum ether:Ethyl acetate=1:1) to give 54a (130 mg, 59.4%) as a light yellow solid.

Step 2:

To a solution of 54a (130 mg) in DCM (5 mL) was added TFA (450 mg, 3.95 mmol, 10 eq) and Et3SiH (92 mg, 789 umol, 2 eq) at 25 °C. The mixture was stirred at 25 °C for 1 h. TLC (Petroleum ether:Ethyl acetate=1:1) showed the starting material was consumed completely, and one major new spot was detected. The reaction mixture was diluted with $CH_2Cl_2$ (10 mL) and concentrated under reduced pressure to dryness at a temperature below 10 °C. The residue was re-dissolved in $CH_2Cl_2$ (10 mL), treated with Amberlyst A21 (0.1 g) and stirred for another 0.5 hr. After filtering, the cake was washed with $CH_2Cl_2$ (5 mL×2) and the filtrates were concentrated under reduced pressure to dryness. The residue was re-dissolved in MeCN (2 mL) and distilled $H_2O$ (2 mL) and then lyophilized to provide the titled product Ex.54 (51.1 mg, 56.5%) as a light yellow solid; $^1H$ NMR: 400 MHz $CD_3OD$, δ 7.60 (s, 1H), 7.34 (d, 2H), 2.93 (dt, J=13.74, 6.72 Hz, 1H), 2.45 (s, 3H), 1.27 (d, J=7.04 Hz, 6

H8.22 (dd, J=1.6, 5.2 Hz, 1H), 7.71 (dd, J=1.6, 7.2 Hz, 1H), 7.57-7.49 (m, 1H), 7.44 (d, J=1.2 Hz, 1H), 7.33 (d, J=11.2 Hz, 1H), 7.19 (d, J=10.0 Hz, 1H), 7.08 (dd, J=5.2, 7.2 Hz, 1H), 3.96 (s, 3H); LC-MS: m/z $[M+H]^+$=230.

Example 55: Preparation of 2-hydroxy-4-(5-methylpyridin-3-yl)cyclohepta-2,4,6-trien-1-one (Ex.55)

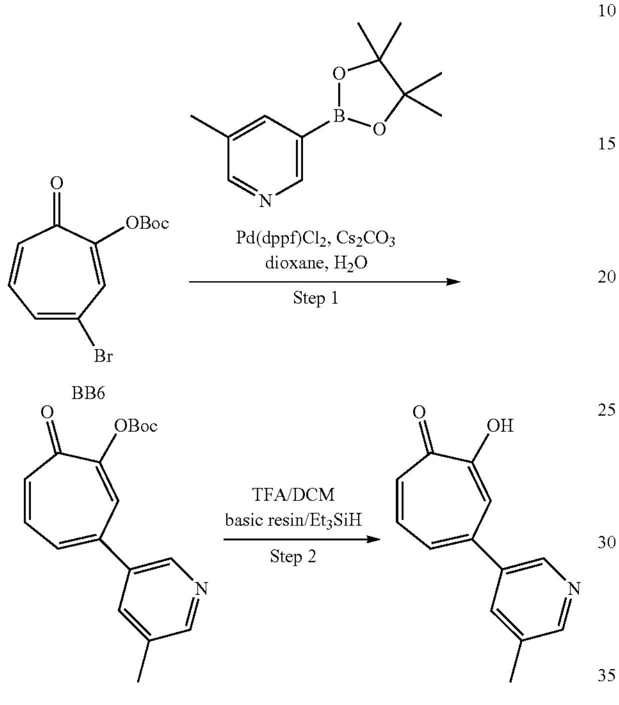

BB6, 55a, Ex. 55

Step 1:

To a mixture of building block BB6 (150 mg, 498 umol, 1.0 eq) and 3-methyl-5-(4,4,5,5-tetramethyl-1,3,2-dioxaborolan-2-yl)pyridine (130 mg, 598 umol, 1.2 eq) in dioxane (2.1 mL) and $H_2O$ (0.1 mL) was added $Cs_2CO_3$ (325 mg, 996 umol, 2 eq) and Pd(dppf)$Cl_2$·$CH_2Cl_2$ (81 mg, 99 umol, 0.2 eq) in one portion at 25 °C under $N_2$. The mixture was degassed and recharged with nitrogen, repeated three times. The mixture was heated and stirred at 120 °C for 25 minutes. TLC (Petroleum ether:Ethyl acetate=1:1) showed the starting material was consumed completely and one major new spot was detected. After cooling, the mixture was filtered, and the filter cake was washed with ethyl acetate (10 mL×2). The combined filtrates were washed with brine (10 mL), dried over $Na_2SO_4$, filtered and concentrated under reduced pressure to dryness. The residue was purified by prep-TLC ($SiO_2$, Ethyl acetate:MeOH=10:1) to give 55a (54 mg, 34.6%) as yellow oil.

Step 2:

To a solution of 55a (54 mg, 173 umol, 1 eq) in DCM (3 mL) was added $Et_3SiH$ (60 mg, 0.52 mmol, 3 eq) and TFA (197 mg, 1.73 mmol, 10 eq) at 25 °C. The mixture was stirred at 25 °C for 1 h. TLC (Petroleum ether:Ethyl acetate=1:1) showed the starting material was consumed completely and one major new spot was detected. The reaction mixture was diluted with $CH_2Cl_2$ (10 mL) and concentrated under reduced pressure to dryness at a temperature below 10 °C. The residue was redissolved in acetonitrile (10 mL), treated with Amberlyst A21 (0.1 g) and stirred for another 0.5 hr. After filtering, the solid cake was washed with acetonitrile (5 mL×2) and the filtrate was lyophilized to afford the titled product Ex.55 (14 mg, 38.1%) as a yellow solid; $^1$H NMR: 400 MHz $CD_3OD$, δ 78.54 (d, J=2.0 Hz, 1H), 8.42 (s, 1H), 7.89 (s, 1H), 7.42-7.34 (m, 1H), 7.29 (s, 1H), 7.11 (d, J=11.2 Hz, 1H), 6.95 (d, J=10.0 Hz, 1H), 2.44 (s, 3H); LC-MS: m/z $[M+H]^+$=214.1.

Example 56: Preparation of 4-(6-amino-5-methylpyridin-3-yl)-2-hydroxycyclohepta-2,4,6-trien-1-one (Ex.56)

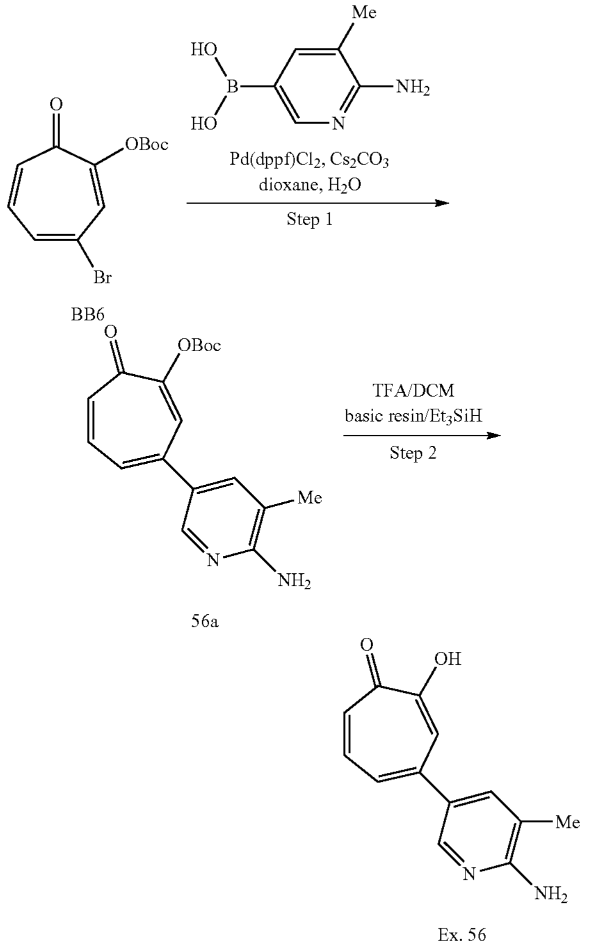

BB6, 56a, Ex. 56

Step 1:

To a mixture of building block BB6 (200 mg, 574 umol, 1 eq) and 5-bromo-3-methyl-pyridin-2-amine (128 mg, 689 umol, 1.2 eq) in dioxane (2.8 mL) and $H_2O$ (0.2 mL) was added $Cs_2CO_3$ (374 mg, 1.15 mmol, 2 eq) and Pd(dppf)$Cl_2$·$CH_2Cl_2$ (93 mg, 115 umol, 0.2 eq) at 25 °C under $N_2$. The mixture was degassed and then charged with nitrogen three times. The resulting mixture was heated and stirred at 120 °C for 20 minutes under $N_2$. TLC (Petroleum ether: Ethyl acetate=1:1) showed the starting material was consumed completely and one major new spot was detected. The mixture was filtered, and the filter cake was washed with ethyl acetate (10 mL×2), the combined filtrates were concentrated in vacuum to dryness. The residue was purified by pre-HPLC (column: Waters Xbridge 150×25 5 u; mobile phase: [water (10 mM $NH_4HCO_3$)-ACN]; B %: 25%-45%, 20 min) and lyophilized to afford 56a (40 mg, 21.2%) as a yellow solid.

Step 2:

To a solution of 56a (40 mg) in dichloromethane (3 mL) was added TFA (139 mg, 1.22 mmol, 10 eq) at 25 °C. The mixture was stirred at 25 °C for 1 h. TLC (Petroleum ether:Ethyl acetate=1:1) showed the starting material was consumed completely and one major new spot was detected. The reaction mixture was diluted with $CH_2Cl_2$ (10 mL) and concentrated under reduced pressure to dryness at a temperature below 10 °C. The residue was re-dissolved in $CH_2Cl_2$ (10 mL), treated with Amberlyst A21 (0.1 g) and stirred for another 0.5 hr. After filtering, the solid cake was washed with $CH_2Cl_2$ (5 mL×2) and the filtrate was concentrated under reduced pressure to provide the titled product Ex.56 (21.2 mg, 76.2%) as a yellow solid; $^1$H NMR: 400 MHz $CD_3OD$, δ 8.08 (d, J=2.4 Hz, 1H), 7.66 (d, J=1.6 Hz, 1H), 7.58-7.48 (m, 2H), 7.35-7.21 (m, 2H), 2.22 (s, 3H); LC-MS: m/z $[M+H]^+$=229.1.

Example 57: Preparation of 4-(5-fluoro-6-methylpyridin-3-yl)-2-hydroxycyclohepta-2,4,6-trien-1-one (Ex.57)

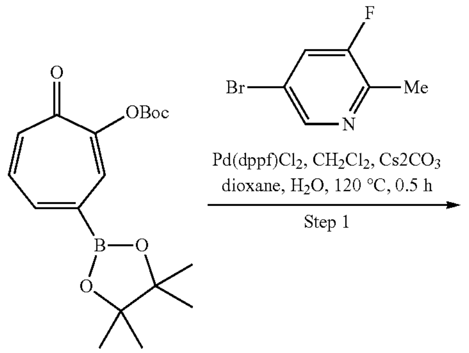

BB10

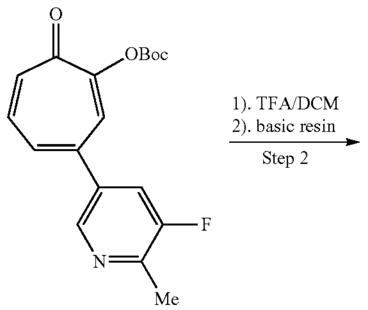

57a

-continued

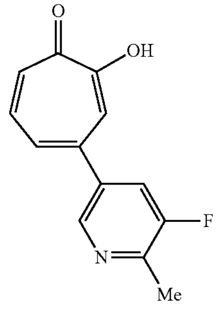

Ex. 57

To a mixture of building block BB10 (320 mg, 919.02 umol, 1 eq) and 5-bromo-3-fluoro-2-methylpyridine (175 mg, 919 umol, 1 eq) in dioxane (5 mL) and $H_2O$ (0.3 mL) was added $Cs_2CO_3$ (598.87 mg, 1.84 mmol, 2 eq) and $Pd(dppf)Cl_2 \cdot CH_2Cl_2$ (150.10 mg, 183.80 umol, 0.2 eq) in one portion at 25 °C under $N_2$ atmosphere. The system was degassed and recharged with nitrogen, repeated three times. The resulting mixture was heated and stirred at 120 °C for 0.5 hours. LCMS showed the starting material was consumed completely and one main peak with desired mass was detected. After cooling, the mixture was filtered through a pad of Celite and the filter cake was washed with $CH_2Cl_2$ (30 mL×3). The filtrate was concentrated under reduced pressure to dryness. The residue was purified by prep-HPLC (column: Xtimate C18 150*25 mm*5 um; mobile phase: [water (10 mM $NH_4HCO_3$)-ACN]; B %: 40%-60%, 10.5 min) to afford 57a (100 mg, 32.84%) as a yellow solid.

Step 2:

To a solution of 57a (100 mg) in $CH_2Cl_2$ (2 mL) was added TFA (0.5 mL) in one portion at 0 °C. The mixture was warmed and stirred at 25 °C for 1 hr. LCMS showed the starting material was consumed completely and one main peak with desired mass was detected. The reaction mixture was diluted with $CH_2Cl_2$ (10 mL) and concentrated under reduced pressure to dryness below 10 °C. The residue was further purified by prep-HPLC (column: Nano-micro Kromasil C18 100*30 mm 5 um; mobile phase: [water (0.1% TFA)-ACN]; B %: 50%-65%, 10 min) to give the titled product Ex.57 (45 mg, 30.1%) as a yellow solid after lyophilization; $^1$H NMR: 400 MHz $CD_3OD$, δ 8.53 (s, 1H), 7.86 (br d, J=10.4 Hz, 1H), 7.64-7.53 (m, 2H), 7.40-7.29 (m, 2H), 2.57 (d, J=2.8 Hz, 3H); LC-MS: m/z $[M+H]^+$=232.0.

Example 58: Preparation of 4-(5-fluoro-2-methylpyridin-3-yl)-2-hydroxycyclohepta-2,4,6-trien-1-one (Ex.58)

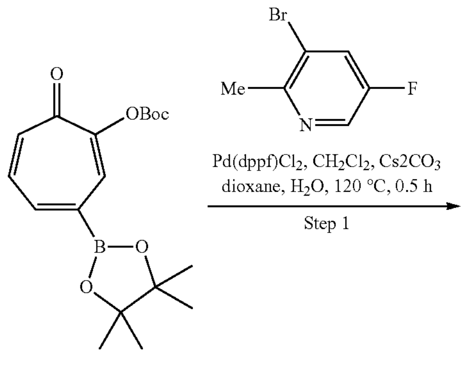

BB10

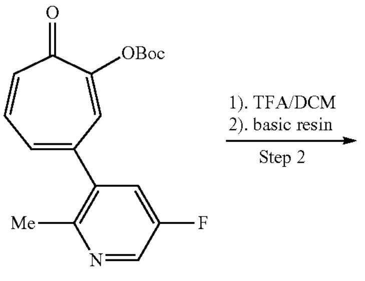

58a

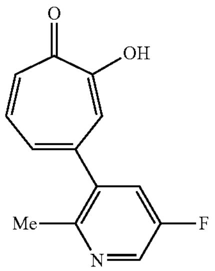

Ex. 58

Step 1:

To a mixture of building block BB10 (400 mg, 1.15 mmol, 1 eq), 3-bromo-5-fluoro-2-methylpyridine (220 mg, 1.15 mmol, 1 eq) and $Cs_2CO_3$ (748.58 mg, 2.30 mmol, 2 eq) in dioxane (7 mL) and $H_2O$ (0.4 mL) was added Pd(dppf) $Cl_2 \cdot CH_2Cl_2$ (180 mg, 220 umol, 0.2 eq) in one portion at 25 °C under a $N_2$ atmosphere. The system was degassed and recharged with nitrogen, repeated the process three times. The resulting mixture was heated and stirred at 120 °C for 0.5 hour. LCMS showed the desired product mass was observed and the starting material was consumed. After cooling to 25 °C, water (20 mL) was added and then extracted with $CH_2Cl_2$ (10 mL×3). The combined organic phases were washed with water (10 mL), brine (20 mL), dried over anhydrous $Na_2SO_4$, filtered and concentrated under reduced pressure to dryness. The residue was purified by prep-HPLC (column: Xtimate C18 150*25 mm*5 um; mobile phase: [water (10 mM $NH_4HCO_3$)-ACN]; B %: 40%-75%, 10.5 min) to give 58a (150 mg, 36.2%) as a yellow solid.

Step 2:

To a solution of 58a (150 mg) in $CH_2Cl_2$ (2 mL) was added TFA (0.8 mL) in one portion at 0 °C. The mixture was warmed and stirred at 20 °C for 1 hour. TLC (petroleum ether:EtOAc=1:1) indicated the starting material was consumed, and one major new spot with large polarity was detected. The reaction mixture was diluted with $CH_2Cl_2$ (10 mL) and concentrated under reduced pressure to dryness at a temperature below 10 °C. The residue was re-dissolved in $CH_2Cl_2$ (10 mL), treated with Amberlyst A21 (1 g) and stirred at 25 °C for another 0.5 hr. After filtering, the solid cake was washed with $CH_2Cl_2$ (5 mL×2) and the filtrate was concentrated under reduced pressure to afford the titled product Ex.58 (100 mg, 95.5%) as a yellow solid; $^1H$ NMR: 400 MHz $CD_3OD$, δ 8.48 (d, J=2.8 Hz, 1H), 7.69 (dd, J=2.8, 8.8 Hz, 1H), 7.56 (dd, J=10.0, 11.2 Hz, 1H), 7.44-7.33 (m, 1H), 7.28 (d, J=1.2 Hz, 1H), 7.10-7.02 (m, 1H), 2.53-2.43 (m, 3H); LC-MS: m/z $[M+H]^+$=232.0.

Example 59: Preparation of 5-(5-fluoro-6-methylpyridin-3-yl)-2-hydroxycyclohepta-2,4,6-trien-1-one (Ex.59)

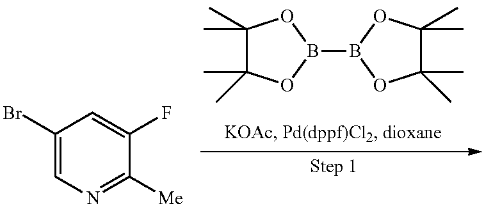

59a

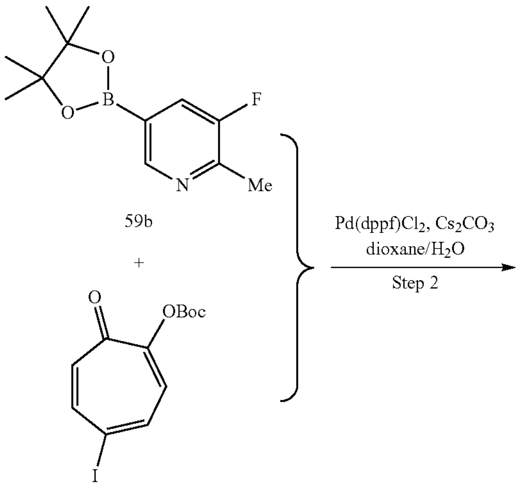

59b

+

BB8

-continued

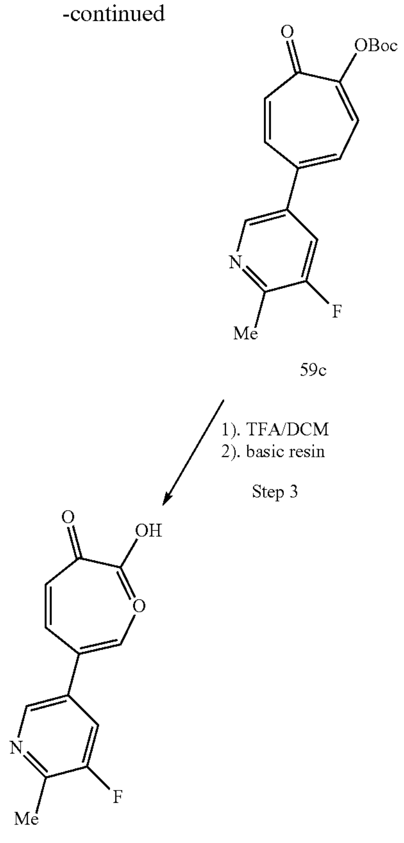

59c

Ex. 59

Step 1.

To a mixture of 5-bromo-3-fluoro-2-methyl pyridine 59a (100 mg, 526 umol, 1 eq) and bis(pinacolato)diboron (147 mg, 579 umol, 1.1 eq) in dioxane (2 mL) was added KOAc (155 mg, 1.58 mmol, 3 eq) and $Pd(dppf)Cl_2$ (77 mg, 105 umol, 0.2 eq) in one portion at 25 °C under $N_2$. The system was degassed and recharged with nitrogen, repeated three times. The resulting mixture was heated and stirred at 70 °C for 16 hours. LCMS showed the starting material was consumed completely and one main new peak with the desired product mass was detected. After cooling, the mixture was filtered through a pad of Celite and the filter cake was washed with $CH_2Cl_2$ (30 mL×3). The filtrates were concentrated under reduced pressure to dryness to give 59b (200 mg, crude) as a brown oil, which was used in the next step without further purification. Total 800 mg of 59b was obtained from 2 batches of preparations.

Step 2:

To a mixture of BB8 (1.17 g, 3.37 mmol, 1 eq) and 59b (800 mg) in dioxane (15 mL) and $H_2O$ (0.8 mL) was added $Cs_2CO_3$ (2.20 g, 6.75 mmol, 2 eq) and $Pd(dppf)Cl_2 \cdot CH_2Cl_2$ (551 mg, 674 umol, 0.2 eq) in one portion at 25 °C under a $N_2$ atmosphere. The system was degassed and recharged with nitrogen, repeated the process three times. The resulting mixture was heated and stirred at 120 °C for 0.5 hour. LCMS showed the starting material was consumed completely and one main new peak with desired product mass was detected. After cooling, the mixture was filtered through a pad of Celite and the filter cake was washed with $CH_2Cl_2$ (30 mL×3). The filtrate was concentrated under reduced pressure to dryness. The residue was purified by prep-HPLC (column: Xtimate C18 10μ 250 mm*50 mm; mobile phase: [water (10 mM $NH_4HCO_3$)-ACN]; B %: 30%-50%, 28 min) to afford 59c (700 mg, 2.02 mmol, 59.9%) as a yellow solid.

Step 3:

To a solution of 59c (200 mg) in $CH_2Cl_2$ (3 mL) was added TFA (0.8 mL) in one portion at 0 °C. The mixture was warmed and stirred at 25 °C for 1 hr. LCMS showed the starting material was consumed completely and one main peak with desired product mass was detected. The reaction mixture was diluted with $CH_2Cl_2$ (10 mL) and concentrated under reduced pressure to dryness at temperature below 10 °C. The residue was re-dissolved in $CH_2Cl_2$ (10 mL), treated with Amberlyst A21 (0.5 g) and stirred for another 0.5 hr. After filtering, the filter cake was washed with $CH_2Cl_2$ (10 mL×2) and the combined filtrates were concentrated under reduced pressure to dryness. The mixture was re-dissolved in MeCN (2 mL) and distilled $H_2O$ (2 mL) and then lyophilized to afford the titled product Ex.59 (67 mg, 50.2%) as a yellow solid; $^1H$ NMR: 400 MHz $CD_3OD$, δ 8.49 (s, 1H), 7.84-7.81 (d, 1H), 7.76-7.73 (d, 2H), 7.43-7.40 (d, 2H), 2.54 (s, 3H); LC-MS: m/z $[M+H]^+$=232.0.

Example 60: Preparation of 5-(5-fluoro-2-methylpyridin-3-yl)-2-hydroxycyclohepta-2,4,6-trien-1-one (Ex.60)

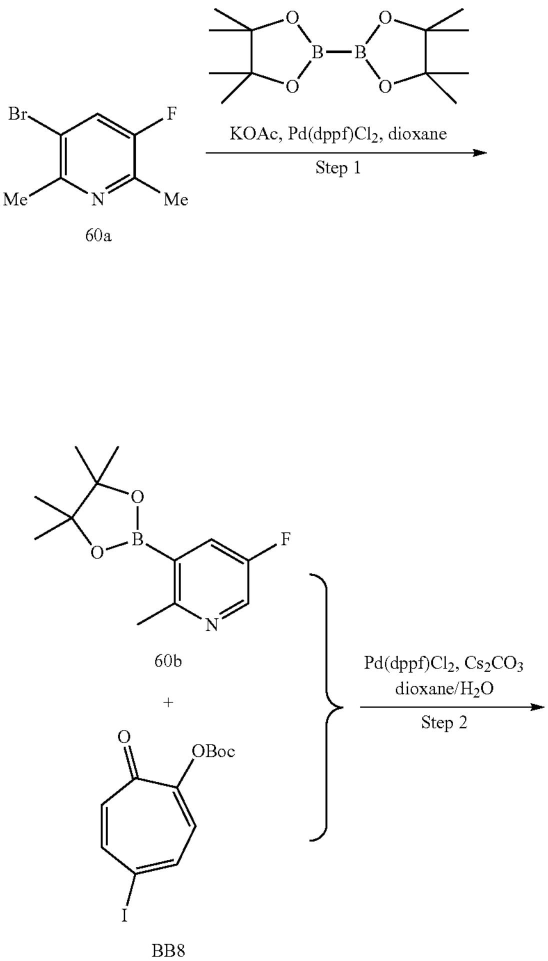

60a

60b

+

BB8

-continued

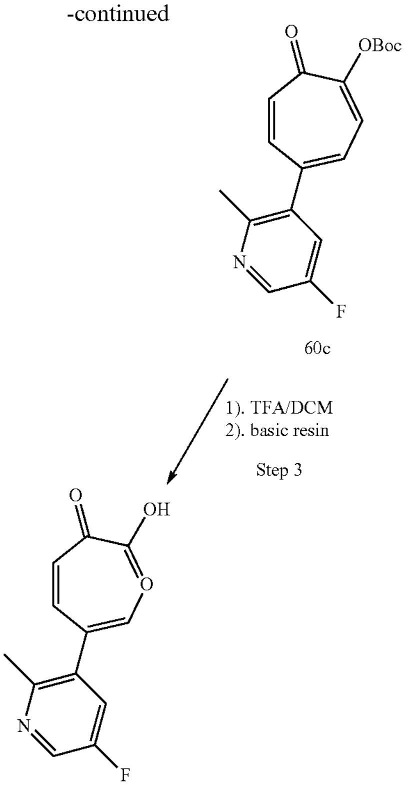

60c

Ex. 60

Step 1:

To a mixture of 3-bromo-5-fluoro-2-methyl pyridine 60a (700 mg, 3.68 mmol, 1 eq), bis(pinacolato)diboron (1.03 g, 4.05 mmol, 1.1 eq) and KOAc (1.08 g, 11.1 mmol, 3 eq) in dioxane (10 mL) was added Pd(dppf)$Cl_2$ (539 mg, 737 umol, 0.2 eq) in one portion at 25 °C under a $N_2$ atmosphere. The system was degassed and recharged with nitrogen, repeated the process three times. The resulting mixture was heated and stirred at 70 °C for 16 hours. LCMS showed the desired product mass was observed and the starting material was consumed. After cooling, the mixture was filtered through a pad of Celite and the filter cake was washed with $CH_2Cl_2$ (30 mL×3). The filtrate was concentrated under reduced pressure to dryness to give crude 60b (1.4 g, crude) as a brown oil, which was used in the next step without further purification.

Step 2:

To a mixture of building block BB8 (800 mg, 3.34 mmol, 1 eq), 60b (1.16 g, 3.34 mmol, 1 eq) and $Cs_2CO_3$ (2.18 g, 6.69 mmol, 2 eq) in dioxane (20 mL) and $H_2O$ (1.2 mL) was added Pd(dppf)$Cl_2$·$CH_2Cl_2$ (546 mg, 669 umol, 0.2 eq) in one portion at 25 °C under $N_2$ atmosphere. The system was degassed and recharged with nitrogen, repeated the process three times. The resulting mixture was heated and stirred at 120 °C for 0.5 hour. LCMS showed the desired product MS was observed and the starting material was consumed. After cooling to 25 °C, water (25 mL) was added and then extracted with $CH_2Cl_2$ (15 mL×3). The combined organic phases were washed with water (15 mL), brine (25 mL), dried over anhydrous $Na_2SO_4$, filtered and concentrated under reduced pressure to dryness. The residue was purified by prep-HPLC (column: Agela Durashell 10 u 250*50 mm; mobile phase: [water (10 mM $NH_4HCO_3$)-ACN]; B %: 33%-48%, 22 min) to give 60c (580 mg, 50.1%) as a yellow solid.

Step 3:

To a solution of 60c (100 mg) in MeCN (3 mL) was added TFA (1.2 mL) in one portion at 0 °C. The mixture was warmed and stirred at 20 °C for 1 hour. TLC (petroleum ether:EtOAc=1:1) indicated the starting material was consumed and one major new spot with large polarity was detected. The mixture was concentrated under reduced pressure to dryness, and then re-dissolved in MeCN (5 mL). Amberlyst A21 (500 mg) was added, and the suspension was stirred for another 20 min. After filtering, the solid cake was washed with MeCN (5 mL×2) and the combined filtrates were concentrated under reduced pressure to dryness. The residue was re-dissolved in MeCN (2 mL) and distilled $H_2O$ (2 mL) and then lyophilized to afford the titled product Ex.60 (30 mg, 42.5%) as a brown solid; $^1H$ NMR: 400 MHz DMSO-$d_6$, δ 8.49 (d, J=2.8 Hz, 1H), 7.69 (dd, J=2.8, 9.2 Hz, 1H), 7.42 (d, J=11.6 Hz, 2H), 7.24 (d, J=11.6 Hz, 2H), 2.38 (s, 3H); LC-MS: m/z $[M+H]^+$=232.0.

Example 61: Preparation of 2-(5-fluoropyridin-3-yl)-7-hydroxy-4-isopropylcyclohepta-2,4,6-trien-1-one (Ex.61)

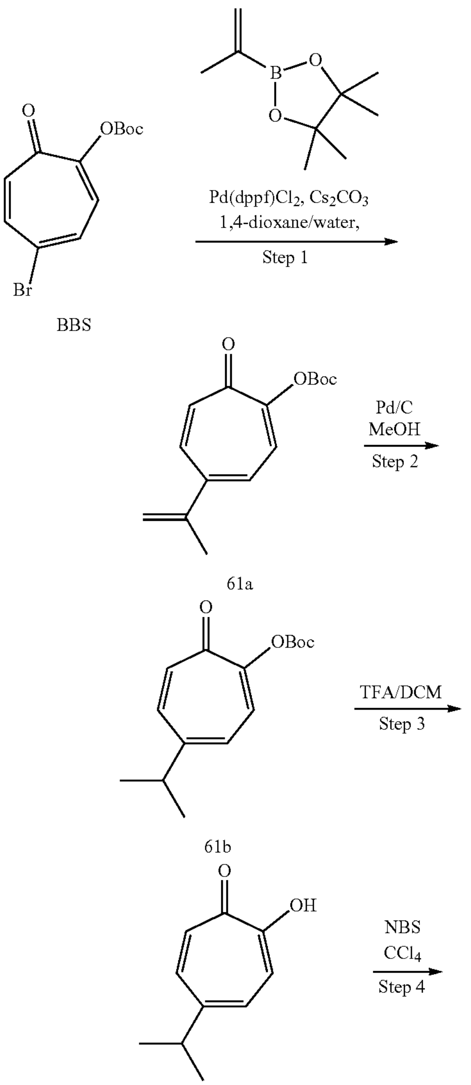

BBS

61a

61b

61c

-continued

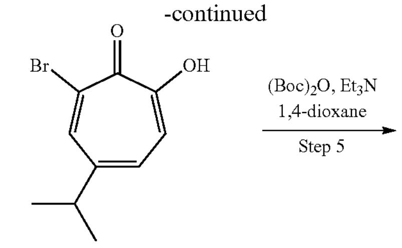

61d

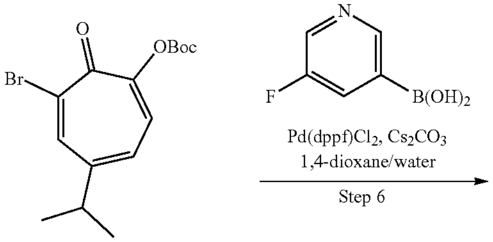

61e

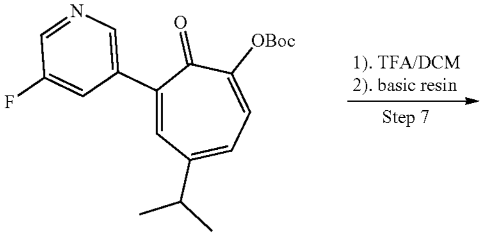

61f

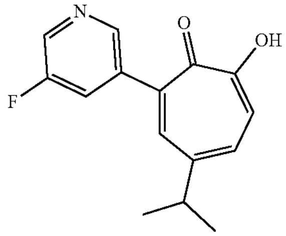

Ex. 61

Step 1:

To a mixture of building block BB5 (2.00 g, 5.74 mmol, 1 eq) and 2-isopropenyl-4,4,5,5-tetramethyl-1,3,2-dioxaborolane (1.93 g, 11.49 mmol, 2 eq) in 1,4-dioxane (20 mL) and water (4 mL) was added $Cs_2CO_3$ (4.68 g, 14.3 mmol, 2.5 eq) and Pd(dppf)$Cl_2$ (469 mg, 574 umol, 0.1 eq) at 25 °C under a $N_2$ atmosphere. The system was degassed and recharged with nitrogen, repeated three times. The resulting mixture was heated and stirred at 120 °C for 50 min under $N_2$. TLC (Petroleum ether:Ethyl acetate=3:1) showed the starting material was consumed completely and a new spot was observed. After cooling to room temperature, water (30 mL) was added and the aqueous mixture was extracted with ethyl acetate (50 mL×3). The combined organic phases were washed with water (20 mL), brine (20 mL), dried over anhydrous $Na_2SO_4$. After filtering, the filtrate was concentrated under reduced pressure to a residue, which was purified by silica gel chromatography eluting with Petroleum ether/Ethyl acetate (100/1 to 20/1) to give 61a (0.50 g, 1.91 mmol, 33.2%) as a yellow solid.

Step 2:

To a solution of 61a (500 mg, 1.91 mmol, 1 eq) in MeOH (5 mL) was added 10% Pd/C (0.30 g) under a $N_2$ atmosphere. The suspension was degassed under vacuum and purged with $H_2$ three times. The mixture was stirred under $H_2$ (15 psi) at 25 °C for 1 hour. LCMS showed the starting material was consumed completely and the desired product mass was observed. Then the mixture was filtered through a pad of Celite and the filter cake was washed with MeOH (10 mL×2). The combined filtrates were concentrated to dryness under reduced pressure to a residue. The residue was purified by silica gel column chromatography (Petroleum ether: Ethyl acetate=20:1 to 3:1) to give 61b (400 mg, 79.4%) as a yellow oil.

Step 3:

To a solution of 61b (400 mg, 1.51 mmol, 1 eq) in DCM (2 mL) was added TFA (2 mL) in one portion at 0 °C. The mixture was warmed and stirred at 25 °C for 1 hour. TLC (Ethyl acetate:Petroleum ether=1:1, Rf=0.2) indicated the starting material was consumed completely and one major new spot with larger polarity was detected. The mixture was diluted with $CH_2Cl_2$ (5 mL) and concentrated under reduced pressure to dryness to give 61c (200 mg, 80.5%) as a brown oil.

Step 4:

To a solution of 61c (200 mg, 1.22 mmol, 1 eq) in $CCl_4$ (3 mL) was added NBS (216 mg, 1.22 mmol, 1 eq) in portions at 25 °C under a $N_2$ atmosphere. The mixture was heated and stirred at 80 °C for 1 h. LCMS showed the starting material was almost consumed and the desired product mass was observed as a major peak. After cooling, a saturated aqueous sodium thiosulfate solution (10 mL) was added drop-wise to the above mixture and stirred for another 10 min. The aqueous layer was extracted with ethyl acetate (20 mL×3). The combined organic phases were washed with brine (20 mL), dried over anhydrous $Na_2SO_4$, filtered and concentrated under reduced pressure to dryness to provide crude 61d (290 mg, 97.9%) as a brown solid, which was used in the next step without further purification.

Step 5:

To a solution of 61d (290 mg, 1.19 mmol, 1 eq) in 1,4-dioxane (10 mL) was added $Boc_2O$ (781 mg, 3.58 mmol, 3 eq) and $Et_3N$ (362 mg, 3.58 mmol, 3 eq) in one portion at 25 °C. Then the mixture was heated and stirred at 120 °C for 2 h. TLC (Petroleum ether:Ethyl acetate=3:1) indicated the starting material was consumed completely and a new spot was observed. After cooling, the mixture was concentrated under reduced pressure to a residue. The residue was purified by silica gel column chromatography (Petroleum ether/Ethyl acetate=20/1 to 3/1) to afford 61e (200 mg, 48.9%) as a yellow oil.

Step 6:

To a mixture of 61e (200 mg, 583 umol, 1 eq) and 3-fluoro-5-(4,4,5,5-tetramethyl-1,3,2-dioxaborolan-2-yl) pyridine (389 mg, 1.75 mmol, 3 eq) in 1,4-dioxane (10 mL) and water (1 mL) was added $Cs_2CO_3$ (474 mg, 1.46 mmol, 2.5 eq) and Pd(dppf)$Cl_2$ (42 mg, 58.3 umol, 0.1 eq) in one portion under a $N_2$ atmosphere. The system was degassed and recharged with nitrogen, repeated the process three times. The resulting mixture was heated and stirred at 120 °C for 1 h under $N_2$. TLC (Ethyl acetate:Petroleum ether=1:2) indicated the starting material was consumed completely and a new spot was observed. After cooling to room temperature, water (20 mL) was added and then extracted with ethyl acetate (30 mL×3). The combined organic phases were washed with water (20 mL), brine (20 mL), dried over anhydrous $Na_2SO_4$, filtered, and the filtrate was concentrated under reduced pressure to a residue. The residue was purified by silica gel column chromatography (Petroleum ether:Ethyl acetate=20:1 to 2:1) first followed by prep- HPLC (column: Nano-micro Kromasil C18 100*30 mm 5 um; mobile phase: [water (0.1% TFA)-ACN]; B %: 50%-65%, 10 min) to give 61f (70 mg, 33.5%) as a yellow oil.

Step 7:

To a solution of 61f (70 mg, 195 umol, 1 eq) in DCM (2 mL) was added TFA (2 mL) in one portion at 25 °C. Then the mixture was stirred at 25 °C for 0.5 h. TLC (Ethyl acetate:Petroleum ether=1:1) indicated the starting material was consumed completely and a new spot was observed. The reaction mixture was diluted with $CH_2Cl_2$ (10 mL) and concentrated under reduced pressure to dryness at a temperature below 10 °C. The residue was re-dissolved in $CH_2Cl_2$ (10 mL), treated with Amberlyst A21 (0.2 g) and stirred for another 0.5 hr. After filtering, the cake was washed with $CH_2Cl_2$ (5 mL×2) and the filtrate was concentrated under reduced pressure to dryness. The mixture was redissolved in MeCN (1 mL) and distilled $H_2O$ (2 mL) and then lyophilized to afford the titled product Ex.61 (38.5 mg, 76.2%) as a gray solid; $^1H$ NMR: 400 MHz $CDCl_3$, S 8.53-8.59 (m, 2H) 7.93-7.99 (m, 1H) 7.62 (d, J=1.6 Hz, 1H) 7.46-7.50 (m, 1H) 7.39-7.43 (m, 1H) 2.96-3.03 (m, 1H) 1.30 (d, J=6.8 Hz, 6H); LC-MS: m/z $[M+H]^+$=260.1.

Example 62: Preparation of 7-(5-fluoropyridin-3-yl)-2-hydroxy-3-isopropylcyclohepta-2,4,6-trien-1-one (Ex.62)

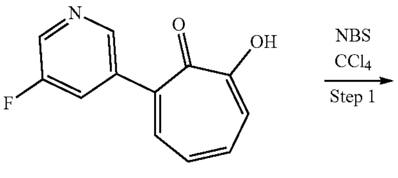

62a

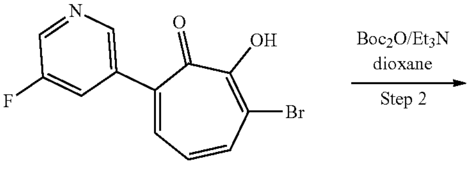

62b

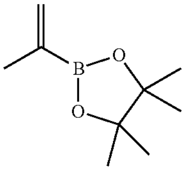

62d

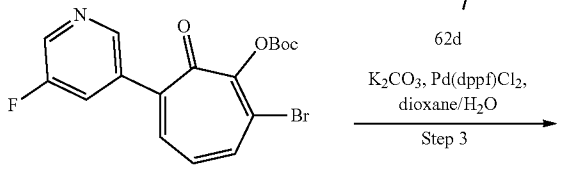

62c

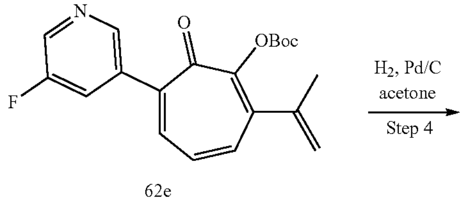

62e

-continued

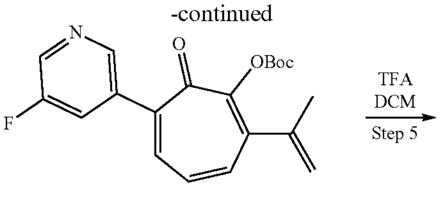

62f

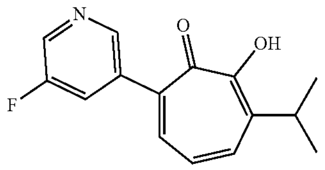

Ex. 62

Step 1:

To a solution of 62a (500 mg, 2.30 mmol, 1.00 eq) in $CCl_4$ (20 mL) NBS (410 mg, 2.30 mmol, 1.00 eq) was added at 20 °C. The reaction mixture was heated and stirred at 80 °C for 0.5 hr under $N_2$ atmosphere. LCMS showed 60% of desired compound was detected. After cooling to room temperature, the reaction mixture was poured into $H_2O$ (10 mL) and then extracted with ethyl acetate (30 mL×3). The combined organic layers were washed with brine (10 mL), dried over anhydrous $Na_2SO_4$ and concentrated under reduced pressure to give compound 62b (390 mg, crude) as a yellow solid.

Step 2:

To a mixture of 62b (390 mg, 1.32 mmol, 1.00 eq) and $(Boc)_2O$ (908 uL, 3.00 eq) in dioxane (15 mL) TEA (533 mg, 5.27 mmol, 4.00 eq) was added in one portion at 25 °C under $N_2$. The reaction mixture was heated and stirred at 118 °C for 30 min. TLC (Petroleum ether/Ethyl acetate=1/1, $R_f$ (material)=0.0, $R_f$(product)=0.5) showed the reaction was completed. The mixture was concentrated under reduced pressure to give a residue, which was purified by column chromatography ($SiO_2$, Petroleum ether/Ethyl acetate=78/22) to give compound 62c (503 mg, 1.27 mmol, 96.4% yield) as a red oil.

Step 3:

To a mixture of 62c (503 mg, 1.27 mmol, 1.00 eq), 62d (427 mg, 2.54 mmol, 2.00 eq) and $K_2CO_3$ (351 mg, 2.54 mmol, 2.00 eq) in dioxane (10 mL) and $H_2O$ (2.5 mL) Pd(dppf)$Cl_2$·$CH_2Cl_2$ (104 mg, 127 umol, 0.10 eq) was added under $N_2$, then the system was degassed and charged with nitrogen three times. The reaction mixture was heated to 118 °C and stirred for 0.5 hour. TLC (Petroleum ether/Ethyl acetate=1/1, $R_f$(material)=0.4, $R_f$(product)=0.2) showed the starting material was consumed completely. After cooling to room temperature, the reaction mixture was poured into $H_2O$ (100 mL) and then extracted with ethyl acetate (35 mL×3). The combined organic layers were washed with brine (50 mL), dried over anhydrous $Na_2SO_4$ and concentrated under reduced pressure to give a residue. The residue was purified by column chromatography ($SiO_2$, Petroleum ether/Ethyl acetate=79/21) to give compound 62e (290 mg, 811 umol, 63.9% yield) as a yellow oil.

Step 4:

To a solution of 62e (150 mg, 420 umol, 1.00 eq) in acetone (5 mL) Pd/C (10%, 150 mg) was added under Ar. The suspension was degassed under reduce pressure and purged with $H_2$ several times, then the reaction mixture was stirred under $H_2$ (15 psi) at 25 °C for 1 hour. LCMS showed the reaction was completed. The reaction mixture was filtered and concentrated under reduced pressure to give a residue. The residue was purified by prep-HPLC (TFA condition) to give compound 62f (14 mg, 39.0 umol, 9.28% yield) as a yellow oil.

Step 5:

To a solution of 62f (14 mg, 39.0 umol, 1.00 eq) in DCM (3 mL) TFA (0.75 mL) was added in one portion at 20 °C. The reaction mixture was stirred at 20 °C for 30 min. TLC (Petroleum ether/Ethyl acetate=1/1, $R_f$ (material)=0.5, $R_f$ (product)=0.0) showed the reaction was completed. The reaction mixture was concentrated under reduced pressure to afford the titled compound Ex.62 (14 mg, TFA salt) as a white solid. $^1H$ NMR: MeOD 400 MHz; δ ppm 1.31 (d, J=6.8 Hz, 6H) 3.71-3.81 (m, 1H) 7.16-7.30 (m, 1H) 7.59 (d, J=10.0 Hz, 1H) 7.67 (d, J=10.4 Hz, 1H) 7.97 (dd, J=9.6, 1.6 Hz, 1H) 8.48-8.63 (m, 2H); HPLC: MS: (M+1): 260.0

Example 63: Preparation of 4-(5-fluoro-4-methylpyridin-3-yl)-7-hydroxy-2-methylcyclohepta-2,4,6-trien-1-one (Ex.63)

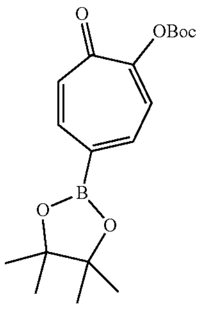

63a

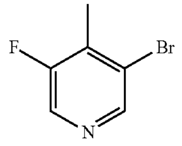

63b

Pd(dppf)$Cl_2$, $K_2CO_3$,
Dioxane/$H_2O$
Step 1

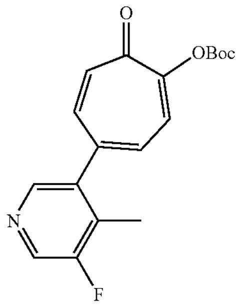

63c

1) TFA, DCM
2) base resin
Step 2

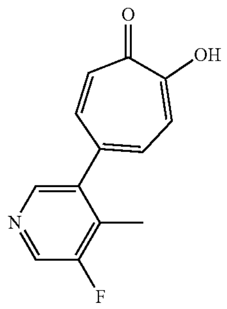

63d

NBS
$CCl_4$
Step 3

-continued

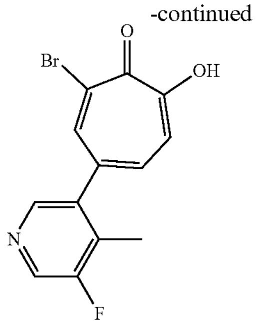

63e $(Boc)_2O$
TEA, dioxane
Step 4

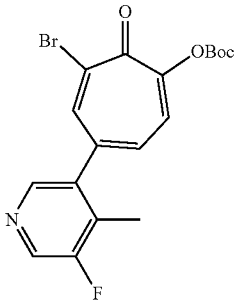

63F $MeB(OH_2)$
Pd(dppf)$Cl_2$, $K_2CO_3$
dioxane, $H_2O$
Step 5

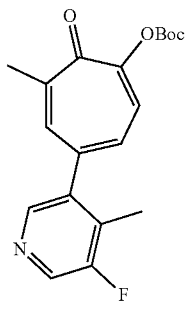

63g

TFA
DCM
Step 6

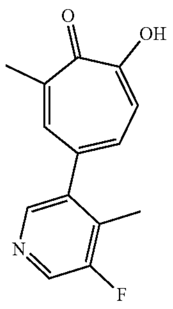

Ex. 63

Step 1:

To a mixture of 63a (1.00 g, 2.87 mmol, 1.00 eq), 63b (654 mg, 3.45 mmol, 1.20 eq) and $K_2CO_3$ (992 mg, 7.18 mmol, 2.50 eq) in 1,4-dioxane (10 mL) and $H_2O$ (2 mL) Pd(dppf)$Cl_2$·$CH_2Cl_2$ (234 mg, 287 umol, 0.10 eq) was added under $N_2$, then the system was degassed and charged with nitrogen three times. The reaction mixture was heated to 120 °C and stirred for 0.5 hour. LCMS showed the reaction was completed. After cooling to the room temperature, the mixture was filtered and concentrated in vacuo. The residue was purified by column chromatography ($SiO_2$, Petroleum ether/Ethyl acetate=100/1 to 3/1) to give 63c (760 mg, 2.29 mmol, 79.8% yield) as a yellow solid.

Step 2:

To a solution of 63c (760 mg, 2.29 mmol, 1.00 eq) in DCM (4 mL) TFA (2 mL) was added. The reaction mixture was stirred at 20 °C for 0.5 hr. LCMS showed the reaction was completed. The mixture was concentrated under reduced pressure to remove the solvent. Then the mixture was re-dissolved in $CH_2Cl_2$ (10 mL) and added Amberlyst A21 (0.1 g) and stirred for another 0.5 hr. After filtering, the filter cake was washed with $CH_2Cl_2$ (5 mL×2) and the filtrate was concentrated under reduced pressure to provide crude product 63d (500 mg, crude) as a yellow solid.

Step 3:

To a solution of 63d (500 mg, 2.16 mmol, 1.00 eq) in $CCl_4$ (6 mL) NBS (192 mg, 1.08 mmol, 0.50 eq) was added at 20 °C. The reaction mixture was heated to 80 °C and stirred for 0.5 hr. LCMS showed the reaction was completed. After cooling, the mixture was concentrated under reduced pressure to remove solvent to give 63e (760 mg, crude) as a yellow solid.

Step 4:

To a solution of 63e (760 mg, 2.45 mmol, 1.00 eq) in 1,4-dioxane, triethylamine (TEA, 9.80 mmol, 1.36 mL, 4.00 eq) and $Boc_2O$ (7.35 mmol, 1.69 mL, 3.00 eq) were added. The reaction mixture was heated to 120 °C and stirred for 0.5 hr. LCMS showed the reaction was completed. After cooling to the room temperature, the mixture was filtered and concentrated in vacuo to dryness. The residue was purified by column chromatography ($SiO_2$, Petroleum ether/Ethyl acetate=100/1 to 4/1) to give 63f (100 mg, 243 umol, 9.9% yield) as a pink oil.

Step 5:

To a mixture of 63f (100 mg, 243 umol, 1.00 eq), methylboronic acid (146 mg, 2.44 mmol, 10.0 eq) and $K_2CO_3$ (67.4 mg, 487 umol, 2.00 eq) in 1,4-dioxane (5 mL) and $H_2O$ (1 mL) $Pd(dppf)Cl_2 \cdot CH_2Cl_2$ (20 mg, 24.4 umol, 0.1 eq) was added under $N_2$, then the system was degassed and charged with nitrogen three times. The reaction mixture was heated to 120 °C and stirred for 0.5 hr. LCMS showed the reaction was completed. After cooling to room temperature, the mixture was filtered and concentrated in vacuo. Then the residue was purified by column chromatography ($SiO_2$, Petroleum ether/Ethyl acetate=100/1 to 9/1) to give 63g (40 mg, 115 umol, 47.5% yield) as a yellow oil.

Step 6:

To a solution of 63g (40 mg, 115 umol, 1.00 eq) in DCM (1 mL) TFA (0.5 mL) was added. The mixture was stirred at 20 °C for 0.5 hr. The reaction mixture was diluted with $CH_2Cl_2$ (10 mL) and concentrated under reduced pressure to dryness. The residue was washed with n-hexane (10 mL) to afford the titled product Ex.63 (12 mg, TFA salt) as a yellow solid. $^1H$ NMR: MeOD 400 MHz; δ=8.53 (s, 1H), 8.37 (s, 1H), 7.66 (s, 1H), 7.44-7.34 (m, 2H), 2.48 (s, 3H), 2.30 (d, J=2.4 Hz, 3H); HPLC: LCMS: (M+1): 246

Example 64: Preparation of 4-(5-fluoro-4-methylpyridin-3-yl)-7-hydroxy-2-isopropylcyclohepta-2,4,6-trien-1-one (Ex.64)

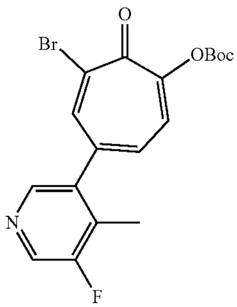

64a

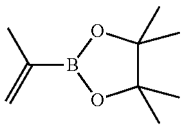

64b

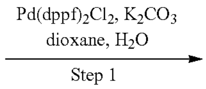

-continued

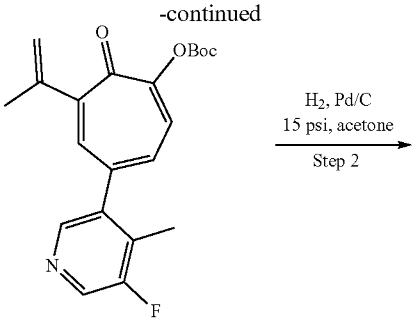

64c

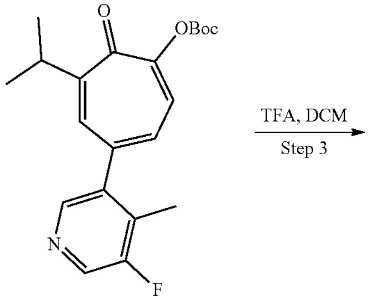

64d

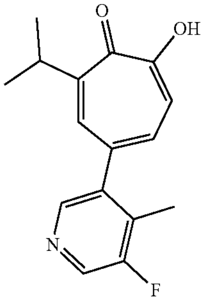

Ex. 64

Step 1:

To a mixture of 64a (200 mg, 488 umol, 1.00 eq), 64b (98 mg, 585 umol, 1.20 eq) and $K_2CO_3$ (135 mg, 975 umol, 2.00 eq) in 1,4-dioxane (0.5 mL) and $H_2O$ (0.1 mL) Pd(dppf) $Cl_2 \cdot CH_2Cl_2$ (40 mg, 48.8 umol, 0.10 eq) was added at 25 °C under $N_2$. The system was degassed and then charged with nitrogen three times. The reaction mixture was heated and stirred at 120 °C for 0.5 hr. TLC (Petroleum ether/Ethyl acetate=1/1, Rf=0.3) showed the starting material was consumed completely and one new spot observed. After cooling to room temperature, water (30 mL) was added and the reaction mixture was extracted with ethyl acetate (40 mL×3). The combined organic layers were washed with brine (30 mL), dried over anhydrous $Na_2SO_4$, filtered and concentrated under reduced pressure to give a residue. The residue was purified by column chromatography ($SiO_2$, Petroleum ether/Ethyl acetate=2/1) to give compound 64c (35 mg, 94.2 umol, 19.3% yield) as a yellow oil.

Step 2:

To a solution of 64c (35 mg, 94.2 umol, 1.00 eq) in acetone (2 mL) Pd/C (10%, 50 mg) was added at 20 °C. The suspension was degassed under reduce pressure and purged with $H_2$ several times. The mixture was stirred under $H_2$ (15 psi) at 20 °C for 15 min. LCMS showed the reaction was completed. The mixture was filtered through a pad of Celite and the filter cake was washed with acetone (5 mL×3). The filtrate was concentrated under reduced pressure to dryness. The residue was purified by prep-HPLC (TFA condition) to give compound 64d (10 mg, 26.8 umol, 28.4% yield) as a yellow oil.

Step 3:

To a solution of 64d (18 mg) in DCM (1 mL) TFA (0.2 mL) was added in one portion at 20 °C. The reaction mixture was stirred at 20 °C for 0.5 hr. LCMS showed the reaction was completed. The reaction mixture was diluted with $CH_2Cl_2$ (10 mL) and concentrated under reduced pressure to dryness to afford the titled product Ex.64 (12 mg, TFA salt) as a yellow oil.

$^1$H NMR: ET22755-309-P1B MeOD 400 MHz

δ=8.53 (d, J=1.2 Hz, 1H), 8.38 (s, 1H), 7.51 (d, J=1.2 Hz, 1H), 7.42-7.35 (m, 2H), 3.77 (td, J=6.8, 13.6 Hz, 1H), 2.31 (d, J=2.0 Hz, 3H), 1.26 (d, J=6.8 Hz, 6H)

HPLC: ET22755-309-P1A2

LCMS: (M+1): 274

Example 65: Preparation of 5-(4-fluorophenoxy)-2-hydroxycyclohepta-2,4,6-trien-1-one (Ex.65)

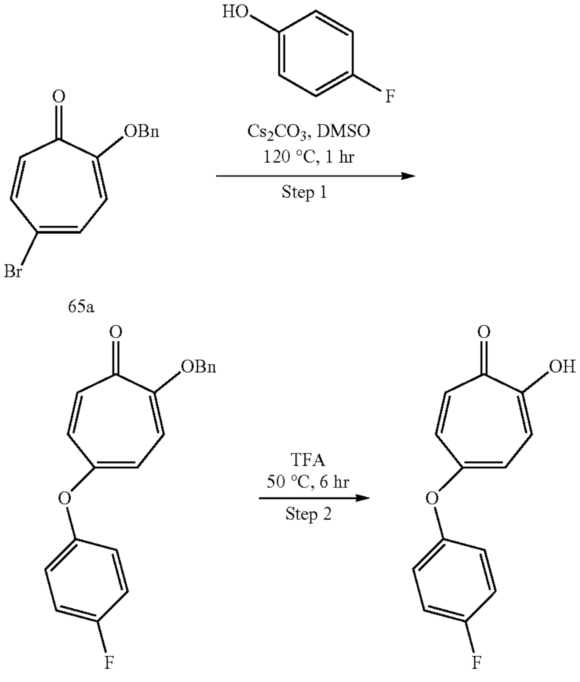

65a 65b 65c

Step 1:

To a mixture of 65a (0.30 g, 1.03 mmol, 1.00 eq) and 4-fluorophenol (347 mg, 3.09 mmol, 3.00 eq) in DMSO (6 mL) $Cs_2CO_3$ (1.34 g, 4.12 mmol, 4.00 eq) was added in one portion at 25 °C under $N_2$. The mixture was heated and stirred at 120 °C for 1 hour. TLC (Petroleum ether:Ethyl acetate=10:1, $R_f$ (material)=0.4, $R_f$(product)=0.2) showed the reaction was completed. After cooling to the room temperature, the reaction mixture was diluted with water (20 mL) and then extracted with ethyl acetate (20 mL×3). The combined organic layers were washed with water (20 mL), brine (20 mL), dried over anhydrous $Na_2SO_4$, filtered and concentrated under reduced pressure to give a residue. The residue was purified by column chromatography ($SiO_2$, Petroleum ether/Ethyl acetate=100/1 to 74/26) to give 65b (92 mg, 285 umol, 27.7% yield) as a yellow solid.

Step 2:

65b (92.0 mg, 285 umol, 1.00 eq) was added into TFA (4 mL) at 25 °C. The mixture was heated and stirred at 50 °C for 6 hours. LCMS showed the reaction was completed. After cooling to room temperature, the reaction mixture was diluted with DCM (20 mL) and concentrated under reduced pressure to give a residue. The residue was purified by prep-HPLC (TFA condition) to afford the titled product Ex.65 (66 mg, 284 umol, 99.6% yield) as a yellow solid. $^1$H NMR: MEOD 400 MHz; δ ppm 7.01-7.08 (m, 2H) 7.11-7.18 (m, 2H) 7.23 (s, 2H) 7.29-7.36 (m, 2H); HPLC: MS: (M+1): 233.1

Example 66: Preparation of 3-(4-fluorophenoxy)-2-hydroxycyclohepta-2,4,6-trien-1-one (Ex.66)

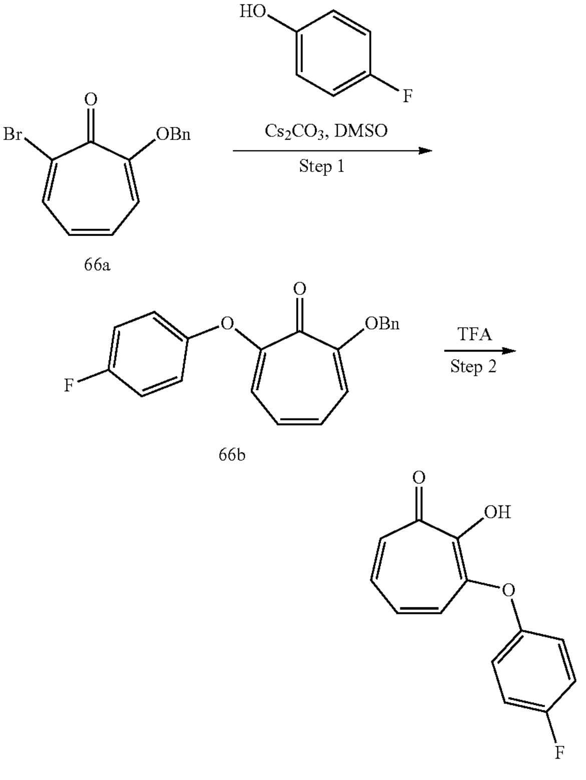

66a 66b Ex. 66

Step 1:

To a mixture of 66a (100 mg, 343 umol, 1.00 eq) and 4-fluorophenol (115 mg, 1.03 mmol, 3.00 eq) in DMSO (5 mL) $Cs_2CO_3$ (447 mg, 1.37 mmol, 4.00 eq) was added in one portion at 25 °C. The mixture was heated to 120 °C and stirred for 1 hour. LCMS showed material was consumed completely and one main peak with desired mass was detected. After cooling, the reaction mixture was poured into $H_2O$ (10 mL) and then extracted with EtOAc (20 mL×3). The combined organic layers were washed with brine (10 mL), dried over $Na_2SO_4$, filtered and concentrated under reduced pressure to give a residue. The residue was purified by column chromatography ($SiO_2$, Petroleum ether/Ethyl acetate=100/0 to 5/1) to give 66b (84 mg, 260 umol, 25.2% yield) as a yellow solid.

Step 2:

A solution of 66b (112 mg, 347 umol, 1.00 eq) in TFA (2 mL) was heated to 50 °C and stirred for 6 hours. LCMS showed the material was consumed completely and one main peak with desired mass was detected. The reaction mixture was diluted with DCM (20 mL) and concentrated under reduced pressure to dryness. The residue was slurried by n-hexane (10 mL) to afford the titled product Ex.66 (49 mg, 211 umol, 60.7% yield) as a yellow solid. $^1H$ NMR: MeOD 400 MHz; δ ppm 6.99-7.08 (m, 3H) 7.09-7.16 (m, 2H) 7.35-7.40 (m, 2H) 7.48 (d, J=10.0 Hz, 1H); HPLC: MS: (M+): 232.05

Example 67: Preparation of 3-(2,4-difluorophenoxy)-2-hydroxycyclohepta-2,4,6-trien-1-one (Ex.67)

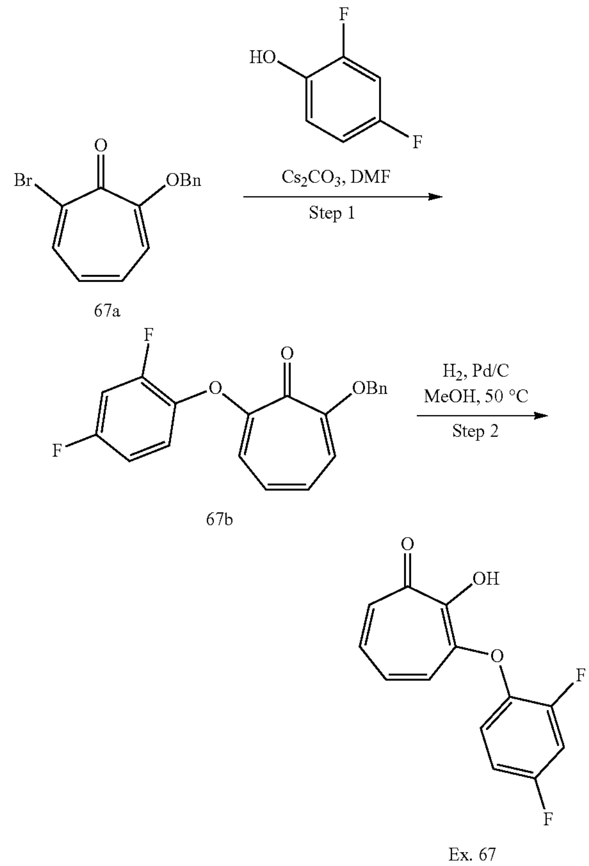

67a

67b

Ex. 67

Step 1:

To a mixture of 67a (3 g, 13.0 mmol, 1.00 eq) in DMF (dimethylformamide, 30 mL) $Cs_2CO_3$ (12.7 g, 39.1 mmol, 3.00 eq) and 2,4-difluorophenol (2.54 g, 19.6 mmol, 1.50 eq) was added at 25 °C. The reaction mixture was stirred at 25 °C for 2 hr. TLC (Petroleum ether:Ethyl acetate=1:1, Rf=0.3) showed the starting material was consumed completely and a new spot observed. The reaction mixture was diluted with water (60 mL) and then extracted with ethyl acetate (60 mL×3). The combined organic layers were washed with water (30 mL), brine (30 mL), dried over anhydrous $Na_2SO_4$, filtered and concentrated under reduced pressure to give a residue. The residue was purified by column chromatography ($SiO_2$, Petroleum ether/Ethyl acetate=1/0 to 3/1) to give 67b (4.00 g, 11.8 mmol, 90.2% yield) as a white solid.

Step 2:

To a solution of 67b (3 g, 8.82 mmol, 1.00 eq) in MeOH (40 mL) Pd/C (75 mg, 8.82 mmol, 10% purity, 1.00 eq) was added under $N_2$ atmosphere. The system was degassed and then charged with $H_2$ three times. The mixture was heated and stirred under $H_2$ (15 psi) at 50 °C for 2 hrs. TLC (Petroleum ether:Ethyl acetate=1:1, Rf=0.0) showed the starting material was consumed completely and a new spot observed. After cooling, the mixture was filtered through a pad of Celite and the filter cake was washed with MeOH (10 mL×3). The filtrate was concentrated under reduced pressure to dryness. The residue was purified by re-crystallization from acetone (40 mL) to afford the titled product Ex.67 (1.75 g, 6.99 mmol, 79.4% yield) as a yellow solid. $^1$HNMR: $CDCl_3$ 400 MHz Example 68: Preparation of 3-(2,6-difluorophenyl)-2-hydroxycyclohepta-2,4,6-trien-1-one (Ex.68)

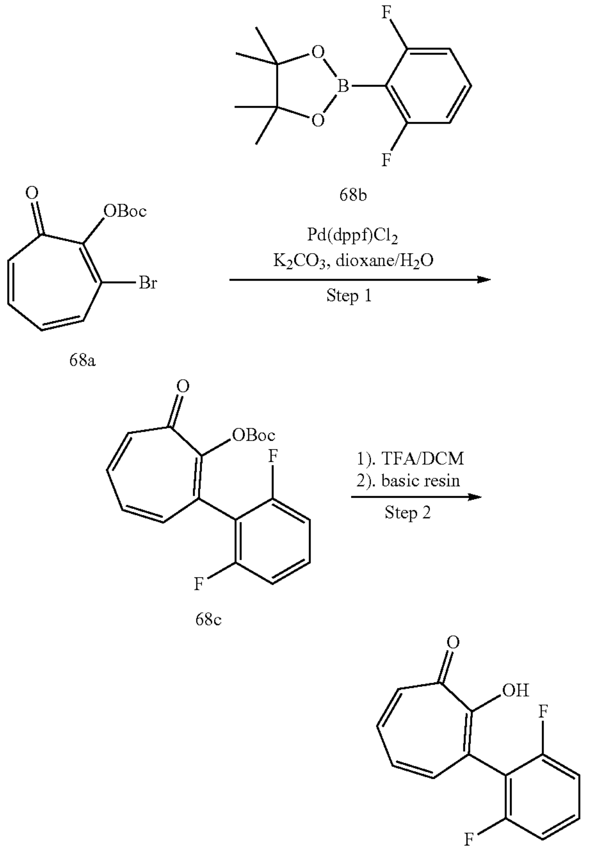

68a

68b

68c

Ex. 68

Step 1:

To a mixture of 68a (200 mg, 664 umol, 1.00 eq), 68b (419 mg, 2.66 mmol, 4.00 eq) and $Cs_2CO_3$ (649 mg, 1.99 mmol, 3.00 eq) in 1,4-dioxane (10 mL) and water (1 mL) $Pd(dppf)Cl_2·CH_2Cl_2$ (54 mg, 66.4 umol, 0.10 eq) was added under under $N_2$. The system was degassed and then charged with nitrogen three times. The mixture was heated and stirred at 120 °C for 2 hrs. TLC (Ethyl Acetate/Petroleum Ether=1/3, $R_f$=0.4) indicated the material was consumed completely and one major spot detected. After cooling, the mixture was concentrated in vacuo to dryness, which was purified by column chromatography ($SiO_2$, Petroleum ether/Ethyl acetate=100/1 to 3/1, $R_f$=0.4) and then purified by prep-HPLC (TFA condition) again to get 68c (100 mg, 299 umol, 45.0% yield) as a yellow oil.

Step 2:

To a solution of 68c (100 mg, 299 umol, 1.00 eq) in DCM (2 mL) TFA (0.5 mL) was added. Then the reaction mixture was stirred at 25 °C for 0.5 hr. TLC (Ethyl Acetate/Petroleum Ether=1/1, $R_f$=0.2) showed material was consumed completely and one major new spot with large polarity detected. The reaction mixture was diluted with $CH_2Cl_2$ (10 mL) and concentrated under reduced pressure to dryness below 10 °C. Then the mixture was re-dissolved in $CH_2Cl_2$ (5 mL) and added Amberlyst A21 (0.1 g) and stirred at 25 °C for another 0.5 hr. After filtering, the cake was washed with $CH_2Cl_2$ (5 mL×2) and the filtrate was concentrated under reduced pressure to afford the titled product Ex.68 (50 mg, 213 umol, 71.3% yield) as a yellow solid. $^1$H NMR (400 MHz, METHANOL-d4) δ ppm 7.52-7.60 (m, 2H) 7.41-7.50 (m, 2H) 7.16 (t, J=10 Hz, 1H) 7.03-7.10 (m, 2H); LCMS (Rt=1.54 min): [M+1]: 235; HPLC (Rt=2.70 min)

Example 69: Preparation of 3-(6-fluoropyridin-2-yl)-2-hydroxycyclohepta-2,4,6-trien-1-one (Ex.69)

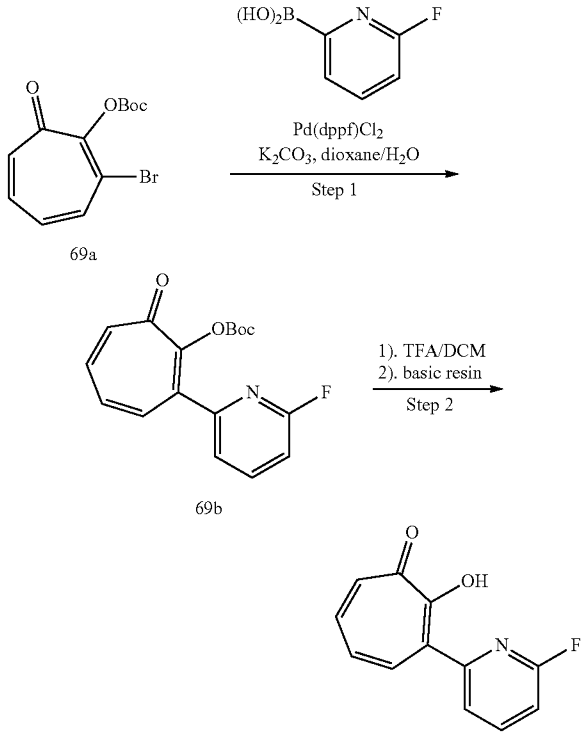

69a

69b

Ex. 69

Step 1:

To a solution of 69a (0.5 g, 1.66 mmol, 1.00 eq) in dioxane (10 mL) and $H_2O$ (2 mL) $K_2CO_3$ (573 mg, 4.15 mmol, 2.50 eq), (6-fluoro-2-pyridyl)boronic acid (351 mg, 2.49 mmol, 1.50 eq) and $Pd(dppf)Cl_2 \cdot CH_2Cl_2$ (136 mg, 166.04 umol, 0.10 eq) were added. The system was degassed and charged with nitrogen three times. The mixture was heated and stirred at 118 °C for 16 hrs under $N_2$ atmosphere. TLC (Petroleum ether:Ethyl acetate=3:1) showed the starting material was consumed completely and a new spot observed. The reaction mixture was quenched by addition of $H_2O$ (50 mL) at 0 °C, and then extracted with EtOAc (50 mL×3). The combined organic phases were washed with brine (50 mL), dried over anhydrous $Na_2SO_4$, filtered and concentrated under reduced pressure to give a residue. The residue was purified by column chromatography (SiO2, Petroleum ether/Ethyl acetate=100/0 to 3/1) to give 69b (450 mg, 85.4% yield) as a yellow oil.

Step 2:

To a solution of 69b (50 mg) in DCM (3 mL) TFA (1 mL) was added at 25 °C, and the mixture was stirred for 30 min. TLC (Petroleum ether:Ethyl acetate=3:1) showed the starting material was consumed completely and a new spot observed. The reaction mixture was diluted with $CH_2Cl_2$ (10 mL) and concentrated under reduced pressure to dryness below 10 °C. Then the mixture was re-dissolved in $CH_2Cl_2$ (5 mL) and added Amberlyst A21 (0.1 g) and stirred at 25 °C for another 0.5 hr. After filtering, the cake was washed with $CH_2Cl_2$ (5 mL×2) and the filtrate was concentrated under reduced pressure to afford the titled product Ex.69 (14 mg, 40.3% yield, 98.6% purity) as a yellow solid. $^1$H NMR: METHANOL 400 MHz; δ ppm 7.07 (dd, J=8.4, 2.8 Hz, 1H) 7.16-7.27 (m, 1H) 7.43 (s, 1H) 7.52 (d, J=10.0 Hz, 1H) 7.88 (br d, J=2.4 Hz, 1H) 8.00 (d, J=8.8 Hz, 2H); HPLC: MS: (M+1):218.2

Example 70: Preparation of 3-(4-fluoropyridin-2-yl)-2-hydroxycyclohepta-2,4,6-trien-1-one (Ex.70)

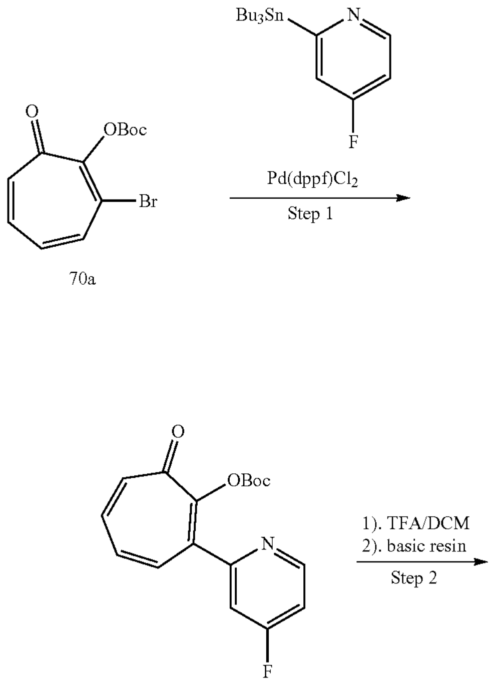

70a

70b

-continued

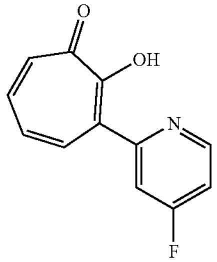

Ex. 70

Step 1:

To a solution of 70a (0.2 g, 664 umol, 1.00 eq) in toluene (3 mL) tributyl-(4-fluoro-2-pyridyl)stannane (256 mg, 664 umol, 1.00 eq), CuI (51 mg, 266 umol, 0.40 eq) and Pd(dppf)$Cl_2$·$CH_2Cl_2$ (108 mg, 133 umol, 0.20 eq) were added. The system was degassed and then charged with nitrogen three times. The mixture was heated and stirred at 120 °C for 2.5 hrs under $N_2$. LC-MS showed the starting material was consumed completely and one main peak with desired mass was detected. After cooling to room temperature, water (150 mL) was added and then extracted with ethyl acetate (50 mL×3). The combined organic phases were washed with brine (50 mL), dried over anhydrous $Na_2SO_4$. After filtering, the filtrate was concentrated under reduced pressure to dryness. The residue was purified by column chromatography ($SiO_2$, Petroleum ether/Ethyl acetate=100/0 to 30/10) to afford 70b (80 mg, 37.9% yield) as a yellow solid.

Step 2:

To a solution of 70b (20 mg) in DCM (2 mL) TFA (1 mL) was added in one portion at 25 °C. The mixture was stirred at 25 °C for 20 min. TLC (Petroleum ether:Ethyl acetate=1:1) showed the starting material was consumed completely and a new spot observed. The reaction mixture was diluted with $CH_2Cl_2$ (10 mL) and concentrated under reduced pressure to dryness below 10 °C. Then the mixture was re-dissolved in $CH_2Cl_2$ (5 mL) and added Amberlyst A21 (0.1 g) and stirred at 25 °C for another 0.5 hr. After filtering, the cake was washed with $CH_2Cl_2$ (5 mL×2) and the filtrate was concentrated under reduced pressure to afford the titled product Ex.70 (11 mg, 80.1% yield) as a yellow solid. $^1$H NMR: 400 MHz; δ ppm 7.08 (dd, J=8.0, 5.6 Hz, 1H) 7.15-7.25 (m, 1H) 7.40-7.55 (m, 2H) 7.84 (dd, J=10.4, 2.4 Hz, 1H) 8.20 (d, J=10.4 Hz, 1H) 8.65-8.79 (m, 1H); HPLC: MS: (M+1): 218

Example 71: Preparation of 3-(3-fluoropyridin-2-yl)-2-hydroxycyclohepta-2,4,6-trien-1-one (Ex.71)

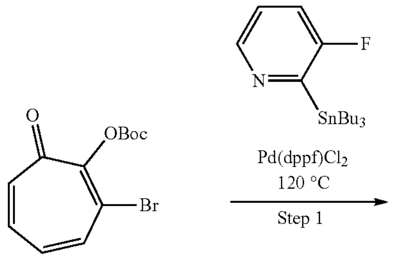

71a

-continued

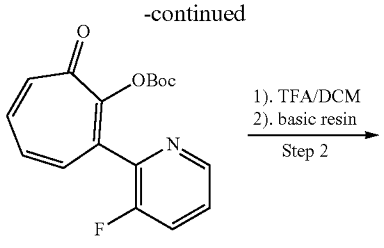

71b

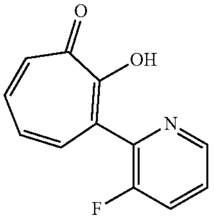

Ex. 71

Step 1:

To a solution of 71a (0.4 g, 1.33 mmol, 1 eq) in toluene (5 mL) tributyl-(3-fluoro-2-pyridyl)stannane (513 mg, 1.33 mmol, 1 eq), CuI (101 mg, 531.33 umol, 0.4 eq) and Pd(dppf)$Cl_2$·$CH_2Cl_2$ (217 mg, 266 umol, 0.20 eq) were added. The system was degassed and then charged with nitrogen three times. The mixture was heated and stirred at 120 °C for 2.5 hr under $N_2$ atmosphere. LC-MS showed the starting material was consumed completely and one main peak with desired mass was detected. After cooling, the reaction mixture was filtered and concentrated under reduced pressure to give a residue. The residue was purified by prep-HPLC (TFA condition, column: Phenomenex Luna C18 100*30 mm*5 um; mobile phase: [water (0.1% TFA)-ACN]; B %: 20%-50%, 10 min) to give 71b (99 mg, 23.5% yield) as a yellow solid.

Step 2:

To a solution of 71b (20 mg) in DCM (2 mL) TFA (1 mL) was added in one portion at 25 °C. The mixture was stirred at 25 °C for 20 min. TLC (Petroleum ether:Ethyl acetate=1:1) showed the starting material was consumed completely and a new spot observed. The reaction mixture was diluted with $CH_2Cl_2$ (10 mL) and concentrated under reduced pressure to dryness below 10 °C. Then the mixture was re-dissolved in $CH_2Cl_2$ (5 mL) and added Amberlyst A21 (0.1 g) and stirred at 25 °C for another 0.5 hr. After filtering, the cake was washed with $CH_2Cl_2$ (5 mL×2) and the filtrate was concentrated under reduced pressure to afford the titled product Ex.71 (11 mg, 78.3% yield, 97.4% purity) as a yellow solid. $^1$H NMR: CDCl3 400 MHz; δ ppm 7.11-7.20 (m, 1H) 7.41 (dd, J=8.4, 4.0 Hz, 1H) 7.44-7.57 (m, 3H) 7.75 (d, J=10.0 Hz, 1H) 8.51-8.59 (m, 1H); HPLC: MS: (M+1): 218

Example 72: Preparation of 3-(5-fluoropyridin-2-yl)-2-mercaptocyclohepta-2,4,6-trien-1-one (Ex.72)

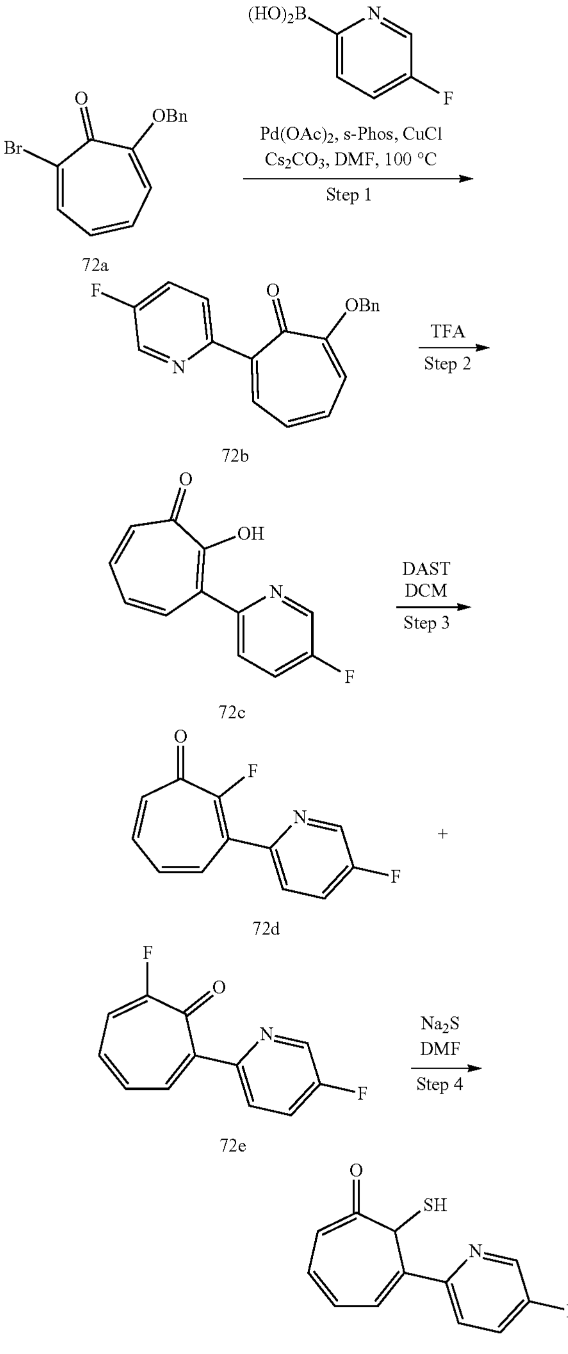

Ex. 72

Step 1:

To a mixture of 72a (2.8 g, 9.62 mmol, 1.00 eq) and (5-fluoro-2-pyridyl)boronic acid (2.03 g, 14.4 mmol, 1.50 eq) in DMF (25 mL) CuCl (952 mg, 9.62 mmol, 1.00 eq), s-Phos (1.58 g, 3.85 mmol, 0.40 eq), $Cs_2CO_3$ (12.5 g, 38.4 mmol, 4.00 eq) and $Pd(OAc)_2$ (216 mg, 962 umol, 0.10 eq) were added in one portion at 25 °C under $N_2$. The system was degassed and then charged with nitrogen three times. The mixture was heated and stirred at 100 °C for 1 hour. TLC (petroleum ether:ethyl acetate=1:1, $R_f$=0.5) indicated 72a was consumed completely and one new spot formed. The reaction was clean according to TLC. After cooling, the reaction mixture was quenched by addition of $H_2O$ (30 mL) at 25 °C, and then extracted with EtOAc (20 mL×3). The combined organic layers were washed with brine (20 mL), dried over anhydrous $Na_2SO_4$, filtered and concentrated under reduced pressure to give a residue. The residue was purified by column chromatography ($SiO_2$, Petroleum ether/Ethyl acetate=100/1 to 30/1) to give 72b (600 mg, 6.77% yield) as a yellow solid.

Step 2:

A mixture of 72b (600 mg, 1.95 mmol, 1.00 eq) in TFA (5 mL) was heated and stirred at 50 °C for 1 hr under $N_2$. TLC (petroleum ether:ethyl acetate=3:1, $R_f$=0.4) showed 72b was consumed completely and desired mass was detected. The reaction mixture was diluted with DCM (15 mL) and concentrated under reduced pressure to give a residue. The crude product was purified by re-crystallization from MeOH (3 mL) at 15 °C to give 72c (360 mg, 84.9% yield) as a yellow solid.

Step 3:

To a mixture of 72c (360 mg, 1.66 mmol, 1.00 eq) in DCM (4 mL) was added DAST (802 mg, 4.97 mmol, 3.00 eq) in one portion at 0 °C under $N_2$. The mixture was stirred at 20 °C for 16 hours. LC-MS showed 72c was consumed completely and one main peak with desired mass was detected. The reaction was quenched by $NaHSO_4$ slowly and then extracted with DCM (20 mL×5). The combined organic phases were washed with brine (10 mL), dried over anhydrous $Na_2SO_4$, filtered and concentrated in vacuo to dryness. The residue was purified by prep-HPLC (TFA condition) to give 72d and 72e (235 mg, 64.7% yield) as a yellow solid.

Step 4:

To a solution of 72d (175 mg, 798 umol, 1.00 eq) in DMF (8 mL) was added $Na_2S$ (187 mg, 2.40 mmol, 3.00 eq) in one portion at 15 °C. The mixture was stirred at 15 °C for 20 min. LC-MS showed the reactant was consumed completely and one main peak with desired mass was detected. The reaction mixture was quenched by addition of HCl (1M, 10 mL) at 15 °C, and then diluted with $H_2O$ (10 mL) and extracted with EtOAc (10 mL×4). The combined organic layers were washed with brine (10 mL), dried over anhydrous $Na_2SO_4$, filtered and concentrated under reduced pressure to give a residue. The residue was purified by prep-HPLC (TFA condition) to afford the titled product Ex.72 (20 mg, 10.7% yield) as a yellow solid. $^1H$ NMR: 400 MHz; 1H NMR (400 MHz, METHANOL-d4) δ ppm 7.40-7.49 (m, 1H) 7.53-7.58 (m, 1H) 7.63-7.68 (m, 3H) 7.69-7.76 (m, 1H) 8.52 (d, J=2.4 Hz, 1H); HPLC: MS (M+H): 234.1

Example 73: Preparation of 3-(5-chloropyridin-2-yl)-2-mercaptocyclohepta-2,4,6-trien-1-one (Ex.73)

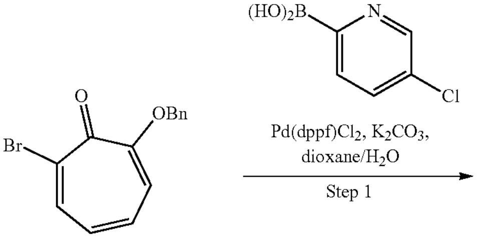

73a

-continued

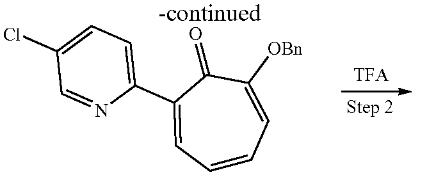

73b

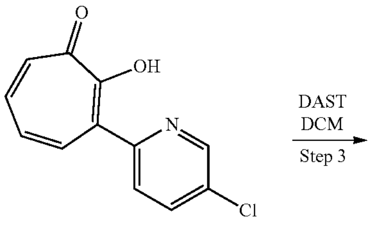

73c

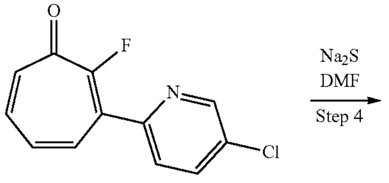

73d

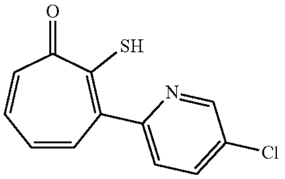

Ex. 73

Step 1:

To a solution of 73a (1.50 g, 5.15 mmol, 1.00 eq) in dioxane (3 mL) and $H_2O$ (0.6 mL) $K_2CO_3$ (1.42 g, 10.3 mmol, 2.00 eq), (5-chloro-2-pyridyl)boronic acid (973 mg, 6.18 mmol, 1.20 eq) and Pd(dppf)$Cl_2$·$CH_2Cl_2$ (421 mg, 515 umol, 0.10 eq) were added under $N_2$. The system was degassed and then charged with nitrogen three times. The mixture was heated and stirred at 118 °C for 0.5 hr under $N_2$. TLC (Petroleum ether:Ethyl acetate=3:1) indicated the starting material was consumed completely and one new spot formed. After cooling, the reaction mixture was diluted with $H_2O$ (30 mL) and extracted with EtOAc (30 mL×3). The combined organic layers were washed with brine (30 mL), dried over $Na_2SO_4$, filtered and concentrated under reduced pressure to give a residue. The residue was purified by column chromatography ($SiO_2$, Petroleum ether/Ethyl acetate=I/O to 3/1) to give 73b (70.0 mg, 4.20% yield) as a yellow solid.

Step 2:

To a solution of 73b (0.20 g, 618 umol, 1 eq) TFA (1 mL) was added in one portion at 25 °C. The mixture was heated and stirred at 50 °C for 2 hr. TLC (Petroleum ether:Ethyl acetate=3:1) showed the starting material was consumed completely and a new spot observed. The reaction mixture was diluted with sat.$NaHCO_3$.aq (10 mL) and then extracted with DCM (30 mL×3). The combined organic layers were washed with brine (10 mL), dried over $Na_2SO_4$, filtered and concentrated under reduced pressure to give 73c (150 mg, crude) as a yellow solid.

Step 3:

To a solution of 73c (80 mg, 342 umol, 1.00 eq) in DCM (5 mL) DAST (83.0 mg, 514 umol, 1.50 eq) was added dropwise at 0 °C. The mixture was stirred at 25 °C for 2 hrs. LC-MS showed the starting material was consumed completely and one main peak with desired mass was detected. The reaction was quenched by $NaHSO_4$ slowly and then extracted with DCM (20 mL×5). The combined organic phases were washed with brine (10 mL), dried over anhydrous $Na_2SO_4$, filtered and concentrated in vacuo to dryness to give 73d (100 mg, crude) as a brown solid.

Step 4:

To a solution of 73d (0.20 g, 849 umol, 1.00 eq) in DMF (2 mL) $Na_2S$ (199 mg, 2.55 mmol, 3 eq) in DMF (2 mL) was added in one portion at 25 °C. The mixture was stirred at 25 °C for 0.5 hr. LC-MS showed the starting material was consumed completely and one main peak with desired mass was detected. The reaction mixture was quenched by addition of HCl (1M, 10 mL) at 15 °C, and then diluted with $H_2O$ (10 mL) and extracted with EtOAc (10 mL×4). The combined organic layers were washed with brine (10 mL), dried over anhydrous $Na_2SO_4$, filtered and concentrated under reduced pressure to give a residue. The residue was purified by prep-HPLC (TFA condition; column: Phenomenex Luna C18 100*30 mm*5 um; mobile phase: [water (0.1% TFA)-ACN]; B %: 50%-60%, 10 min) to afford the titled product Ex.73 (12.0 mg, 5.66% yield) as a yellow solid. $^1$HNMR: CDCl3 400 Hz; δ 7.44 (br dd, J=10.0, 5.60 Hz, 1H) 7.51-7.61 (m, 2H) 7.64 (d, J=4.8 Hz, 2H) 7.92 (br d, J=8.4 Hz, 1H) 8.59 (s, 1H); HPLC: MS: (M+1): 251

Example 74: Preparation of 5-(2-(3-fluoro-6-(2-hydroxy-3-oxocyclohepta-1,4,6-trien-1-yl)pyridin-2-yl)ethyl)thiophen-2(5H)-one (Ex.74)

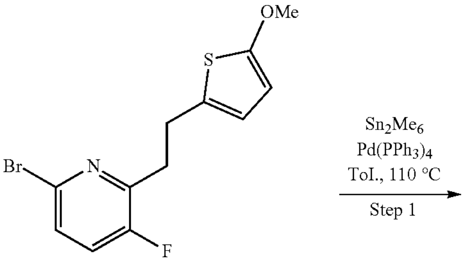

74a

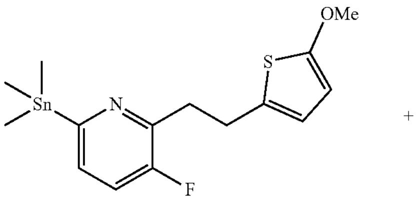

74b

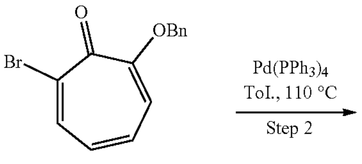

74c

-continued

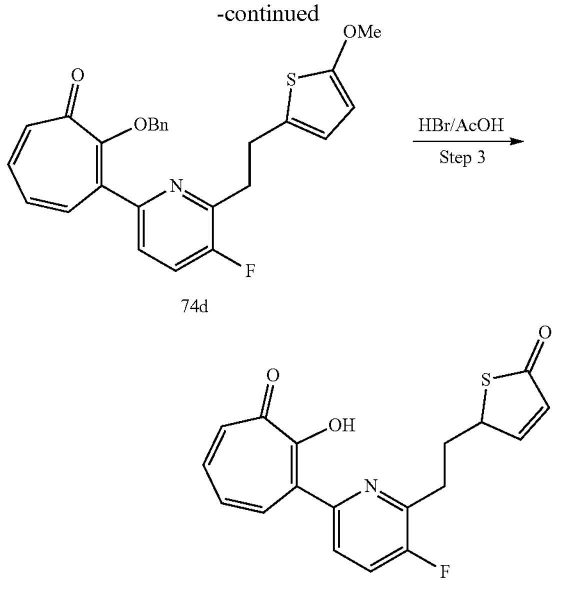

74d

Ex. 74

Step 1:

To a solution of 74a (500 mg, 1.58 mmol, 1.00 eq) in toluene (10 mL) trimethyl(trimethylstannyl)stannane (518 mg, 1.58 mmol, 1.00 eq) and $Pd(PPh_3)_4$ (190 mg, 164 umol, 0.1 eq) were added at 25 °C under $N_2$. Then the mixture was heated to 110 °C and stirred for 1 h under $N_2$. LCMS showed the starting material was consumed and desired MS was found. After cooling to 20 °C, the mixture in solvent was used for the next step.

Step 2:

To a solution of 74b (600 mg, 1.50 mmol, 1.00 eq) and 74c (1.31 g, 4.50 mmol, 3.00 eq) in toluene (10 mL) $Pd(PPh_3)_4$ (173 mg, 150 umol, 0.10 eq) was added at 25 °C under $N_2$. The suspension was degassed under vacuum and purged with $N_2$ three times. Then the mixture was heated to 110 °C and stirred for 16 h under $N_2$. LCMS showed the starting material was consumed and the desired MS was observed. After cooling, a saturated solution of $NH_4Cl$ (10 mL) was added into the mixture and extracted with EtOAc (20 mL×3). Then the combined organic phases were washed with water (20 mL), saturated brine (20 mL×2), dried over anhydrous $Na_2SO_4$, filtered and concentrated under reduced pressure to dryness to give a residue, which was purified by reversed-phase HPLC (0.1% TFA condition) to give 74d (340 mg, 50.7% yield) as a yellow gum.

Step 3:

To a solution of 74d (300 mg, 670 umol, 1.00 eq) in AcOH (2 mL) was added aq. HBr (4.00 mL, 40% purity) at 25 °C under $N_2$ atmosphere. Then the mixture was heated to 80 °C and stirred for 0.5 h under $N_2$. LCMS showed the starting material was consumed and desired MS was observed. After cooling, the reaction mixture was concentrated under reduced pressure to remove solvent. Water (10 mL) was added and the residue extracted with EtOAc (10 mL×3). Then the combined organic phases were washed with saturated brine (10 mL×2), dried over with anhydrous $Na_2SO_4$, filtered and concentrated under reduced pressure to dryness to give a residue, which was purified by pre-HPLC (TFA condition) to afford the titled product Ex.74 (70 mg, 30.4% yield) as a brown gum. $^1$HNMR: DMSO 400 MHz; δ ppm 7.96 (d, J=9.2 Hz, 1H) 7.82-7.89 (m, 2H) 7.70-7.79 (m, 1H) 7.45-7.54 (m, 1H) 7.35 (d, J=9.6 Hz, 1H) 7.21 (t, J=9.6 Hz, 1H) 6.42 (dd, J=6.2, 1.6 Hz, 1H) 4.82-4.91 (m, 1H) 2.91-3.13 (m, 3H) 2.08-2.19 (m, 1H); HPLC: MS (M+H): 344.1

Example 75: Preparation of 2-hydroxy-3-(thiazol-5-yl)cyclohepta-2,4,6-trien-1-one (Ex.75)

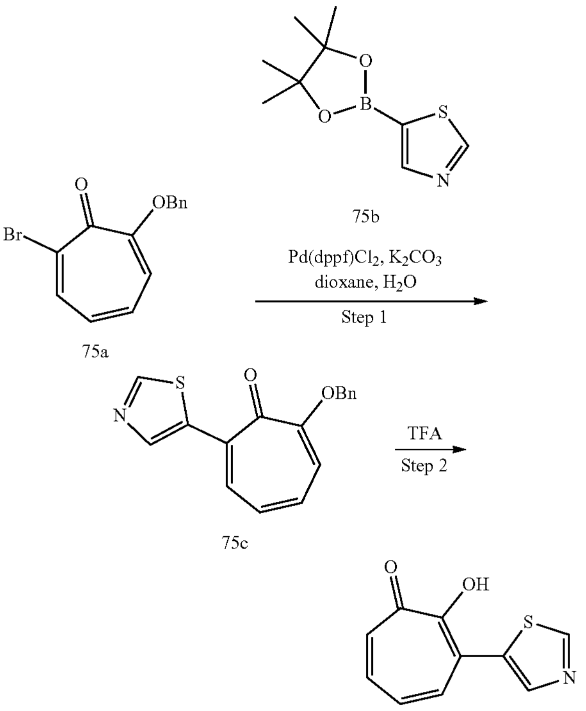

75b

75a

75c

Ex. 75

Step 1:

To a mixture of 75a (500 mg, 1.72 mmol, 1.00 eq) and 75b (435 mg, 2.06 mmol, 1.20 eq) in dioxane (5 mL) and $H_2O$ (1 mL) $K_2CO_3$ (474 mg, 3.43 mmol, 2.00 eq) and Pd(dppf)$Cl_2$ (125 mg, 171 umol, 0.1 eq) were added at 20 °C under $N_2$. The system was degassed and then charged with nitrogen three times. The mixture was heated and stirred at 120 °C for 1 hr. TLC (petroleum ether/ethyl acetate=3/1) showed the starting material was consumed and new spot was observed. After cooling, water (20 mL) was added to the reaction mixture and extracted with ethyl acetate (20 mL×3). The combined organic phases were washed with brine (20 mL), dried over anhydrous $Na_2SO_4$, filtered and concentrated in vacuo to dryness. The residue was purified by silica gel chromatography (Petroleum ether/Ethyl acetate=100/1 to 100/45) to give 75c (190 mg, 26.9% yield, 72% purity) as a yellow oil.

Step 2:

75c (190 mg, 643 umol, 1.00 eq) was added into TFA (3 mL) at 25 °C. The mixture was heated and stirred at 50 °C for 0.5 hr. LCMS showed the starting material was consumed and the desired MS was detected. The mixture was concentrated in vacuum to dryness. The residue was purified by pre-HPLC (column: Xtimate C18 100*30 mm*3 um; mobile phase: [water (0.2% FA)-ACN]; B %: 10%-40%, 9 min) to afford the titled product Ex.75 (0.06 g, 44.54% yield) as a yellow solid. $^1$H NMR: δ 9.09 (s, 1H), 8.63 (s, 1H), 8.48 (d, J=10.0. Hz, 1H), 7.57-7.41 (m, 2H), 7.25 (t, J=10.0 Hz, 1H); HPLC: MS: 206.0

Example 76: Preparation of 2-hydroxy-3-(thiazol-4-yl)cyclohepta-2,4,6-trien-1-one (Ex.76)

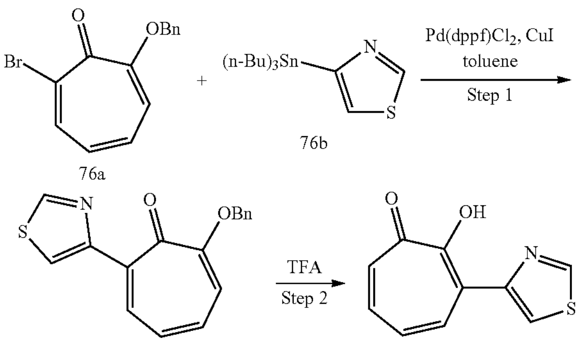

76a 76b 76c Ex. 76

Step 1:

To a mixture of 76a (3.20 g, 10.9 mmol, 1.65 eq) and 76b (3.00 g, 8.02 mmol, 1.20 eq) in toluene (20 mL) Pd(dppf) $Cl_2 \cdot CH_2Cl_2$ (545 mg, 668 umol, 0.10 eq) and CuI (508 mg, 2.67 mmol, 0.40 eq) were added, then the mixture was degassed and purged with $N_2$ for 3 times. The reaction mixture was stirred at 120 °C for 16 hr under $N_2$ atmosphere. LCMS showed ~24% of reactant remained. Several new peaks were shown on LCMS and ~27% of desired compound was detected. After cooling, the reaction mixture was quenched by addition of $H_2O$ (10 mL) at 15 °C, and then extracted with EtOAc (50 mL×4). The combined organic layers were washed with brine (10 mL), dried over $Na_2SO_4$, filtered and concentrated under reduced pressure to give a residue. The residue was purified by column chromatography ($SiO_2$, Petroleum ether/Ethyl acetate=85/1 to 15/1) to give compound 76c (2.3 g, 7.79 mmol, 69% yield) as a yellow oil.

Step 2:

76c (2.30 g, 7.79 mmol, 1.00 eq) was added into TFA (5 mL) and the mixture was heated to 50 °C and stirred for 2 hr. LCMS showed 76c was consumed completely and one main peak with desired mass was detected. The mixture was diluted with DCM (20 mL) and concentrated under reduced pressure to give a residue. The crude product was triturated with MeOH at 25 °C for 5 min, and the precipitate was collected and dried in vacuo to afford the titled product Ex.76 (1.00 g, 62.6% yield) as a yellow solid. $^1H$ NMR: $CDCl_3$ 400 MHz Example 77: Preparation of 3-(2,4-difluorophenoxy)-2-hydroxy-7-methylcyclohepta-2,4,6-trien-1-one (Ex.77)

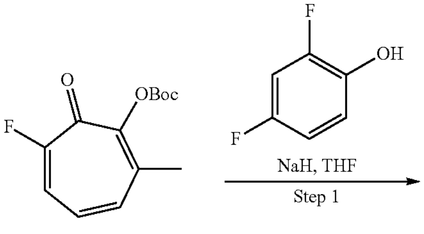

77a

-continued

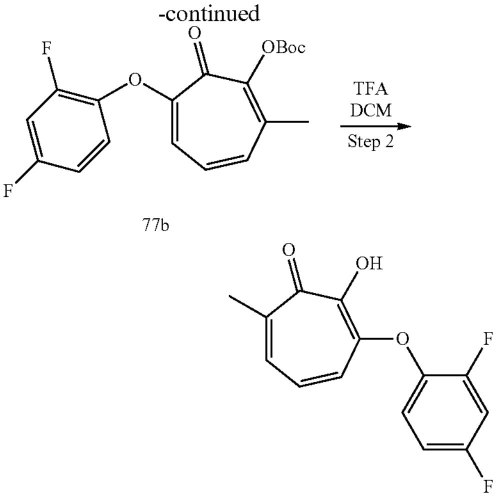

77b Ex. 77

Step 1:

To a solution of 2,4-difluorophenol (153 mg, 1.18 mmol, 1.50 eq) in THE (4 mL) NaH (47.0 mg, 1.18 mmol, 60% purity, 1.50 eq) was added at 0 °C. After stirring at 0 °C for 30 min, a solution of 77a (200 mg, 787 umol, 1.00 eq) in THE (4 mL) was added to the mixture at 0 °C. The mixture was heated and stirred at 50 °C for 3 hr. LCMS showed the reaction was completed. After cooling to room temperature, water (10 mL) was added to the reaction mixture and extracted with ethyl acetate (15 mL×3). The combined organic phase was washed with brine (20 mL), dried over anhydrous $Na_2SO_4$, filtered and concentrated under reduced pressure to give a residue. The residue was purified by silica gel chromatography (Petroleum ether/Ethyl acetate=100/1 to 100/8) to give 77b (46.0 mg, 11.1% yield) as an off-white solid.

Step 2:

To a solution of 77b (46.0 mg, 126 umol, 1.00 eq) in DCM (1 mL) TFA (0.5 mL) was added at 25 °C. The mixture was stirred at 25 °C for 0.5 hr. LCMS showed the starting material was consumed and the desired MS was detected. The mixture was concentrated under reduced pressure to give a residue. The residue was purified by pre-HPLC (column: Xtimate C18 100*30 mm*3 um; mobile phase: [water (0.2% FA)-ACN]; B %: 30%-60%, 9 min) to afford the titled product Ex.77 (10.0 mg, 29.4% yield, 98.0% purity) as an off-white solid. $^1H$ NMR: MeOD 400 MHz; δ 7.45 (d, J=10.4 Hz, 1H), 7.24 (br d, J=10.4 Hz, 1H), 7.20-7.10 (m, 2H), 7.03-6.93 (m, 2H), 2.49 (s, 3H); HPLC: MS: 265.0

Example 78: Preparation of 2-hydroxy-7-methyl-3-phenoxycyclohepta-2,4,6-trien-1-one (Ex.78)

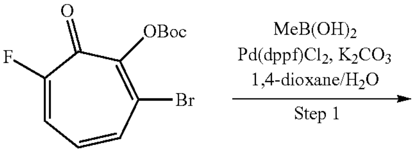

78a

-continued

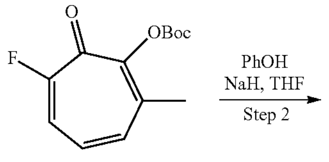

78b

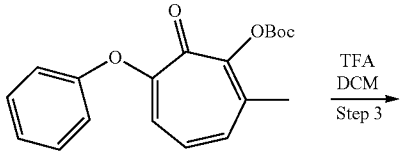

78c

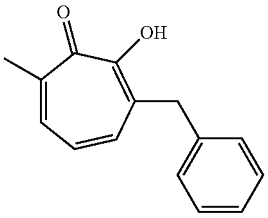

Ex. 78

Step 1:

To a mixture of 78a (1.00 g, 3.13 mmol, 1.00 eq) and methylboronic acid (1.88 g, 31.3 mmol, 10.0 eq) in dioxane (10 mL) and $H_2O$ (2 mL) $K_2CO_3$ (866 mg, 6.27 mmol, 2.00 eq) was added at 20 °C under $N_2$. Then Pd(dppf)$Cl_2$ (230 mg, 313 umol, 0.10 eq) was added to the mixture under $N_2$. The system was degassed and then charged with nitrogen three times. The mixture was heated and stirred at 110 °C for 0.5 hr. LCMS showed the starting material was consumed and the desired MS was detected. After cooling to room temperature, water (20 mL) was added to the reaction mixture and extracted with ethyl acetate (20 mL×2). The combined organic phase was washed with brine (20 mL), dried over anhydrous $Na_2SO_4$, filtered and concentrated under reduced pressure to give a residue. The residue was purified by silica gel chromatography (Petroleum ether/Ethyl acetate=100/1 to 100/8) to give 78b (0.35 g, 43.9% yield) as a yellow solid.

Step 2:

To a solution of phenol (83.3 mg, 885 umol, 1.50 eq) in THE (3 mL) NaH (35.0 mg, 885 umol, 60% purity, 1.50 eq) was added at 0 °C, and the mixture was stirred at 0 °C for 30 min. 78b (0.15 g, 590 umol, 1.00 eq) in THE (3 mL) was added to the mixture at 0 °C. The mixture was heated and stirred at 50 °C for 4 hr. LCMS showed the starting material was consumed and the desired MS was detected. After cooling to room temperature, water (10 mL) was added to the reaction mixture and extracted with ethyl acetate (15 mL×3). The combined organic phases were washed with brine (20 mL), dried over anhydrous $Na_2SO_4$, filtered and concentrated under reduced pressure to give a residue. 78c (300 mg, crude) was obtained as a black oil.

Step 3:

To a solution of 78c (280 mg, 853 umol, 1.00 eq) in DCM (2 mL) TFA (1 mL) was added at 25 °C. The mixture was stirred at 25 °C for 0.5 hr. LCMS showed the starting material was consumed and the desired MS was detected. The mixture was concentrated under reduced pressure to give a residue. The residue was purified by pre-HPLC (column: 3_Phenomenex Luna C18 75*30 mm*3 um; mobile phase: [water (0.2% FA)-ACN]; B %: 33%-53%, 7 min) to afford the titled product Ex.78 (45.0 mg, 22.9% yield) as a yellow solid. $^1$H NMR: MeOD 400 MHz; δ 7.45 (d, J=10.6 Hz, 1H), 7.42-7.36 (m, 2H), 7.28 (d, J=10.6 Hz, 1H), 7.20-7.14 (m, 1H), 7.02-6.94 (m, 3H), 2.50 (s, 3H); MS (M+H): 229.1

Example 79: Preparation of 2-hydroxy-3-(oxazol-4-yl)cyclohepta-2,4,6-trien-1-one (Ex.79)

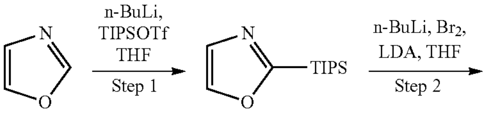

79a

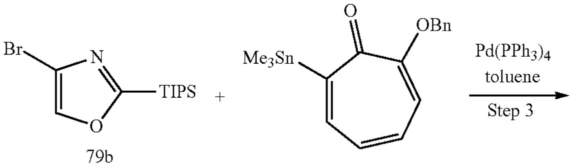

79b

79c

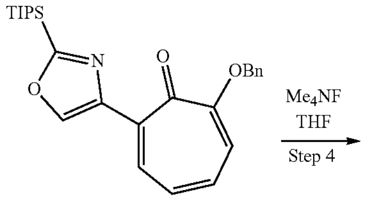

79d

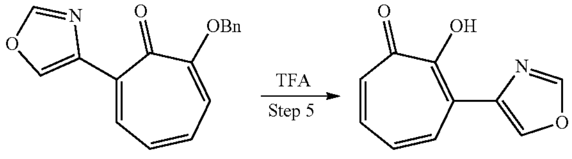

79e

Ex. 79

Step 1:

To a solution of oxazole (600 mg, 8.69 mmol, 555 uL, 1.00 eq) in THE (5 mL) n-BuLi (2.5 M, 3.82 mL, 1.10 eq) was added dropwise at −78 °C under $N_2$. After stirring for an additional 45 min at −78 °C, TIPSOTf (2.66 g, 8.69 mmol, 2.34 mL, 1.00 eq) in THE (2 mL) was added slowly to reaction mixture at −78 °C. After completion of addition, the reaction mixture was slowly allowed to warm to 0 °C and stirred for 1 h. A new spot was observed on TLC (Petroleum ether:Ethyl acetate=10:1, $R_f$=0.3). The reaction mixture was quenched with n-hexane (20 mL) and volatiles were evaporated under reduced pressure to give yellow gum. The obtained crude material was purified by silica gel column chromatography (Petroleum ether:Ethyl acetate=100:1 to 100:10) to afford 79a (1.70 g, 86.8% yield) as a yellow gum.

Step 2:

To a solution of 79a (1.30 g, 5.77 mmol, 1.00 eq) in THE (20 mL) n-BuLi (2.5 M, 2.54 mL, 1.10 eq) was added drop-wise at −78 °C. The reaction mixture was stirred for additional 30 min, and $Br_2$ (1.01 g, 6.34 mmol, 327 uL, 1.10 eq) was added drop-wise at −78 °C. The solution was warmed to −30 °C over 40 min and then cooled to −78 °C. A solution of LDA (2.00 M in hexane, 3.17 mL, 1.10 eq) was added drop-wise at −78 °C, and the mixture was stirred at temperature for an additional 35 min. Then water (207 mg, 11.5 mmol, 207 uL, 2.00 eq) was added drop-wise, and the reaction mixture was warmed up to 25 °C for 4 hours. A new spot was observed on TLC (Petroleum ether:Ethyl acetate=10:1, $R_f$=0.25). Saturated aqueous $NH_4Cl$ (40 mL) was added to the stirred mixture. Hexanes and THE were evaporated in vacuo, and the residue was extracted with EtOAc (20 mL×3). The organic layer was separated, washed with brine (50 mL×2), dried over $Na_2SO_4$ and evaporated in vacuo to dryness. The residue was purified by flash chromatography on silica gel (Petroleum ether:Ethyl acetate from 100:1 to 100:30) to give 79b (1.60 g, 91.1% yield) as a yellow gum.

Step 3:

To a mixture of 79b (300 mg, 1.0 mmol, 1.00 eq) and 79c (390 mg, 1.0 mmol, 1.00 eq) in toluene (5 mL) $Pd(PPh_3)_4$ (50 mg) was added at 25 °C under $N_2$ atmosphere. The suspension was degassed under vacuum and purged with $N_2$ three times. Then the mixture was heated to 110 °C and stirred for 16 h under $N_2$ atmosphere. LCMS showed the starting material was consumed and the desired MS was observed. After cooling, a saturated solution of $NH_4Cl$ (10 mL) was added into the mixture and extracted with EtOAc (20 mL×3). Then the combined organic phases were washed with water (20 mL), saturated brine (20 mL×2), dried over anhydrous $Na_2SO_4$, filtered and concentrated under reduced pressure to dryness to give a residue, which was purified by silica gel column (Petroleum ether:Ethyl acetate=100/10 to 100/15) to give 79d (150 mg, 33.0% yield) as a yellow gum.

Step 4:

A mixture of 79d (80.0 mg, 179 umol, 1.00 eq) and $Me_4NF$ (33.4 mg, 359 umol, 2.00 eq) in THE (1.00 mL) was heated to 60 °C and stirred for 2 hours under $N_2$. The reaction was detected by LCMS and desired MS was observed. After cooling, brine (10 mL) was added to the mixture and then extracted with EtOAc (10 mL×3). The combined original layers were washed with water (10 mL), saturated brine (10 mL×2), dried over anhydrous $Na_2SO_4$, filtered and concentrated under reduced pressure to dryness to give a residue. The residue was purified by pre-TLC (Petroleum ether:Ethyl acetate=3/1) to give the desired 79e (51 mg, 98.2% yield) as a yellow solid.

Step 5:

A solution of 79e (50.0 mg, 172 umol, 1.00 eq) in TFA (2 mL) was heated and stirred at 50 °C for 1 h. A peak observed on HPLC. After cooling, the reaction mixture was diluted with $CH_2Cl_2$ (10 mL) and concentrated under reduced pressure to dryness below 10 °C. Then the mixture was re-dissolved in $CH_2Cl_2$ (5 mL) and added Amberlyst A21 (0.1 g) and stirred at 25 °C for another 0.5 hr. After filtering, the cake was washed with $CH_2Cl_2$ (5 mL×2) and the filtrate was concentrated under reduced pressure to afford the titled product Ex.79 (26.0 mg, 137 umol, 79.5% yield) as a yellow solid. $^1$HNMR: ($D_2O$, 400 MHz); δ 9.01 (s, 1H), 8.81 (d, J=10.0 Hz, 1H), 8.27 (s, 1H), 7.56-7.41 (m, 2H), 7.34-7.24 (m, 1H); HPLC: MS: 190.1

Example 80: Preparation of 2-hydroxy-3-(thiazol-2-yl)cyclohepta-2,4,6-trien-1-one (Ex.80)

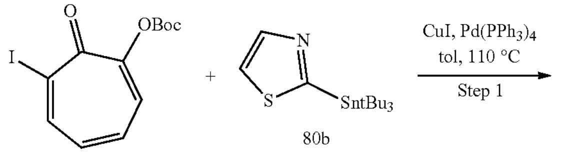

80a 80b

-continued

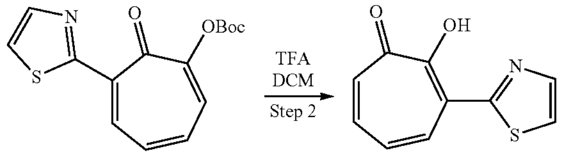

80c Ex. 80

Step 1:

A mixture of 80a (195 mg, 561 umol, 1.00 eq), 80b (210 mg, 561 umol, 176 uL, 1.00 eq), CuI (42.7 mg, 224 umol, 0.400 eq) and $Pd(PPh_3)_4$ (129 mg, 112 umol, 0.200 eq) in toluene (2 mL) was degassed and purged with $N_2$ for 3 times, and then the mixture was heated and stirred at 118 °C for 0.5 hr under $N_2$. LCMS showed 80a was consumed completely and one main peak with desired mass was detected. After cooling, the reaction mixture was quenched by addition of $H_2O$ (10 mL) at 15 °C and extracted with EtOAc (20 mL×4). The combined organic layers were washed with $H_2O$ (10 mL), brine (10 mL), dried over $Na_2SO_4$, filtered and concentrated under reduced pressure to give a residue. The residue was purified by column chromatography ($SiO_2$, Petroleum ether/Ethyl acetate=85/1 to 15/1) to give compound 80c (110 mg, 360 umol, 64.1% yield) as a brown oil.

Step 2:

To a solution of 80c (110 mg, 360 umol, 1.00 eq) in DCM (1.00 mL) TFA (41.0 mg, 360 umol, 26.6 uL, 1.00 eq) was added in one portion at 25 °C. The mixture was stirred at 25 °C for 30 min. LCMS showed 80c was consumed completely and one main peak with desired mass was detected. The reaction mixture was filtered and concentrated under reduced pressure to give a residue. The residue was purified by prep-HPLC (TFA condition) to afford the titled product Ex.80 (50.0 mg, 67.6% yield) as a yellow solid. $^1$H NMR: MeOD 400 MHz; δ: ppm 7.35 (t, J=10.0 Hz, 1H) 7.49 (d, J=10.0 Hz, 1H) 7.60 (d, J=10.0 Hz, 1H) 7.77 (d, J=3.2 Hz, 1H) 8.04 (d, J=3.2 Hz, 1H) 9.21 (d, J=10.0 Hz, 1H)

Example 81: Preparation of 7-fluoro-2-hydroxy-3-(thiazol-4-yl)cyclohepta-2,4,6-trien-1-one (Ex.81)

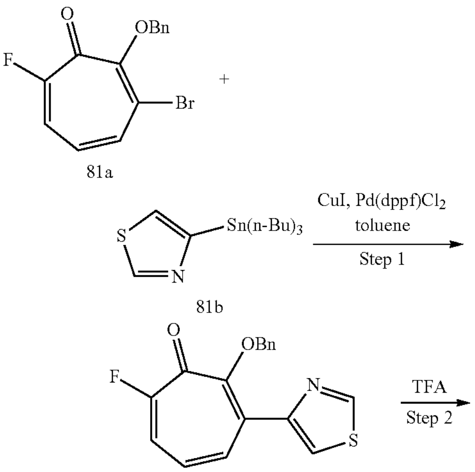

81a 81b 81c

-continued

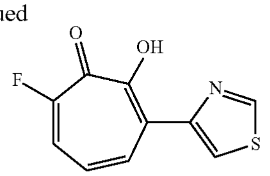

Ex. 81

Step 1:

To a mixture of 81a (100 mg, 323 umol, 1.00 eq) and 81b (145 mg, 388 umol, 1.20 eq) in toluene (1.00 mL) Pd(dppf) $Cl_2$ (24.0 mg, 32.3 umol, 0.10 eq) and CuI (25.0 mg, 129 umol, 0.40 eq) were added at 20 °C under $N_2$. The system was degassed and then charged with nitrogen three times. The mixture was heated and stirred at 110 °C for 1 hr. LCMS showed the starting materials was consumed and the desired MS was detected. After cooling, water (10 mL) was added to the reaction mixture and then extracted with ethyl acetate (10 mL×3). The combined organic phases were washed with brine (10 mL), dried with anhydrous $Na_2SO_4$, filtered and concentrated in vacuum. The residue was purified by prep-TLC (Petroleum ether/Ethyl acetate=3/1, $R_f$=0.4) to give 81c (40 mg, 35.5% yield) as a yellow oil.

Step 2:

A solution of 81c (100 mg, 319 umol, 1.00 eq) in TFA (0.5 mL) was heated and stirred at 50 °C for 1 hr. LCMS showed the starting material was consumed completely and the desired MS observed. The mixture was diluted with DCM (15 mL) and concentrated in vacuum to dryness. The residue was purified by prep-HPLC (column: 3_Phenomenex Luna C18 75*30 mm*3 um; mobile phase: [water (0.2% FA)-ACN]; B %: 10%-45%, 9 min) to afford the titled product Ex.81 (27.0 mg, 37.5% yield) as a yellow solid. $^1$HNMR: (MeOH, 400 MHz); δ 9.07 (br s, 1H), 8.74 (br d, J=11.6 Hz, 2H), 7.67 (br dd, J=10.4, 18.4 Hz, 1H), 7.19 (br s, 1H); HPLC: MS: 224.1

Example 82: Preparation of 7-chloro-2-hydroxy-3-(thiazol-4-yl)cyclohepta-2,4,6-trien-1-one (Ex.82)

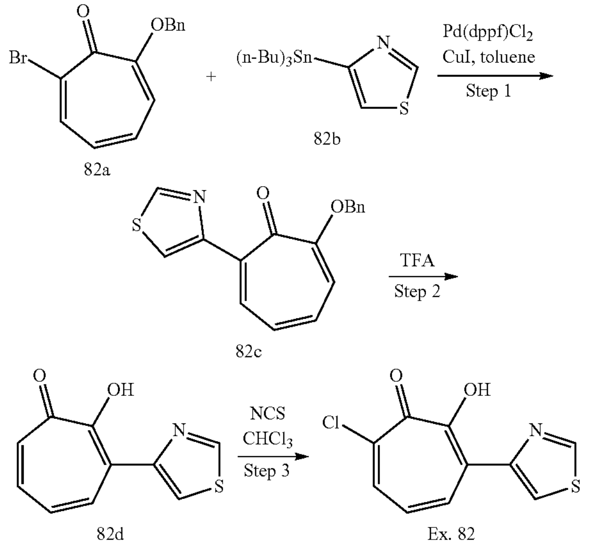

82a 82b 82c 82d Ex. 82

Step 1:

To a mixture of 82a (1.41 g, 4.86 mmol, 1.00 eq) and 82b (2.18 g, 5.83 mmol, 1.20 eq) in toluene (12.0 mL) Pd(dppf) $Cl_2 \cdot CH_2Cl_2$ (793 mg, 971 umol, 0.20 eq) and CuI (370 mg, 1.94 mmol, 0.40 eq) were added under $N_2$. The system was degassed and then charged with nitrogen three times. The mixture was heated and stirred at 120 °C for 2.5 hr under $N_2$. LCMS showed 82a was consumed completely and one main peak with desired mass was detected. After cooling, the reaction mixture was quenched by addition of $H_2O$ (10 mL) at 15 °C, and then extracted with EtOAc (20 mL×4). The combined organic layers were washed with brine (20 mL), dried over $Na_2SO_4$, filtered and concentrated under reduced pressure to give a residue. The residue was purified by column chromatography ($SiO_2$, Petroleum ether/Ethyl acetate=85/1 to 15/1) to give compound 82c (900 mg, 62.7% yield) as yellow oil.

Step 2:

A solution of 82c (900 mg, 3.05 mmol, 1.00 eq) in TFA (5.00 mL) was heated to 50 °C and stirred for 2 hours. LCMS showed 82c was consumed completely and one main peak with desired mass was detected. The mixture was diluted with DCM (20 mL) and concentrated under reduced pressure to give a residue. The crude product was triturated with MeOH at 25 °C for 5 min and the precipitate was collected, dried in vacuo to give compound 82d (500 mg, 79.9% yield) as a yellow solid.

Step 3:

To a solution of 82d (200 mg, 974 umol, 1.00 eq) in toluene (2.00 mL) NCS (169 mg, 1.27 mmol, 1.30 eq) was added in one portion at 15 °C under $N_2$. The reaction mixture was heated to 120 °C and stirred for 30 min. LCMS showed 82d was consumed completely and one main peak with desired mass was detected. After cooling, the reaction mixture was quenched by addition of $H_2O$ (10 mL) at 15 °C, and then extracted with EtOAc (20 mL×5). The combined organic layers were washed with brine (20 mL), dried over $Na_2SO_4$, filtered and concentrated under reduced pressure to give a residue. The residue was purified by prep-HPLC (TFA condition) to afford the titled product Ex.82 (40.0 mg, 17.1% yield) as a yellow solid. $^1$H NMR: 400 MHz; 1H NMR (400 MHz, METHANOL-d4) δ ppm 7.13 (t, J=10.8 Hz, 1H) 7.89 (dd, J=10.8, 0.63 Hz, 1H) 8.73 (d, J=2.0 Hz, 1H) 8.80 (d, J=10.4 Hz, 1H); 9.06 (d, J=2.01 Hz, 1H)

Example 83: Preparation of 5-fluoro-2-hydroxy-3-(thiazol-4-yl)cyclohepta-2,4,6-trien-1-one (Ex.83)

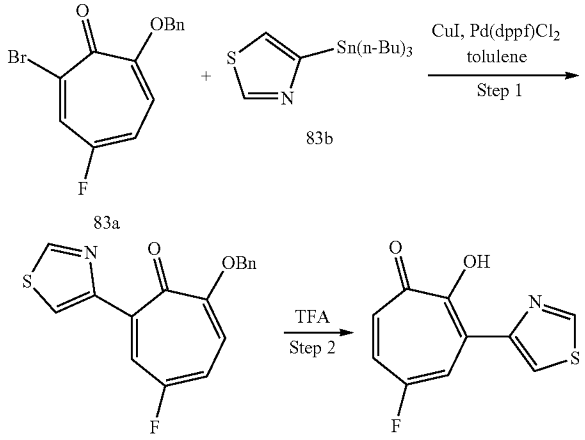

83a 83b 83c Ex. 83

Step 1:

To a mixture of 83a (110 mg, 356 umol, 1.00 eq) and 83b (160 mg, 427 umol, 1.20 eq) in toluene (10.0 mL) CuI (27.0 mg, 142 umol, 0.40 eq) and Pd(dppf)$Cl_2$·$CH_2Cl_2$ (29.0 mg, 36.0 umol, 0.10 eq) were added in one portion at 25 °C under $N_2$ atmosphere. The system was degassed and then charged with nitrogen three times. The mixture was heated and stirred at 120 °C for 60 min. LCMS showed 83a was consumed completely and one main peak with desired mass was detected. After cooling, the reaction mixture was quenched by addition of $H_2O$ (10 mL) and then extracted with EtOAc (10 mL×3). The combined organic layers were washed with brine (10 mL), dried over $Na_2SO_4$, filtered and concentrated under reduced pressure to dryness. The residue was purified by column chromatography ($SiO_2$, Petroleum ether/Ethyl acetate=100/1 to 3/1) to give 83c (108 mg, 96.8% yield) as a yellow solid.

Step 2:

A solution of 83c (106 mg, 338 umol, 1.00 eq) in TFA (3.00 mL) was heated and stirred at 50 °C under $N_2$ for 1 hr. TLC (Petroleum ether/Ethyl acetate=3/1) indicated 83c was consumed completely and one new spot formed. The reaction mixture was diluted with DCM (10 mL) and concentrated under reduced pressure to dryness. The residue was purified by prep-HPLC (FA condition, column: 3_Phenomenex Luna C18 75*30 mm*3 um; mobile phase: [water (0.2% FA)-ACN]; B %: 40%-70%, 10 min) to afford the titled product Ex.83 (49.0 mg, 64.9% yield) as a yellow solid. $^1$H NMR: MeOD 400 MHz; δ: 7.34-7.40 (m, 2H) 8.87-8.99 (m, 1H) 8.99-9.08 (m, 2H) HPLC: MS (M+H): 224.0

Example 84: Preparation of methyl 2-(3-fluoro-4-((2-hydroxy-3-oxocyclohepta-1,4,6-trien-1-yl)oxy)phenyl)acetate (Ex.84)

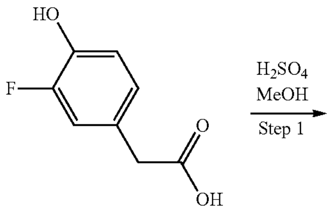

84a

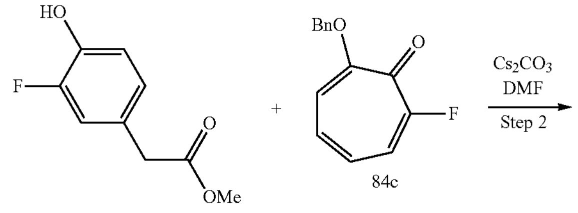

84b

84c

-continued

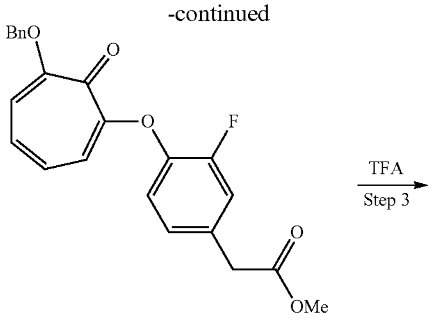

84d

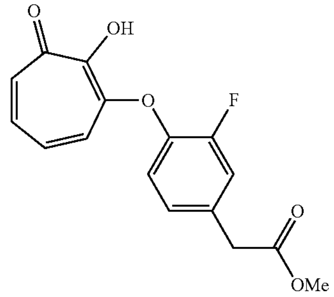

Ex. 84

Step 1:

To a solution of 84a (1.00 g, 5.88 mmol, 1.00 eq) in MeOH (10.0 mL) $H_2SO_4$ (0.1 mL) was added at 20 °C. The mixture was heated and stirred at 68 °C for 1 hr. TLC (petroleum ether/ethyl acetate=3/1) showed the starting material was consumed and new spot observed. After cooling, the residue was poured into water (20 mL) and stirred for 5 min. The aqueous phase was extracted with ethyl acetate (20 mL×2) and the combined organic phase was washed with brine (20 mL×2), dried over anhydrous $Na_2SO_4$, filtered and concentrated in vacuum to dryness to give 84b (1.08 g, 95.7% yield) as yellow oil.

Step 2:

To a mixture of 84c (500 mg, 2.17 mmol, 1.00 eq) and 84b (482 mg, 2.60 mmol, 1.20 eq) in DMF (5 mL) $Cs_2CO_3$ (1.42 g, 4.34 mmol, 2.00 eq) was added in one portion at 25 °C. The mixture was stirred at 25 °C for 1 hr. LCMS showed the starting materials was consumed and the desired MS was detected. Water (15 mL) was added to quench the reaction and then extracted with ethyl acetate (15 mL×3). The combined organic phases were washed with brine (10 mL×2), dried over anhydrous $Na_2SO_4$, filtered and concentrated in vacuum to give crude 84d (950 mg, crude) as a yellow oil.

Step 3:

A solution of 84d (500 mg, 1.27 mmol, 1.00 eq) in TFA (4.00 mL) was heated and stirred at 50 °C for 1 hour. LCMS showed the starting material was consumed completely and the desired MS observed. After cooling, the mixture was diluted with DCM (20 mL) and concentrated in vacuum to dryness. The residue was purified by prep-HPLC (column: Phenomenex Luna C18 200*40 mm*10 um; mobile phase: [water (0.2% FA)-ACN]; B %: 20%-60%, 8 min) to afford the titled product Ex.84 (180 mg, 46.6% yield) as a yellow solid. $^1$HNMR: (MeOH, 400 MHz); δ 7.52-7.46 (m, 1H), 7.40-7.31 (m, 2H), 7.24 (dd, J=1.6, 11.6 Hz, 1H), 7.14-7.10 (m, 1H), 7.09-7.02 (m, 2H), 3.71 (s, 3H), 3.70 (s, 2H); LCMS: MS: 305.0

Example 85: Preparation of 2-hydroxy-3-(isothiazol-5-yl)cyclohepta-2,4,6-trien-1-one (Ex.85)

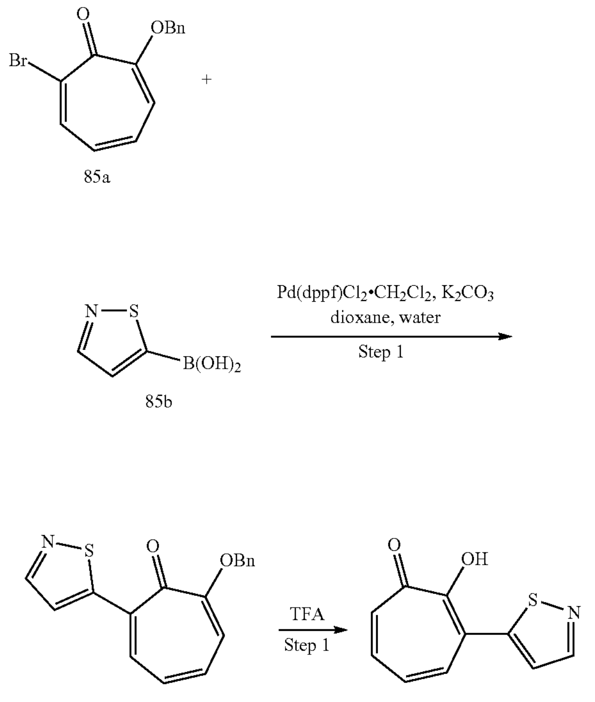

85a

85b

85c

Ex. 85

Step 1:

To a mixture of 85a (170 mg, 584 umol, 1.00 eq) and 85b (75.3 mg, 584 umol, 1.00 eq) in dioxane (2 mL) and $H_2O$ (0.4 mL) $K_2CO_3$ (161 mg, 1.17 mmol, 2.00 eq) and Pd(dppf)$Cl_2 \cdot CH_2Cl_2$ (47.7 mg, 58.4 umol, 0.100 eq) were added at 20 °C under $N_2$. The system was degassed and then charged with nitrogen three times. The mixture was heated and stirred at 105 °C for 15 min. LCMS showed the starting materials was consumed and the desired MS was detected. After cooling, water (10 mL) was added to the reaction mixture and extracted with ethyl acetate (10 mL×3). The combined organic phase was washed with brine (20 mL), dried over anhydrous $Na_2SO_4$, filtered and concentrated in vacuum to give a residue. The residue was purified by silica gel chromatography (Petroleum ether/Ethyl acetate=100/1 to 100/45) to give 85c (40 mg, 84.0 umol, 14.4% yield, 62% purity) as a yellow oil.

Step 2:

85c (40 mg, 135 umol, 1.00 eq) was added to TFA (1.00 mL) at 25 °C. The reaction mixture was heated and stirred at 50 °C for 3 hrs. LCMS showed the starting materials was consumed completely and the desired MS was detected. After cooling, the reaction mixture was concentrated in vacuum to dryness. The residue was purified by prep-HPLC (column: 3_Phenomenex Luna C18 75*30 mm*3 um; mobile phase: [water (0.2% FA)-CAN]; B %: 10%-40%, 8 min) to afford the titled product Ex.85 (6 mg, 28.3 umol, 20.9% yield, 96.7% purity) as a yellow solid. $^1$HNMR: (MeOH, 400 MHz); δ: 8.74 (d, J=10.0 Hz, 1H), 8.55 (d, J=2.0 Hz, 1H), 8.10 (d, J=2.0 Hz, 1H), 7.68-7.61 (m, 1H), 7.56-7.51 (m, 1H), 7.37 (t, J=10.0 Hz, 1H); LCMS Example 86: Preparation of methyl 3-fluoro-4-((2-hydroxy-3-oxocyclohepta-1,4,6-trien-1-yl)oxy)benzoate (Ex.86)

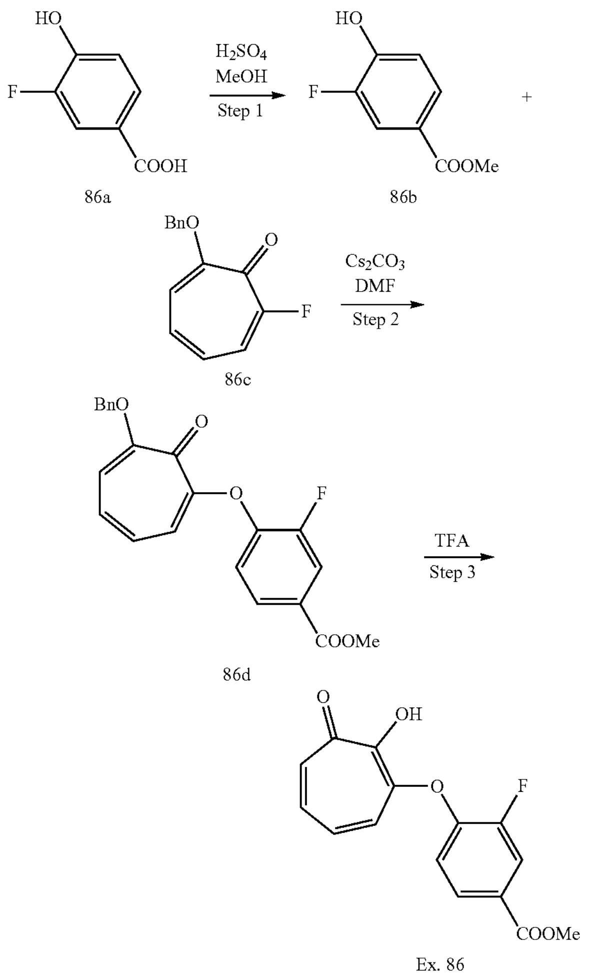 [SMILES: O=C(O)c1ccc(O)c(F)c1 ; COC(=O)c1ccc(O)c(F)c1 ; O=c1c(F)ccccc1OCc1ccccc1 ; COC(=O)c1ccc(Oc2ccccc(OCc3ccccc3)c2=O)c(F)c1 ; COC(=O)c1ccc(Oc2ccccc(=O)c2O)c(F)c1]

86a

86b

86c

86d

Ex. 86

Step 1:

To a solution of 86a (1.00 g, 6.41 mmol, 1.00 eq) in MeOH (10 mL) $H_2SO_4$ (0.10 mL) was added at 20 °C. The mixture was heated and stirred at 80 °C for 12 hrs. TLC (petroleum ether:ethyl acetate=3:1, UV 254 nm as developer, Rf=0.4) showed the starting material was consumed and new spot observed. After cooling, the residue was poured into water (20 mL) and stirred for 5 min. The aqueous phase was extracted with ethyl acetate (20 mL×2). The combined organic phases were washed with brine (20 mL×2), dried over anhydrous $Na_2SO_4$, filtered and concentrated in vacuum. The residue was purified by silica gel chromatography (Petroleum ether/Ethyl acetate=100/1 to 100/15) to give 86b (1.00 g, 5.41 mmol, 84.4% yield, 92.0% purity) as a white solid.

Step 2:

To a mixture of 86c (500 mg, 2.17 mmol, 1.00 eq) and 86b (443 mg, 2.60 mmol, 1.20 eq) in DMF (5 mL) $Cs_2CO_3$ (1.42 g, 4.34 mmol, 2.00 eq) was added in one portion at 25 °C. The mixture was stirred at 25 °C for 5 hrs. LCMS showed the starting materials was consumed and the desired MS was detected. After cooling, water (15 mL) was added to the reaction mixture and extracted with ethyl acetate (15 mL×3).

The combined organic phase was washed with brine (10 mL×2), dried with anhydrous $Na_2SO_4$, filtered and concentrated in vacuum to give a residue. The residue was purified by silica gel chromatography (Petroleum ether/Ethyl acetate=100/1 to 100/28) to give 86d (900 mg, 1.70 mmol, 78.5% yield, 72.0% purity) as a yellow solid.

Step 3:

86d (470 mg, 1.24 mmol, 1.00 eq) was added into TFA (4 mL) at 25 °C. The mixture was heated and stirred at 50 °C for 0.5 hr. LCMS showed the starting material was consumed completely and the desired MS observed. After cooling, the mixture was concentrated in vacuum to dryness. Then the crude product was purified by re-crystallization from MeCN (0.5 mL) at 25 °C to afford the titled product Ex.86 (120 mg, 405 umol, 78.3% yield, 97.9% purity) as a yellow solid. $^1$HNMR: (MeOH, 400 MHz); δ 7.86 (dd, J=2, 11.6 Hz, 1H), 7.80 (br d, J=8.8 Hz, 1H), 7.61 (d, J=10.0 Hz, 1H), 7.54-7.44 (m, 2H), 7.18-7.11 (m, 1H), 7.00 (t, J=8.4 Hz, 1H), 3.92 (s, 3H); LCMS: MS: 291.0

Example 87: Preparation of 2-hydroxy-5-(1-hydroxy-3-phenylpropan-2-yl)-3-(thiazol-4-yl)cyclohepta-2,4,6-trien-1-one (Ex.87)

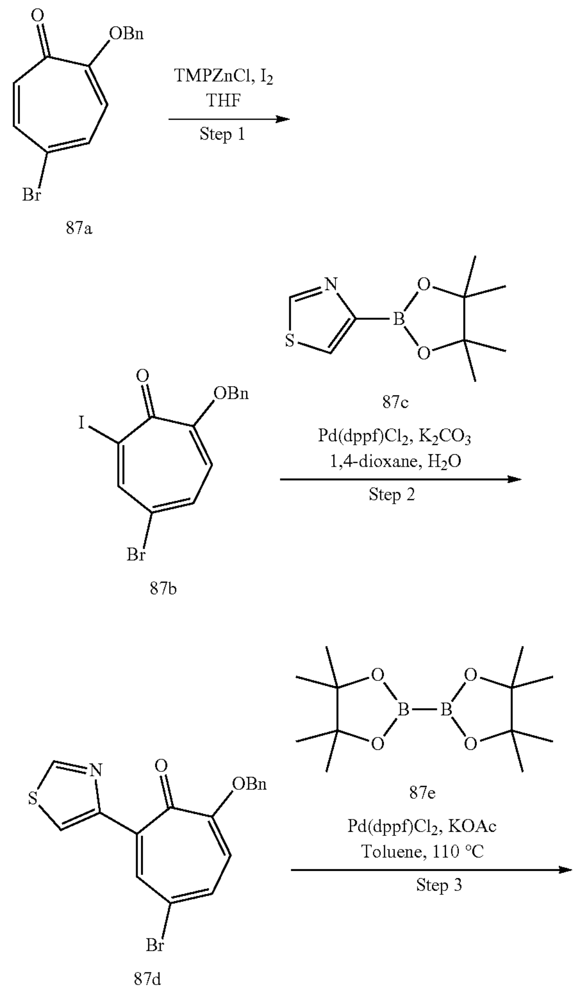

87a

87c

87b

87e

87d

-continued

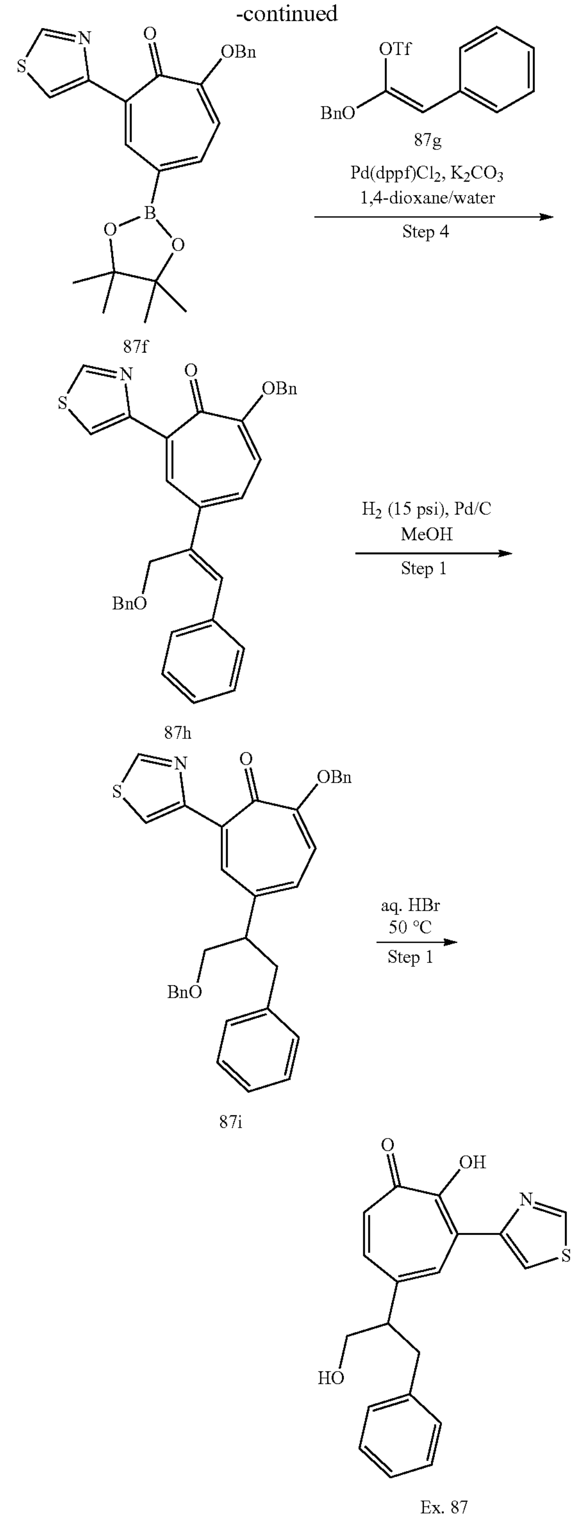

87f

87g

87h

87i

Ex. 87

Step 1:

To the solution of 87a (2.00 g, 6.87 mmol, 1.00 eq) in THE (15 mL) a solution of chloro-(2,2,6,6-tetramethyl-1-piperidyl)zinc (TMPZnCl) (0.4 M in THF, 42.9 mL, 2.50 eq) was added in THE drop-wise at 0 °C under $N_2$. After stirring at 0-10 °C for 30 min, a solution of 12 (3.49 g, 13.7 mmol, 2.77 mL, 2.00 eq) in THE (5 mL) was added to the mixture at 0 °C, and the resulting yellow solution was stirred at 0 °C for another 30 min. New spot was observed on TLC (Petroleum ether:Ethyl acetate=3:1, $R_f$=0.3). The reaction was quenched with aqueous $Na_2SO_3$ (10%, 100 mL) and stirred at 25 °C for 30 min. Then the mixture was extracted with EtOAc (50 mL×3), and the combined organic layers were washed with brine (50 mL), dried over $Na_2SO_4$, filtered and concentrated under reduced pressure to dryness. The residue was purified by silica gel column (Petroleum ether:Ethyl acetate=10/1 to 5/1) to give 87b (1.00 g, 2.40 mmol, 34.9% yield) as a yellow solid.

Step 2:

To a mixture of 87b (1.00 g, 2.40 mmol, 1.00 eq), compound 87c (506 mg, 2.40 mmol, 1.00 eq) and $K_2CO_3$ (662 mg, 4.80 mmol, 2.00 eq) in dioxane (2 mL) and water (0.03 mL) $Pd(dppf)Cl_2$ (175 mg, 239 umol, 0.10 eq) was added under $N_2$. The system was degassed and then charged with nitrogen three times. The mixture was heated and stirred at 110 °C for 1 hour under $N_2$. LCMS shown desired MS was observed and material was consumed completely. After cooling to 25 °C, the mixture was filtered through a pad of Celite and the filter cake was washed with $CH_2Cl_2$ (10 mL×3). The filtrate was concentrated under reduced pressure to dryness. The residue was purified by silica gel column (Petroleum ether:Ethyl acetate=10/1 to 5/1) to give 87d (100 mg, 267 umol, 11.1% yield) as a yellow solid.

Step 3:

To a mixture of 87d (100 mg, 267 umol, 1.00 eq), compound 87e (81 mg, 320 umol, 1.2 eq) and KOAc (53 mg, 534 umol, 2.00 eq) in toluene (2 mL) $Pd(dppf)Cl_2 \cdot CH_2Cl_2$ (22 mg, 26.7 umol, 0.10 eq) was added at 25 °C under $N_2$. The system was degassed and then charged with nitrogen three times. The mixture was heated and stirred at 110 °C for 1 hour under nitrogen. LCMS showed the material consumed completely and desired MS observed. After cooling to 25 °C, the mixture was filtered through a pad of Celite and the filter cake was washed with $CH_2Cl_2$ (10 mL×3). The filtrate was concentrated under reduced pressure to dryness to give the crude product 87f (130 mg, crude) as a yellow solid.

Step 4:

To a mixture of 87f (350 mg, 830 umol, 1.00 eq), 87g (402 mg, 1.08 mmol, 1.30 eq) and $K_2CO_3$ (230 mg, 1.66 mmol, 2.00 eq) in dioxane (2 mL) and water (0.03 mL) $Pd(dppf)Cl_2$ (60.7 mg, 83.0 umol, 0.10 eq) was added under $N_2$. The system was degassed and then charged with nitrogen three times. The reaction mixture was heated and stirred at 110 °C and stirred for 1 hour under $N_2$. The reaction mixture was detected by LCMS and desired MS was observed. After cooling to room temperature, the mixture was filtered through a pad of Celite and the filter cake was washed with $CH_2Cl_2$ (10 mL×2). The filtrate was concentrated under reduced pressure to dryness. The residue was purified by silica column (Petroleum ether:Ethyl acetate=100/1 to 100/10) to give the desired 87h (280 mg, 540 umol, 65.1% yield) as a yellow gum.

Step 5:

To a solution of 87h (280 mg, 540 umol, 1.00 eq) in MeOH (3 mL) was added Pd/C (100 mg, 540 umol, 50% purity, 1.00 eq) under $N_2$. The system was degassed and then charged with $H_2$ three times. The reaction mixture was stirred under $H_2$ (15 psi) at 25 °C for 1 hour. LCMS showed the reaction was completed. The mixture was filtered through a pad of Celite and the filter cake was washed with MeOH (10 mL×2). The filtrate was concentrated under reduced pressure to dryness. The residue was purified by pre-HPLC (column: Phenomenex Gemini-NX 150*30 mm*5 um; mobile phase: [water (0.1% TFA)-ACN]; B %: 55%-85%, 9 min) to give 87i (50 mg, 9.62 umol, 17.8% yield) as a yellow gum.

Step 6:

To a suspension of 87i (60 mg, 115 umol, 1.00 eq) in water (1 mL) was added HBr (0.5 mL, 40% aqueous solution) at 25 °C. Then the resulting yellow mixture was heated to 50 °C and stirred for 40 min. The reaction mixture was detected by HPLC, new peak was observed and the 87i disappeared. Brine (5 mL) was added to the mixture and then extracted with EtOAc (10 mL×2). The combined organic layers were concentrated under reduced pressure to give a residue, which was purified by pre-HPLC (column: Phenomenex Synergi C18 150*25*10 um; mobile phase: [water (0.1% TFA)-ACN]; B %: 35%-60%, 10 min) to afford the titled product Ex.87 (11 mg, 32.4 umol, 28.1% yield) as a yellow gum. $^1H$ NMR: MeOD 400 MHz; δ ppm 9.06 (brs, 1H), 8.88 (s, 1H), 8.79 (s, 1H), 7.29 (s, 2H), 7.20-7.02 (m, 5H), 3.83 (br d, J=4.4 Hz, 2H), 3.22-3.12 (m, 2H), 2.88 (br t, J=10.8 Hz, 1H); HPLC: MS: (M+1): 340.1

Example 88: Preparation of 2-hydroxy-3-(isothiazol-3-yl)cyclohepta-2,4,6-trien-1-one (Ex.88)

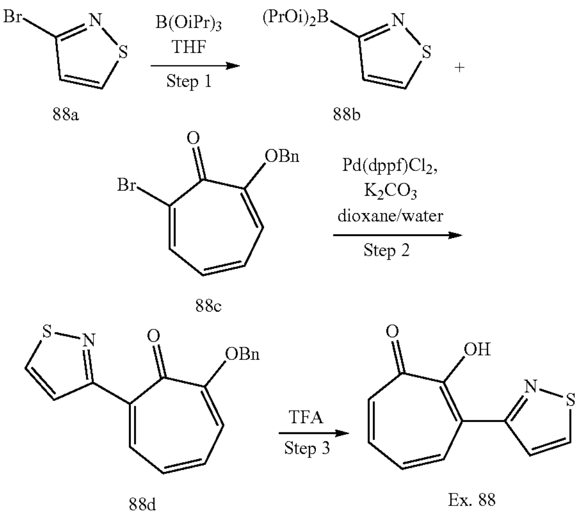

88a 88b 88c 88d Ex. 88

Step 1:

To a mixture of 88a (0.30 g, 1.83 mmol, 1.00 eq) and triisopropyl borate (482 mg, 2.56 mmol, 589 uL, 1.40 eq) in THF (4 mL) n-BuLi (2.5 M, 1.02 mL, 1.40 eq) was added drop-wise at −70 °C under $N_2$. The reaction mixture was stirred at −70 °C for 1 hr. LCMS showed the starting material was consumed completely. Water (8 mL) was added to the reaction mixture at 0 °C, and then extracted with ethyl acetate (20 mL×2). The combined organic layers were dried over $Na_2SO_4$, filtered and concentrated under reduced pressure to give 88b (0.34 g, crude) as a brown oil.

Step 2:

To a mixture of 88c (0.35 g, 1.20 mmol, 1.00 eq) and $K_2CO_3$ (332 mg, 2.40 mmol, 2.00 eq) in dioxane (3 mL) and $H_2O$ (0.6 mL) 88b (256 mg, 1.20 mmol, 1.00 eq) and $Pd(dppf)Cl_2$ (98 mg, 120 umol, 0.10 eq) were added at 25 °C under $N_2$. The system was degassed and then charged with nitrogen three times. The reaction mixture was heated and stirred at 118 °C for 20 min. LCMS showed the starting material was consumed completely and major desired MS was observed. After cooling, the mixture was extracted with ethyl acetate (20 mL×3). The combined organic phases were washed with brine (10 mL), dried over anhydrous $Na_2SO_4$, filtered and concentrated under reduced pressure to give a residue. The residue was purified by prep-TLC ($SiO_2$, Petroleum ether:Ethyl acetate=1:1) to give 88d (20 mg, crude) as a brown oil.

Step 3:

A solution of 88d (20 mg, crude) in TFA (0.5 mL) was heated and stirred at 50 °C for 30 min. LCMS showed the starting material was consumed completely and major desired MS was observed. The mixture was concentrated under reduced pressure to give a residue. The residue was purified by prep-HPLC (TFA condition) to afford the titled product Ex.88 (3 mg) as a yellow solid. $^1H$ NMR: MEOD 400 MHz; δ ppm 5.84 (d, J=10.4 Hz, 1H) 7.11 (br t, J=9.6 Hz, 1H) 7.35-7.45 (m, 2H) 7.70-7.84 (m, 2H); HPLC: MS: (M+1): 206.1

C. Effects of Tropolone Derivatives on the Regulation of Fe (Iron) Transport

In certain embodiments, the effects of tropolone derivatives on the regulation of Fe transport were determined by separate assays, including but not necessarily limited to: (1) ligand facilitated Fe(III) efflux from liposomes; and (2) shDMT1-Caco2 55Fe transport assay to assess ligand ability in transporting Fe (III).

Assay 1: Ligand Facilitated Fe(III) Efflux from Liposomes

Preparation of POPC (1-palmitoyl-2-oleoyl-sn-glycero-3-phosphocholine): Cholesterol Liposomes:

A 1M buffer solution of MES and Tris was prepared by dissolving 121.14 grams of Tris base and 213.25 grams of MES hydrate in 500 mL of MilliQ water and adjusted to pH7.0 using an 18M HCl solution before bringing the total volume of the solution to 1 L. A 500 mM solution of $FeCl_3$ was prepared by dissolving 0.811 grams of anhydrous $FeCl_3$ in 10 mL of a 0.1M $H_2SO_4$ aqueous solution. Inside buffer is prepared in a 50 mL falcon tube, which was added with 25 mL of MilliQ water, 1.61 g of sodium citrate, 1.5 mL of the above FeCl3 solution, and 2.5 mL of the 1M MES/Tris HCl buffer (pH=7.0), and finally additional MilliQ $H_2O$ to bring to a 50 mL final volume. The inside buffer prepared will be a solution with final concentrations of 15 mM of FeCl3, 125 mM of sodium citrate, and 50 mM of MES/Tris HCl at pH7.0.

Lipid solution is prepared by dissolving 206.9 mg of POPC (1-palmitoyl-2-oleoyl-sn-glycero-3-phosphocholine) and 8.6 mg of cholesterol in 10 mL of ethanol.

The lipids solution and the inside buffer solution are independently loaded into 10 mL luer lock syringes for loading into a virgin cartridge on a Precision Nanosystems NanoAssembler to prepare unilamaller liposomes with the following parameters: 7.5 mL total volume, 1.5:1 mixing ratio of inside buffer:lipids solution, 8 mL/min flow rate, ambient temperature, 0.35 mL start waste, and 0.05 mL of end waste. 7.5 mL of liposomes is harvested for purification on a 6-inch long, 1-inch diameter Sephadex G-50 column wetted in 600 mM sodium ascorbate and 50 mM MES/Tris HCl pH 7.0 buffer. This buffer also serves as the column running buffer. The crude liposome solution is carefully loaded with minimal volume of running buffer above the top of the Sphadex, allowed to enter the matrix, and the column is run with the continued addition of running buffer. The eluting liposomes, observed as a milky and turbid solution, are collected until free iron begins to elute (observed as a deep purple color) and the fractions are pooled for phosphorus quantitation.

Determination of Phosphorus Content:

Phosphorus content of eluted liposomes was determined by the process outlined below. 10 uL of liposome elution and a running buffer blank are added to a 5 mL glass vial containing 450 uL of a 8.9 M aqueous $H_2SO_4$ solution, the mixture is heated to 225 °C for 25 minutes in an aluminum heat block to hydrolyze POPC and cooled for 5 minutes. 200 ul of a 30% hydrogen peroxide aqueous solution is added to each vial and heated to 225 °C for 25 minutes. After cooling, the phosphorus content was determined using an Abcam Phosphate Assay kit, with buffer subtracted phosphorus levels determined against a standard curve of phosphate included in the kit. Liposomes were diluted to 1 mM phosphate in Running Buffer for use in assays after accounting for dilutions made during phospholipid digestion.

Determination of the Iron Transporting Rate Constant of the Ligands:

Determination of the rate at which a small molecule ligand liberates (transport) Ferric iron from liposomes is performed in clear bottom black 384-well plates on a Spectramax i3x set to read the absorbance at 562 nm in the kinetic mode every 60 seconds for 120 minutes. 1 uL of serially diluted DMSO stock solution of a small molecule ligand is added to wells in triplicate to give the final concentrations of 40, 20, 10, 5, 2.5, and 1.25 uM of the ligand at 80 μL final volume, followed by addition of 1 μL of 100 mM Ferrozine in water to give a final concentration of 1 mM ferrozine. 78 uL of liposomes diluted to 1 mM phosphorus in running buffer is added to wells as quickly as possible (using a digital repeater mulchannel pipette) with the kinetic read initiated as rapidly as possible after addition of liposomes to all wells. Typically, eight compounds at six concentrations are tested in triplicate simultaneously.

Upon completion of kinetic read, the data for individual reads is fitted to a single phase association regression with the equation $Y=(Y_0-Y_{Max})^{(-kX)}+Y_{Max}$, with Y being the 562 absorbance value and X being time in minutes. The k value from the individual replicate values is averaged from the triplicates runs for each compound concentration. The ligand's ability in liberating iron from within liposome is represented by the rate, k, at a given concentration. Rate k is considered as the efflux rate and ligands are ranked by the efflux rate at 10 uM ligand concentration at which they effect Ferric iron efflux. $K_{efflux}$ at 10 uM is reported in Tables 1 and 2.

Assay 2: shDMT1-Caco2 $^{55}Fe$ Transport Assay to Assess Ligand Ability in Transporting Fe (III)

Materials and Methods

Cells: DMT1-deficient Caco-2 cells (alias: "shDMT1," or "4A" cells) were from Grillo et al. *Science,* 2017, and were cryopreserved in liquid nitrogen prior to use.

Reagents and supplies: $^{55}FeCl_3$ was obtained from PerkinElmer (Boston, MA). Iron(III) chloride ($FeCl_3$) hexahydrate was obtained from Sigma. Dulbecco's Modified Eagle Medium (DMEM), fetal bovine serum (FBS), L-glutamine, MEM nonessential amino acids, penicillin-streptomycin, G418, formic acid, methanol, high-purity water, ammonium formate, dimethyl sulfoxide (DMSO) were purchased from Fisher Scientific. Propranolol, atenolol and carbutamide were obtained from Sigma-Aldrich Chemical Company (St Louis, MO). Scintillation cocktail was obtained from Research Product International Co. (Mount Prospect, IL).

Stericup filter system (PES membrane, 0.22 um pore size) was purchased from Fisher Scientific. Coming item #3378 24-well transwell insert plates. Test articles: known compounds hinokitiol and deferiprone were purchased from Sigma. They are tested side by side with the small molecule ligands disclosed in this application. DMSO stocks (10 mM, which is 1,000× of the 10 μM dose level) of hinokitiol or test articles were prepared. A stock solution of 25 mM deferiprone in DMSO was prepared. The DMSO stock solutions were stored at −20 °C or below when not in use.

The growth medium was prepared according to the following table

| Component | Stock | Final | For 1 L (mL) |
|---|---|---|---|
| DMEM | — | — | 1,000 |
| FBS | — | 10% total | 116.2 |
| Glutamine | 200 mM | 4 mM (2%) | 23.2 |
| PEN-STREP | 1000 μg/mL | 100 μg/mL (1%) | 11.6 |
| N.E. Amino Acids | — | 1% total | 11.6 |
| Geneticin G418 disulfate | | 800 mg/L | |

Apical media (serum free DMEM, 10 mM MES, pH 6.5) was prepared. Apical master mix media was prepared fresh with the addition of 200 nM $^{55}Fe$ before each experiment. For the negative control propranolol and atenolol wells, 200 nM of non-radioactive iron was used.

The basolateral media was serum-free DMEM, 10 mM HEPES, 2% bovine serum albumin (BSA), pH 7.4.

For each experiment, cells were seeded into the 24-well transwell plates (0.5 mL of 50,000 cells/mL) with growth media. The basolateral companion plate was loaded with 1 mL of growth media. After 12-24 hr, both the apical and basolateral chamber were replaced with growth media. The apical media was changed 3× per week for 21-28 days, including a media change exactly 48 hr before the assay date.

On the assay day, the TEER values were measured and the average TEER values was obtained. Individual wells with TEER vaule >35% lower than the average of all wells were excluded. For the qualified wells, the apical layer (twice) and basolaterial (once) chambers were washed with PBS. The basolateral companion plate was then filled with 1 mL of basolateral media. Via addition down the side-wall of the apical well, 300 μL per well of the apical assay master mix, with the indicated dose level of test article, was added. Each dose was tested in triplicate. The plates were incubated (5% $CO_2$ and 90% humidity at 37 °C) for the indicated timepoints. At each indicated timepoint, the basolateral supernatant was gently mixed via pipetting, and 200 μL of the basolateral supernatant was transferred to scintillation vials. To each scintillation counting vial, 5 mL of scintillation cocktail fluid was added. For each scintillation vial, the radioactivity (CPM) was determined with liquid scintillation counter LS6500. The counting time per vial was 5 min.

Data Processing:

All raw CPM values are divided by the average value of blank DMSO solution to give a fold of change above the DMSO value. The mean and standard deviation of each compound at each concentration level and at each time point measured was calculated to give the fold change (fc) value.

For rank order compounds, the fc value of a ligand at 4 h time point is further divided by the fold change (fc) value of hinokitiol (a positive control compound) at an equimolar concentration to arrive at the FC (normalized fold of change) value. Data reported in Tables 1 and 2 is 4 hr time point FC=fc-ligand @ 3 uM/fc-hino @ 3 uM, and FC hino=1.

Example 89. Experimental Results of (1) Ligand Facilitated Fe(III) Efflux from Liposomes; (2) shDMT1-Caco2 55Fe Transport Assay to Assess Ligand Ability in Transporting Fe (III)

TABLE 1

Results of Assays (1)-(2) for Selected Compounds

| Structure | Liposome Fe transport $k_{efflux}$ at 10 μM | Caco2 shDMT1 transport FC @ 3 μM, 4 h |
|---|---|---|
| 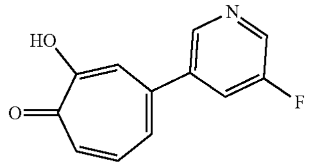 [SMILES: O=c1cccc(-c2cncc(F)c2)cc1O] | 5-7.5 | 0.01-0.5 |
| 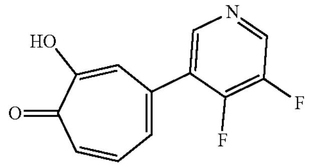 [SMILES: O=c1cccc(-c2cncc(F)c2F)cc1O] | 0.1-5 | 0.01-0.5 |
| 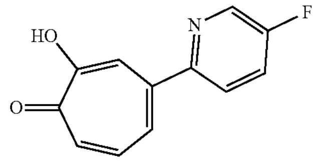 [SMILES: O=c1cccc(-c2ccc(F)cn2)cc1O] | 5-7.5 | 0.01-0.5 |

TABLE 1-continued
| Results of Assays (1)-(2) for Selected Compounds | | |
|---|---|---|
| Structure | Liposome Fe transport $k_{efflux}$ at 10 μM | Caco2 shDMT1 transport FC @ 3 μM, 4 h |
| 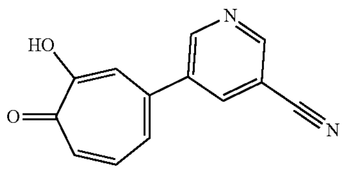 [SMILES: N#Cc1cncc(-c2cccc(=O)c(O)c2)c1] | 0.1-5 | 0.01-0.5 |
| 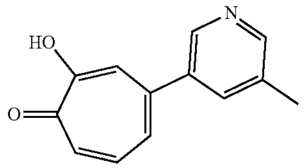 [SMILES: Cc1cncc(-c2cccc(=O)c(O)c2)c1] | 0.1-5 | N/A |
| 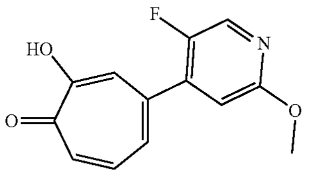 [SMILES: COc1cc(-c2cccc(=O)c(O)c2)c(F)cn1] | 7.5-10 | 0.01-0.5 |
| 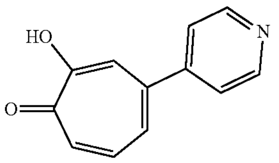 [SMILES: O=c1cccc(-c2ccncc2)cc1O] | 0.1-5 | N/A |
| 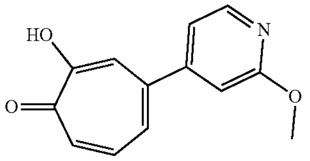 [SMILES: COc1cc(-c2cccc(=O)c(O)c2)ccn1] | 7.5-10 | 0.01-0.5 |
| 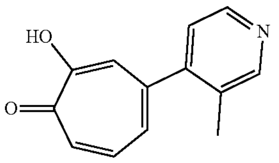 [SMILES: Cc1cnccc1-c1cccc(=O)c(O)c1] | 0.1-5 | 0.01-0.5 |
| 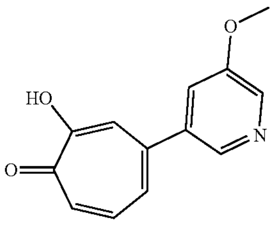 [SMILES: COc1cncc(-c2cccc(=O)c(O)c2)c1] | 0.1-5 | 0.01-0.5 |
| 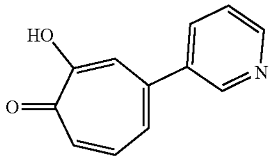 [SMILES: O=c1cccc(-c2cccnc2)cc1O] | 0.1-5 | 0.01-0.5 |

TABLE 1-continued
| Results of Assays (1)-(2) for Selected Compounds | | |
|---|---|---|
| Structure | Liposome Fe transport $k_{efflux}$ at 10 μM | Caco2 shDMT1 transport FC @ 3 μM, 4 h |
| 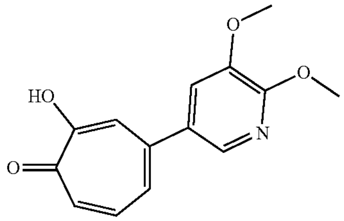 [SMILES: COc1cc(-c2cccc(=O)c(O)c2)cnc1OC] | 7.5-10 | 0.5-1 |
| 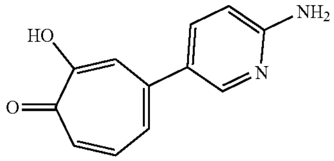 [SMILES: Nc1ccc(-c2cccc(=O)c(O)c2)cn1] | 0.1-5 | N/A |
| 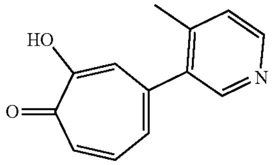 [SMILES: Cc1ccncc1-c1cccc(=O)c(O)c1] | 0.1-5 | N/A |
| 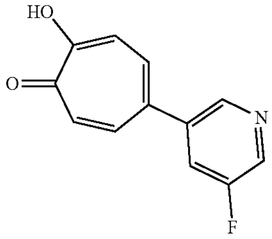 [SMILES: O=c1ccc(-c2cncc(F)c2)ccc1O] | 5-7.5 | 0.01-0.5 |
| 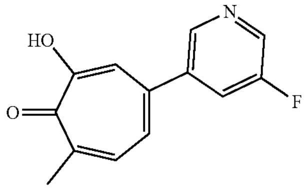 [SMILES: Cc1ccc(-c2cncc(F)c2)cc(O)c1=O] | 10-25 | 0.5-1 |
| 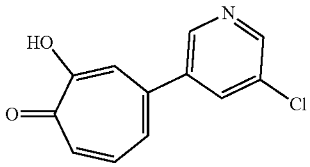 [SMILES: O=c1cccc(-c2cncc(Cl)c2)cc1O] | 5-7.5 | 0.01-0.5 |
| 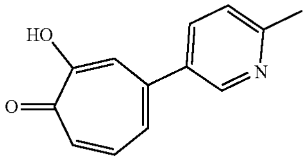 [SMILES: Cc1ccc(-c2cccc(=O)c(O)c2)cn1] | 0.1-5 | 0.01-0.5 |

TABLE 1-continued
| Results of Assays (1)-(2) for Selected Compounds | | |
|---|---|---|
| Structure | Liposome Fe transport $k_{efflux}$ at 10 μM | Caco2 shDMT1 transport FC @ 3 μM, 4 h |
| 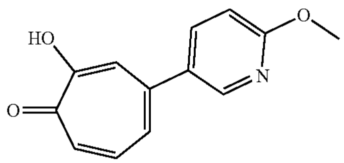 [SMILES: COc1ccc(-c2cccc(=O)c(O)c2)cn1] | 0.1-5 | 0.01-0.5 |
| 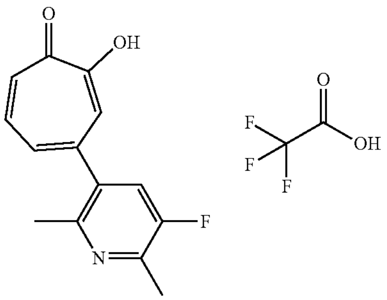 [SMILES: Cc1nc(C)c(-c2cccc(=O)c(O)c2)cc1F ; O=C(O)C(F)(F)F] | 0.1-5 | N/A |
| 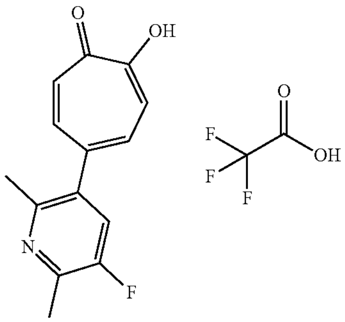 [SMILES: Cc1nc(C)c(-c2ccc(O)c(=O)cc2)cc1F ; O=C(O)C(F)(F)F] | 0.1-5 | N/A |
| 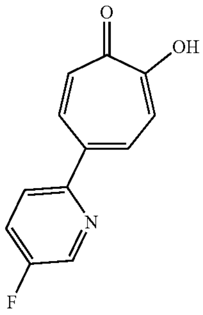 [SMILES: O=c1ccc(-c2ccc(F)cn2)ccc1O] | 0.1-5 | N/A |
| 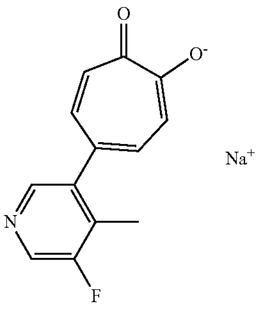 [SMILES: Cc1c(F)cncc1-c1ccc([O-])c(=O)cc1 ; [Na+]] | 10-25 | 0.01-0.5 |

TABLE 1-continued
Results of Assays (1)-(2) for Selected Compounds
| Structure | Liposome Fe transport $k_{efflux}$ at 10 μM | Caco2 shDMT1 transport FC @ 3 μM, 4 h |
|---|---|---|
| 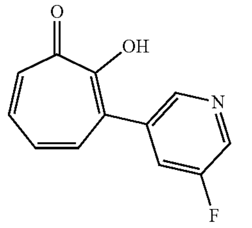 [SMILES: O=c1ccccc(-c2cncc(F)c2)c1O] | 7.5-10 | 0.01-0.5 |
| 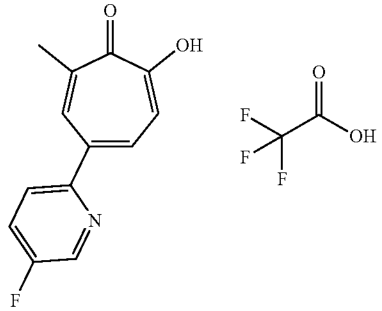 [SMILES: Cc1cc(-c2ccc(F)cn2)ccc(O)c1=O ; O=C(O)C(F)(F)F] | 5-7.5 | N/A |
| 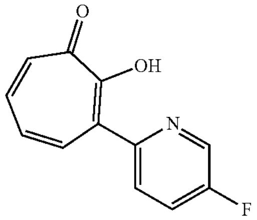 [SMILES: O=c1ccccc(-c2ccc(F)cn2)c1O] | 10-25 | 0.01-0.5 |
| 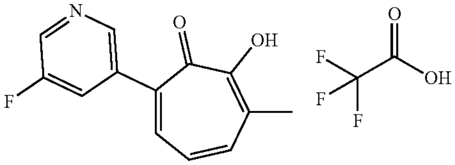 | 10-25 | N/A |
| 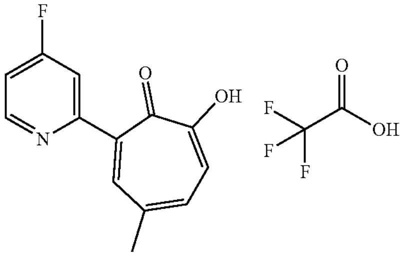 | 10-25 | 0.5-1 |
| 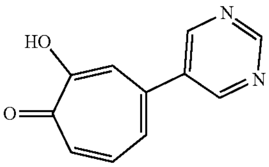 [SMILES: O=c1cccc(-c2cncnc2)cc1O] | 5-7.5 | 0.01-0.5 |

TABLE 1-continued
Results of Assays (1)-(2) for Selected Compounds
| Structure | Liposome Fe transport $k_{efflux}$ at 10 μM | Caco2 shDMT1 transport FC @ 3 μM, 4 h |
|---|---|---|
| 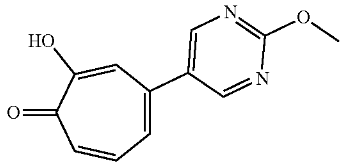 [SMILES: COc1ncc(-c2cccc(=O)c(O)c2)cn1] | 0.1-5 | 0.01-0.5 |
| 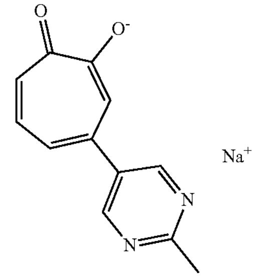 [SMILES: Cc1ncc(-c2cccc(=O)c([O-])c2)cn1 ; [Na+]] | 0.1-5 | 0.01-0.5 |
| 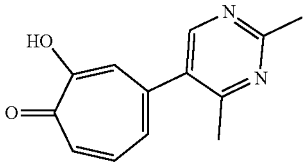 [SMILES: Cc1ncc(-c2cccc(=O)c(O)c2)c(C)n1] | 5-7.5 | 0.01-0.5 |
| 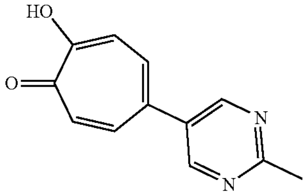 [SMILES: Cc1ncc(-c2ccc(O)c(=O)cc2)cn1] | 0.1-5 | 0.01-0.5 |
| 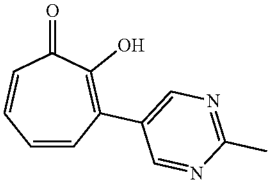 [SMILES: Cc1ncc(-c2ccccc(=O)c2O)cn1] | 0.1-5 | 0.01-0.5 |
| 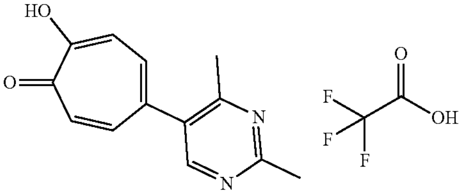 | 7.5-10 | 0.01-0.5 |
| 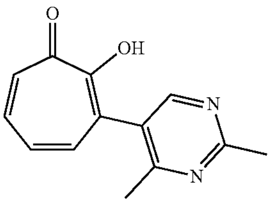 [SMILES: Cc1ncc(-c2ccccc(=O)c2O)c(C)n1] | 5-7.5 | 0.01-0.5 |

TABLE 1-continued
Results of Assays (1)-(2) for Selected Compounds
| Structure | Liposome Fe transport $k_{efflux}$ at 10 μM | Caco2 shDMT1 transport FC @ 3 μM, 4 h |
|---|---|---|
| 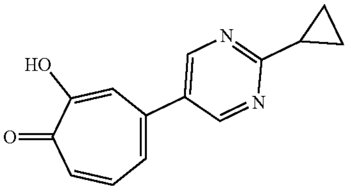 [SMILES: O=c1cccc(-c2cnc(C3CC3)nc2)cc1O] | 5-7.5 | 0.01-0.5 |
| 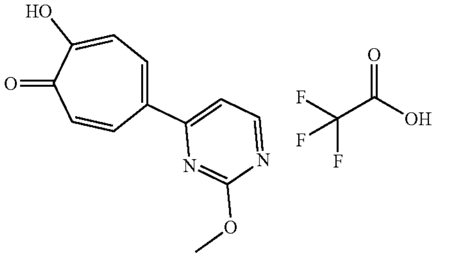 | 0.1-5 | 0.01-0.5 |
| 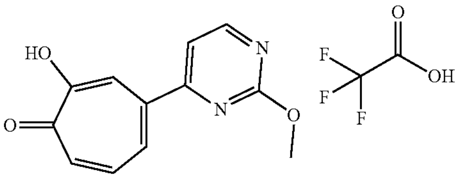 | 0.1-5 | 0.01-0.5 |
| 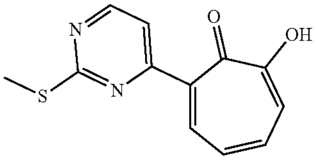 [SMILES: CSc1nccc(-c2ccccc(O)c2=O)n1] | 5-7.5 | N/A |
| 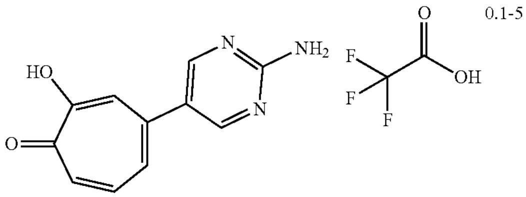 $C_{13}H_{10}F_3N_3O_4$ | 0.1-5 | N/A |
| 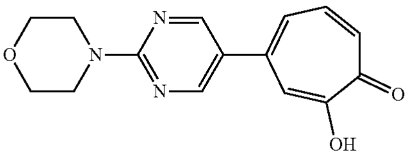 [SMILES: O=c1cccc(-c2cnc(N3CCOCC3)nc2)cc1O] | 7.5-10 | 0.01-0.5 |
| 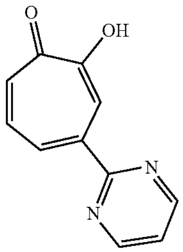 [SMILES: O=c1cccc(-c2ncccn2)cc1O] | 5-7.5 | N/A |

TABLE 1-continued
Results of Assays (1)-(2) for Selected Compounds
| Structure | Liposome Fe transport $k_{efflux}$ at 10 μM | Caco2 shDMT1 transport FC @ 3 μM, 4 h |
|---|---|---|
| 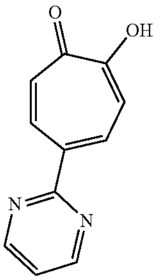 [SMILES: O=c1ccc(-c2ncccn2)ccc1O] | 0.1-5 | N/A |
| 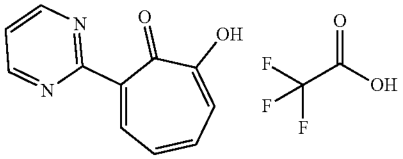 | 0.1-5 | N/A |
| 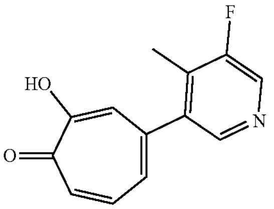 [SMILES: Cc1c(F)cncc1-c1cccc(=O)c(O)c1] | 5-7.5 | 0.01-0.5 |
| 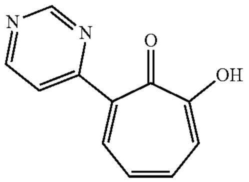 [SMILES: O=c1c(O)ccccc1-c1ccncn1] | 0.1-5 | 0.01-0.5 |
| 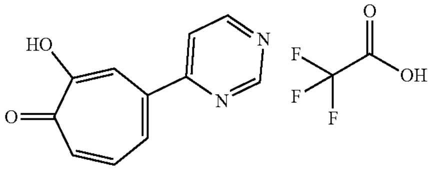 | 0.1-5 | 0.01-0.5 |
| 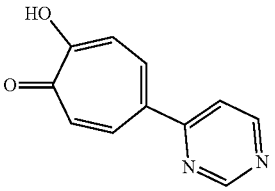 [SMILES: O=c1ccc(-c2ccncn2)ccc1O] | 0.1-5 | 0.01-0.5 |
| 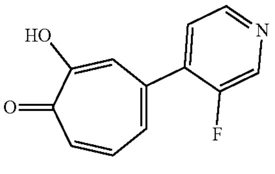 [SMILES: O=c1cccc(-c2ccncc2F)cc1O] | 0.1-5 | 0.01-0.5 |

TABLE 1-continued
Results of Assays (1)-(2) for Selected Compounds
| Structure | Liposome Fe transport $k_{efflux}$ at 10 μM | Caco2 shDMT1 transport FC @ 3 μM, 4 h |
|---|---|---|
| 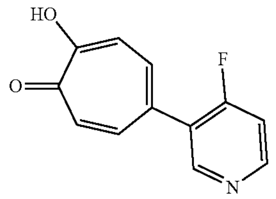 [SMILES: O=c1ccc(-c2cnccc2F)ccc1O] | 5-7.5 | 0.01-0.5 |
| 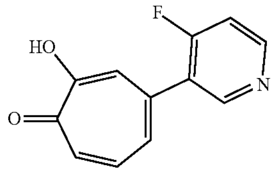 [SMILES: O=c1cccc(-c2cnccc2F)cc1O] | 0.1-5 | 0.01-0.5 |
| 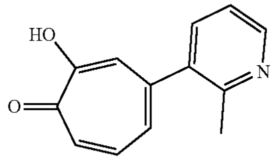 [SMILES: Cc1ncccc1-c1cccc(=O)c(O)c1] | 0.1-5 | 0.01-0.5 |
| 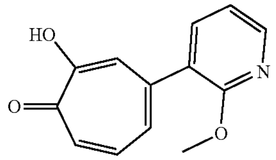 [SMILES: COc1ncccc1-c1cccc(=O)c(O)c1] | 10-25 | 0.01-0.5 |
| 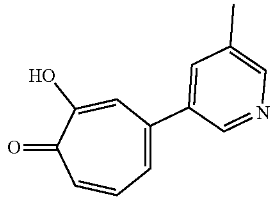 [SMILES: Cc1cncc(-c2cccc(=O)c(O)c2)c1] | 0.1-5 | N/A |
| 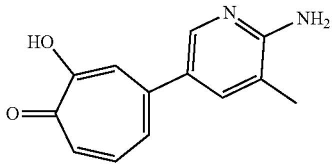 [SMILES: Cc1cc(-c2cccc(=O)c(O)c2)cnc1N] | 0.1-5 | 0.01-0.5 |
| 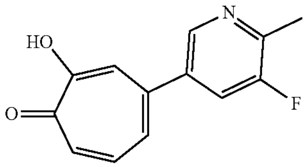 [SMILES: Cc1ncc(-c2cccc(=O)c(O)c2)cc1F] | 7.5-10 | 0.01-0.5 |
| 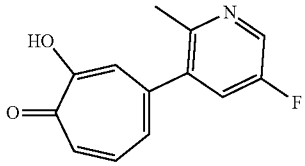 [SMILES: Cc1ncc(F)cc1-c1cccc(=O)c(O)c1] | 0.1-5 | 0.01-0.5 |

TABLE 1-continued
| Results of Assays (1)-(2) for Selected Compounds | | |
|---|---|---|
| Structure | Liposome Fe transport $k_{efflux}$ at 10 µM | Caco2 shDMT1 transport FC @ 3 µM, 4 h |
| 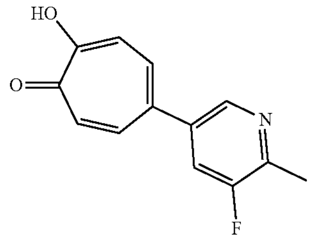 [SMILES: Cc1ncc(-c2ccc(O)c(=O)cc2)cc1F] | 5-7.5 | 0.01-0.5 |
| 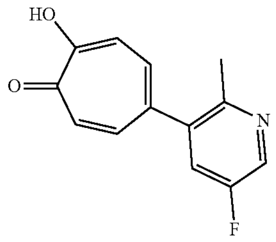 [SMILES: Cc1ncc(F)cc1-c1ccc(O)c(=O)cc1] | 0.1-5 | N/A |
| 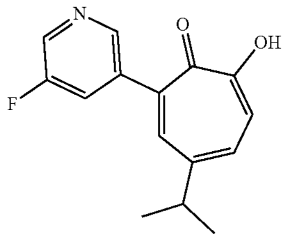 [SMILES: CC(C)c1ccc(O)c(=O)c(-c2cncc(F)c2)c1] | 7.5-10 | 0.01-0.5 |

TABLE 1-continued

| Results of Assays (1)-(2) for Selected Compounds | | |
|---|---|---|
| Structure | Liposome Fe transport $k_{efflux}$ at 10 μM | Caco2 shDMT1 transport FC @ 3 μM, 4 h |
| 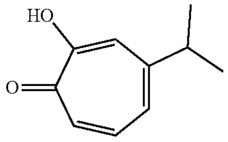<br>hinokitiol | 7.77 | 1 |
| 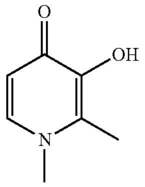<br>deferiprone | 0 | 0.02-0.03 |

Reference compounds: hinokitiol; and deferiprone.

TABLE 2

| Results of Assays (1)-(2) for Additional Selected Compounds | | |
|---|---|---|
| Structure | Liposome Fe transport $K_{efflux}$ at 10 μM | Caco2 shDMT1 transport FC @ 3 μM, 4 h |
| 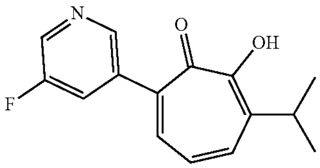 [SMILES: CC(C)c1cccc(-c2cncc(F)c2)c(=O)c1O] | <0.1 | N/A |
| 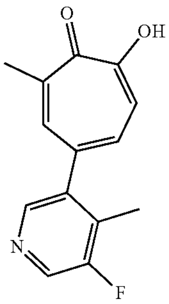 [SMILES: Cc1c(F)cncc1-c1ccc(O)c(=O)c(C)c1] | 10-25 | N/A |

TABLE 2-continued

| Results of Assays (1)-(2) for Additional Selected Compounds | | |
|---|---|---|
| Structure | Liposome Fe transport $K_{efflux}$ at 10 μM | Caco2 shDMT1 transport FC @ 3 μM, 4 h |
| 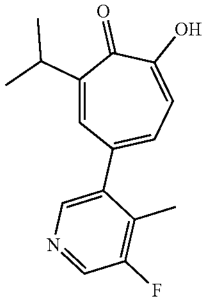 [SMILES: Cc1c(F)cncc1-c1ccc(O)c(=O)c(C(C)C)c1] | <0.1 | N/A |
| 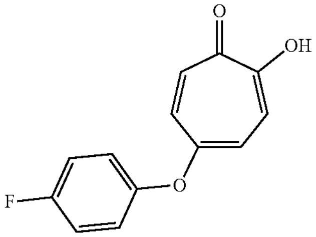 [SMILES: O=c1ccc(Oc2ccc(F)cc2)ccc1O] | 5-7.5 | N/A |

TABLE 2-continued
| Results of Assays (1)-(2) for Additional Selected Compounds | | |
|---|---|---|
| Structure | Liposome Fe transport $K_{efflux}$ at 10 μM | Caco2 shDMT1 transport FC @ 3 μM, 4 h |
| 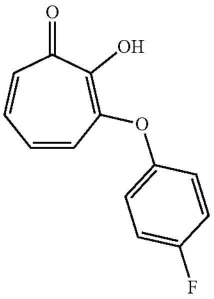 [SMILES: O=c1ccccc(Oc2ccc(F)cc2)c1O] | 0.1-5 | N/A |
| 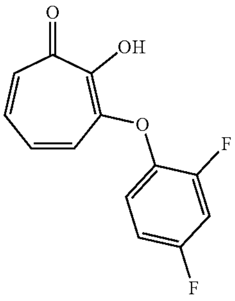 [SMILES: O=c1ccccc(Oc2ccc(F)cc2F)c1O] | <0.1 | 0.01-0.5 |
| 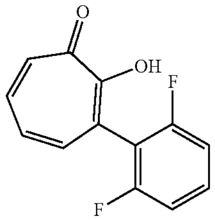 [SMILES: O=c1ccccc(-c2c(F)cccc2F)c1O] | 7.5-10 | N/A |
| 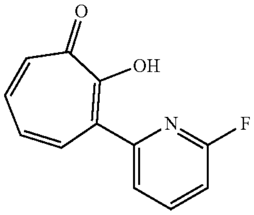 [SMILES: O=c1ccccc(-c2cccc(F)n2)c1O] | 10-25 | 0.01-0.5 |
| 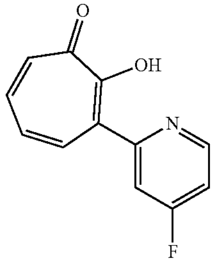 [SMILES: O=c1ccccc(-c2cc(F)ccn2)c1O] | 10-25 | 0.01-0.5 |
TABLE 2-continued
| Results of Assays (1)-(2) for Additional Selected Compounds | | |
|---|---|---|
| Structure | Liposome Fe transport $K_{efflux}$ at 10 μM | Caco2 shDMT1 transport FC @ 3 μM, 4 h |
| 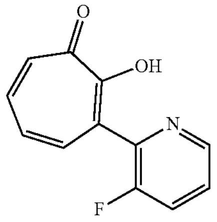 [SMILES: O=c1ccccc(-c2ncccc2F)c1O] | 0.1-5 | N/A |
| 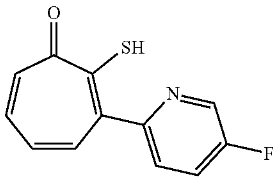 [SMILES: O=c1ccccc(-c2ccc(F)cn2)c1S] | 7.5-10 | N/A |
| 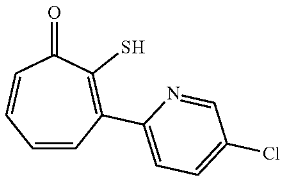 [SMILES: O=c1ccccc(-c2ccc(Cl)cn2)c1S] | 7.5-10 | N/A |
| 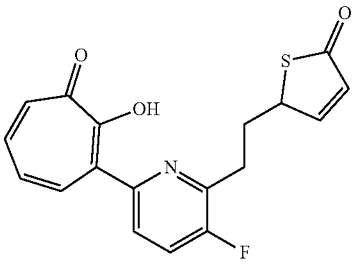 [SMILES: O=C1C=CC(CCc2nc(-c3ccccc(=O)c3O)ccc2F)S1] | 0.1-5 | N/A |
| 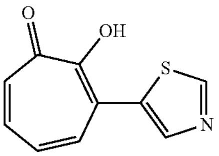 [SMILES: O=c1ccccc(-c2cncs2)c1O] | 0.1-5 | 0.5-1 |
| 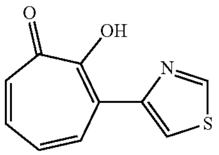 [SMILES: O=c1ccccc(-c2cscn2)c1O] | | 0.5-1 |
| 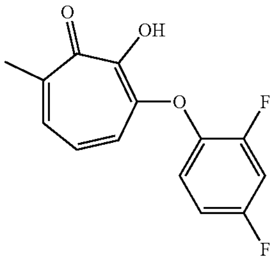 [SMILES: Cc1cccc(Oc2ccc(F)cc2F)c(O)c1=O] | 0.1-5 | N/A |

TABLE 2-continued

Results of Assays (1)-(2) for Additional Selected Compounds

| Structure | Liposome Fe transport $K_{efflux}$ at 10 μM | Caco2 shDMT1 transport FC @ 3 μM, 4 h |
| --- | --- | --- |
| 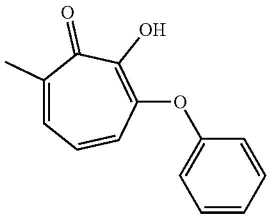 [SMILES: Cc1cccc(Oc2ccccc2)c(O)c1=O] | 0.1-5 | N/A |
| 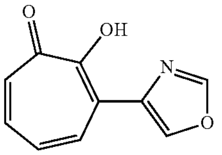 [SMILES: O=c1ccccc(-c2cocn2)c1O] | 5-7.5 | N/A |
| 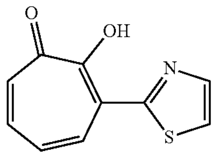 [SMILES: O=c1ccccc(-c2nccs2)c1O] | 5-7.5 | N/A |
| 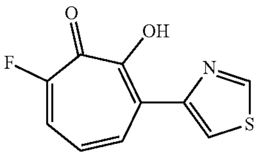 [SMILES: O=c1c(F)cccc(-c2cscn2)c1O] | 7.5-10 | N/A |
| 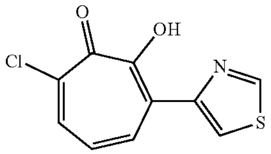 [SMILES: O=c1c(Cl)cccc(-c2cscn2)c1O] | 0.1-5 | N/A |
| 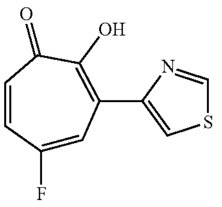 [SMILES: O=c1ccc(F)cc(-c2cscn2)c1O] | 0.1-5 | N/A |
| 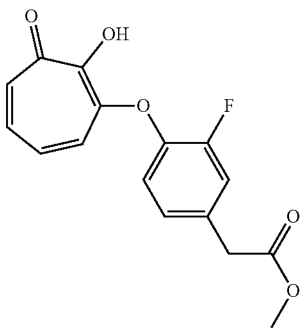 [SMILES: COC(=O)Cc1ccc(Oc2ccccc(=O)c2O)c(F)c1] | 5-7.5 | N/A |
| 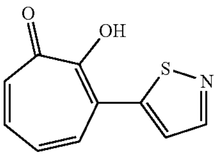 [SMILES: O=c1ccccc(-c2ccns2)c1O] | 0.1-5 | N/A |
| 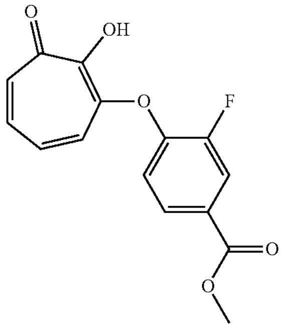 [SMILES: COC(=O)c1ccc(Oc2ccccc(=O)c2O)c(F)c1] | 0.1-5 | N/A |
| 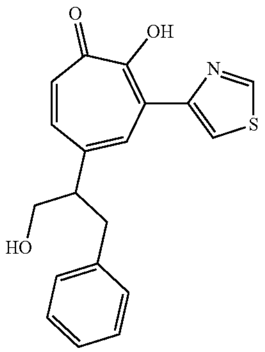 [SMILES: O=c1ccc(C(CO)Cc2ccccc2)cc(-c2cscn2)c1O] | 0.1-5 | N/A |
| 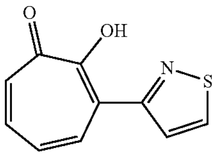 [SMILES: O=c1ccccc(-c2ccsn2)c1O] | N/A | N/A |
| 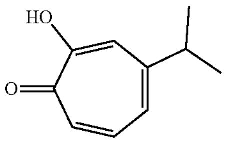 hinokitiol | 7.77 | 1.00 |

Reference compounds: hinokitiol.

D. Effects of Tropolone Derivatives on Anemia of Inflammation

In certain embodiments, the effects of the compounds of the present disclosure are evaluated according to assay 3.

Assay 3: Turpentine Oil Induced Anemia of Inflammation

This is a model of anemia of inflammation by turpentine oil injection in combination with phlebotomy.

Conditioning: Mice receive 3 doses of turpentine oil subcutaneously within 2 weeks. Mice are anesthetized and then administered 0.1 mL/20 g body weight of turpentine oil (TO) via subcutaneous injection in the scapular fat area using syringe and 27 G needle on Day 1, 7, and 14. On day 14, after the final injection of turpentine oil, a controlled 10% hemorrhage (approximately 200 uL) is accomplished via anesthetized orbital sinus bleed to increase the magnitude of anemia. The bleeding uses orbital blood sampling technique, 200 uL capillary bleeding device (essentially a vacutainer tube with a glass capillary tube attached). The eye is clean gauze light pre-soaked with sterile saline held over eye immediately following hemorrhage to promote hemostasis.

Treatment: On day 15, 16 hours post last dose of turpentione oil, sham group and TO plus bleeding group is terminated. These two groups are used as part of control.

On day 15, vehicle group and compound treatment groups will receive proper vehicle or compounds at a specified dose accordingly, treatments can be oral once a day or oral twice a day. The treatment will continue for 7 days, and then terminated on day 21.

On day 21, 3 hours post last treatment of test articles, the vehicle and treatment group are terminated. At the time of blood collection and tissue harvest, mice are weighed then anesthetized with isoflurane anesthesia (3-4% with oxygen to a surgical plane of anesthesia). Depth of anesthesia is monitored by toe pinch method. Collect blood through cardiac puncture which is a terminal procedure. Blood samples are placed into tubes with EDTA anticoagulated to undergo CBC analysis. The remaining of the blood is placed into serum separator to collect serum for the test of Total Iron, Ferritin and TIBC by clinical chemical analyzer and, in some instances, a proinflammatory cytokine panel, including e.g., cytokines selected from IL-6, TNF-α, IL-10, IL-1α, IL-4, IL-6, IL-13, IFNα and IL-1β or a 9-cytokine panel such as those commercially available from Luminex. Ferritin measurement allows for assessment of transferrin saturation, a significant and clinically relevant measure of correction of anemia due to anemia of inflammation. The leftover serum is used for assessment of drug concentration at termination. After blood sampling the tissues of duodenum, spleen and liver are snap frozen (in multiple aliquots per organ) in liquid nitrogen and stored at −80 degree for later determination of iron content and assessment of hepcidin gene expression and Ferroportin gene and protein expression.

Data analysis: The iron mobilization impact of the compounds are assessed based on the serum iron level, transferrin saturation and TIBC; the ability of restoring normal iron homeostasis and metabolism and subsequent rescue of anemia are assessed by comparing the hemoglobin and hematocrit levels of test article treated groups with vehicle treated group.

Example 90. Compounds of the Present Disclosure have Advantageous Absorption, Distribution, Metabolism, Excretion (ADME) and Drug Metabolism and Pharmacokinetics (DMPK) Properties Compounds of the present disclosure were further evaluated in standard in vitro and in vivo Absorption, Distribution, Metabolism, Excretion (ADME) and Drug Metabolism and Pharmacokinetics (DMPK) assays to assess drug profiles important for further drug development.

Such assessments included human and mouse liver microsomal stability assays as well as 6-hour mouse PK studies. Compounds of the present disclosure demonstrated desirable ADME and DMPK characteristics, including e.g., improved in vitro liver microsomal stability and/or in vivo PK properties as compared to hinokitiol. For example, as shown in Tables 3 and 4, compounds of the present disclosure, including e.g., Ex.26 and others, displayed a longer clearence half-life ($t_{1/2}$) and/or lower intrinsic clearence ($CL_{int}$) than hinokitiol in one or both of mouse and human liver microsomal stability assays.

TABLE 3

Liver Microsomal Stability Results for Example 26

| | Human | | Mouse | |
|---|---|---|---|---|
| | $t_{1/2}$ (min) | $CL_{int}$ (μL/min/mgprotein) | $t_{1/2}$ (min) | $CL_{int}$ (μL/min/mgprotein) |
| Hinokitiol | 11.59 | 119.59 | 29.68 | 46.70 |
| 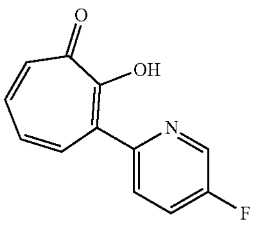 [SMILES: O=c1ccccc(-c2ccc(F)cn2)c1O] Ex. 26 | >150 | <24.99 | >150 | <24.99 |

TABLE 4
Liver Microsomal Stability Results for Additional Selected Compounds
| | | Human | | Mouse | |
|---|---|---|---|---|---|
| | | $t_{1/2}$ (min) | $CL_{int}$ (μL/min/mg protein) | $t_{1/2}$ (min) | $CL_{int}$ (μL/min/mg protein) |
| Hinokitiol | | 9.20 | 149.90 | 32.00 | 43.40 |
| Ex.1 | 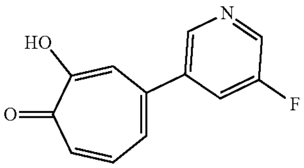 [SMILES: O=c1cccc(-c2cncc(F)c2)cc1O] | >120 | <11.55 | >120 | <11.55 |
| Ex.32 | 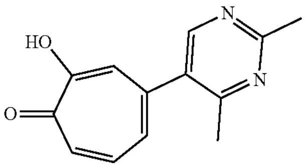 [SMILES: Cc1ncc(-c2cccc(=O)c(O)c2)c(C)n1] | >120 | <11.55 | >120 | <11.55 |
| Ex.3 | 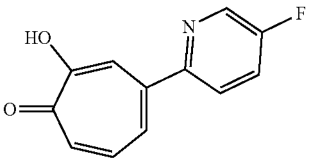 [SMILES: O=c1cccc(-c2ccc(F)cn2)cc1O] | >120 | <11.55 | >120 | <11.55 |
| Ex.37 | 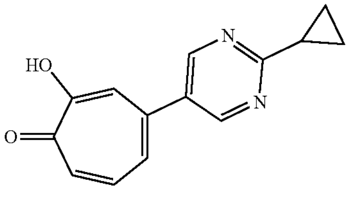 [SMILES: O=c1cccc(-c2cnc(C3CC3)nc2)cc1O] | >120 | <11.55 | >120 | <11.55 |
| Ex.57 | 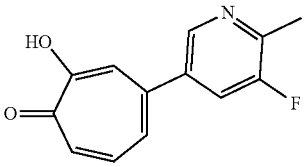 [SMILES: Cc1ncc(-c2cccc(=O)c(O)c2)cc1F] | >120 | <11.55 | >120 | <11.55 |
| Ex.23 | 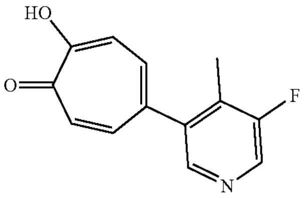 [SMILES: Cc1c(F)cncc1-c1ccc(O)c(=O)cc1] | >120 | <11.55 | >120 | <11.55 |
| Ex.16 | 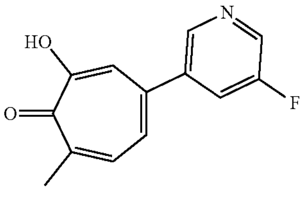 [SMILES: Cc1ccc(-c2cncc(F)c2)cc(O)c1=O] | >120 | <11.55 | 82.99 | 16.70 |

TABLE 4-continued

| Liver Microsomal Stability Results for Additional Selected Compounds | | | | | |
|---|---|---|---|---|---|
| | | Human | | Mouse | |
| | | $t_{1/2}$ (min) | $CL_{int}$ (μL/min/mg protein) | $t_{1/2}$ (min) | $CL_{int}$ (μL/min/mg protein) |
| Ex.31 | 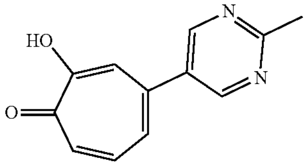 [SMILES: Cc1ncc(-c2cccc(=O)c(O)c2)cn1] | >120 | <11.55 | >120 | <11.55 |

In addition, as shown in Table 5, numerous compounds, including Ex. 1, Ex. 3, Ex. 16, Ex. 23, Ex. 26, Ex. 31, Ex. 32, Ex. 37, Ex. 57, Ex. 67, and Ex. 76, displayed one or more improved mouse 6-hour PK properties compared to hinokitiol.

TABLE 5

| Mouse 6-hour PK Results | | | | |
|---|---|---|---|---|
| Compound ID | | Cmax (ng/ml) | $AUC_{last}$ 0-6 hr (hr * ng/mL) | $t_{1/2}$ (hr) |
| Hinokitiol | | 956 | 584 | 1.11 |
| Ex.1 | 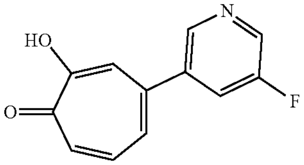 [SMILES: O=c1cccc(-c2cncc(F)c2)cc1O] | 5000-19999 | 5000-19999 | <1.25 |
| Ex.3 | 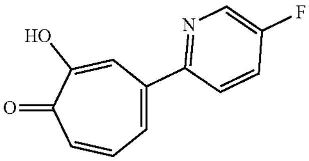 [SMILES: O=c1cccc(-c2ccc(F)cn2)cc1O] | 1500-4999 | 5000-19999 | 1.25-4.99 |
| Ex.16 | 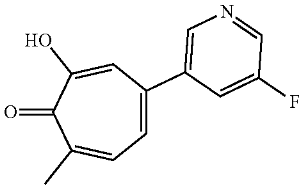 [SMILES: Cc1ccc(-c2cncc(F)c2)cc(O)c1=O] | 5000-19999 | >20000 | 1.25-4.99 |
| Ex.23 | 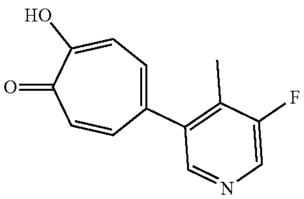 [SMILES: Cc1c(F)cncc1-c1ccc(O)c(=O)cc1] | 5000-19999 | >20000 | 1.25-4.99 |

TABLE 5-continued
| Mouse 6-hour PK Results | | | | |
|---|---|---|---|---|
| Compound ID | | Cmax (ng/ml) | $AUC_{last}$ 0-6 hr (hr * ng/mL) | $t_{1/2}$ (hr) |
| Ex.26 | 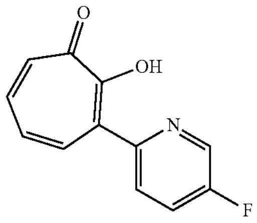 [SMILES: O=c1ccccc(-c2ccc(F)cn2)c1O] | 1500-4999 | 1500-4999 | 1.25-4.99 |
| Ex.31 | 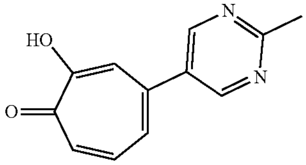 [SMILES: Cc1ncc(-c2cccc(=O)c(O)c2)cn1] | 1500-4999 | 1500-4999 | 1.25-4.99 |
| Ex.32 | 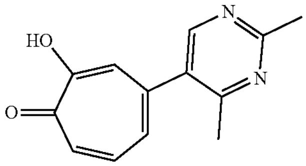 [SMILES: Cc1ncc(-c2cccc(=O)c(O)c2)c(C)n1] | 1500-4999 | 5000-19999 | 1.25-4.99 |
| Ex.37 | 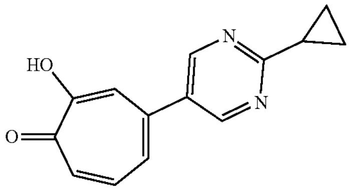 [SMILES: O=c1cccc(-c2cnc(C3CC3)nc2)cc1O] | 500-1499 | 1500-4999 | 1.25-4.99 |
| Ex.57 | 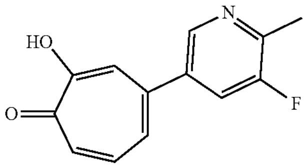 [SMILES: Cc1ncc(-c2cccc(=O)c(O)c2)cc1F] | 500-1499 | 1500-4999 | 1.25-4.99 |
| Ex.67 | 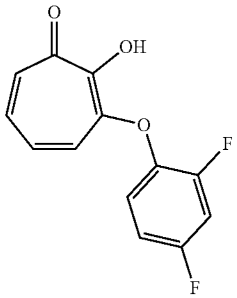 [SMILES: O=c1ccccc(Oc2ccc(F)cc2F)c1O] | 1500-4999 | 1500-4999 | 1.25-4.99 |
| Ex.76 | 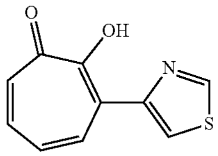 [SMILES: O=c1ccccc(-c2cscn2)c1O] | 1500-4999 | 500-1499 | <1.25 |

Accordingly, the results presented above demonstrate that compounds of the present disclosure have desireable ADME and DMPK characteristics, including, e.g., where such characteristics are improved compared to hinokitiol.

EQUIVALENTS

The foregoing written specification is considered to be sufficient to enable one skilled in the art to practice the present disclosure. The present disclosure is not to be limited in scope by examples provided, since the examples are intended as a single illustration of one aspect of the present disclosure and other functionally equivalent embodiments are within the scope of the present disclosure. Various modifications of the present disclosure in addition to those shown and described herein will become apparent to those skilled in the art from the foregoing description and fall within the scope of the appended claims. The advantages and objects of the present disclosure are not necessarily encompassed by each embodiment of the present disclosure.

What is claimed is:

1. A compound or a tautomer thereof, or a pharmaceutically acceptable salt of either, represented by Formula Ia:

Formula Ia

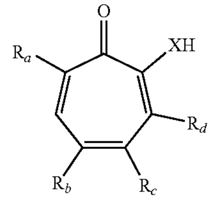

wherein:

X represents sulfur or oxygen;

and wherein:

$R_a$, $R_b$, and $R_d$ represent hydrogen; and $R_c$ represents heteroaryl or substituted heteroaryl according to Formula II, or aryloxy, substituted aryloxy, heteroaryloxy, or substituted heteroaryloxy according to Formula IIa;

or wherein:

$R_a$, $R_c$, and $R_d$ represent hydrogen; and $R_b$ represents heteroaryl or substituted heteroaryl according to Formula II or heteroaryloxy or substituted heteroaryloxy according to Formula IIa;

or wherein:

$R_a$, $R_b$, and $R_c$ represent hydrogen; and $R_d$ represents substituted heteroaryl according to Formula II;

or wherein:

$R_a$ represents alkyl;

one and only one of $R_b$, $R_c$, and $R_d$ represents heteroaryl or substituted heteroaryl according to Formula II, or one and only one of $R_b$ and $R_c$ represents aryloxy, substituted aryloxy, heteroaryloxy, or substituted heteroaryloxy according to Formula IIa; and two of $R_b$, $R_c$, and $R_d$ represent hydrogen;

or wherein:

$R_a$ represents heteroaryl or substituted heteroaryl according to Formula II or aryloxy, substituted aryloxy, heteroaryloxy, or substituted heteroaryloxy according to Formula IIa;

one and only one of $R_b$, $R_c$, and $R_d$ represents alkyl; and two of $R_b$, $R_c$, and $R_d$ represent hydrogen;

or wherein:

$R_a$ represents substituted heteroaryl according to Formula II; and each of $R_b$, $R_c$, and $R_d$ represent hydrogen; and wherein Formula II is Formula II

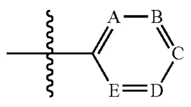

and wherein Formula IIa is:

Formula IIa

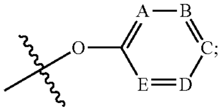

wherein each of A, B, C, D, and E independently represents CH, N, or CR; and wherein for each instance of Formula II, the total number of nitrogen atoms among A, B, C, D, and E is 1 or 2 and for each instance of Formula IIa, the total number of nitrogen atoms among A, B, C, D, and E is 0, 1, or 2; and wherein each instance of R independently represents halo, alkyl, heteroalkyl, cycloalkyl, heterocycloalkyl, hydroxy, alkoxy, alkoxyalkyl, cycloalkoxy, cyano, amino, alkenyl, heteroalkenyl, cycloalkenyl, heterocycloalkenyl, alkynyl, or heteroalkynyl;

wherein said alkyl, heteroalkyl, cycloalkyl, heterocyloalkyl, alkoxy, alkoxyalkyl, cycloalkoxy, alkenyl, cycloalkenyl, heteocycloalkenyl, or alkynyl is unsubstituted or optionally substituted with alkyl, halogen or fluoroalkyl; or wherein the compound or tautomer thereof is selected from

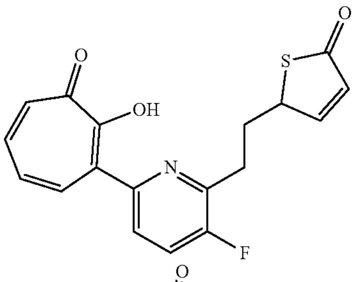

, and

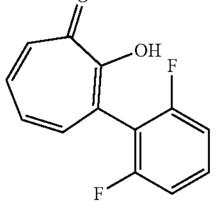

.

2. The compound or tautomer, or a pharmaceutically acceptable salt of either, of claim 1, wherein each instance of R independently represents chloro, fluoro, bromo, iodo, cyano, trifluoromethyl, amino, hydroxy, ($C_1$-$C_{12}$) alkyl, ($C_3$-$C_{12}$) cycloalkyl, ($C_1$-$C_{12}$) alkoxy, ($C_3$-$C_{12}$) cycloalkoxy, or ($C_3$-$C_{12}$) heterocycloalkyl; and heterocycloalkyl comprises one or two oxygen atoms, one or two nitrogen atoms, one or two sulfur atoms, or any combination of two atoms selected from the group consisting of oxygen, nitrogen, and sulfur atoms.

3. The compound or tautomer, or a pharmaceutically acceptable salt of either, of claim 1, wherein:

$R_a$, $R_b$, and $R_d$ represent hydrogen; and $R_c$ represents heteroaryl or substituted heteroaryl according to Formula II.

4. The compound or tautomer, or a pharmaceutically acceptable salt of either, of claim 3, wherein said compound or tautomer is selected from the group consisting of:

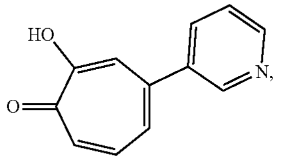

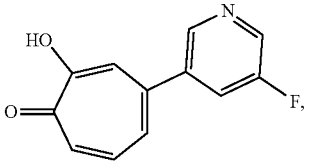

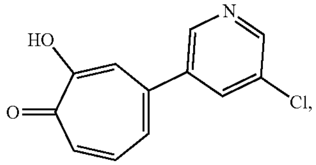

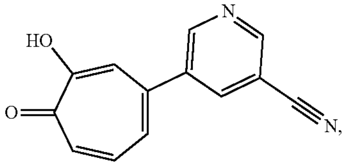

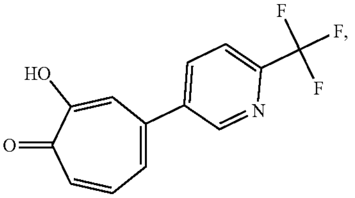

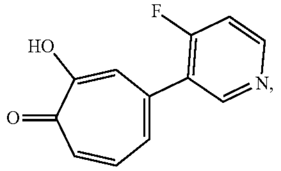

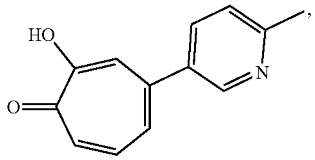

-continued

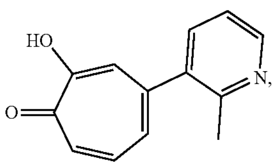

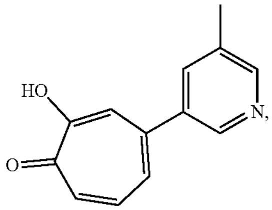

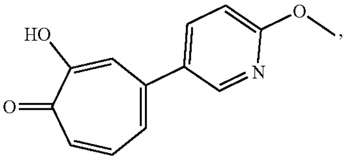

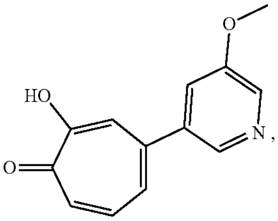

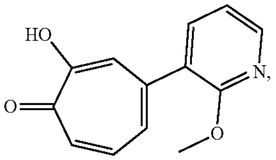

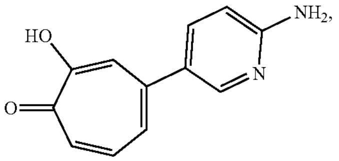

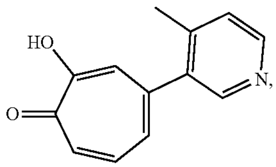

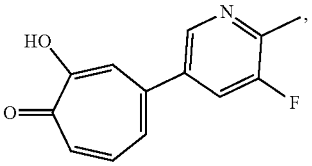

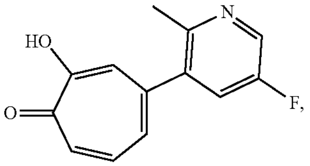

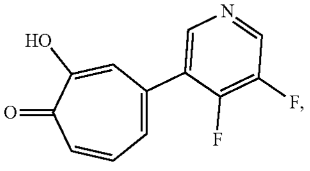

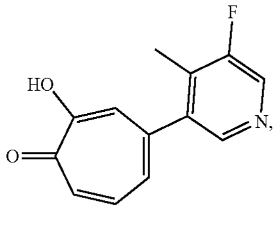

-continued

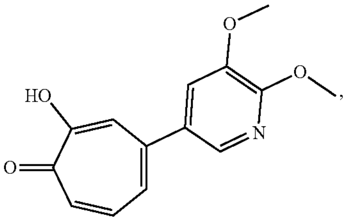

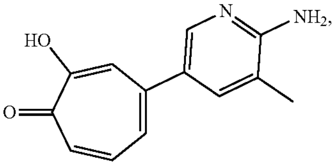

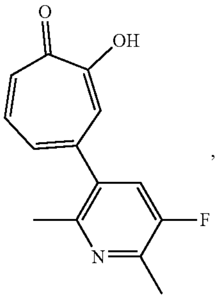

,

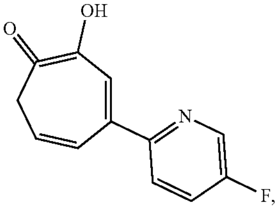

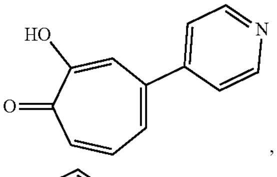

,

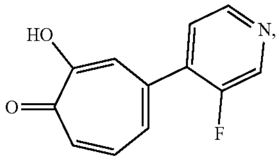

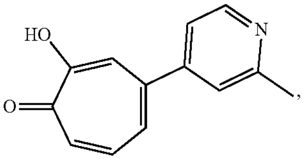

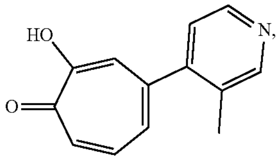

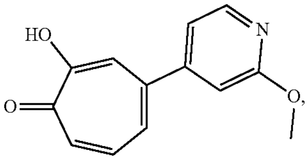

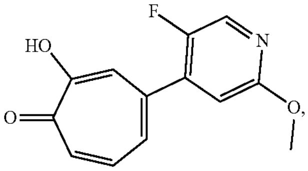

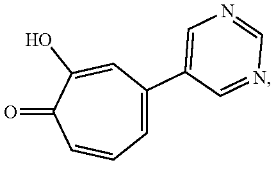

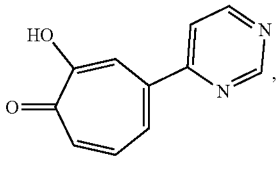

-continued

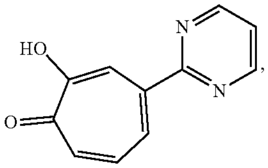

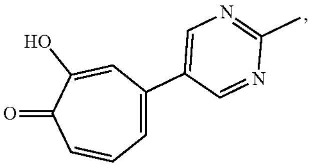

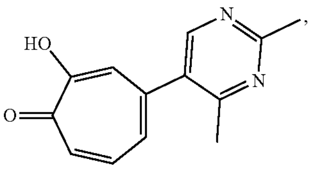

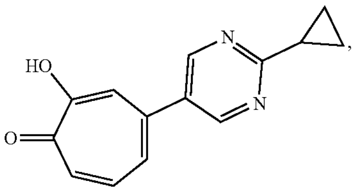

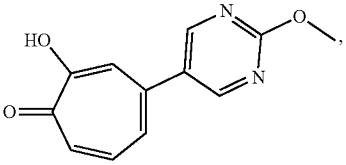

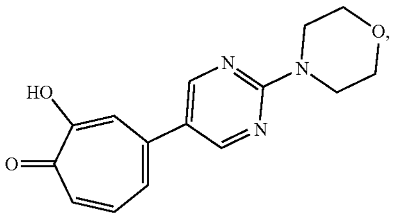

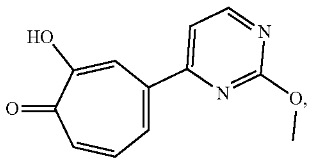

and

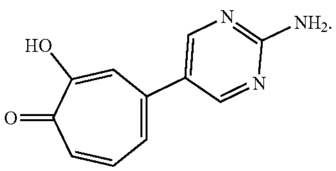

5. The compound or tautomer, or a pharmaceutically acceptable salt of either, of claim 1, wherein:

$R_a$, $R_c$, and $R_d$ represent hydrogen; and $R_b$ represents heteroaryl or substituted heteroaryl according to Formula II.

6. The compound or tautomer, or a pharmaceutically acceptable salt of either, of claim 5, wherein said compound or tautomer is selected from the group consisting of:

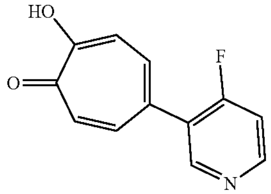
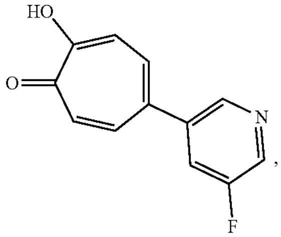
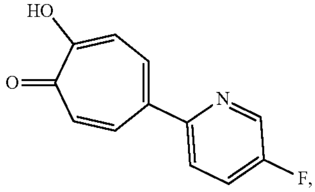
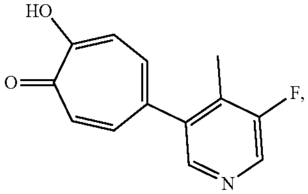
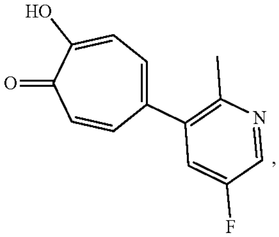
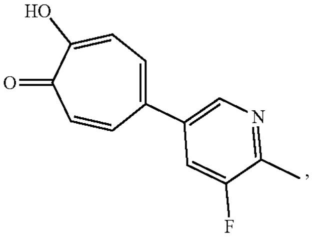
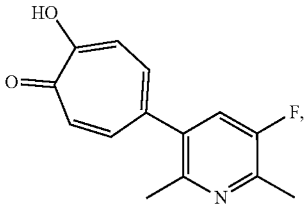
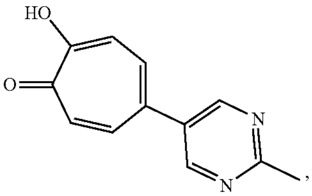
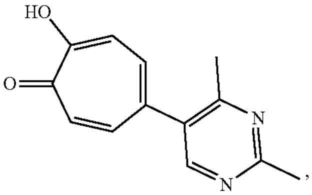

-continued

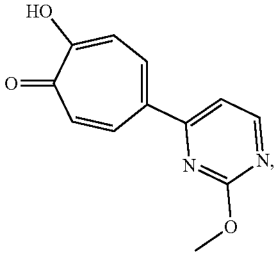
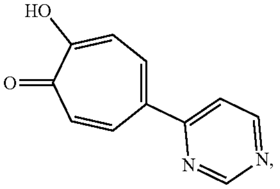
and
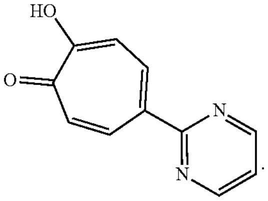

7. The compound or tautomer, or a pharmaceutically acceptable salt of either, of claim 1, wherein:

$R_a$, $R_b$, and $R_c$ represent hydrogen; and $R_d$ represents substituted heteroaryl according to Formula II.

8. The compound or tautomer, or a pharmaceutically acceptable salt of either, of claim 7, wherein said compound or tautomer is selected from the group consisting of:

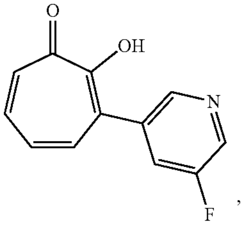
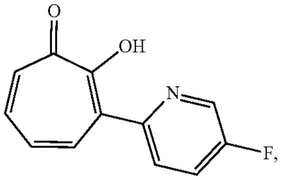
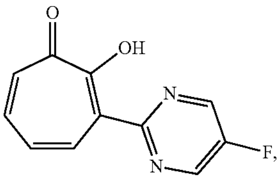
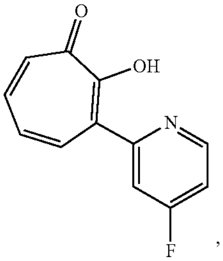
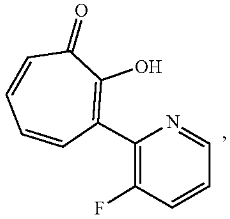
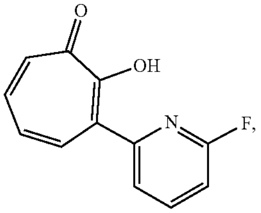

-continued

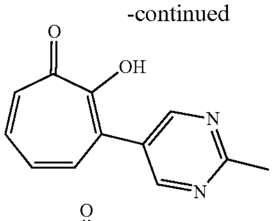

, and

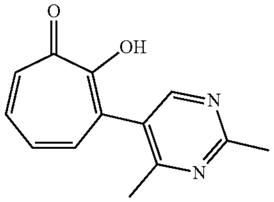

.

9. The compound or tautomer, or a pharmaceutically acceptable salt of either, of claim 1, wherein said compound or tautomer is selected from the group consisting of:

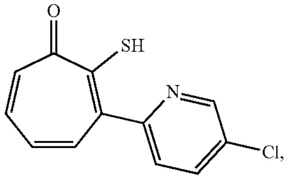

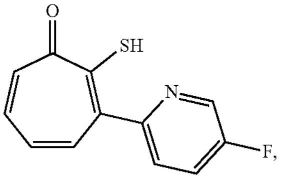

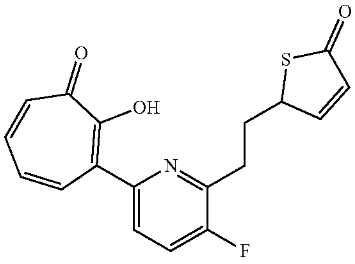

, and

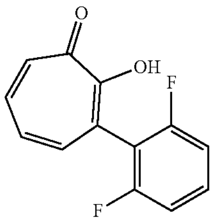

.

10. The compound or tautomer, or a pharmaceutically acceptable salt of either, of claim 1, wherein:

$R_a$ represents alkyl;

one and only one of $R_b$, $R_c$, and $R_d$ represents heteroaryl or substituted heteroaryl according to Formula II; and two of $R_b$, $R_c$, and $R_d$ represent hydrogen.

11. The compound or tautomer, or a pharmaceutically acceptable salt of either, of claim 10, wherein said compound or tautomer is selected from the group consisting of:

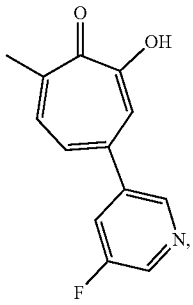

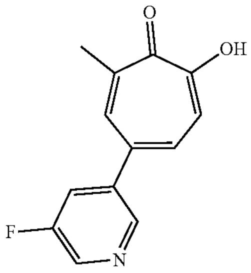

,

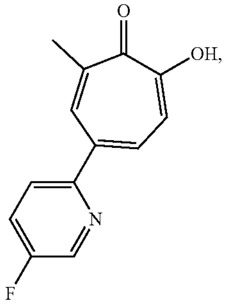

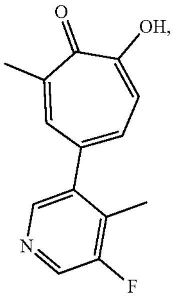

and

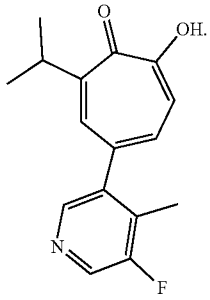

12. The compound or tautomer, or a pharmaceutically acceptable salt of either, of claim 1, wherein:

$R_a$ represents heteroaryl or substituted heteroaryl according to Formula II;

one and only one of $R_b$, $R_c$, and $R_d$ represents alkyl; and two of $R_b$, $R_c$, and $R_d$ represent hydrogen.

13. The compound or tautomer, or a pharmaceutically acceptable salt of either, of claim 12, wherein said compound or tautomer is selected from the group consisting of:

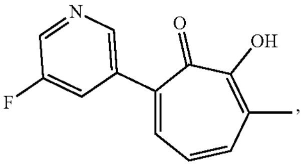

,

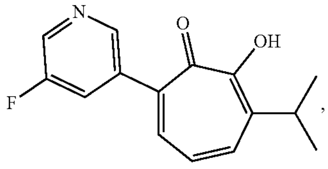

,

-continued

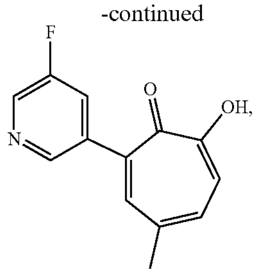

and

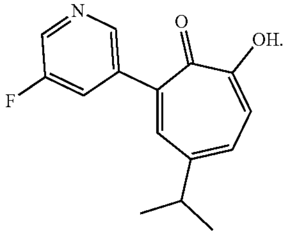

14. The compound or tautomer, or a pharmaceutically acceptable salt of either, of claim 1, wherein:

$R_a$ represents substituted heteroaryl according to Formula II; and each of $R_b$, $R_c$, and $R_d$ represent hydrogen.

15. The compound or tautomer, or a pharmaceutically acceptable salt of either, of claim 14, wherein said compound or tautomer is:

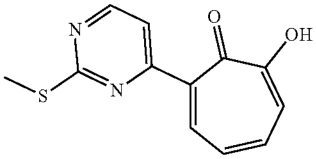 [SMILES: CSc1nccc(-c2ccccc(O)c2=O)n1]

16. The compound or tautomer, or a pharmaceutically acceptable salt of either, of claim 1, wherein:

$R_a$, $R_b$, and $R_d$ represent hydrogen; and $R_c$ represents an aryloxy, substituted aryloxy, heteroaryloxy, or substituted heteroaryloxy according to Formula IIa; or $R_a$, $R_c$, and $R_d$ represent hydrogen; and $R_b$ represents heteroaryloxy or substituted heteroaryloxy according to Formula IIa; or $R_a$ represents alkyl;

one and only one of $R_b$, and $R_c$ represents an aryloxy, substituted aryloxy, heteroaryloxy, or substituted heteroaryloxy according to Formula IIa; and two of $R_b$, $R_c$, and $R_d$ represent hydrogen; or $R_a$ represents an aryloxy, substituted aryloxy, heteroaryloxy, or substituted heteroaryloxy according to Formula IIa;

one and only one of $R_b$, $R_c$, and $R_d$ represents alkyl; and two of $R_b$, $R_c$, and $R_d$ represent hydrogen.

17. A pharmaceutical composition, comprising the compound or tautomer, or a pharmaceutically acceptable salt of either, of claim 1; and a pharmaceutically acceptable carrier.

18. A method of treating a disease or condition associated with iron dysregulation or dysfunctional iron homeostasis, comprising administering to a subject in need thereof a therapeutically effective amount of the compound or tautomer, or a pharmaceutically acceptable salt of either, of claim 1.

19. The compound or tautomer, or a pharmaceutically acceptable salt of either, of claim 1, wherein X is oxygen.

* * * * *